(12) United States Patent
Kasibhatla et al.

(10) Patent No.: US 7,544,672 B2
(45) Date of Patent: Jun. 9, 2009

(54) ALKYNYL PYRROLO[2,3-D]PYRIMIDINES AND RELATED ANALOGS AS HSP90-INHIBITORS

(75) Inventors: Srinivas Rao Kasibhatla, San Diego, CA (US); Marco Antonio Biamonte, San Diego, CA (US); Jiandong Shi, San Diego, CA (US); Marcus F. Boehm, San Diego, CA (US)

(73) Assignee: Conforma Therapeutics Corporation, San Diego, CA (US)

( * ) Notice: Subject to any disclaimer, the term of this patent is extended or adjusted under 35 U.S.C. 154(b) by 72 days.

(21) Appl. No.: 11/277,918

(22) Filed: Mar. 29, 2006

(65) Prior Publication Data

US 2006/0223797 A1    Oct. 5, 2006

Related U.S. Application Data

(60) Provisional application No. 60/666,899, filed on Mar. 30, 2005.

(51) Int. Cl.
  C07D 487/04 (2006.01)
  C07F 9/38 (2006.01)
  A61K 31/519 (2006.01)
  A61K 31/662 (2006.01)

(52) U.S. Cl. .................. 514/81; 514/265.1; 544/243; 544/280

(58) Field of Classification Search .......... 544/117, 544/280, 244, 229, 243; 514/234.5, 265.1, 514/252.16, 81, 63
See application file for complete search history.

(56) References Cited

U.S. PATENT DOCUMENTS

| | | | |
|---|---|---|---|
| 3,595,955 | A | 7/1971 | Boer et al. |
| 4,261,989 | A | 4/1981 | Sasaki et al. |
| 4,495,190 | A | 1/1985 | Hagberg et al. |
| 4,533,254 | A | 8/1985 | Cook et al. |
| 4,547,573 | A | 10/1985 | Jung et al. |
| 4,617,304 | A | 10/1986 | Ashton et al. |
| 4,699,877 | A | 10/1987 | Cline et al. |
| 4,738,958 | A | 4/1988 | Franco et al. |
| 4,748,177 | A | 5/1988 | Sircar |
| 4,772,606 | A | 9/1988 | Sircar |
| 4,774,325 | A | 9/1988 | Casadio et al. |
| 4,806,642 | A | 2/1989 | Sircar et al. |
| 4,918,162 | A | 4/1990 | Slamon et al. |
| 4,921,859 | A | 5/1990 | Sircar et al. |
| 4,923,885 | A | 5/1990 | Hupe |
| 4,968,603 | A | 11/1990 | Slamon et al. |
| 5,002,950 | A | 3/1991 | Malone et al. |
| 5,098,906 | A | 3/1992 | Sircar et al. |
| 5,110,818 | A | 5/1992 | Allgeier |
| 5,204,353 | A | 4/1993 | Meier |
| 5,217,866 | A | 6/1993 | Summerton et al. |
| 5,332,744 | A | 7/1994 | Chakravarty |
| 5,369,008 | A | 11/1994 | Arlinghaus |
| 5,387,584 | A | 2/1995 | Schnur |
| 5,602,156 | A | 2/1997 | Kohn et al. |
| 5,656,629 | A | 8/1997 | Bacon et al. |
| 5,789,394 | A | 8/1998 | Nugyen-Ba et al. |
| 5,846,749 | A | 12/1998 | Slamon et al. |
| 5,861,503 | A | 1/1999 | Barrio et al. |
| 5,917,042 | A | 6/1999 | Daluge |
| 5,932,566 | A | 8/1999 | Schnur et al. |
| 5,955,610 | A | 9/1999 | Nguyen-Ba et al. |
| 5,994,361 | A | 11/1999 | Penney |
| 6,005,107 | A | 12/1999 | Nguyen-Ba et al. |
| 6,025,126 | A | 2/2000 | Westbrook |
| 6,140,374 | A | 10/2000 | May et al. |
| 6,143,743 | A | 11/2000 | Wilde |
| 6,174,875 | B1 | 1/2001 | DeFranco et al. |
| 6,177,460 | B1 | 1/2001 | Camden |
| 6,210,974 | B1 | 4/2001 | Gold |
| 6,262,254 | B1 | 7/2001 | Barrio et al. |
| 6,333,331 | B1 | 12/2001 | Moschel |
| 6,369,092 | B1 | 4/2002 | Pamukcu |
| 6,444,656 | B1 | 9/2002 | Nguyen-Ba et al. |
| 6,723,727 | B1 | 4/2004 | Peyman et al. |
| 7,129,244 | B2 | 10/2006 | Kasibhatla et al. |
| 7,138,401 | B2 | 11/2006 | Kasibhatla et al. |
| 7,148,228 | B2 | 12/2006 | Kasibhatla et al. |

(Continued)

FOREIGN PATENT DOCUMENTS

EP    55239 B1    6/1982

(Continued)

OTHER PUBLICATIONS

Bouma-ter Steege, J. et al., "Angiostatic Proteins and Peptides," Crit. Rev. Eukaryotic Gene Expression 11(4):319-333 (2001).

(Continued)

*Primary Examiner*—Brenda L Coleman
*Assistant Examiner*—Susanna Moore
(74) *Attorney, Agent, or Firm*—Finnegan

(57) ABSTRACT

Alkynyl pyrrolo[2,3-d]pyrimidines and related analogs are described and demonstrated to have utility as Heat Shock Protein 90 (HSP90) inhibiting agents used in the treatment and prevention of various HSP90 mediated disorders. Methods of synthesis and use of such compounds are also described and claimed.

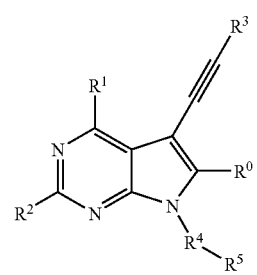

13 Claims, 5 Drawing Sheets

U.S. PATENT DOCUMENTS

| | | |
|---|---|---|
| 2002/0156277 A1 | 10/2002 | Fick et al. |
| 2002/0161014 A1 | 10/2002 | Sadhu et al. |
| 2003/0022864 A1 | 1/2003 | Ishaq et al. |
| 2003/0078413 A1 | 4/2003 | Dempcy et al. |
| 2003/0113331 A1 | 6/2003 | Brooks et al. |
| 2004/0063668 A1 | 4/2004 | Choi et al. |
| 2004/0097526 A1 | 5/2004 | Gillespie et al. |
| 2004/0102458 A1 | 5/2004 | Chiosis et al. |
| 2004/0116447 A1 | 6/2004 | Gillespie et al. |
| 2004/0241706 A1 | 12/2004 | Shah et al. |
| 2004/0242490 A1 | 12/2004 | Brooks et al. |
| 2005/0043239 A1 | 2/2005 | Douangpanya et al. |
| 2005/0049263 A1 | 3/2005 | Kasibhatla et al. |
| 2005/0107343 A1 | 5/2005 | Kasibhatla et al. |
| 2005/0113339 A1 | 5/2005 | Kasibhatla et al. |
| 2005/0113340 A1 | 5/2005 | Kasibhatla et al. |
| 2005/0119282 A1 | 6/2005 | Kasibhatla et al. |
| 2006/0035909 A1 | 2/2006 | Fuksova et al. |
| 2007/0111996 A1 | 5/2007 | Kasibhatla et al. |
| 2007/0111997 A1 | 5/2007 | Kasibhatla et al. |
| 2007/0173483 A1 | 7/2007 | Kasibhatla et al. |
| 2007/0185064 A1 | 8/2007 | Kasibhatla et al. |

FOREIGN PATENT DOCUMENTS

| | | |
|---|---|---|
| EP | 156559 B1 | 10/1985 |
| EP | 159264 B1 | 10/1985 |
| EP | 178178 A2 | 4/1986 |
| EP | 206415 B1 | 12/1986 |
| EP | 0184322 B1 | 12/1989 |
| EP | 363320 A2 | 4/1990 |
| EP | 0151528 B1 | 7/1990 |
| EP | 465297 B1 | 1/1992 |
| EP | 502690 B1 | 9/1992 |
| EP | 565377 B1 | 10/1993 |
| EP | 675123 A1 | 10/1995 |
| JP | 06080670 A2 | 3/1994 |
| JP | 08041035 A2 | 2/1996 |
| JP | 08208687 A2 | 8/1996 |
| JP | 09020776 A2 | 1/1997 |
| JP | 09169758 A2 | 6/1997 |
| JP | 10025294 A2 | 1/1998 |
| JP | 2000-072733 A2 | 3/2000 |
| JP | 2003-113181 A2 | 4/2003 |
| WO | WO-86-05518 A1 | 9/1986 |
| WO | WO-89-10923 A1 | 11/1989 |
| WO | WO-92-05180 A1 | 4/1992 |
| WO | WO-93-14215 A1 | 7/1993 |
| WO | WO-95-07695 A1 | 3/1995 |
| WO | WO-95-08327 A1 | 3/1995 |
| WO | WO-98-01448 A1 | 1/1998 |
| WO | W0-98-39344 A1 | 9/1998 |
| WO | WO-98-51702 A1 | 11/1998 |
| WO | WO-99-01454 A1 | 1/1999 |
| WO | WO-99-02162 A1 | 1/1999 |
| WO | WO-99-12927 A1 | 3/1999 |
| WO | WO-1999-16465 A | 4/1999 |
| WO | WO-99-24432 A1 | 5/1999 |
| WO | WO-99-32122 A1 | 7/1999 |
| WO | WO-99-51223 A1 | 10/1999 |
| WO | WO-00-06573 | 2/2000 |
| WO | WO-00-37050 A1 | 6/2000 |
| WO | WO-00-53394 A1 | 7/2000 |
| WO | WO-00-44750 A1 | 8/2000 |
| WO | WO-00-61578 A1 | 10/2000 |
| WO | WO-00-68230 A1 | 11/2000 |
| WO | WO-01-38584 A2 | 5/2001 |
| WO | WO-01-49688 A1 | 7/2001 |
| WO | WO-01-72779 A1 | 10/2001 |
| WO | WO-02-085905 A1 | 10/2001 |
| WO | WO-01-81346 A2 | 11/2001 |
| WO | WO-02-02123 A1 | 1/2002 |
| WO | WO-02-09696 A1 | 2/2002 |
| WO | WO-02-36075 A2 | 5/2002 |
| WO | WO-02-36171 | 5/2002 |
| WO | WO-02-055082 A1 | 7/2002 |
| WO | WO-02-055083 | 7/2002 |
| WO | WO-02-055521 A1 | 7/2002 |
| WO | WO-02-057288 A1 | 7/2002 |
| WO | WO-02-069900 A2 | 9/2002 |
| WO | WO-02-088079 A2 | 11/2002 |
| WO | WO-02-088080 A2 | 11/2002 |
| WO | WO-02-094196 A2 | 11/2002 |
| WO | WO-02-102314 A2 | 12/2002 |
| WO | WO-03-000200 A2 | 1/2003 |
| WO | WO-03-002565 A1 | 1/2003 |
| WO | WO-03-026571 A2 | 4/2003 |
| WO | WO-03-035938 A2 | 5/2003 |
| WO | WO-03-037860 A2 | 5/2003 |
| WO | WO-03-041643 A2 | 5/2003 |
| WO | WO-03-050295 A2 | 6/2003 |
| WO | WO-03-056030 A3 | 7/2003 |
| WO | WO-03-066005 A2 | 8/2003 |
| WO | WO-03-072794 A1 | 9/2003 |
| WO | WO-03-086381 A1 | 10/2003 |
| WO | WO-03-106458 A1 | 12/2003 |
| WO | WO-2004-014913 A2 | 2/2004 |
| WO | WO-2004-024082 A2 | 3/2004 |
| WO | WO-2004-029064 A1 | 4/2004 |
| WO | WO-2004-087734 A | 10/2004 |
| WO | WO-2005-012324 A2 | 2/2005 |
| WO | WO-2005-016348 A1 | 2/2005 |
| WO | WO-2005-016349 A1 | 2/2005 |
| WO | WO-2005-028434 A2 | 3/2005 |
| WO | WO-2005-028479 A2 | 3/2005 |
| WO | WO-2005-058925 A1 | 6/2005 |
| WO | WO-2005-058926 A1 | 6/2005 |
| WO | WO-2005-067901 A2 | 7/2005 |
| WO | WO-2005-079812 A1 | 9/2005 |
| WO | WO-2005-085470 A1 | 9/2005 |
| WO | WO-2005-092892 A1 | 10/2005 |
| WO | WO-2006-105372 | 10/2006 |

OTHER PUBLICATIONS

Hicklin, D.J. et al., "Monoclonal antibody strategies to block angiogenesis," Drug Discovery Today 6(10):517-528 (2001).

Hodivala-Dilke,K. et al., "Integrins in angiogenesis: Multitalented molecules in a balancing act," Cell Tissue Res. 314(1):131-144 (2003).

Kumar, C.C., "Integrin Alphavbeta3 as a Therapeutic Target for Blocking Tumor-induced Angiogenesis," Curr. Drug Targets 4(2):123-131 (2003).

Marneros, A.G. et al., "The role of collagen-derived proteolytic fragments in angio genesis," Matrix Biology 20:337-345 (2001).

Meerovitch, K. et al., "A novel RGD antagonist that targets both alphavbeta3 and alpha5beta1 induces apoptosis of angiogenic endothelial cells on type I collagen," Vasc. Pharma, 40:77-89 (2003).

Nimmanapalli et al., "Geldanamycin and its analogue 17-allylamino-17-demethoxygeldanamycin lowers Bcr-Abl levels and induces apaptosis and differentiation of Bcr-Abl-positive human leukemic blasts," Cancer Res. 61:1799-1804 (2001).

Schulte, T. "The benzoquinone ansamycin 17-allyamino-17-demethoxygeldanamycin binds to HSP90 and shares important biologic activities with geldanamycin," Cancer Chemother. Pharmacol. 42:273-279 (1998).

U.S. Appl. No. 60/371,668, filed Apr. 10, 2002, Ulm et al.
U.S. Appl. No. 60/359,484, filed Feb. 25, 2002, Short et al.
U.S. Appl. No. 60/340,762, filed Dec. 12, 2001, Kamal et al.
U.S. Appl. No. 60/337,919, filed Nov. 9, 2001, Kasibhatla et al.
U.S. Appl. No. 60/335,391, filed Oct. 30, 2001, Kasibhatla et al.
U.S. Appl. No. 60/331,893, filed Nov. 21, 2001, Zhang et al.
U.S. Appl. No. 60/326,639, filed Sep. 24, 2001, Zhang et al.
U.S. Appl. No. 60/293,246, filed May 23, 2001, Rosen et al.

U.S. Appl. No. 10/945,851, filed Sep. 20, 2004, Kasibhatla et al.
U.S. Appl. No. 10/494,414, filed Oct. 4, 2004, Kasibhatla et al.
U.S. Appl. No. 10/946,645, filed Sep. 20, 2004, Kasibhatla et al.
U.S. Appl. No. 10/946,637, filed Sep. 20, 2004, Kasibhatla et al.
U.S. Appl. No. 10/469,469, filed Aug. 27, 2003, Fritz et al.
Abblard, J. et al., "Preparation et determination de structure de nouvelles pyridines halogenees Mecanisme de l'halagenation," Bull. Soc. Chim. Fr. 1972, 2466.
Abramovith Pyridine and its derivatives, Supp. Part 2, Wiley & Sons, 1974, pp. 1-261. Table of Contents.
Akao et al., Genes, Chromosomes & Cancer, Apr. 2000 27(4):412-417.
Alhede, J., "A Simple and Efficient Synthesis of 9-Substituted Guanines. Cyclodesulfurization of 1-Substituted-5;[(Thiocarbamoyl)amino]imidazole-4-carboxamides under Aqueous Basic Conditions, " J. Org. Chem. 1991, 2139.
An et al., Cell Growth and Differentiation, Jul. 2000, 11:355-360.
Andricopulo, A.D. and Yunes, R.A., "Structure-activity relationships for a collection of structurally diverse inhibitors of purine nucleoside phosphorylase," Chem. & Pharm. Bull. 49(1), 10-17 (2001).
Ashton, W.T. et al., "Synthesis and Antiherpetic Activity of (∓)-9-[[(Z)-2-(Hydroxymethyl)cyclopropyl]methyl]guanine and Related Compounds," J. Med. Chem. 1988, 31, 2304-2315.
Ashwell, M. et al., "An improved route to guanines substituted at N-9," J. of the Chem. Soc., Chem. Comm. (14), 955-6 (1990).
Aurelio et al., Mol. And Cell Biol. Feb. 2000, 20:770-778.
Ausubel et al., Current Protocols in Molecular Biology, John Wiley & Sons, NY 1994, Table of Contents.
Baffa et al., PNAS 23, May 1995, 93(11):4922-1926.
Baker, et al., "Irreversible Enzyme Inhibitors. XCV. 8-(m-Bromoacetamidobenzylthio) hypoxanthine, and Active-Site-Directed Irreversible Inhibitor of Xanthine Oxidase," J. Medicinal Chem. 10(4), 682 (1967). See compounds 6, 8a, 12, 14, 15, 17.
Bakkestuen, A. K., et al., "9-Benzylpurines with inhibitory activity against Mycobacterium tuberculosis," Biorg. & Med. Chem. Ltrs., 10(11), 1207-1210 (2000).
Balo, C. et al, "Synthesis of novel carbocyclic nucleosides with a cyclopentenyl ring: homocarbovir and analogs," Tetrahedron 54(12), 2833-2842 (1998).
Balo, M. et al, "Synthesis and antiviral activities of some novel carbocyclic nucleosides," Nucleosides & Nucleotides 15(7&8), 1335-1346 (1996).
Barltrop et al., Biorg. & Med. Chem. Lett., 1991, 1:611-614.
Barr, F., Nat. Genet., Jun. 1998, 19:121-124.
Bayar et al., Cancer Genet. Cytogenet., Jul. 1, 1996 89:177-180.
Bedard, J. et al., "Comparative study of the anti-human cytomegalovirus activities and toxicities of a tetrahydrofuran phosphonate analog of guanosine and cidofovir," Antimocrobial Agents & Chemo. 43(3), 557-567 (1999).
Bennet, L.L., et al., "Mode of action of 2-amino-6-chloro-1-deazapurine," Biochem. Pharmacol. 33(2), 261-71 (1984).
Bennett, S.M., "Synthesis and Antiviral Activity of Some Acyclic and C-Acyclic Pyrrolo[2,3-d]pyrimidine Nucleoside Analogues," J. Med. Chem. 1990, 33, 2162.
Berge et al., "Pharmaceutical Salts," J. Pharm. Sci. 1977, 66:1-19.
Blagosklonny, M. et al., FASEB J., Oct. 2000, 14:1901-1907.
Blagosklonny, M. et al., Oncogene 1995, 11:933-939.
Blanco, J.M. et al., "Synthesis and antiviral and antineoplastic activities of some novel carbocyclic guanosine analogs with cyclobutane ring," Chem. & Pharm. Bulletin, 47(9), 1314-1317, (1999).
Blanco, J.M. et al., "Synthesis and antiviral and cytostatic activities ofcarbocyclic nucleosides ncorporating a modified cyclopentane ring. 1. Guanosine analogs.," Nucleosides & Nucleotides 16(1&2), 159-171 (1997).
Blanz, E.J. et al., "Carcinostatic Activity of Thiosemicarbazones of Formyl Heteroaromatic Compounds. VII. 2-Formylpyridine Derivatives Bearing Additional Ring Sustituents," J. Med. Chem. 1970, 13, 1124.
Borkhardt et al., Genes, Chromosomes & Cancer, Sep. 2001, 32(1):83-88.
Borrow et al., Nat. Genet. Feb. 1996, 12(2):159-167.
Brachmann et al., PNAS Apr. 1996, 93:4091-4095..

Brathe, A. et al., "Cytotoxic activity of 6-alkynyl-and 6-alkenylpurines," Biorg. & Med. Chem. Ltrs. 13(5), 877-880 (2003.
Bruckner, A.M. et al., "Nucleo-β-amino acids: synthesis and oligomerization of β-homoalanyl-PNA," Helvetica Chimica Acta 85(11), 3855-3866 (2002).
Bubenik, M. et al., "A stereoselective route to bioactive nucleotide phosphonate analogs," Tetrahedron Ltrs. 44(45), 8261-8263 (2003).
Bubenik, M. et al., "Novel nucleotide phosphonate analogues with potent antitumor activity," Biorg. & Med. Chem. Ltrs. 12(21), 3063-3066 (2002).
Buchner, J., "Hsp90 & Co.-a holding for folding," YIBS, Apr. 1999, 24:136-141.
Buchwald, H. et al., "Long-term, continuous intravenous heparin administration by an implantable infusion pump in ambulatory patients with recurrent venou thrombosis," Surgery, 1980, 88, 507.
Buijis et al., Oncogene, Apr. 20, 1995, 10(8):1511-1519.
Bundgaard, H. "Design and Application of Prodrugs" in A Textbook of Drug Design and Development, Krosgaard-Larsen and H. Bundgaard, Ed., 1991, Chapter 5, p. 113-191.
Bundgaard, H., Advanced Drug Delivery Review, 1992, 8, 1-38.
Burger, A. et al., "Synthesis of 8-(O-Hydroxyalkyl)-, 8-(o-Hydroxyalk-1-enyl)-, and 8-(o-Hydroxyalk-1-ynyl)adenines Using the tert-Butyldimethylsilyloxymethyl Group, a New and Versatile Protecting Group of Adenine," J. Org. Chem. 2000, 65, 7825-7832.
Busson-Le Coniat et al., Leukemia, Feb. 1999, 13(2):302-306.
Caamano, O. et al, "Carbocyclic nucleosides with a modified cyclopentane skeleton," Nucleosides & Nucleotides 14(3-5), 295-7 (1995).
Caplan, A., "Hsp90's secrets unfold: new insights from structural and functional studies," Trends in Cell Biol. 1999, 9:262-268.
Cazzaniga et al., Blood, Dec. 15, 1999, 94:4370-4373.
Cesnek, M. et al., "New 2-alkynyl derivatives of the acyclic nucleoside 9-(2,3-dihydroxypropyl)adenine and their 6-guanidinopurine counterparts as potential effectors of adenosine receptors," Collection of Czechoslovak Chem. Comm. 68(11), 2201-2218 (2003).
Chen et al., EMBO J., 1993, 12(3):1161-1167.
Chen et al., Stem Cells, Jan. 1995, 13(1):22-31.
Chene et al., Int. J. Cancer, 1999, 82:17-22.
Chene, P., J. Mol. Biol. 1998, 281:205-209.
Cheng et al., "Rearrangement of 4-Amino-6-chloro-1-methlypyrazolo (3,4-d)pyrimidine in Basic Solution," J. Org. Chem. 1959, vol. 24, pp. 1570-1571.
Chern, J.W. et al., "Certain 8-Amino-9-(benzul)guanines as potential purine nucleoside phosphorylase inhibitors," Eur. J. Med. Chem. 1994, 29(1), 3-9.
Chiosis et al., A Small Molecule Designed to Bind to the Adenine Nucleotide Picket of HSP90 Causes HER2 Degradation and the Growth Arrest and Differentiation of Breast Cancer Cells, Chem. & Biol. 8, 289-299 (2001).
Chissoe et al., Genomics (1995) 27:67-82.
Choi, B.G. et al, "Synthesis and antiviral activity of novel exomethylene cyclopropyl nucleosides," Nucleosides, Nucleotides & Nucleic Acids 20(4-7), 1059-1062 (2001).
Choi, J. et al., "A Novel Class of Phosphonate Nucleosides. 9-[(1-Phosphonomethoxycyclopropyl)methyl]guanine as a Potent and Selective Anti-HBV Agent," J. Med. Chem. 2004, 47, 2864-2869.
Chong, S. et al., Pharma. Res. 14(12):1835-1837 (1997).
Chowdhury, S.F. et al., "Design, Synthesis and Evaluation of Inhibitors of Trypanosomal and Leishmanial Dihtdorofolate Reductase," J. Med. Chem. 1999, 42, 4300.
Cimino et al., Cancer Res., Dec. 15, 1991, 51(23):6712-6714.
Cory, A. et al., "Use of an aqueous soluble tetrazolium/formazan assay for cell growth assays in culture," Cancer Comm. 1991, 3, 207-212.
Cotter et al., Am. J. Clin.Nutr. 50:794-800 (1989).
Crook et al., Oncogene 2000, 19:3439-3444.
Dai et al., "Physical interaction of mammalian CDC37 with CDK4," J. Biol. Chem. 1996, 271:22030-22034.
De Cat, A., "Synthetic Applications of Difluorocarbene," Bull. Soc. Chim. Belg. 1965, 74, 270-280.
De La Torre-Bueno, J. et al., 2000, Modern Pathology 13:221A.

De Napoli, L., "Reaction of 3',4'-Di-O-acetyl-2'-deoxyinosine with the Chlorinating Agent PPh3-CCl4: Synthesis of the 6-chloroderivative and of a new base linked dimmer, useful intermediate to 15N-1-labelled2'-deoxyinosine," J. Chem. Soc., Perkin Trans 1, 1994.

Deb, D. et al., Int. J. Oncol. 1999, 15:413-422.

Deng, H.F., "Studyon the synthesis of N6 aromatic heterocyclic methyl substituted adenosine and adenine by Dimroth rearrangement reaction," Chinese Chem. Ltrs. 5(4), 271-4 (1994).

Deninger et al., Cancer Res. Apr. 1, 2000, 60:2049-2055.

Design of Prodrugs, Bundgaard, A. Ed., Elseview, 1985, Table of Contents.

Diekmann et al., Nature 351:400-402(May 30, 1991).

Dierlamm et al., Genes, Chromosomes & Cancer, Jun. 1998, 22(2):87-94.

Dridi et al., Am. J. Med. Genet. (1999) 87:134-138.

Egorin, M. et al., Cancer Chemother. Pharmacol. 49:7-19 (2002).

Eguchi et al., Blood, Feb. 15, 1999, 93(4):1355-1363.

Erikson et al., PNAS, Mar. 1986, 83:1807-1811.

Erion, M.D. et al., Sructure-based design of inhibitors of purine nucleoside phophorylase.3. 9-arylmethyl derivatives of 9-deazaguanine substituted on the arylmethyl group. J. of Med. Chem. 37(7), 1034 (1994).

Erion, M.D. et al., "Structure-Based Design of Inhibitors of Purine Nucleoside Phosphorylase.3. 9-Arylmethyl Derivatives of 9-Deazaguanine Substituted on the Methylene Group," J. Med. Chem. 1993, 36, 3771-3783.

Erlichman, C. et al., "A Phase I Trial of 17-Allyl-Amino-Geldanamycin in Patients with Advanced Cancer," Proc. AACR (2001), 42, Abstract 4474.

Federal Register 66(129):35443-35444, 2001.

Fisher, B.E. et al., "The Structure of Isomaltol," J. Org. Chem. 1964, 29, 776.

Ford et al., PNAS, Apr. 1998, 95(8):4584-4588.

Frebourg et al., PNAS, Jul. 1992, 89:6413-6417.

Gangjee et al., "Design, Synthesis and X-ray Crystal Structure of a Potent Dual Inhibitor of Thymidylate Synthase and Dihydrofolate REductase as an Antitumor Agent," J. Am. Chem. Soc. 2000, vol. 43, No. 21, pp. 3837-3851.

Gauwerky et al., Semin. In Cancer Biol., Dec. 1993, 4(6):333-340.

Goodman and Gilman, The Pharmacological Basis of Therapeutics,current ed., Pergamon Press, 2006 Table of Contents.

Goodson, J., "Medical Applications of Controlled Release," 1984, vol. 2, pp. 115-138.

Gracia-Cueller et al., Oncogene, Mar. 30, 2000, 19(14):1744-1751.

Grosveld et al., Mol. and Cell. Biol., Feb. 1986, 6(2):607-616.

Guan, H. et al., "Synthesis of phosphonate derivatives of methylenecyclopropane nucleoside analogues by alkylatin-elimination method and unusual opening of cyclopropane ring," Tetrahedron 58(30), 6047-6059 (2002).

Guillarme et al., "Rapid Access to acyclic nucleosides via conjugate addition,"Tetrahedron, 59:12, Mar. 17, 2003, pp. 2177-2184.

Hainaut et al., Adv. Cancer Res., 2000, 77:81-137.

Halazy, S. et al., "Phosphonate derivatives of N9-benzylguanine: a new class of potent purine nucleoside phosphorylase inhibitors," Biorg. & Med. Chem. Ltrs. 2(5), 407-10 (1992).

Halazy, S. et al., "Fluorophosphonate derivatives of N9-benzylguanine as potent, slow-binding multisubstrate analog inhibitors of purine nucleoside phosphorylase," Tetrahedron, 52(1), 177-84 (1996).

Halbfinger, E. et al., "Molecular Recognition of Modified Nucleotides by the P2Y1-Receptor. 1. A Synthetic, Biochemical, and NMR Approach," J. Med. Chem. 1999, 42, 5325.

Han et al., Arthritis & Rheumat., Jun. 1999, 42(6): 1088-1092.

Han, M.J. et al., "Polynucleotide analogs. VI. Synthesis and characterization of alternating copolymers of maleic anhydride and dihydropyran-containing guanine derivatives," J. of Polymer Science, Part A: Polymer Chemistry 33(11), 1829-39 (1995).

Harlow et al., Antibodies: A Laboratory Manual, 2nd Ed., Cold Spring Harbor Laboratory Press, Cold Spring Harbor, NY 1988, Table of Contents.

Harris et al., N. Eng. Med., Oct. 28, 1993, 329(18):1318-1327.

Hartmann et al., "Effects of the tyrosine-kinase inhibitor gelanamycin on ligand-induced her-2/heu activation, receptor expression and proliferation on her-2-positive malignant cell lines," Int. J. Cancer, 1997, 70:221-229.

Hayashi et al., Cancer Res., Feb. 15, 2000, 60(4):1139-1145.

Herdewijn, P. et al., "Synthesis and Structure-Activity Relationships o Analogs of 2'-Deoxy-2'-(3-mehoxybenzamido)adenosine, a Selective Inhibitor of Trypanosomal Glycosomal lyceraldehyde-3-phosphate Dehydrogenase," J. Med. Chem. 1995, 38, 3838.

Holy, A. et al., "Acyclic nucleotide analogs. VI. Synthesis of (3-hydroxy-2-phosphonylmethoxypropyl) derivatives of heterocyclic bases," Collection of Czechoslovak Chemical Communications 54(9), 2470-501 (1989).

Holy, A. et al., "Structure-Antiviral Activity Relationship in the Series of Pryimidine and Purine N-[2-(2-Phosphonomethoxy)ethyl] Nucleotide Analogues. 1. Derivatives Substituted at the Carbon Atoms of the Base," J. Med. Chem. 1999, 42, 2064-2086.

Honma et al., Int. J. Cancer, 1995, 60:685-688.

Horiike et al., Leukemia, Aug. 1999, 13(8):1235-1242.

Hossain, N. et al., "Synthesis of homo-N-nucleosides, a series of C1' branched-chain nucleosides," Tetrahedron 52(15), 5563-78 (1996).

Hotoda, H. et al., "Biologically active oligodeoxyribonucleotides. X. Anti-HIV-1 activity and stability of modified hexanucleotides containing glycerl-skeleton," Nucleosides and Nucleotides 17(1-3), 243-252 (1998).

Houlton, A. et al, "Synthesis, structure and redox properties of ferrocenylmethylnucleobases," J. of the Chem. Society, Dalton Transactions: Inorganic Chem. 1999, 18, 3229-3234.

Hunger et al., Blood, Jun 15, 1993, 81(12):3197-3203.

Iljima et al., Blood, Mar. 15, 2000, 95(6):2126-2131.

Jacobson, K. A. et al., "Structure-Activity Relationships of Bisphosphate Nucleotide Derivatives as P2Y, Receptor Antanonists and Partial Agonists," J. Med Chem. 1999, 42, 1625.

Jaju et al., Blood, Jul 15, 1999, 94(2):773-780.

Janeba, Z., Collection of Czechoslovak Chemical Communications 66(9), 1393-1406 (Sep. 2001).

Jeromin, G.E. et al., "Seitenkettenchlorierungen von N-Heterocyclen mit Trichlorisocyanursaure (TCC)," Chem. Ber. 1987, 120, 649.

Kanth et al., "Selective Reduction of Carboxylic Acids into Alcohols Using NaBH4 and I2", J. Org. Chem. 1991, 56, 5964-5965.

Kaur, G. et al., Clin. Cancer Res. 10:4813-4821 (2004).

Kelley, J.L. et al., "6-(Alkylamino)-9-alkylpurines. A New Class of Potential Antipsychotic Agents," J. Med. Chem. 1997, 40, 3207-3216.

Kelley, J.L. et al., "9-[Phosphonoalkyl)benzyl]guanines. Multisubstrate Analogue Inhibitors of Human Erythrocyte Purine Nucleoside Phosphorylase," J. Med. Chem. 1993, 36, 3455-3463.

Kelley, J.L. et al., "Synthesis and Structure-Activity Relationships of 2-Substituted-6-(dimethylamino)-9-(4-methylbenzyl)-9H-purines with Antirhinovirus Activity," J. Med. Chem. 1989, 32, 218-224.

Kim, D.K. et al., "Synthesis and evaluation of 2-amino-6-fluoro-9-(2-hydroxyethoxymethyl)purine esters as potential prodrugs of acyclovir," Biorg. Med. Chem. 6(12), 2525-30 (1998).

Kim, K. and McComas, W., "Chemoselective high-throughput purification mediated by solid-supported reagents: Its application to the first 6,9-disubstituted purine library synthesis," Cominatorial Chem. & High Throughput Screening, 3(2), 125-129 (2000).

Kjellberg, J. and Johansson, N.G., "Characterization of N-7 and N-9 alkylated purines analogs by proton and carbon-13 NMR," Tetrahydron 42(23), 6541-44 (1985).

Kjellberg, J. and Johansson, N.G., "Studies on the Alkylation of Derivaties of Guanine," Nucleosides & Nucleotides, 8(2), 225-256 (1989).

Knezevich et al., Nat. Genet., Feb. 1998, 18:184-187.

Kobayashi et al., Leukemia and Lymphoma, 1997;28:43-50.

Kolibaba et al., Biochim. Et. Biophys. Acta, 1997, 1333:F217-F248.

Kos et al., "Deamination of 6-Amino-and-6-(Alkylamino)-9-alkylpurines and Demethylation of Methylthiopurines by Sodium in Liquid Ammonia," J. Org. Chem. 1981, 46, 5000-5003. See Table 1, last 2 compounds.

Kotra, L.P. et al., "Structure-Activity Relationships of 2'-Deoxy-2',2'-difluoro-1-erythro-pentofuranosyl Nucleosides," J. Med. Chem. 40, 3635-3644 (1997).

Kourlas et al., PNAS, Feb. 29, 2000, 97(5):2145-2150.
Kozai, S. and Maruyama, T., "Synthesis and biological activity of 9-(2,6-difluorobenzyl)-9H-purines bearing chlorine," Chem. & Pharm. Bulletin, 47(4), 574-575 (1999).
Krauter et al., Genes, Chromosomes & Cancer, 2001, 304(4):342-348.
Kurokawa, H. et al., "Inhibition of HER2/neu(erbB-2) and Mitogen-activated Protein Kinases Enhances Tamoxifen Action against HER2-overexpressing, Tamoxifen-resistant Breast Cancer Cells," Cancer Res. 2000, 60, 5887-5894.
Kusmierek, J.T. et al., "Preparative electrochemical reductuion of 2-amino-6-chloropurine and synthesis of 6-deoxyacyclovir, a fluorescent subsrate of xanthine oxidase and a prodrug of acyclovir, " Acta Chem Scan B 41(10), 701-7 (1987).
Kuwada et al., Cancer Res., Mar 15, 2001, 61(6):2665-2669.
Kwak, E.Y. et al, "Synthesis and antiviral activity of novel methylene cyclopropyl nucleosides," Archives of Pharm. Res. 23(6), 559-563 (2000).
Langer, R., "New Methods of Drug Delivery," Science 1990, 249:1527-1533.
Langli, G. et al., "Regiochemistry in Stille couplings in 2,6-dihalopurines," Tetrahedron, 52(15), 5625-38 (1996).
Le et al., Eur. J. Haematol., 1998, 60:217-225.
Lee, Y.R. et al., "Design and synthesis of novel fluorocyclopropanoid nucleosides," Nucleosides, Nucleotides & Nucleic Acids 29(4-7), 677-679 (2001).
Legraverend, M. et al., "Synthesis and in vitro evaluation of novel 2,6,9-trisubsituted purines acting as cyclin-dependent kinase inhibitors," Biorg. & Med. Chem. (7), 1281-1293 (1999).
Liang, B. et al., J. Org. Chem. 2005, 70,391.
Liefer et al., Cancer Res., Aug. 1, 2000, 60:4016-4020.
Lin, X., "Mild and Efficient Functionalization at C6 of Purine 2'-Deoxynucleosides and Ribonucleosides," Org. Letters 2000, 2, 3497.
Lindgren et al., Am. J. Genet., May 1992, 50(5):988-997.
Linn, J.A. et al., "1,4-Diazabicyclo[2.2.2.]octane (DABCO)-catalyzed hydrolysis and alcoholysis reactions of 2-amino-9-benzyl-6-chloro-9H-purine," J. of the Chem. Soc., Chem. Comm. (8), 913-914 (1994).
Liu et al., EMBO J., 2000, 19(8):1827-1838.
Liu, F. et al., "Addition and cycloaddition to 2-and 8-vinylpurines," Acta CXhemica Scandinavica, 53(4), 269-279 (1999).
Looker, J.H. et al., "Bromomaltol: Structure and Conversion to Novel Pyridone and Pyridine Derivatives," J. Org. Chem. 1979, 44, 3407.
Luo et al., Mol. Cell Biol., Aug. 2001, 21(16):5678-5687.
Ma et al., Blood, Jan. 15, 1996, 87(2):734-745.
Mallory et al., "Pyrimido[4,5-c]pyridazines. 3. Preferential formation of 8-amino-1H-pyrimido[4,5-c]-1,2-diazepin-6(7H)-ones by cyclizations with .alpha., .gamma..-dioxoesters," J. Org. Chem. 1982, vol. 47, pp. 667-674.
Martinelli et al., Haematologica, May 2000, 85(5):552-554.
Marutani et al., Cancer Res., Oct. 1, 1999, 59:4765-4769.
Meegalla, S. et al., "Synthesis of 1-quinolyl derivatives of adenine and guanine," Synlett (1), 61-2 (1993).
Meerabux et al., Oncogene, Mar. 1994, 9(3):893-898.
*Methods in Enzymology*, Drug and Enzyme Targeting, Producing Kinetics, Widder, K. and Green, R. Eds., Academic Press, Inc. 1985, vol. 112, pp. 309-396—"Theory and Practice of Prodrug Kinetics" by Robert W, Notari.
Miles et al., J. of Parenteral and Enteral Nutrition 15:37-41 (1991).
Miller et al., "Depletion of the erbB-2-gene product p185 by benzoquinoid anasymcins," Cancer Res. 1994, 54:2724-2730.
Mimnaugh et al., "Polyubiquitination and proteaseomal degradation of the p185c-erbB-2 receptor protein-tyrosine kinase induced by geldanamycin," J. Biol. Chem. 1996, 271:22796-22801.
Mitani et al., Blood, Apr. 15, 1995, 85(8):2017-2024.
Mitchell, M.S. and Press, M. F., "The Role of Immunohistochemistry and Fluorescence in Situ Hybridization for HER-2/neu in Assessing the Prognosis of Breast Cancer," Oncol. Supp. 1999, 12, 108-116.
Montgomery, J.A. et al., "Synthesis of potential anticancer agents. XXX. (1-Aziridinyl)purines," J. of Med. & Pharm. Chem. 5, 15-24 (1962).

Morisawa, Y. et al., "Studies on Anticoccidial Agents. 1. Synthesis and Anticoccidial Activity of 4-Deoxypyridoxol and Its Esters," J. Med .Chem. 1974, 17, 1083.
Morrissey et al., Blood, Mar. 1, 1993, 81(5):1124-1131.
Muise-Heimericks et al., "Cyclin D expression is controlled post-transcriptionally via a phosphatidylinositol 3-kinase/Akt-dependent pathway," J. Biol. Chem. 1998, 273(45):29864-29872.
Murthy, D. et al., "9-[(Hydroxymethylphenyl_methyl]purine nucleoside analogues: Synthesis, antiviral and cytotoxic properties against cancer cells," Med. Chem. Res. 12(1), 13-25 (2003).
Nakamura et al., PNAS, May 15, 1993, 90(10):4631-4635.
Naritomi et al., Hum. Genet., 1988, 80:201-202.
Negrini et al., Cancer Res., Oct. 1, 1993, 53(19):4489-4492.
Ng et al., Oncogene 2000, 19:1885-1890.
Nguyen-Ba, P. et al., "Design and SAR study of a novel class of nucleoside analogues as potent anti-HCMV agents," Nucleosides & Nucleotides 18(4&5), 821-827 (1999).
Nguyen-Ba, P. et al., "Design and synthesis of a novel class of nucleotide analogs with anti-HCMV activity," Bioorg. & Med. Chem. Ltrs. 8(24), 3555-3560 (1998).
Nguyen-Ba, P. et al., "Identification of novel nucleotide phosphonate analogs with potent anti-HCMV activity," Bioorg. & Med. Chem. Ltrs. 8(24), 3561-3566 (1998).
Noelle et al., "Potential Purine Antagonists. XX. The Preparation and Reactions of Some Methylthiopurines," J. Am. Chem. Soc. 81, 5997-6007 (1959). See species of Tables ii-iV, Scheme IV.
Novak, J. et al., "Synthesis of 7-Hydroxy(phenyl)ethylguanines by Alkylation of 2-amino-6-chloropurine with allyl-protected bromohydrins," Org. Ltrs. 5(5), 637-639 (2003).
O'Connor et al., Br. J. Hematol., 1997, 99:597-604.
O'Connor et al., Leuk. And Lymphoma, 1999, 33(1-2):53-63.
Ogawa et al., Oncogene, Jul. 1996, 13(1):183-191.
Okuda et al., Oncogene, Sep. 19, 1996, 13(6):1147-1152.
Onishi, T. and Tsuji, T., "Synthesis of cylcobutane analogs of the antiviral cyclopropane nucleoside A-5021," Nucleosides, Nucleotides & Nucleic Acids 20 (12), 1941-1948 (2001).
Onishi, T. et al., "A practical synthesis of antiviral cyclopropane nucleoside A-5021," Tetrahedron Ltrs. 40(50), 8845-8847 (1999).
Ono et al., Cancer Res., Jan. 15, 2002, 62(2):333-337.
Osada et al., Nature Med., Jul. 1998, 4(7):839-843.
Ozeki, N. et al., "A New Sandmeyer Iodination of 2-Aminopurines in Non-Aqueous Conditions: Combination of Alkali Metal Iodide and Iodine as Iodine Sources," Heterocycles, vol. 55, No. 3, pp. 461-464, 2001.
Panagopoulos et al., Genes, Chromosomes & Cancer, Aug. 2000, 28(4):415-424.
Panaretou et al., "ATP binding and hydrolysis are essential to the function of the Hsp90 molecular chaperone in vivo," EMBO J. 1998, 17 (16):4829-4836.
Panouse, J.J., Pharm. Francaises 2000, 58(5), 291-302.
Papadopoulos et al., Cancer Res., Jan. 1, 1995, 55(1):34-38.
Park et al., Oncogene, 1994, 9:1899-1906.
Park, J. et al., "Synthesis of [1'-fluoro-2',2'-bis-(hydroxymethyl)-cyclopropylmethyl]purines as antiviral agents," Nucleosides, Nucleotides & Nucleic Acids 22(5-8), 995-957 (2003).
Parkanyi C. et al., "Synthesis of Acyclic Nucleoside Analogs of 6-Substitutred 2-Aminopurines and 2-Amino-8-azapurines," J. Het. Chem. 1990, 27(5).
Peterson, M.L. and Vince. R., "Synthesis and biological evaluation of carbocyclic analogues of lyxofuranosides of 2-amino-t-substituted-purines and 2-amino-6-substituted-8-azapurines," J. Med. Chem. 33(4), 1214-9 (1990).
Pierra, C. et al., "Synthesis and antiviral activities of enantiomeric 1-[2-(hydroxymethyl)cyclopropyl] methyl nucleosides," Nucleosides, Nucleotides & Nucleic Acids 19 (1&2), 253-268 (2000).
Poirel et al., Blood, Mar. 15, 1996, 87(6):2496-2505.
Prasad et al., PNAS, Aug. 16, 1994, 91(17):8107-8111.
Press, M. et al., Modern Pathology 2000, 13 225A, 1326.
Preuss et al., Int. J. Cancer, 2000, 88:162-171.
Prodromou, C. et al., "Identification and Structural Characterization of the ATP/ADP-Binding Site in the Hsp90 Molecular Chaperone," Cell 90:1997, 65-75.

Qiu, Y. and Zemlicka, J., "Synthesis of new nucleoside analogues comprising a geminal difluorocyclopropane moiety as potential antiviral/antitumor agents," Nucleosides & Nucleotides 18(10), 2285-2300 (1999).

Quintela et al., "Pyrazolopyrimidines: synthesis, effect on histamine release from rat peritoneal mast cells and cytotoxic activity," Eur. J. Med. Chem. 2001, vol. 36, pp. 321-332.

Rabbitts, T., Nature, Nov. 10, 1994, 372:143-149.

Raboisson, P. et al., "Design, synthesis and structure-activity relationships of a series of 9-substituted adenine derivatives as selective phosphodiesterase type-4 inhibitors," Eur. J. of Medicinal Chem. 38 (2003) 199-214.

Remington Pharmaceutical Sciences, 20th ed, Ch. 47, pp. 913-914, Mack Publishing Co., Easton PA USA, 2000.

Remington Pharmaceutical Sciences, Osol., A. ed., 18th ed., Mack Publishing Co., Easton PA USA 1990, Table of Contents.

Revy, P. et al., Cell, Sep. 1, 2000, 102:565-575.

Rinehart et al., "Progress in the Chemistry of Organic Natural Products", Chemistry of the Ansamycin Antibiotics, 33:231-307 (1976).

Riss et al., Mol. Biol. Cell 3 (Suppl.), Sep. 1992, 3:184A.

Robins, M.J., "Nucleic Acid Related Compounds. 8. Direct Conversion f2'-Deoxyinosine to 6-Chloropurine 2'-Deoxyriboside and Selected 6-Substituted Deoxynucleosides and Their Evaluation as Substrates of Adenosine Deaminase," Can. J. Chem. 1973, 12, 3161.

Rollenhagen et al., Int. J. Cancer, 1998, 78:372-376.

Romana et al., Blood, Jun. 15, 1995, 85(12):3662-3670.

Roulston et al., Blood, Dec. 1, 1993, 82(11):3424-3429.

Rowley, J., Semin. Hematol., Oct. 1999, 36(4), Suppl 7:59-72.

Rubnitz et al., Blood, Sep 15, 1994, 84(6):1747-1752.

Rubnitz et al., Leukemia, Jan. 1999, 13(1):6-13.

Salomon-Nguyen et al., PNAS, Jun. 6, 2000, 97(12):6757-6762.

Sambrook et al, Molecular Cloning: A Laboratory Manual, 2nd ed. (1989), Cold Spring Harbor Laboratory Press, Cold Spring Harbor NY, Table of Contents.

Satana, L. et al., "Synthesis and biological activity of some 2-aminopurine carbonucleosides," Nucleosides & Nucleotides 16(7-9), 1337-1339 (1997).

Santana, L. et al., "Synthesis of 1,2-disubstituted carbocyclic analogs of pyrimidine and purine nucleosides," Synthesis 10, 1532-1538 (2001).

Saudek, et al., "A Preliminary Trial of the Programmable Implantable Medication System for Insulin Delivery," N. Eng. J. Med. 1989, 321, (574).

Scarpa et al., Leuk. Lymphoma 1997, 26 Suppl. 1:77-82.

Scheibel et al., "The charged region of Hsp90 modulates the function of the N-terminal domain," PNAS USA 1999, 96A:1297-1302.

Schneider et al., "Pharmacologic shifting of a balance between protein refolding and degradation mediated by Hsp90," PNAS USA 1996, 93:14536-14541.

Schnur et al., "Inhibition of the oncogene product p185 in vitro in vivo by geldanamycin and dihydrogeldanamycin deriviates," J. Med. Chem. 1995, 38:3806-3812.

Schulte et al., "Disruption of the Raf-1-Hsp90 molecular complex results in destabilization of Raf-1 and loss of Raf-1-Ras association," J. Biol. Chem. 1995, 270:24585-24588.

Schulte et al., "Geldanamycin-induced destabilization of Raf-1 involves the proteasome," Biochem. Biophys. Res. Commun. 1997, 239:655-659.

Schwartz et al., Cytogenet. Cell Genet., 1991, 51:152-153.

Sedlak, M. et al., "Synthesis and 15N NMR Characterization of 4-Vinylbenzyl Substituted Bases of Nucleic Acids," J. Heterocyclic Chem. 40, 671-675 (2003).

Seeger et al., Blood, 1999, 94(1) Correspondence:374-375.

Seela, F., "7-Desaza-Isostere von 2'-Desoxyxanthosin und 2'-Desoxyspongosin-Synthese via Glycoslierung von 2,3-Dichlor-7H-pyrrolo[2,3-d] pyrmidin," Liebigs. Ann. Chem. 1985, 312-230.

Seela, F., Synthesis 2004,8, 1203.

Sefton, M.V., "Implantable Pumps," 1987, CRC Crit. Ref. Biomed. Eng. 14:201.

Segnitz et al., "The function of steroid hormone receptors is inhibited by the hsp90-specific compound geldanamycin," J. Biol. Chem. 1997, 272:18694-18701.

Sekiyama, T. et al., "Synthesis and Antiviral of Novel Acyclic Nucleosides: Discovery of a Cyclopropyl Nucleoside with Potent Inhibitory Activity against Herpesviruses," J. Med. Chem. 1998, 41, 1284-1298.

Sen, A.K. et al., "Synthesis of compounds related to 4(5)-aminoimidazole-5(4)-carboxamides: part VI—synthesis of 3-(6-methoxyl-8-quinolyl)-7-methylpurin-6(3H)-one," Indian J. of Chem., Sect. B: Org. Chem. Including Medicinal Chem. 23B(9), 870-3 (1984).

Sepehrnia et al., J. Biol. Chem., Jun. 21, 1996, 271(25): 15084-15090.

Sepp-Lorenzo et al., "Herbimycin A indues the 20 S proteasome-and Ubiquitin-dependent degradation of receptor tyrosin kinases," J. Biol. Chem. 1995, 270:16580-16587.

Shealy, Y.F. et al., "Synthesis and antiviral evaluation of carbocyclic analogues of 2-amino-6-substituted-purine 3'-deoxyribofuranosides," J. Med. Chem. 30(6), 1090-4 (1987).

Shiah et al., Leukemia, 2002, 16(2):196-202.

Shurtleff et al., Leukemia, 1995, 9:1985-1989.

Silvany et al., Oncogene 2000, 19:4523-4530.

Sircar, J.C., "8-amino-9-substituted guanines: potent purine nucleoside phosphorylase (PNP) inhibitors," Agents and Actions 21 (3-4), 253-6 (1987).

Slany et al., Mol. Cell. Biol. Jan. 1998, 18(1):122-129.

Slominski et al., Arch. Pathol. Lab Med, Dec. 1999, 123:1246-1259.

Smith et al., "Progesterone receptor structure and function altered by Geldanamycin, an hsp90-binding agent," Mol. Cell. Biol. 1995, 15:6804-6812.

So et al., Cancer Genet. Cytogenet., Feb. 2000, 117(1):24-27.

Springall et al., Leukemia, 1998, 12_2034-2035.

Srivastava et al., Oncogene, 1993, 8:2449-2456.

Stebbins et al, "Crystal structure of an Hsp90-geldanamycin complex;targeting of a protein chaperone by an antitumor agent," Cell, 1997, 89:239-250.

Stepanova et al., "Mammalian p50cdc37 is a protein kinase-targeting subunit of HSP90 that binds and stabilizes Cdk4," Genes Dev. 1996, 10:1491-1502.

Stoffel et al., PNAS, Apr. 1996, 93:3937-3941.

Stryer, Biochemistry, 2nd Ed., pp. 206-211 (1981).

Super et al., Genes, Chromosomes & Cancer, Oct. 1997, 20(2):185-195.

Szoka, F. Jr., et al., Annu. Rev. Biophys. Bioeng. 9:467-508 (1980.

Taki et al., Blood, Jun 1, 1997, 89(11):3945-3950.

Taki et al., Cancer Res., Sep. 1, 1999, 59(17):4261-4265.

Taki et al., Oncogene, Nov. 21, 1996, 13(10):2121-2130.

Taki et al., PNAS, Dec. 7, 1999, 96(25):14535-14540.

Tanabe et al., Blood, Nov. 1, 1996, 88(9):3535-3545.

Tani et al., Neoplasia, Apr. 1999, 1(1):71-79.

Terry, B.J. et al., "Broad-spectrum antiviral activity of the acyclic guanosine phosphonate (R,S)-HPMPG," Antiviral Res. 10(4-5), 235-51 (1988).

Tkachuk et al., Cell, Nov. 13, 1992, 71(4):691-700.

Tohidi, M. and Orgel, L.E., "Some acyclic analogs of necleotides and their template-directed reactions," J. of Mol. Evolution 28(5), 367-373 (1989).

Toyota, A. et al., "Synthesis of nucleosides and related compounds. 31. The alkylation of 2-amino-6-chloropurines with alcohols by Mitsunobu reaction for a synthesis of carbocyclic guanosine analogs," Heterocycles 36(7), 1625-30 (1993).

Traul et al., Food Chem. Toxicol. 38:79-98 (2000).

Treat et al., 1989, Liposomes in the Therapy of Infectious Disease and Cancer, Lopez-Bernstein and Fidler (eds), Liss, NY USA pp. 353-365.

Tse et al., Blood, Feb. 1, 1995, 85(3):650-656.

Uehara et al., Jpn. J. Cancer Res. (GANN), Aug. 1985, 76:672-675.

Uehara et al., Mol. Cell Biol., Jun. 1986, 6:2198-2206.

Ugarkar, B.G., "Adenosine Kinase Inhibitors. 2. Synthesis, Enzyme Inhibition and Antiseizure Activity of Diaryltubercidin Analogues," J. Med. Chem. 2000, 43, 2894-2905.

Ugarkar, B.G., "Adenosine Kinase Inhibitors.. 1. Synthesis, Enzyme Inhibition and Antiseizure Activity of 5-Iodotubercidin Analogues," J. Med. Chem. 2000, 43, 2883-2893.

Van Calenbergh et al., "Synthesis and Structure-Activity Relationships of Analogs of 2'-Deoxy-2'-(3-methoxybenzamido)adenosine, a Selective Inhibitor of Trypanosomal Glycosomal Glyceraldehyde-3-phosphate Dehydrogensase," J. Med. Chem. 1995, 38, 3838-3849, 1995.

Van Oijen et al., Clin. Cancer Res., Jun. 2000, 6:2138-2145.

Vasilevskaya et al., "Effects of geldanamycin on signaling through activator-protein I inhypoxic HT29 human colon adenocarcinoma cells," Cancer Res. 1999, 59:3935-3940.

Veliz, E.A., C6 substitution of inosine using hexamethylphosphorous triamide in conjunction with carbon tetrahalide or N-halosuccinimid, Tetrahedron Lett. 2000, 41, 1695.

Vemuri et al., Pharma. Acta. Helvetiae, 70:95-111 (1995).

Villadsen et al., Cancer Genet. Cytogenet., 2000, 116:28-34.

Viswanatha et al., Blood, Mar. 15, 1998, 91(6):1882-1890.

Wai et al., Oncogene, Feb. 17, 2000, 19(7):906-915.

Wang, R. et al., "Methylene-gem-Difluorocyclopropane Analogues of Nucleosides: Synthesis, Cyclopropene-Methylenecyclopropane Rearrangment, and Biological Activity," J. Med. Chem. 2001, 44, 4019-4022.

Wang, R. et al., "Synthesis of methylenecyclobutane analogues of nucleosides with axial chirality and their phosphoralaninates: A new pronucleotide effective against Epstein-Barr virus," Antiviral Chem. & Chemo. 13(4), 251-262 (2002).

Wedemeyer et al., Genomics, 1997, 46:313-315.

Weidmann, K. et al., "24(2-Pyridylmethyl)sylfinyl]-1H-theino[3,4-d]imidazoles. A Novel Class of Gastric H+/K=-ATPase Inhibitors," J. Med. Chem. 1992, 35, 438.

Whitesell et al., "Inhibition of heat shock protein HSP90-pp60v-src heteroprotein complex formation by benzoquinone ansamycins: essential role for stress proteins in oncogenic transformation," PNAS USA 1994, 91:8324-8328.

Wiemels et al., Blood, Aug. 1, 1999, 94(3):1057-1062.

Wilson et al., ASCO 325 (2001).

Wong et al., Cytogenet., Jul 1, 1995, 82(1):70-72.

Wong, C. et al., " Synthesis and Evaluation of Homoaza Sugars as Glycosidase Inhibitors," J. Org. Chem. 1995, 60, 1492-1501

International Search Report and Written Opinion of the International Searching Authority mailed Mar. 27, 2007 for international application No. PCT/US06/11846, international filing date Mar. 29, 2006.

Yagasaki et al., Genes, Chromosomes & Cancer, 1999, 26:192-202.

Yokomatsu, T. et al., "Synthesis of (2'S,3'S)-9-(4-phosphono-4',4'difluoro-2', 3'-metthanobutyl)guanine and its enantiomer. Evaluation of the inhibitory activity for purine nucleoside phosphorylase," Tetrahedron 53(33), 11297-11306(1997).

Yokomatsu, T. et al., "Synthesis of 1,1-difluoro-5-(1H-9-purinyl)-2-pentenylphosphonic acids and the related methano analoges. Remarkable effect of the nucleobases and the cyclopropane rings on inhibitory activity toward purine nucleoside phosphorylase," Biorg. & Med. Chem. 6(12), 2495-2505 (1998).

Yoneda-Kato et al., Oncogene, 1996, 12:265-275.

Zemlicka, J., "Synthesis and biological properties of 9-(2,4-dihydroxybutyl)adenine and guanine: new analogs of 9-(2,3-dihydroxypropyl)adenine(DHPA) and 9-(2-hydroxyethoxymethyl)guanine(acyclovir)," Nucleosides & Nucleotides 3(3), 245-64 (1984).

Zheng, Q. et al., "Synthesis and preliminary biological evaluation of radiolabeled O6-benzylguanine derivatives, new potential PET imaging agents for the DNA repair protein) 6-alkylguanine-DNA alkytransferase in breast cancer," Nucl. Med. & Biol., 30(4), 405-415 (2003).

ALKYNYL PYRROLO[2,3-D]PYRIMIDINES AND RELATED ANALOGS AS HSP90-INHIBITORS

CROSS-REFERENCE

This application claims the benefit of U.S. Provisional Application No. 60/666,899 filed Mar. 30, 2005, which is herein incorporated by reference in its entirety.

FIELD OF THE INVENTION

The invention relates in general to alkynyl pyrrolopyrimidines and their broad-spectrum utility, e.g., in inhibiting heat shock protein 90 (HSP90) to thereby treat or prevent HSP90-mediated diseases.

BACKGROUND

HSP90s are ubiquitous chaperone proteins that are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner J. *TIBS* 1999, 24, 136-141; Stepanova, L. et al. *Genes Dev.* 1996, 10, 1491-502; Dai, K. et al. *J. Biol. Chem.* 1996, 271, 22030-4). Studies further indicate that certain co-chaperones, e.g., HSP70, p60/Hop/Sti1, Hip, Bag1, HSP40/Hdj2/Hsj1, immunophilins, p23, and p50, may assist HSP90 in its function (see, e.g., Caplan, A. *Trends in Cell Biol.* 1999, 9, 262-68).

HSP90 possesses a binding pocket at its N-terminus. This pocket is highly conserved and has weak homology to the ATP-binding site of DNA gyrase (Stebbins, C. et al., supra; Grenert, J. P. et al. *J. Biol. Chem.* 1997, 272, 23843-50). Further, ATP and ADP have both been shown to bind this pocket with low affinity and to have weak ATPase activity (Proromou, C. et al. *Cell* 1997, 90, 65-75; Panaretou, B. et al. *EMBO J.* 1998, 17, 4829-36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T. H. et al. *Proc. Natl. Acad. Sci. USA* 1999, 96, 1297-302; Schulte, T. W. et al. *J. Biol. Chem.* 1995, 270, 24585-8; Whitesell, L., et al. *Proc. Natl. Acad. Sci. USA* 1994, 91, 8324-8328). HSP90 inhibitors, e.g. ansamycins, have also been demonstrated to inhibit the ATP-dependent release of chaperone-associated protein substrates (Schneider, C. L. et al. *Proc. Natl. Acad. Sci., USA* 1996, 93, 14536-41; Sepp-Lorenzino et al. *J. Biol. Chem.* 1995, 270, 16580-16587). In either event, the substrates are degraded by an ubiquitin-dependent process in the proteasome (Schneider, C. L., supra; Sepp-Lorenzino, L., et al. *J. Biol. Chem.* 1995, 270, 16580-16587; Whitesell, L. et al. *Proc. Natl. Acad. Sci. USA* 1994, 91, 8324-8328).

HSP90 substrate destabilization occurs in tumor and non-transformed cells alike and has been shown to be especially effective on a subset of signaling regulators, e.g., Raf (Schulte, T. W. et al. *Biochem. Biophys. Res. Commun.* 1997, 239, 655-9; Schulte, T. W., et al. *J. Biol. Chem.* 1995, 270, 24585-8), nuclear steroid receptors (Segnitz, B.; U. Gehring *J. Biol. Chem.* 1997, 272, 18694-18701; Smith, D. F. et al. *Mol. Cell. Biol.* 1995, 15, 6804-12), v-Src (Whitesell, L., et al. *Proc. Natl. Acad. Sci. USA* 1994, 91, 8324-8328) and certain transmembrane tyrosine kinases (Sepp-Lorenzino, L. et al. *J. Biol. Chem.* 1995, 270, 16580-16587) such as EGF receptor (EGFR) and Her2/Neu (Hartmann, F., et al. *Int. J. Cancer* 1997, 70, 221-9; Miller, P. et al. *Cancer Res.* 1994, 54, 2724-2730; Mimnaugh, E. G., et al. *J. Biol. Chem.* 1996, 271, 22796-801; Schnur, R. et al. *J. Med. Chem.* 1995, 38, 3806-3812), CDK4, and mutant p53. Erlichman et al. *Proc. AACR* 2001, 42, abstract 4474. The HSP90 inhibitor-induced loss of these proteins leads to the selective disruption of certain regulatory pathways and results in growth arrest at specific phases of the cell cycle (Muise-Heimericks, R. C. et al. *J. Biol. Chem.* 1998, 273, 29864-72), and apoptosis, and/or differentiation of cells so treated (Vasilevskaya, A. et al. *Cancer Res.,* 1999, 59, 3935-40). HSP90 inhibitors thus hold great promise for the treatment and/or prevention of many types of cancers and proliferative disorders, and also hold promise as traditional antibiotics.

In addition to anti-cancer and antitumorigenic activity, HSP90 inhibitors have also been implicated in a wide variety of other utilities, including use as anti-inflammation agents, anti-infectious disease agents, agents for treating autoimmunity, agents for treating stroke, ischemia, multiple sclerosis, cardiac disorders, central nervous system related disorders and agents useful in promoting nerve regeneration (See, e.g., Rosen et al. WO 02/09696 (PCT/US01/23640); Degranco et al. WO 99/51223 (PCT/US99/07242); Gold, U.S. Pat. No. 6,210,974 B1; DeFranco et al., U.S Pat. No. 6,174,875. Overlapping somewhat with the above, there are reports in the literature that fibrogenic disorders including but not limited to scieroderma, polymyositis, systemic lupus, rheumatoid arthritis, liver cirrhosis, keloid formation, interstitial nephritis, and pulmonary fibrosis also may be treatable with HSP90 inhibitors. Strehlow, WO 02/02123 (PCT/US01/20578). Still further HSP90 modulation, modulators and uses thereof are reported in Application Nos. PCT/US03/04283, PCT/US02/35938, PCT/US02/16287, PCT/US02/06518, PCT/US98/09805, PCT/US00/09512, PCT/US01/09512, PCT/US01/23640, PCT/US01/46303, PCT/US01/46304, PCT/US02/06518, PCT/US02/29715, PCT/US02/35069, PCT/US02/35938, PCT/US02/39993, 60/293,246, 60/371,668, 60/335,391, 60/128,593, 60/337,919, 60/340,762, 60/359,484 and 60/331,893.

Recently, purine derivatives, including pyrrolopyrimidines showing HSP90 inhibitory activity have been reported, e.g., in PCT/US02/35069; PCT/US02/36075. U.S. patent application Ser. No. 10/945,851 and PCT/US04/31248. However, a need remains for additional novel and potent pyrrolopyrimidine HSP90 inhibitors that meet the demanding biological and pharmaceutical criteria required to proceed towards human clinical trials.

SUMMARY OF THE INVENTION

The present invention is directed towards alkynyl pyrrolo[2,3-d]pyrimidines and related compounds that show broad utility, e.g., by inhibiting HSP90 and treating diseases that are HSP90-dependent. These compounds differ from a parent pyrrolopyrimidine which was disclosed in prior patent applications in that they are substituted with an alkyne, e.g., acetylene, on the ring carbon at the fifth position (C-5 position) and they exhibit improved HSP90 inhibitory activity over the parent compounds.

In one aspect, the invention comprises alkynyl pyrrolo[2,3-d]pyrimidine compounds of Formula I:

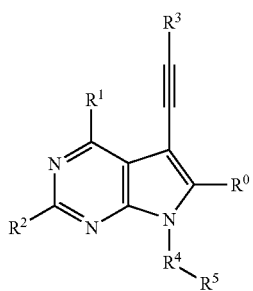

wherein:
$R^0$ is selected from the group consisting of hydrogen, halogen, lower alkyl, —CN, —$SR^8$, —$OR^8$, and —$NHR^8$;
$R^1$ is selected from the group consisting of halogen, —$OR^{11}$, —$SR^{11}$ and lower alkyl;
$R^2$ is —$NHR^8$;
$R^3$ is selected from the group consisting of hydrogen, —CN, —C(O)OH, —$OR^{11}$, —$SR^{11}$, —C(O)$R^9$, —$NR^8R^{10}$, lower alkyl, lower alkenyl, lower alkynyl, lower perhaloalkyl, lower alkylsilyl, aryl, heteroaryl, alicyclyl and heterocyclyl, all optionally substituted, wherein:
  the aryl, heteroaryl, alicyclyl and heterocyclyl groups are mono-, bi- or tri-cyclic;
  $R^8$ and $R^{10}$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;
  the optional substituents on $R^3$ are selected from the group consisting of lower alkyl, lower alkenyl, lower alkynyl, —CN, —C(O)OH, —$NO_2$, —$SR^8$, —$OR^8$, —C(O)$R^9$, —$NR^8R^8$, lower aryl, heteroaryl, alicyclyl, lower heterocyclyl, arylalkyl, heteroarylalkyl, amino, alkylamino, dialkylamino, arylalkylamino, diarylamino, heteroarylamino, diheteroarylamino, arylheteroarylamino, oxo, perhaloalkyl, perhaloalkoxy, perhaloacyl, guanidinyl, pyridinyl, thiophenyl, furanyl, indolyl, indazolyl, phosphonyl, phosphatidyl, phosphoramidyl, sulfanyl, sulfinyl, sulfonyl, sulphonamidyl, carbamyl, uryl, thiouryl and thioamidyl, wherein
    $R^8$ and $R^8$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;
$R^4$ is selected from the group consisting of optionally substituted lower alkylene, —C($R^{12}$)$_2$—, —C(O)—, —C(S)—, —S(O)— and —$SO_2$—;
$R^5$ is selected from the group consisting of aryl, heteroaryl, alicyclyl and heterocyclyl, wherein:
  the aryl group is substituted with 2 to 5 substituents;
  the heteroaryl group is substituted with 2 to 5 substituents;
  the alicyclyl group is substituted with 3 to 5 substituents;
  the heterocyclyl group is substituted with 3 to 5 substituents;
  the substituents on $R^5$ are selected from the group consisting of halogen, lower alkyl, lower alkenyl, lower alkynyl, —CN, —C(O)OH, —$NO_2$, —$SR^8$, —$OR^8$, —C(O)$R^9$, —$NR^8R^{10}$, lower aryl, lower heteroaryl, lower alicyclyl, lower heterocyclyl, arylalkyl, heteroarylalkyl, thioalkyl, amino, alkylamino, dialkylamino, arylalkylamino, oxo, perhaloalkyl, perhaloalkoxy, perhaloacyl, guanidinyl, pyridinyl, thiophenyl, furanyl, indolyl, indazolyl, phosphonyl, phosphatidyl, phosphoramidyl, sulfanyl, sulfinyl, sulfonyl, sulphonamidyl, carbamyl, uryl, thiouryl and thioamidyl, wherein
    $R^8$ and $R^{10}$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;
$R^8$ is selected from the group consisting of hydrogen, lower alkyl, lower alkenyl, lower alkynyl, lower heteroalkyl, lower heteroalkenyl, lower heteroalkynyl, lower aryl, lower heteroaryl and —C(O)$R^9$;
$R^9$ is selected from the group consisting of H, lower alkyl, lower alkenyl, lower alkynyl, lower aryl, lower heteroaryl, —$NR^{10}R^{10}$ and —$OR^{11}$, wherein
  $R^{10}$ and $R^{10}$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;
$R^{10}$ is selected from the group consisting of hydrogen, lower alkyl, lower alkenyl, lower alkynyl, lower heteroalkyl, lower heteroalkenyl, lower heteroalkynyl, lower aryl, lower heteroaryl and —C(O)$R^{11}$;
$R^{11}$ is selected from the group consisting of lower alkyl, lower alkenyl, lower alkynyl, lower aryl and lower heteroaryl; and
$R^{12}$ is selected from the group consisting of hydrogen and lower alkyl.

Also included in the scope of the present invention are stereoisomic forms, including the individual enantiomers and diastereomers, racemic mixtures, and diasteromeric mixtures, and combinations thereof, where appropriate, as well as polymorphs, specific racemates and stereoisomers, solvates, esters, tautomers, pharmaceutically acceptable salts and prodrugs of these compounds.

In another aspect, the invention features pharmaceutical compositions comprising the compounds of the invention, in particular, the compounds of Formula I, or a polymorph, solvate, ester, tautomer, diastereoisomer, enantiomer, pharmaceutically acceptable salt or prodrug thereof, and one or more pharmaceutical excipients, for use in treatment or prevention of diseases and conditions that are HSP90-dependent.

In yet another aspect, the invention is related to methods of preventing or treating HSP90-mediated disorders or conditions by administering a pharmaceutical composition that comprises a pharmaceutically effective amount of a compound of Formula I, or a polymorph, solvate, ester, tautomer, diastereomer, enantiomer, pharmaceutically acceptable salt or prodrug thereof.

In one embodiment, the invention provides a method for treating an individual having a disorder selected from the group of inflammatory diseases, infections, autoimmune disorders, stroke, ischemia, cardiac disorders, neurological disorders, fibrogenic disorders, proliferative disorders, tumors, leukemias, chronic lymphocytic leukemia, acquired immuno-deficiency syndrome, neoplasms, cancers, carcinomas, metabolic diseases, and malignant diseases.

In another embodiment, the invention provides a method for treating an individual having a fibrogenic disorder, such as, for example, scieroderma, polymyositis, systemic lupus, rheumatoid arthritis, liver cirrhosis, keloid formation, interstitial nephritis or pulmonary fibrosis.

In another embodiment, the invention provides a combination therapy comprising the administration of a pharmaceutically effective amount of a compound of Formula I, or a solvate, tautomer, diastereomer, enantiomer, pharmaceutically acceptable salt, polymorph, or prodrug thereof according to any of the preceding aspects or embodiments, and at least one therapeutic agent selected from the group of cytotoxic agents, anti-angiogenesis agents and anti-neoplastic agents. The anti-neoplastic agent may be selected from the group of alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In a further aspect, the invention is related to the use of the compounds of Formula I in the manufacture of a medicament.

In yet a further aspect, the invention is related to the use of the compounds of Formula I in the manufacture of a medicament.for the therapeutical and/or prophylactic treatment of HSP90-dependent diseases and conditions.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
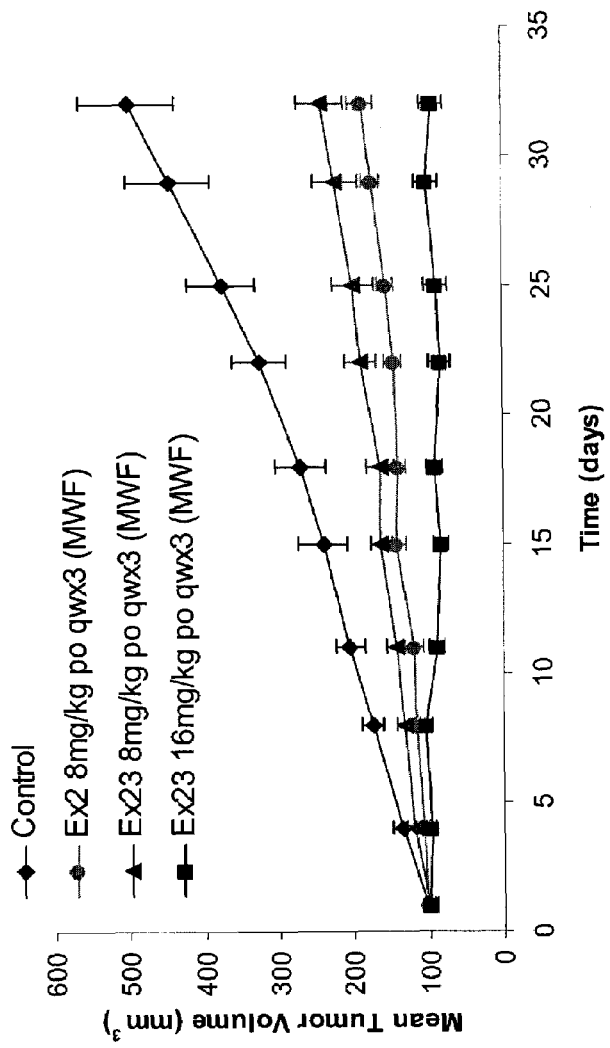
FIG. 1 represents a plot of tumor volume ($mm^3$) against time (days), for animals administered compounds of the present invention (and controls) in a mouse N87 Gastric Carcinoma Xenograft model, as described in example 70.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

A "pharmaceutically acceptable derivative or prodrug" means any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

A "pharmaceutically acceptable salt" may be prepared for any compound of the invention having functionality capable of forming a salt, for example, an acid or base functionality.

Pharmaceutically acceptable salts may be derived from organic or inorganic acids and bases. Compounds of the invention that contain one or more basic functional groups, (e.g., amino, alkylamino), are capable of forming pharmaceutically acceptable salts with pharmaceutically acceptable organic and inorganic acids. These salts can be prepared in situ during the final isolation and purification of the compounds of the invention, or by separately reacting a purified compound of the invention in its free base form with a suitable organic or inorganic acid, and isolating the salt thus formed. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-napthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. See, e.g., Berge et al. "Pharmaceutical Salts", *J. Pharm. Sci.* 1977, 66:1-19. Compounds of the present invention that contain one or more acidic functional groups are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative pharmaceutically acceptable cations include alkali or alkaline earth salts such as lithium, sodium, potassium, calcium, magnesium, and aluminum salts and the like. Illustrative examples of some of the bases that can be used include sodium hydroxide, potassium hydroxide, choline hydroxide, sodium carbonate, $N^+(C_{1-4}\ alkyl)_4$, and the like. Representative organic amines useful for the formation of base addition salts include ethylamine, diethylamine, ethylenediamine, ethanolamine, diethanolamine, piperazine and the like. This invention also envisions the quaternization of any basic nitrogen-containing groups of the compounds disclosed herein. Water or oil-soluble or dispersible products may be obtained by such quaternization. See, for example, Berge et al., supra.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters.

Suitable positions for derivatization of the compounds of the invention to create "prodrugs" include but are not limited, to, 2-amino substitution. Those of ordinary skill in the art have the knowledge and means to accomplish this without undue experimentation. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference.

The term "prodrugs" as employed herein includes, but is not limited to, the following groups and combinations of these groups, for example bis carbomates, or a carbomate and an acyloxyalkyl ester or a cabomate and an amide, etc.

Amine Prodrugs:

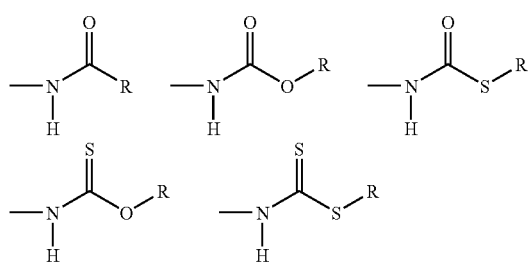

-continued

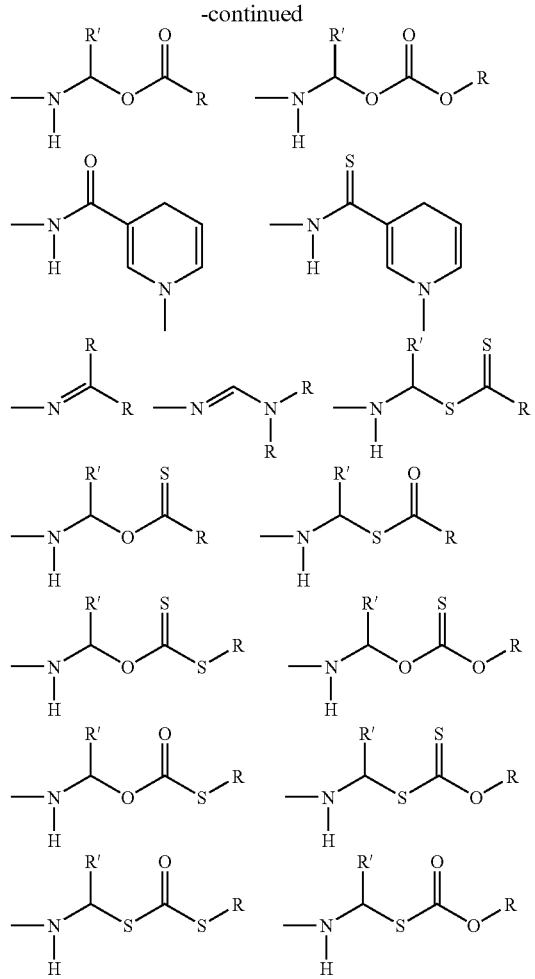

Hydroxy prodrugs include, but are not limited to acyloxy-alkyl esters, alkoxycarbonyloxyalkyl esters, alkyl esters, aryl esters and disulfide containing esters.

The term "alkyl" as used herein, alone or in combination, refers to an optionally substituted straight-chain, or optionally substituted branched-chain saturated hydrocarbon monoradical having from one to about thirty carbons, more preferably one to twelve carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like.

The term "cycloalkyl" as used herein, alone or in combination, refers to cyclic alkyl monoradicals which include monocyclic, bicyclic, tricyclic, and higher multicyclic alkyl radicals wherein each cyclic moiety has from three to about eight carbon atoms. Examples of cycloalkyl radicals include cyclopropyl, cyclobutyl, cyclopentyl, cyclohexyl and the like.

The term "lower alkyl" as used herein, alone or in combination, refers to an alkyl containing fewer carbon atoms, e.g., one containing from one to about six carbon atoms.

The term "alkenyl" as used herein, alone or in combination, refers to an optionally substituted straight-chain, or optionally substituted branched-chain hydrocarbon radical having one or more carbon-carbon double-bonds and having from two to about thirty carbon atoms, more preferably two to about eighteen carbons. Examples of alkenyl radicals include ethenyl, propenyl, butenyl, 1,3-butadienyl and the like.

The term "cycloalkenyl" as used herein, alone or in combination, refers to to cyclic alkenyl radicals which include monocyclic, bicyclic, tricyclic, and higher multicyclic alkenyl radicals wherein each cyclic moiety has from three to about eight carbon atoms.

The term "lower alkenyl" as used herein, alone or in combination, refers to to an alkenyl having from two to about six carbons.

The term "alkynyl" as used herein, alone or in combination, refers to an optionally substituted straight-chain or optionally substituted branched-chain hydrocarbon radical having one or more carbon-carbon triple-bonds and having from two to about thirty carbon atoms, more preferably from two to about twelve carbon atoms, or from two to about six carbon atoms, as well as those having from two to about four carbon atoms. Examples of alkynyl radicals include ethynyl, 2-propynyl, 2-butynyl, 1,3-butadiynyl and the like.

The term "cycloalkynyl" as used herein, alone or in combination, refers to cyclic alkynyl radicals that include monocyclic, bicyclic, tricyclic, and higher multicyclic alkynyl radicals wherein each cyclic moiety has from three to about eight carbon atoms.

The term "lower alkynyl" as used herein, alone or in combination, refers to an alkynyl having from two to about six carbons.

The terms "heteroalkyl", "heteroalkenyl" and "heteroalkynyl" as used herein, alone or in combination, refer to include optionally substituted alkyl, alkenyl and alkynyl structures, as described above, and which have one or more skeletal chain atoms selected from an atom other than carbon, e.g., oxygen, nitrogen, sulfur, phosphorous or combinations thereof.

The terms "lower heteroalkyl", "lower heteroalkenyl" and "lower heteroalkynyl" as used herein, alone or in combination, refer to, respectively, a heteroalkyl, heteroalkenyl and heteroalkynyl having from two to about six carbons.

The term "alkylene" as used herein, alone or in combination, refers to a divalent hydrocarbyl group; because it is divalent, it can link two other groups together. Typically it refers to $-(CH_2)_n-$ where n is 1-8 and preferably n is 1-4, though where specified, an alkylene can also be substituted by other groups, and can be of other lengths, and the open valences need not be at opposite ends of a chain. Thus $-CH(Me)-$ and $-C(Me)_2-$ may also be referred to as alkylenes, as can a cyclic group such as cyclopropan-1,1-diyl. Where an alkylene group is substituted, the substituents include those typically present on alkyl groups as described herein.

The term "lower alkylene" as used herein, alone or in combination, refers to an alkylene group containing fewer carbon atoms, e.g., one containing from one to about six carbon atoms.

The term "carbon chain" as used herein, alone or in combination, refers to any alkyl, alkenyl, alkynyl, or heteroalkyl, heteroalkenyl, or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The term "membered ring" as used herein, alone or in combination, refers to any cyclic structure, including aromatic, heteroaromatic, alicyclic, heterocyclic, monocyclic, polycyclic, and fused rings. The term "membered" is meant to denote the number of skeletal (or ring) atoms that constitute the ring system. Thus, for example, pyrrole, pyrrolidine, succinimide, maleimide, tetrahydrofuran and thiophene are five-membered rings; pyridine, pyran, morpholine, piperazine, piperidine and pyrimidine are six-membered rings; and phthalimide, indole and indane are nine membered fused rings.

The term "aryl" as used herein, alone or in combination, refers to an optionally substituted aromatic hydrocarbon monoradical of six to about twenty ring atoms, and includes mono-aromatic rings and fused aromatic rings. A fused aromatic ring radical contains from two to four fused rings where the ring of attachment is an aromatic ring, and the other individual rings within the fused ring may be aromatic, heteroaromatic, alicyclic or heterocyclic. Further, the term aryl includes mono-aromatic rings and fused aromatic rings containing from six to about twelve carbon atoms, as well as those containing from six to about ten carbon atoms. Examples of aryl groups include, without limitation, phenyl, naphthyl, anthryl, chrysenyl, and benzopyrenyl ring systems.

The term "lower aryl" as used herein, alone or in combination, refers to an aryl having six to about ten skeletal ring carbons, e.g., phenyl and naphthyl ring systems.

The term "heteroaryl" as used herein, alone or in combination, refers to optionally substituted aromatic radicals containing from about five to about twenty skeletal ring atoms and where one or more of the ring atoms is a heteroatom such as, for example, oxygen, nitrogen, sulfur, selenium or phosphorus. The term heteroaryl includes optionally substituted mono-heteroaryl radicals and fused heteroaryl radicals having at least one heteroatom (e.g., quinoline, benzothiazole). A fused heteroaryl radical may contain from two to four fused rings where the ring of attachment is a heteroaromatic ring, the other individual rings within the fused ring system may be aromatic, heteroaromatic, alicyclic or heterocyclic. The term heteroaryl also includes mono-heteroaryls or fused heteroaryls having from five to about twelve skeletal ring atoms, as well as those having from five to about ten skeletal ring atoms. Examples of heteroaryls include, without limitation, furanyl, benzofuranyl, chromenyl, pyridyl, pyrrolyl, indolyl, quinolinyl, pyridyl-N-oxide, pyrimidyl, pyrazinyl, imidazolyl, pyrazolyl, oxazolyl, isoxazolyl, benzothiozolyl, benzimidazolyl, benzoxazolyl, benzothiadiazolyl, benzoxadiazolyl, benzotriazolyl, quinolinyl, isoquinolinyl, indolyl, purinyl, indolizinyl, thienyl and the like and their oxides.

The term "lower heteroaryl" as used herein, alone or in combination, refers to a heteroaryl having five to about ten skeletal ring atoms, e.g., pyridyl, thienyl, pyrimidyl, pyrazinyl, pyrrolyl, or furanyl.

The terms "alicyclic" and "alicyclyl" as used herein, alone or in combination, refer to an optionally substituted saturated or unsaturated nonaromatic hydrocarbon ring system containing from three to about twenty ring atoms. The term alicyclic includes mono-alicyclic and fused alicyclic radicals. A fused alicyclic may contain from two to four fused rings where the ring of attachment is an alicyclic ring, and the other individual rings within the fused-alicyclic radical may be aromatic, heteroaromatic, alicyclic and heterocyclic. The term alicyclic also includes mono-alicyclic and fused alicyclic radicals containing from three to about twelve carbon atoms, as well as those containing from three to about ten carbon atoms. Examples of alicyclics include, without limitation, cyclopropyl, cyclopropenyl, cyclobutyl, cyclopentyl, cyclodecyl, cyclododecyl, cyclopentadienyl, indanyl, and cyclooctatetraenyl ring systems.

The terms "lower alicyclic" and "lower alicyclyl" as used herein, alone or in combination, refer to an alicyclic having three to about ten skeletal ring carbons, e.g., cyclopropyl, cyclopropenyl, cyclobutyl, cyclopentyl, decalinyl, and cyclohexyl.

The terms "heterocyclic" and "heterocyclyl" as used herein, alone or in combination, refer to optionally substituted saturated or unsaturated nonaromatic ring radicals containing from five to about twenty ring atoms where one or more of the ring atoms are heteroatoms such as, for example, oxygen, nitrogen, sulfur, and phosphorus. The term heterocyclic includes mono-heterocyclic and fused heterocyclic ring radicals. A fused heterocyclic radical may contain from two to four fused rings where the attaching ring is a heterocyclic, and the other individual rings within the fused heterocyclic radical may be aromatic, heteroaromatic, alicyclic or heterocyclic. The term heterocyclic also includes mono-heterocyclic and fused alicyclic radicals having from five to about twelve skeletal ring atoms, as well as those having from five to about ten skeletal ring atoms. Example of heterocyclics include without limitation, tetrahydrofuranyl, benzodiazepinyl, tetrahydroindazolyl, dihyroquinolinyl, and the like.

The terms "lower heterocyclic" and "lower heterocyclyl" as used herein, alone or in combination, refer to a heterocyclic ring system having five to about ten skeletal ring atoms, e.g., dihydropyranyl, pyrrolidinyl, dioxolanyl, piperidinyl, piperazinyl, and the like.

The term "alkylaryl" as used herein, alone or in combination, refers to an aryl radical as defined above in which at least one H atom is replaced by an alkyl radical as defined above, such as, for example, tolyl, xylyl and the like.

The terms "arylalkyl" and "araalkyl" as used herein, alone or in combination, refer to an alkyl radical as defined above in which at least one H atom is replaced by an aryl radical as defined above, such as, for example, benzyl, 2-phenylethyl and the like.

The term "heteroarylalkyl" as used herein, alone or in combination, refers to an alkyl radical as defined above in which at least one H atom is replaced by a heteroaryl radical as defined above, each of which may be optionally substituted.

The term "alkoxy" as used herein, alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "lower alkoxy" as used herein, alone or in combination, refers to an alkoxy group having one to about six carbon atoms.

The term "aryloxy" as used herein, alone or in combination, refers to an aryl ether radical wherein the term aryl is defined as above. Examples of aryloxy radicals include phenoxy, thienyloxy and the like.

The terms "alkylthio" and "thioalkyl" as used herein, alone or in combination, refer to an alkyl thio radical, alkyl-S—, wherein the term alkyl is as defined above.

The term "arylthio" as used herein, alone or in combination, refers to an aryl thio radical, aryl-S—, wherein the term aryl is as defined above.

The term "heteroarylthio" as used herein, alone or in combination, refers to the group heteroaryl-S—, wherein the term heteroaryl is as defined above.

The term "acyl" as used herein, alone or in combination, refers to a radical —C(O)R where R includes alkyl, alkenyl, alkynyl, aryl, heteroaryl, alicyclic, heterocyclic, arylalkyl or heteroarylalkyl wherein the alkyl, alkenyl, alkynyl, aryl, heteroaryl, alicyclic, heterocyclic, arylalkyl or heteroaryl alkyl groups may be optionally substituted.

The term "acyloxy" as used herein, alone or in combination, refers to the ester group —OC(O)R, where R is H, alkyl, alkenyl, alkynyl, aryl, heteroaryl, alicyclic, heterocyclic, arylalkyl, or heteroarylalkyl wherein the alkyl, alkenyl, alkynyl, aryl, heteroaryl, alicyclic, heterocyclic, arylalkyl or heteroarylalkyl may be optionally substituted.

The term "carboxy esters" as used herein, alone or in combination, refers to —C(O)OR where R is alkyl, aryl or arylalkyl, wherein the alkyl, aryl and arylalkyl groups may be optionally substituted.

The term "BOC" as used herein, alone or in combination, refers to —C(O)Otbutyl.

The term "carboxamido" as used herein, alone or in combination, refers to

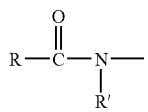

where each of R and R' are independently selected from the group consisting of H, alkyl, aryl, heteroaryl, alicyclic, heterocyclic, arylalkyl and heteroarylalkyl, wherein the alkyl, aryl, heteroaryl, alicyclic, heterocyclic, or arylalkyl groups may be optionally substituted.

The terms "thioamide" and "thioamidyl" as used herein, alone or in combination, refer to

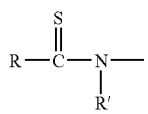

where each of R and R' are independently selected from the group consisting of H, alkyl, aryl, heteroaryl, alicyclic, heterocyclic, arylalkyl and heteroarylalkyl, wherein the alkyl, aryl, heteroaryl, alicyclic, heterocyclic, or arylalkyl groups may be optionally substituted.

The term "oxo" as used herein, alone or in combination, refers to =O.

The term "halogen" as used herein, alone or in combination, refers to F, Cl, Br and I.

The terms "haloalkyl", "haloalkenyl", "haloalkynyl" and "haloalkoxy" as used herein, alone or in combination, refer to alkyl, alkenyl, alkynyl and alkoxy structures, as described above, that are substituted with one or more fluorines, chlorines, bromines or iodines, or with combinations thereof.

The terms "perhaloalkyl", "perhaloalkyloxy" and "perhaloacyl" as used herein, alone or in combination, refer to alkyl, alkyloxy and acyl radicals as described above, in which all the H atoms are replaced by fluorines, chlorines, bromines or iodines, or combinations thereof The terms "lower perhaloalkyl", "lower perhaloalkyloxy" and "lower perhaloacyl" as used herein, alone or in combination, refer to perhaloalkyl, perhaloalkyloxy and perhaloacyl radicals as described above, having from two to about six carbons.

The terms cycloalkyl, arylalkyl, aryl, heteroaryl, alicyclic, heterocyclic, alkyl, alkynyl, alkenyl, haloalkyl, and heteroalkyl include optionally substituted cycloalkyl, arylalkyl, aryl, heteroaryl, alicyclic, heterocyclic, alkyl, alkynyl, alkenyl, haloalkyl and heteroalkyl groups.

The term "alkylsilyl" as used herein, alone or in combination, refers to —NRR'R" where R, R' and R" are alkyls.

The term "lower alkylsilyl" as used herein, alone or in combination, refers to —NRR'R" where R, R' and R" are lower alkyls.

The term "amino" as used herein, alone or in combination, refers to —NH$_2$.

The term "alkylamino" as used herein, alone or in combination, refers to the group —NHR where R is alkyl.

The term "aminoalkyl" as used herein, alone or in combination, refers to the group -alkylene-NH$_2$, wherein alkylene is as defined herein.

The term "dialkylamino" as used herein, alone or in combination, refers to the group —NRR' where R and R' are alkyls.

The term "arylalkylamino" as used herein, alone or in combination, refers to the group —NRR' where R is alkyl, and R' is aryl.

The term "diarylamino" as used herein, alone or in combination, refers to the group —NRR' where R and R' are aryls.

The term "heteroarylamino" as used herein, alone or in combination, refers to the group —NHR where R is heteroaryl.

The term "diheteroarylamino" as used herein, alone or in combination, refers to the group —NRR' where R and R' are heteroaryls.

The term "arylheteroarylamino" as used herein, alone or in combination, refers to the group —NRR' where R is aryl, and R' is heteroaryl.

The term "carbamyl" as used herein, alone or in combination, refers to the —NHC(O)OR and —OC(O)NHR groups, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "uryl" as used herein, alone or in combination, refers to the —NHC(O)NHR group, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "thiouryl" as used herein, alone or in combination, refers to the —NHC(S)NHR group, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "guanidinyl" as used herein, alone or in combination, refers to the —NHC(NH)NHR group, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —S(O$_2$)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—S(O$_2$)CH$_3$) and the like.

The term "phosphite" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The term "phosphoramide" as used herein, alone or in combination, refers to a phosphorus atom covalently linked to four atoms, three of which are nitrogen and one of which is oxygen wherein the formal oxidation state of said phosphorus is (V).

The term "phosphoramidyl" as used herein, alone or in combination, refers to the monoradical derived from a phosphoramide group, as defined above.

The terms "optional" or "optionally" mean that the subsequently described event or circumstance may but need not occur, and that the description includes instances where the event or circumstance occurs and instances in which it does not. For example, "aryl optionally mono- or di-substituted with an alkyl" means that the alkyl may but need not be present, or either one alkyl or two may be present, and the description includes situations where the aryl is substituted with one or two alkyls and situations where the aryl is not substituted with an alkyl.

"Optionally substituted" groups may be substituted or unsubstituted. The substituents of an "optionally substituted" group may include, without limitation, one or more substituents independently selected from the following groups or designated subsets thereof: lower alkyl, lower alkenyl, lower alkynyl, lower aryl, heteroaryl, alicyclic, heterocyclic, arylalkyl, heteroarylalkyl, lower alkoxy, lower aryloxy, amino, alkylamino, dialkylamino, diarylalkylamino, alkylthio, arylthio, heteroarylthio, oxo, oxa, acyl (—C(O)R), (—C(O)), carboxyesters (—C(O)OR), carboxamido (—C(O)NH$_2$), carboxy, acyloxy, —H, halo, —CN, —NO$_2$, —N$_3$, —SH, —OH, —(O)CH$_3$, perhaloalkyl, perhaloalkoxy, perhaloacyl, guanidine, pyridinyl, thiophene, furanyl, indole, indazole, esters, amides, phosphonates, phosphonic acid, phosphates, phosphoramides, sulfonates, sulfones, sulfates, sulphonamides, carbamates, ureas, thioureas, thioamides and thioalkyls. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$).

The term "pyridine-1-oxy" also means "pyridine-N-oxy".

The term "heteroaryl group is substituted with 2 to 5 substituents" encompasses 1-oxy-pyridyl or N-oxy-pyridyl having 1 to 4 substituents, i.e. the oxygen atom of the pyridine-N-oxide should be counted as a substituent.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well. Further, it is possible using well known techniques to separate the various forms, and some embodiments of the invention may feature purified or enriched species of a given enantiomer or diastereomer.

Some of the compounds of the present invention may exist in tautomeric forms. The scope of the present invention is intended to cover all tautomers. As a non-limiting example, compounds of formula (I), wherein R$^0$ is —SR$^8$ or —OR$^8$, and R$^8$ is hydrogen, could exist as either of the tautomers below:

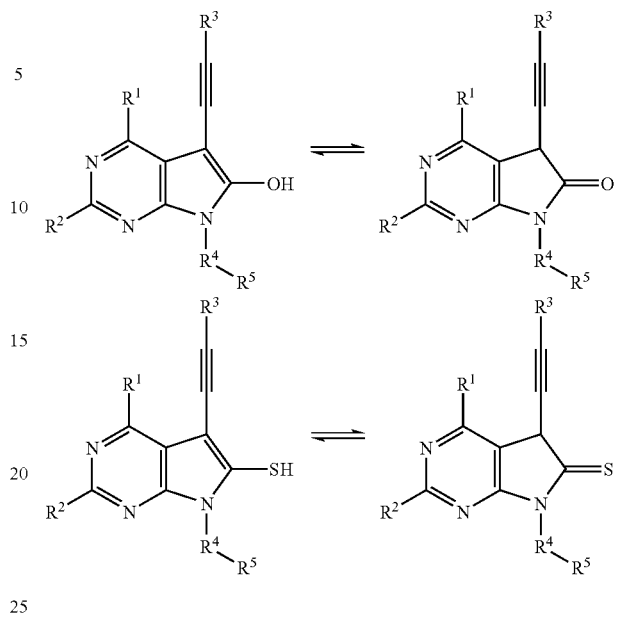

A "pharmacological composition" refers to a mixture of one or more of the compounds described herein, or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

A "pharmaceutically effective amount" means an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate, half-life and maximum tolerated dose (MTD) have yet to be determined but one of ordinary skill in the art can determine these using standard procedures.

In some method embodiments, the preferred therapeutic effect is the inhibition, to some extent, of the growth of cells characteristic of a proliferative disorder, e.g., breast cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

As used herein, the term $IC_{50}$ refers to an amount, concentration or dosage of a particular test compound that achieves a 50% inhibition of a maximal response in an assay that measures such response. In some method embodiments of the invention, the "$IC_{50}$" value of a compound of the invention can be greater for normal cells than for cells exhibiting a proliferative disorder, e.g., breast cancer cells. The value depends on the assay used.

By a "standard" is meant a positive or negative control. A negative control in the context of Her2 expression levels is, e.g., a sample possessing an amount of Her2 protein that correlates with a normal cell. A negative control may also include a sample that contains no Her2 protein. By contrast, a positive control does contain Her2 protein, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick."

By "selectively targeting" is meant affecting one type of cell to a greater extent than another, e.g., in the case of cells with high as opposed to relatively low or normal Her2 levels.

Compounds of the Invention

Compounds of the invention are related to alkynyl pyrrolo[2,3-d]pyrimidines of Formula I

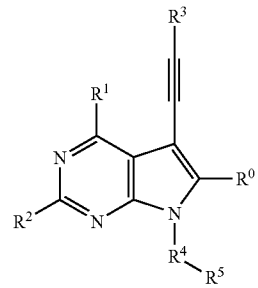

(I)

and their polymorphs, solvates, esters, tautomers, diastereomers, enantiomers, pharmaceutically acceptable salts or prodrugs thereof, which show utility for inhibiting HSP90 and treating and preventing diseases that are HSP90-dependent, wherein:

$R^0$ is selected from the group consisting of hydrogen, halogen, lower alkyl, —CN, —$SR^8$, —$OR^8$, and —$NHR^8$;

$R^1$ is selected from the group consisting of halogen, —$OR^{11}$, —$SR^{11}$ and lower alkyl;

$R^2$ is —$NHR^8$;

$R^3$ is selected from the group consisting of hydrogen, —CN, —C(O)OH, —$OR^{11}$, —$SR^{11}$, —$C(O)R^9$, —$NR^8R^{10}$, lower alkyl, lower alkenyl, lower alkynyl, lower perhaloalkyl, lower alkylsilyl, aryl, heteroaryl, alicyclyl and heterocyclyl, all optionally substituted, wherein:

the aryl, heteroaryl, alicyclyl and heterocyclyl groups are mono-, bi- or tri-cyclic;

$R^8$ and $R^{10}$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;

the optional substituents on $R^3$ are selected from the group consisting of lower alkyl, lower alkenyl, lower alkynyl, —CN, —C(O)OH, —$NO_2$, —$SR^8$, —$OR^8$, —$C(O)R^9$, —$NR^8R^8$, lower aryl, heteroaryl, alicyclyl, lower heterocyclyl, arylalkyl, heteroarylalkyl, amino, alkylamino, dialkylamino, arylalkylamino, diarylamino, heteroarylamino, diheteroarylamino, arylheteroarylamino, oxo, perhaloalkyl, perhaloalkoxy, perhaloacyl, guanidinyl, pyridinyl, thiophenyl, furanyl, indolyl, indazolyl, phosphonyl, phosphatidyl, phosphoramidyl, sulfanyl, sulfinyl, sulfonyl, sulphonamidyl, carbamyl, uryl, thiouryl and thioamidyl, wherein $R^8$ and $R^8$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;

$R^4$ is selected from the group consisting of optionally substituted lower alkylene, —$C(R^{12})_2$—, —C(O)—, —C(S)—, —S(O)— and —$SO_2$—;

$R^5$ is selected from the group consisting of aryl, heteroaryl, alicyclyl and heterocyclyl, wherein:

the aryl group is substituted with 2 to 5 substituents;
the heteroaryl group is substituted with 2 to 5 substituents;
the alicyclyl group is substituted with 3 to 5 substituents;
the heterocyclyl group is substituted with 3 to 5 substituents;

the substituents on $R^5$ are selected from the group consisting of halogen, lower alkyl, lower alkenyl, lower alkynyl, —CN, —C(O)OH, —NO$_2$, —SR$^8$, —OR$^8$, —C(O)R$^9$, —NR$^8$R$^{10}$, lower aryl, lower heteroaryl, lower alicyclyl, lower heterocyclyl, arylalkyl, heteroarylalkyl, thioalkyl, amino, alkylamino, dialkylamino, arylalkylamino, oxo, perhaloalkyl, perhaloalkoxy, perhaloacyl, guanidinyl, pyridinyl, thiophenyl, furanyl, indolyl, indazolyl, phosphonyl, phosphatidyl, phosphoramidyl, sulfanyl, sulfinyl, sulfonyl, sulphonamidyl, carbamyl, uryl, thiouryl and thioamidyl, wherein R$^8$ and R$^{10}$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;

R$^8$ is selected from the group consisting of hydrogen, lower alkyl, lower alkenyl, lower alkynyl, lower heteroalkyl, lower heteroalkenyl, lower heteroalkynyl, lower aryl, lower heteroaryl and —C(O)R$^9$;

R$^9$ is selected from the group consisting of H, lower alkyl, lower alkenyl, lower alkynyl, lower aryl, lower heteroaryl, —NR$^{10}$R$^{10}$) and —OR$^{11}$, wherein R$^{10}$ and R$^{10}$ taken together with the N atom to which they are attached optionally form an optionally substituted ring comprising 3-7 ring atoms, wherein, in addition to said N atom, 0-3 of the ring atoms are heteroatoms selected from the group consisting of O, S and N;

R$^{10}$ is selected from the group consisting of hydrogen, lower alkyl, lower alkenyl, lower alkynyl, lower heteroalkyl, lower heteroalkenyl, lower heteroalkynyl, lower aryl, lower heteroaryl and —C(O)R$^{11}$;

R$^{11}$ is selected from the group consisting of lower alkyl, lower alkenyl, lower alkynyl, lower aryl and lower heteroaryl; and R$^{12}$ is selected from the group consisting of hydrogen and lower alkyl.

In some embodiments, R$^0$ is hydrogen, halogen or —CN. In other embodiments, R$^0$ is hydrogen, lower alkyl, —SR$^8$ or —OR$^8$. In other embodiments, R$^0$ is hydrogen, —SR$^8$, —OR$^8$ or —NHR$^8$. In other embodiments, R$^0$ is —SR$^8$ or —OR$^8$. In other embodiments, R$^0$ is hydrogen.

In some embodiments, R$^1$ is halogen or lower alkyl. In other embodiments, R$^1$ is —OR$^{11}$ or —SR$^{11}$. In some embodiments, R$^1$ is halogen. In some embodiments, R$^1$ is chloro or bromo. In some embodiments, R$^1$ is chloro. In some embodiments, R$^1$ is bromo.

In some embodiments, R$^2$ is —NH$_2$ or —NHC(O)R$^9$. In other embodiments, R$^2$ is —NH-lower alkyl, —NH-lower alkenyl, —NH-lower alkynyl, —NH-lower aryl or —NH-lower heteroaryl. In other embodiments, R$^2$ is —NHC(O)R$^9$ where R$^9$ is lower alkyl, lower alkenyl, lower alkynyl, lower aryl or lower heteroaryl. In other embodiments, R$^2$ is —NH$_2$. In other embodiments, R$^2$ is —NH(O)tBu.

In some embodiments, R$^3$ is hydrogen, lower alkyl, lower alkenyl, lower alkynyl, lower perhaloalkyl, aryl, heteroaryl, alicyclyl, heterocyclyl, —CN or —C(O)R$^9$, all optionally substituted. In other embodiments, R$^3$ is hydrogen, lower alkyl, aryl, heteroaryl, alicyclyl, heterocyclyl or —C(O)R$^9$, all optionally substituted. In other embodiments, R$^3$ is hydrogen, lower alkyl, aryl, heteroaryl, or —C(O)R$^9$, all optionally substituted. In other embodiments, R$^3$ is substituted lower alkyl wherein the substituent on the lower alkyl is selected from the group consisting of lower alkyl, —OR$^8$, —C(O)R$^9$ and —NR$^8$R$^8$. In other embodiments, R$^3$ is lower alkyl, aryl, heteroaryl, —CN or —C(O)R$^9$, all optionally substituted. In other embodiments, R$^3$ is hydrogen. In other embodiments, R$^3$ is optionally substituted lower alkyl. In other embodiments, R$^3$ is optionally substituted phenyl or pyridinyl. In other embodiments, R$^3$ is —(CH$_2$)$_n$OH, where n=1-3. In other embodiments, R$^3$ is —(CH$_2$)$_m$C(R$^{12}$)$_2$(CH$_2$)$_n$OH, where m=0-2 and n=1-2. In other embodiments, R$^3$ is —(CH$_2$)$_n$NR$^8$R$^8$ wherein n=1-3, and each R$^8$ is independently hydrogen or lower alkyl, or —NR$^8$R$^8$ are taken together forming an optionally substituted phthalimide or morpholin. In other embodiments, R$^3$ is —(CH$_2$)$_n$C(O)NR$^{10}$R$^{10}$, wherein n=1-3, and each R$^{10}$ is independently hydrogen or —C(O)R$^{11}$, or —NR$^{10}$R$^{10}$ are taken together forming an optionally substituted piperazine. In other embodiments, R$^3$ is optionally substituted lower alkylsilyl. In other embodiments, R$^3$ is —CO$_2$Et. In other embodiments, R$^3$ is —(CH$_2$)$_n$C(O)NR$^{10}$R$^{10}$ where n=1-3, and each R$^{10}$ is independently hydrogen, or —C(O)R$^{11}$. In other embodiments, R$^3$ is —(CH$_2$)$_n$C(O)NHC(O)OtBu.

In some embodiments, R$^4$ is optionally substituted lower alkylene, —C(O)—, —S(O)— or —SO$_2$—. In other embodiments, R$^4$ is —CH$_2$—, —S(O)— or —SO$_2$. In other embodiements, R$^4$ is —CHR$^{12}$—. In other embodiements, R$^4$ is —CH$_2$—.

In some embodiments, the aryl, heteroaryl, alicyclyl or heterocyclyl group of R$^5$ is monocyclic or bicyclic. In other embodiments, R$^5$ is substituted aryl or heteroaryl and the substituents on said aryl or heteroaryl are selected from the group consisting of halogen, lower alkoxy, lower alkyl, thioalkyl, amino, alkylamino, dialkylamino. In other embodiments, R$^5$ is substituted aryl or heteroaryl and the substituents on the aryl or heteroaryl are selected from the group consisting of halogen, lower alkoxy and lower alkyl.

In some embodiments, R$^0$ is hydrogen, halogen, —SH, —OH, or —CN; R$^1$ is halogen; and R$^2$ is —NH$_2$ or —NH—C(O)R$^9$.

In some embodiments, R$^1$ is chloro or bromo; R$^2$ is —NH$_2$ or —NH—C(O)R$^9$; and R$^3$ is lower alkyl, lower alkenyl, lower alkynyl, lower perhaloalkyl, lower aryl, or lower heteroaryl, all optionally substituted with —OR$^8$, —NR$^8$R$^8$ or —C(O)R$^9$.

In some embodiments, R$^0$ is hydrogen, halogen or —CN; R$^2$ is —NH$_2$ or —NH—C(O)R$^9$; and R$^4$ is —CH$_2$—.

In other embodiments, R$^0$ is hydrogen, halogen, —SH, —OH or —CN; R$^1$ is halogen; R$^2$ is —NH$_2$; R$^3$ is hydrogen, —OR$^{11}$, —SR$^{11}$, —NR$^8$R$^8$, lower alkyl, lower alkenyl, lower alkynyl, lower perhaloalkyl, lower aryl, or lower heteroaryl, wherein the R$^8$ in R$^3$ is hydrogen, lower alkyl, lower heteroalkyl, lower aryl, or —C(O)R$^9$; R$^4$ is —CH$_2$—; and R$^5$ is aryl or heteroaryl, substituted with 2 to 5 substituents.

In some embodiments, R$^0$ is selected from hydrogen, halogen and —CN; R$^1$ is halogen; R$^2$ is —NHR$^8$; R$^3$ is selected from the group consisting of hydrogen, lower alkyl, lower alkenyl, lower alkynyl, lower perhaloalkyl, aryl, heteroaryl, alicyclyl and heterocyclyl, all optionally substituted; R$^4$ is —CHR$^{12}$—; and R$^5$ optionally substituted is aryl or heteroaryl.

In other embodiments, R$^0$ is selected from hydrogen, halogen and —CN; R$^1$ is halogen; R$^2$ is —NH$_2$; R$^3$ is selected from the group consisting of lower alkyl, lower alkenyl, lower alkynyl, all optionally substituted with —OR$^8$, —NR$^8$R$^8$ or —C(O)R$^9$; R$^4$ is —CH$_2$; and R$^5$ is aryl or heteroaryl.

In other embodiments, R$^1$ is chloro or bromo; R$^2$ is —NH$_2$; and R$^5$ is a phenyl having at least three substituents.

In other embodiments, R$^1$ is chloro or bromo; R$^2$ is —NH$_2$; and R$^5$ is a pyridyl having at least two substituents.

In other embodiments, R$^1$ is chloro or bromo; R$^2$ is —NH$_2$; and R$^5$ is 1-oxy-pyridyl (N-oxy-pyridyl) having at least two substituents.

In other selected embodiments, R$^0$ is hydrogen; R$^1$ is chloro or bromo; R$^2$ is —NH$_2$ or —NHC(O)tBu; R$^3$ is selected from the group consisting of hydrogen, lower alkyl, aryl, heteroaryl, —CN, optionally substituted lower alkylsilyl, —CO$_2$Et, —(CH$_2$)$_m$C(CH$_3$)$_n$OH where m=0-2 and n=1-2, —(CH$_2$)$_n$OH where n=1-3, and —(CH$_2$)$_n$NR$^8$R$^{10}$ wherein n=1-3, R$^8$ and R$^{10}$ are independently hydrogen, lower alkyl, or are taken together forming a piperazine, a phthalimide or a morpholine; R$^4$ is —CH$_2$—; R$^5$ is substituted aryl or heteroaryl, and the substituents on the aryl or heteroaryl are selected from the group consisting of halogen, lower alkoxy, lower alkyl, thioalkyl, amino, alkylamino and dialkylamino.

In some selected embodiments, R$^0$ is hydrogen; R$^1$ is chloro or bromo; R$^2$ is —NH$_2$; R$^3$ is selected from the group consisting of hydrogen, lower alkyl, —(CH$_2$)$_n$OH, where n=1-3, —(CH$_2$)$_m$C(CH$_3$)$_n$OH, where m=0-2 and n=1-2, —(CH$_2$)$_2$C(O)NH$_2$, —(CH$_2$)OC(O)CH$_2$N(CH$_3$)$_2$, —(CH$_2$)$_n$NHC(O)OtBu and —(CH$_2$)$_n$NR$^8$R$^8$, wherein n=1-3, R$^8$ and R$^8$ are independently hydrogen, lower alkyl, or are taken together forming an optionally substituted phthalimide or morpholine; R$^4$ is —CH$_2$—; R$^5$ is substituted heteroaryl, and the substituents on said heteroaryl are independently selected from the group consisting of lower alkoxy and lower alkyl.

In some selected embodiments, R$^0$ is hydrogen; R$^1$ is chloro or bromo; R$^2$ is —NH$_2$; R$^3$ is selected from the group consisting of hydrogen, lower alkyl, —(CH$_2$)$_n$OH, where n=1-3, —(CH$_2$)$_m$C(CH$_3$)$_n$OH, where m=0-2 and n=1-2, —(CH$_2$)$_n$C(O)NR10R10 where n=1-3, and, R$^{10}$ and R$^{10}$ are independently hydrogen or —C(O)R$^{11}$, or are taken together forming an optionally substituted piperazine; R$^4$ is —CH$_2$—; R$^5$ is substituted heteroaryl, and the substituents on said heteroaryl are independently selected from the group consisting of lower alkoxy and lower alkyl.

In some selected embodiments R$^3$ is substituted lower alkyl, and in some further selected embodiments R$^3$ is substituted lower alkyl, and the substituent on said lower alkyl is phosphonyl or phosphatidyl.

In other preferred embodiemnts, are the following compounds

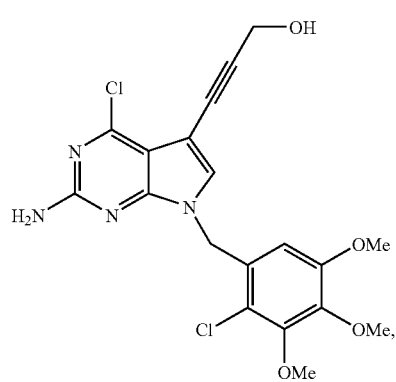

-continued

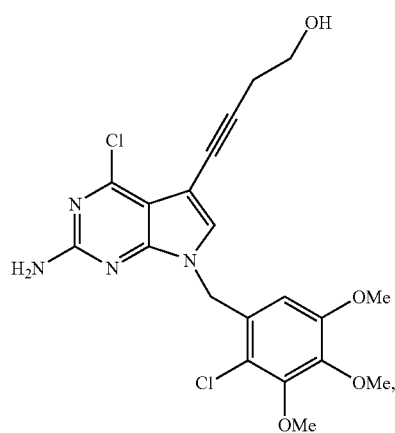

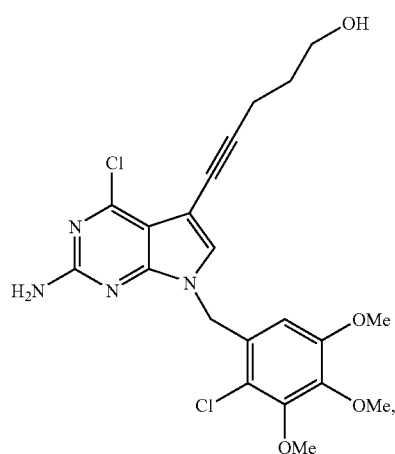

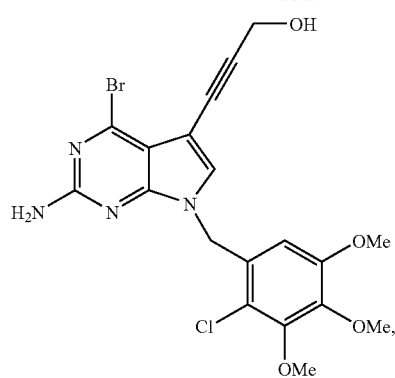

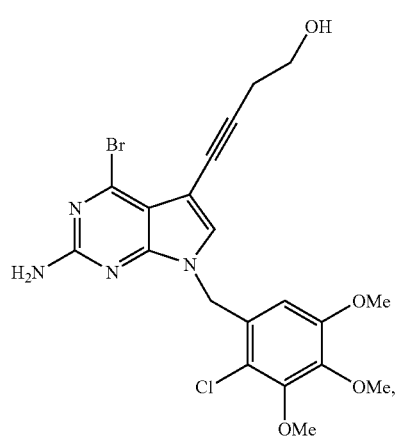

-continued
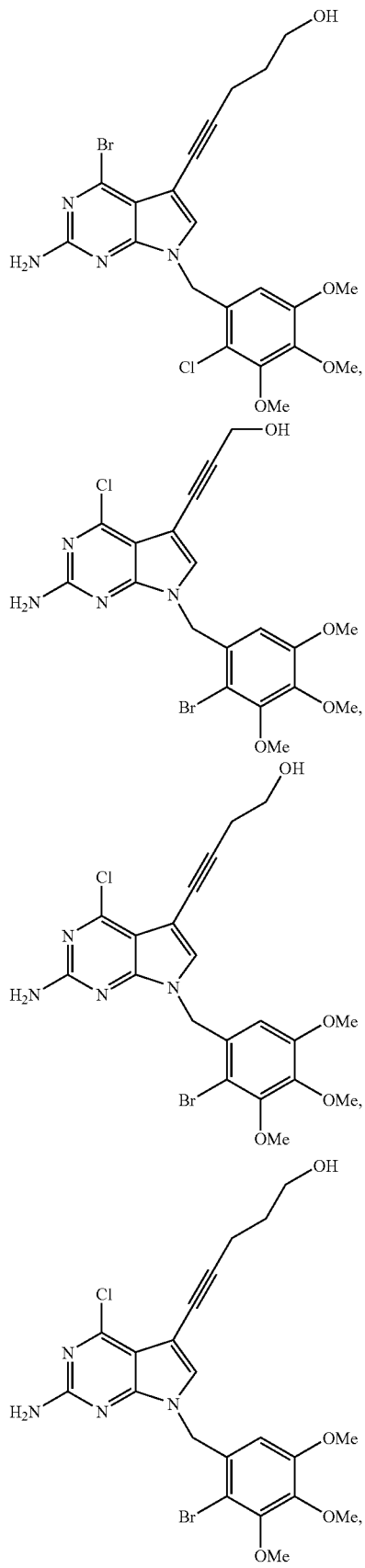
-continued
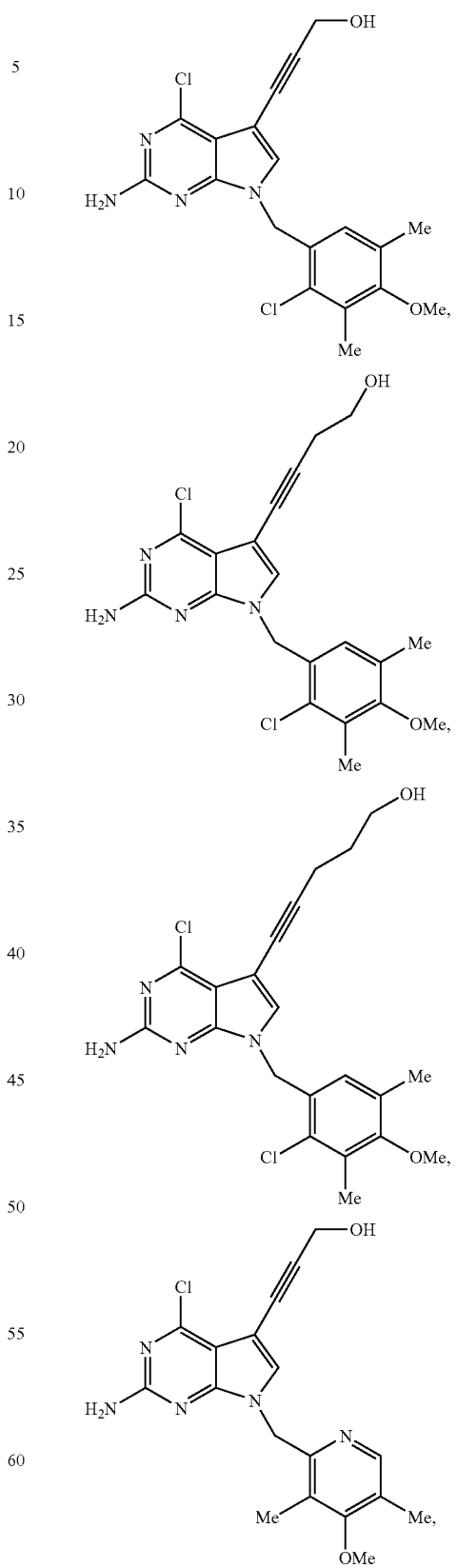

-continued
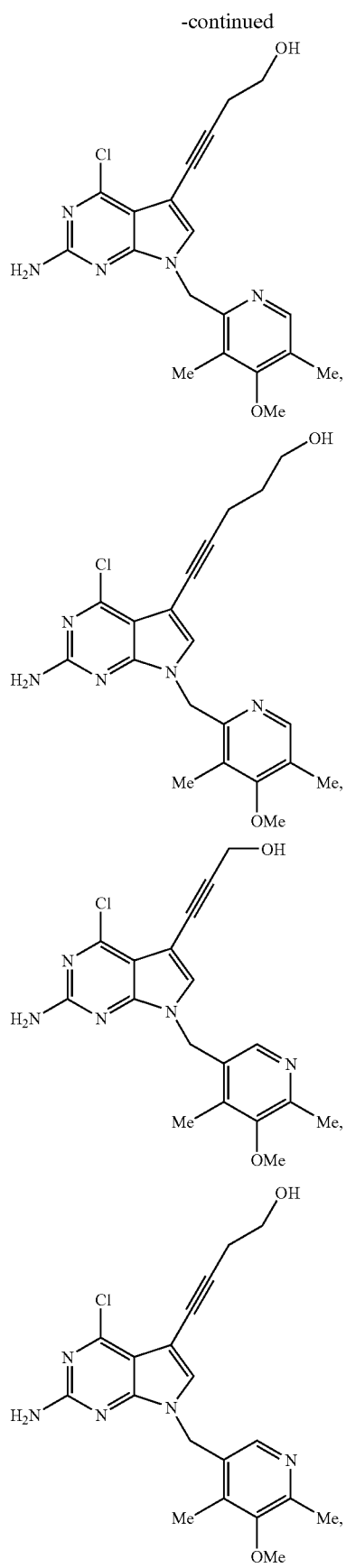
-continued
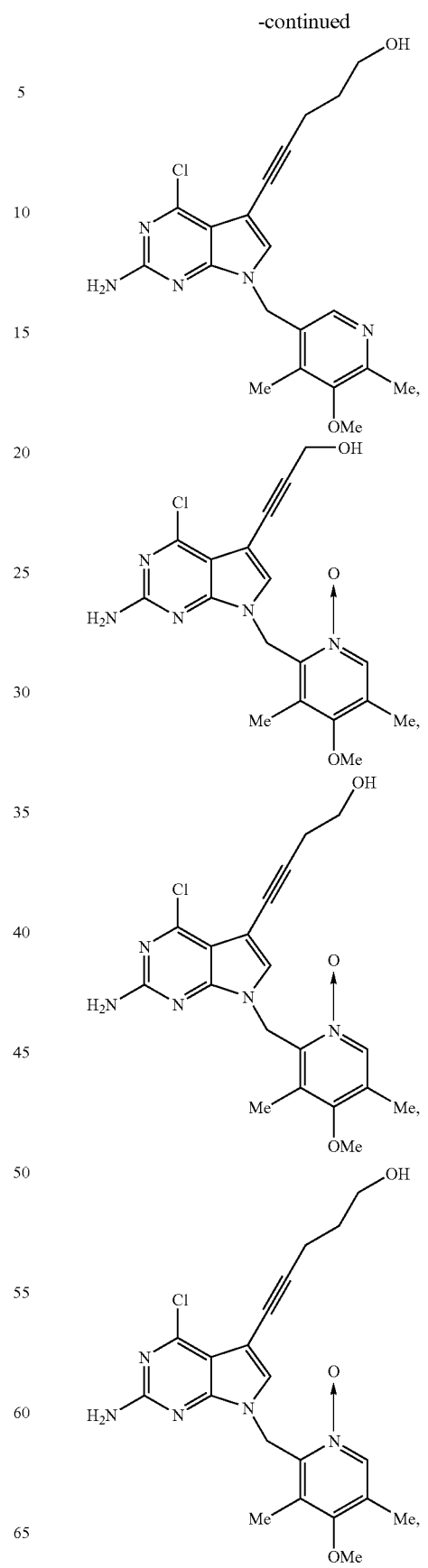

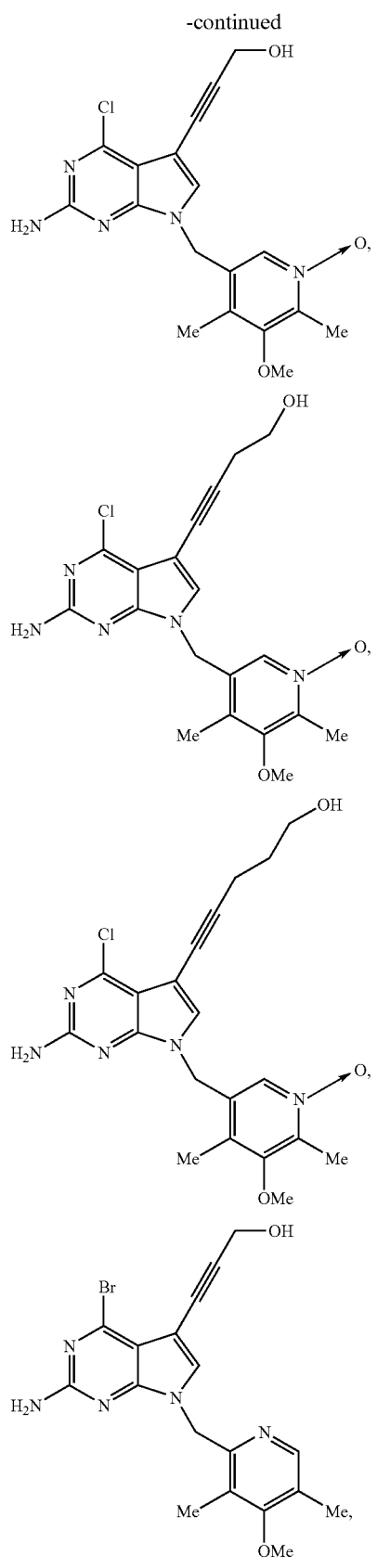
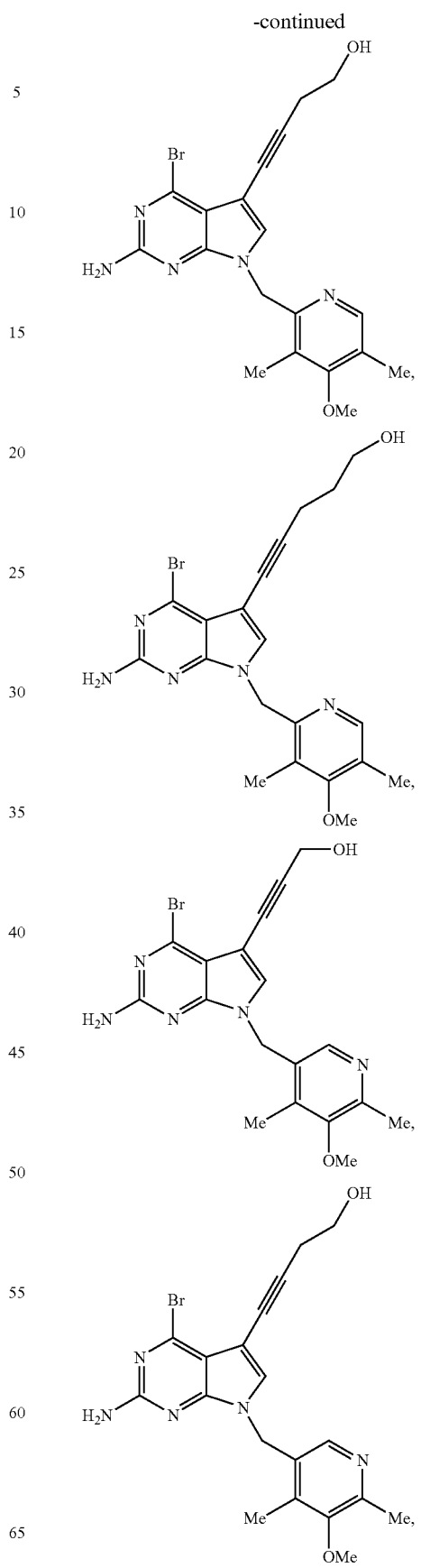

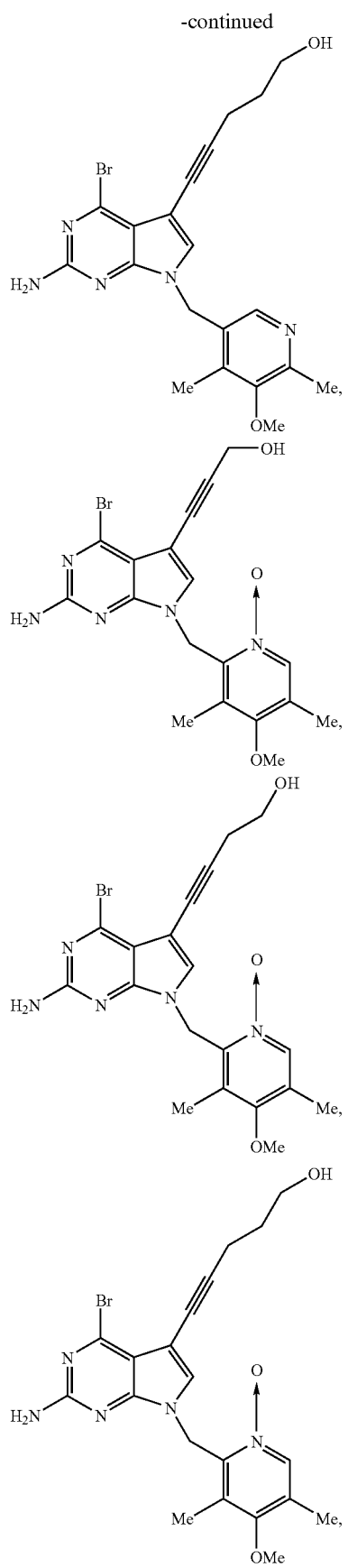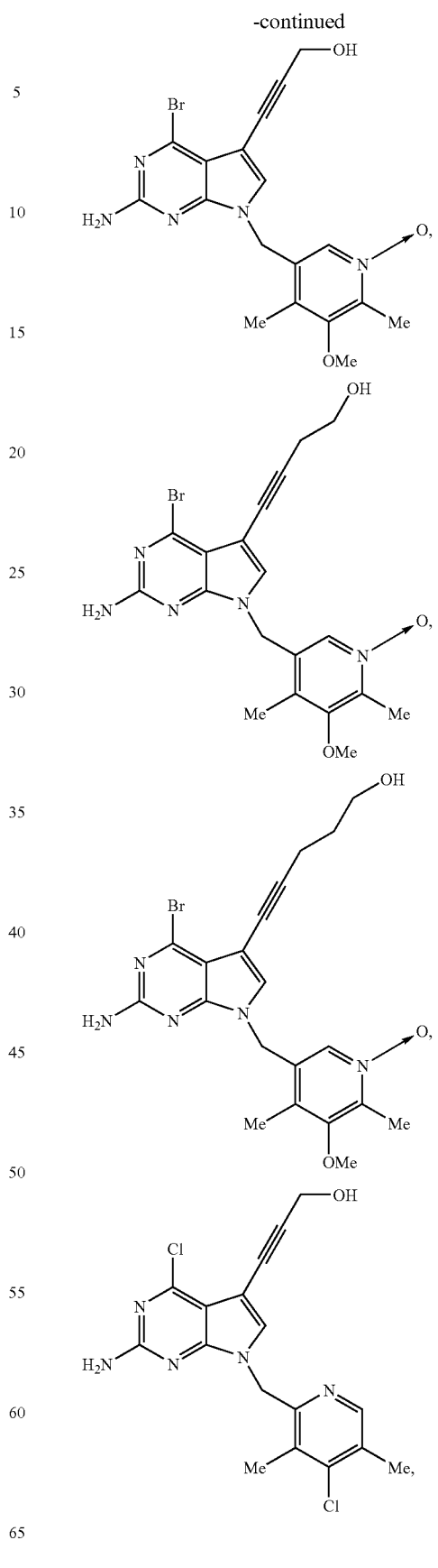

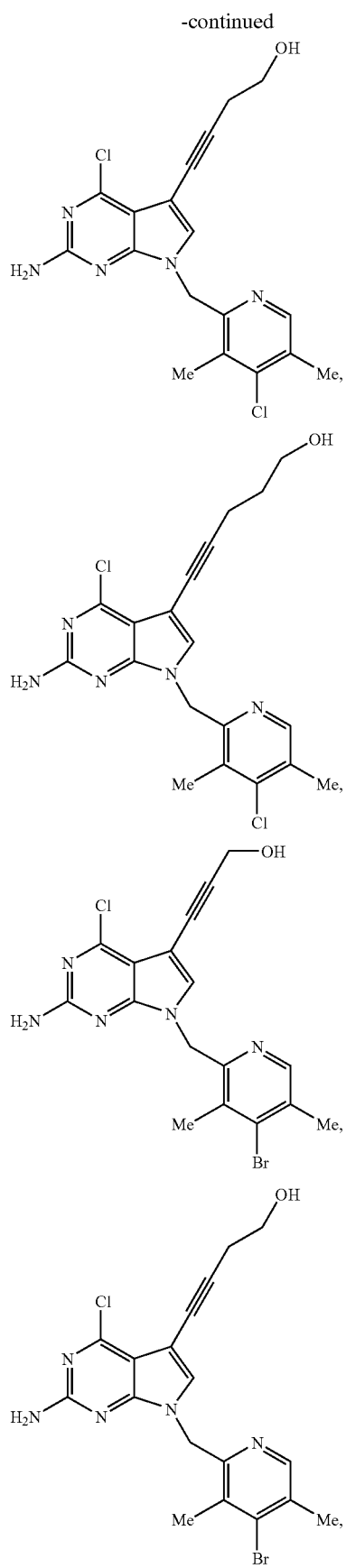
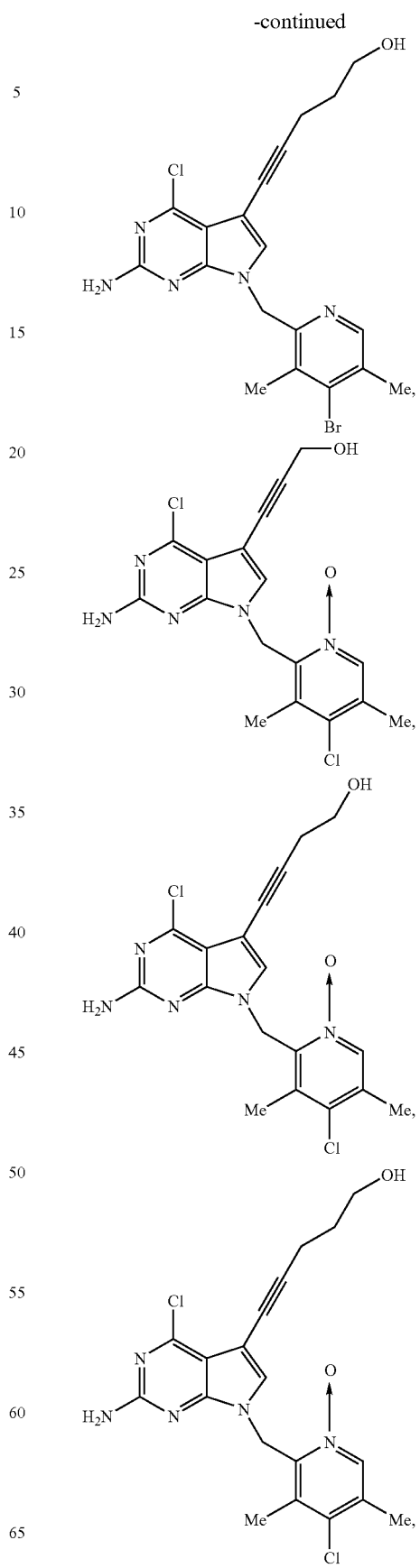

-continued
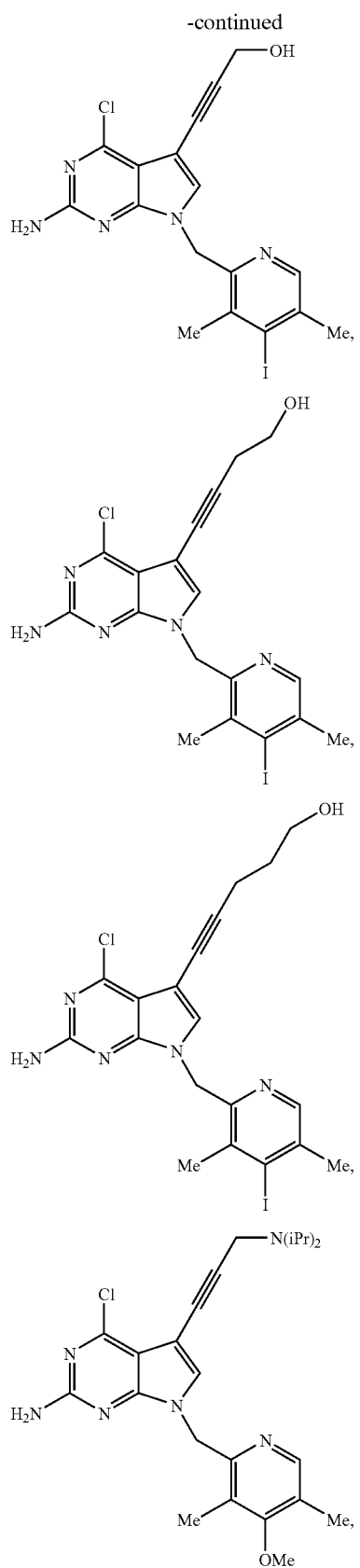
-continued
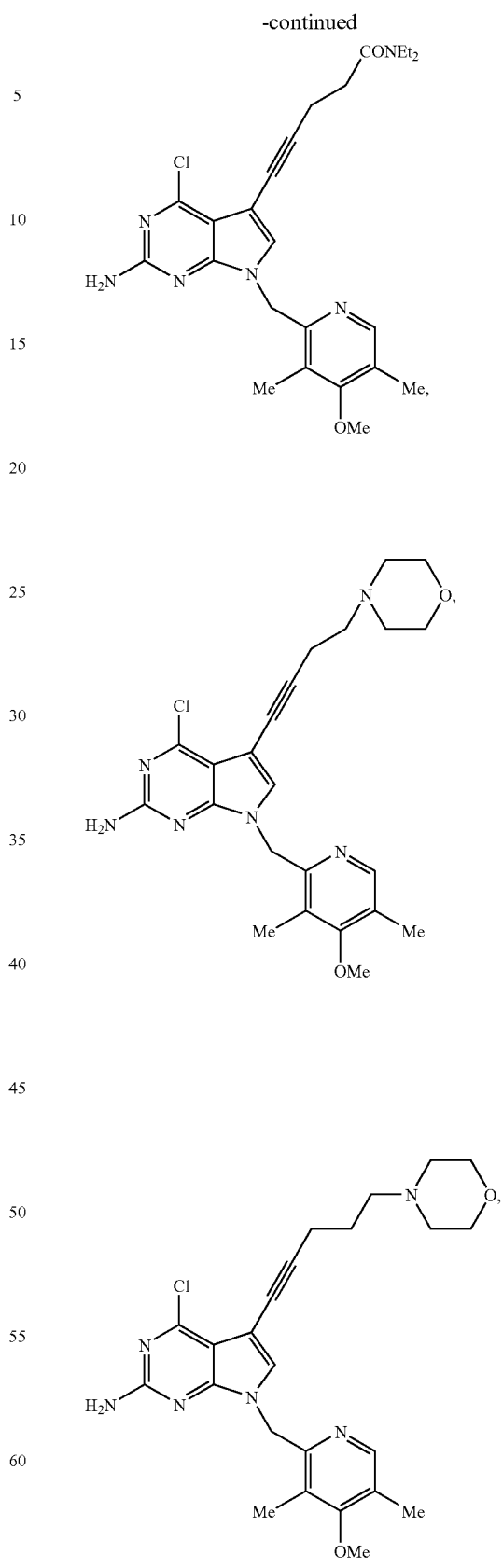

-continued
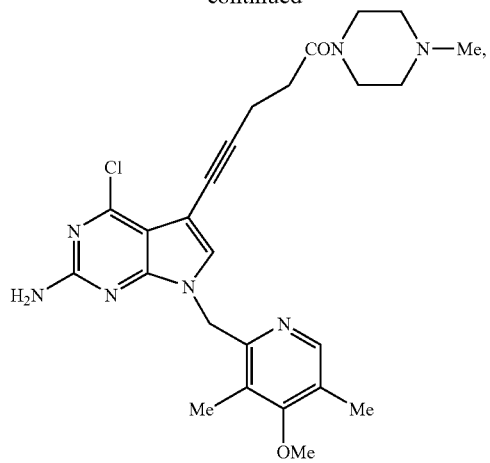
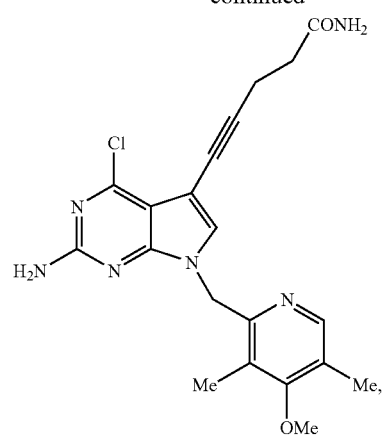
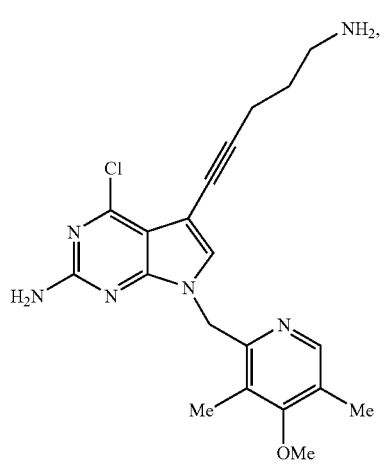
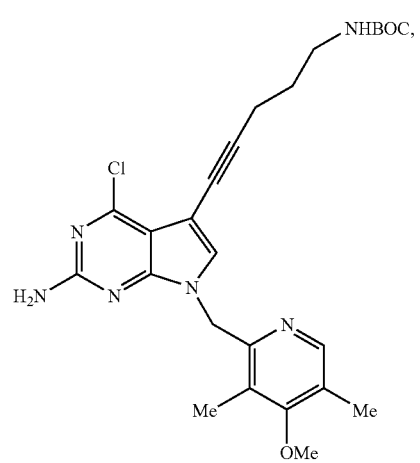
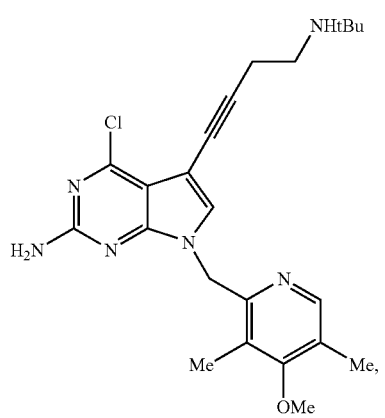
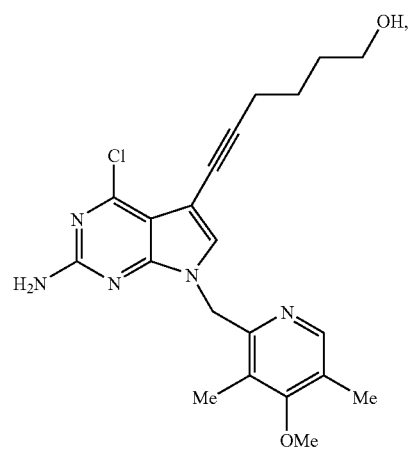

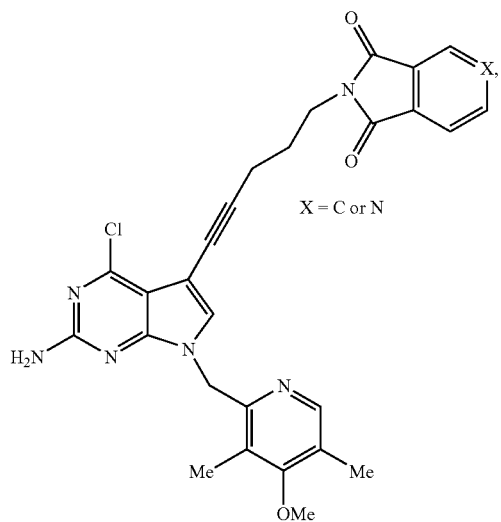
X = C or N
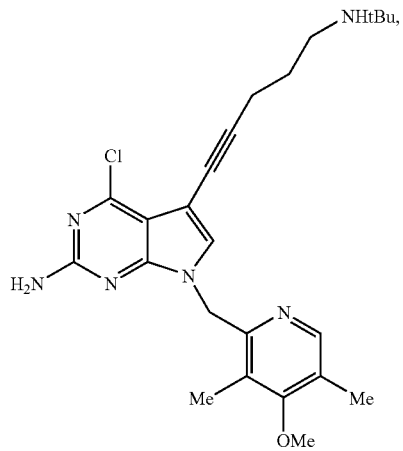
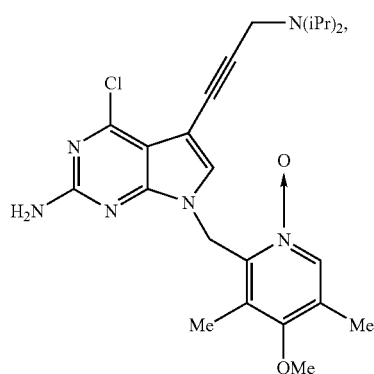
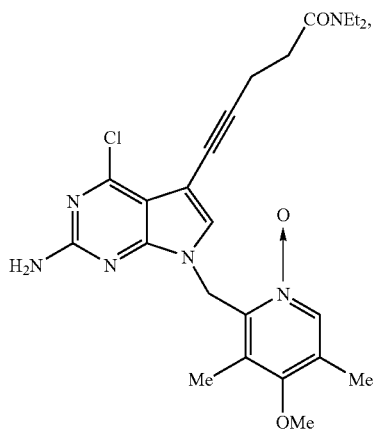
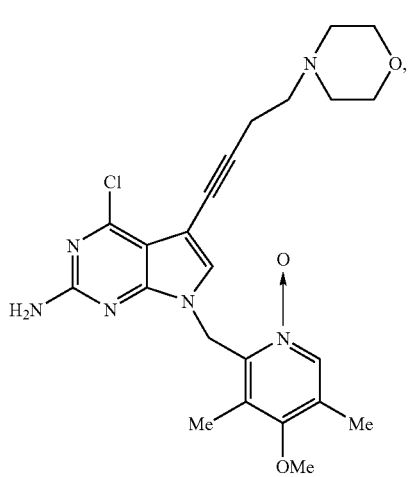
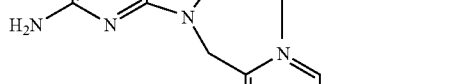

-continued
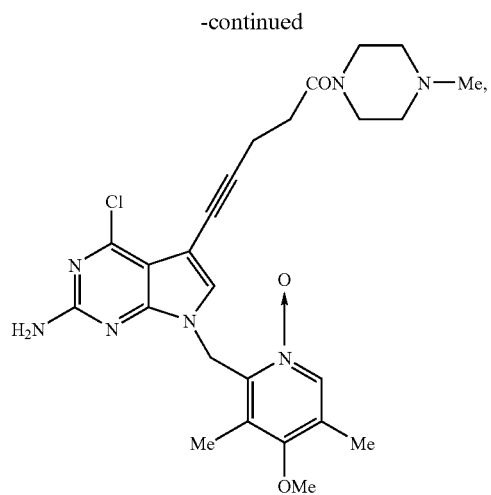
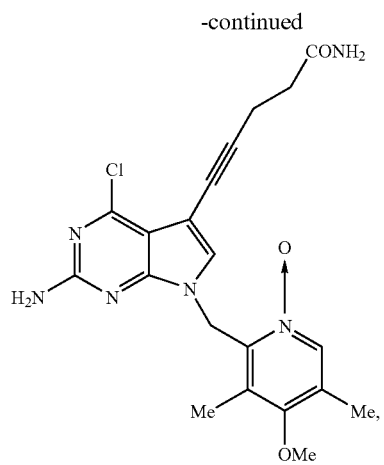
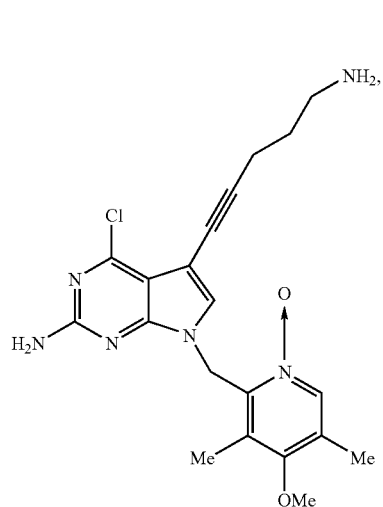
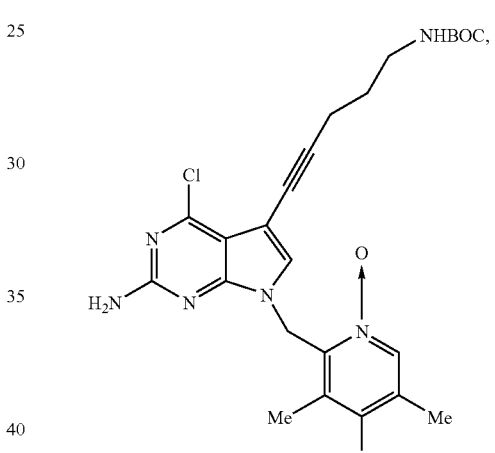
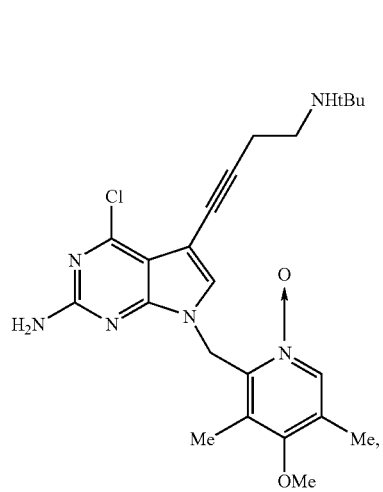
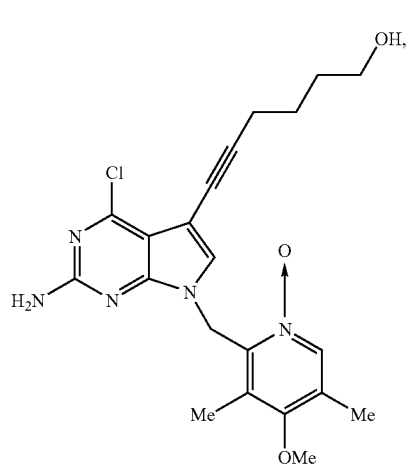

-continued
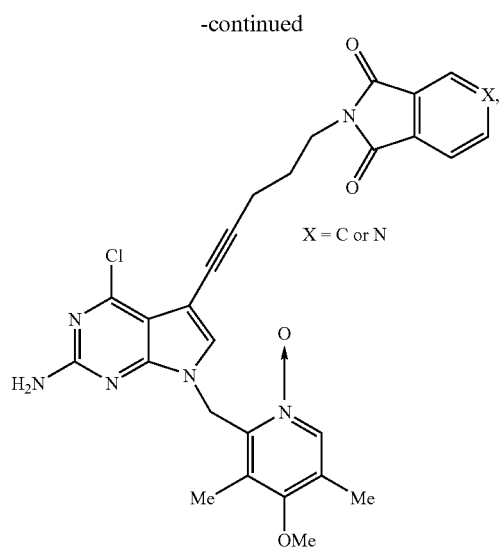
X = C or N
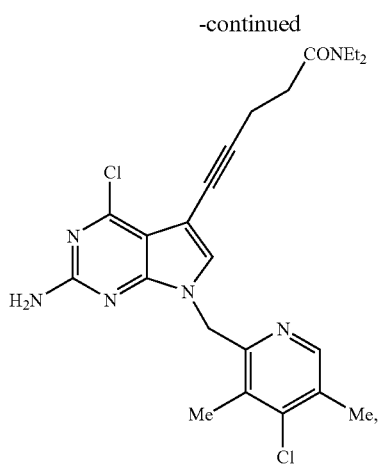
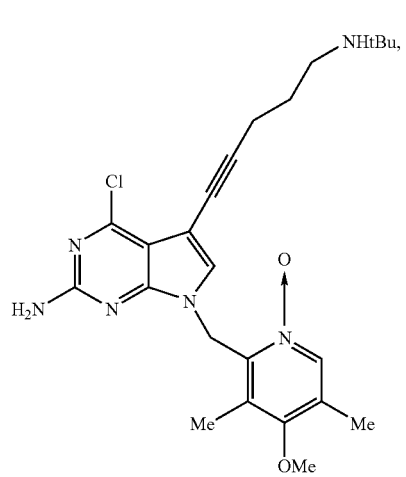
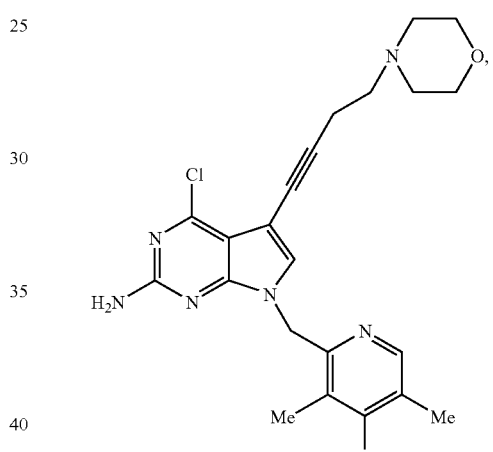
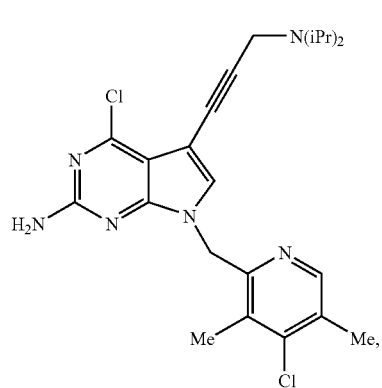
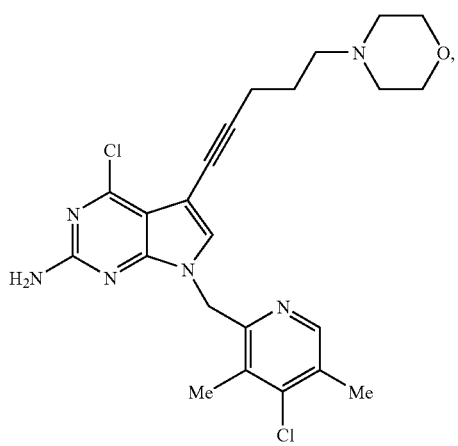

-continued
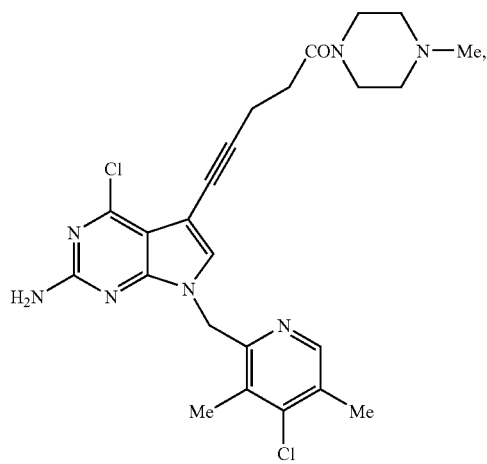
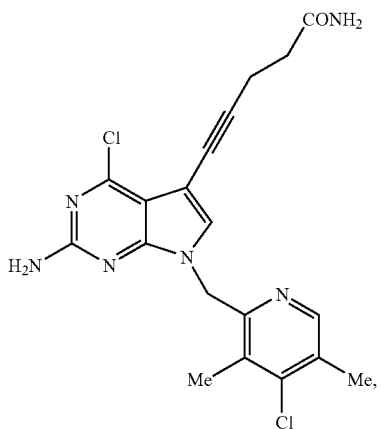
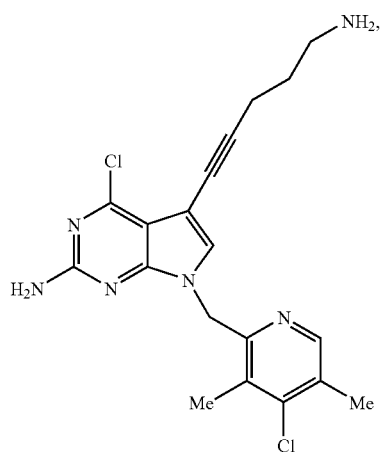
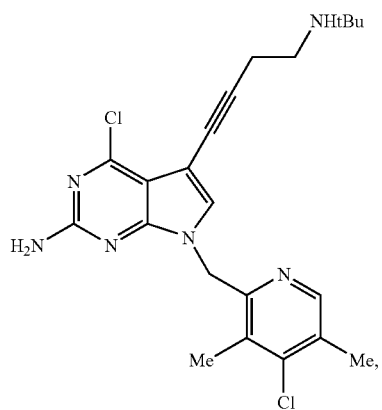

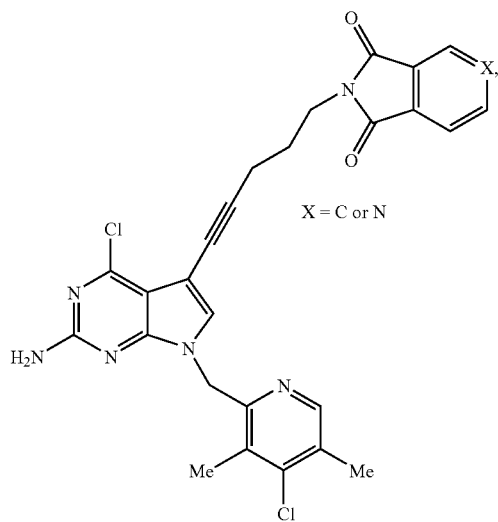
X = C or N
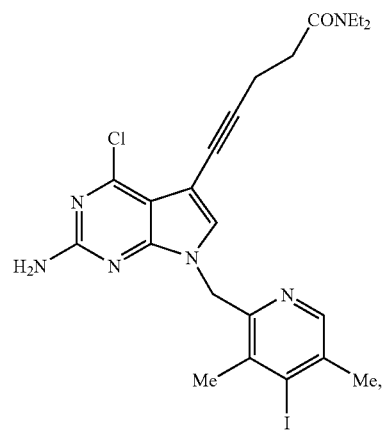
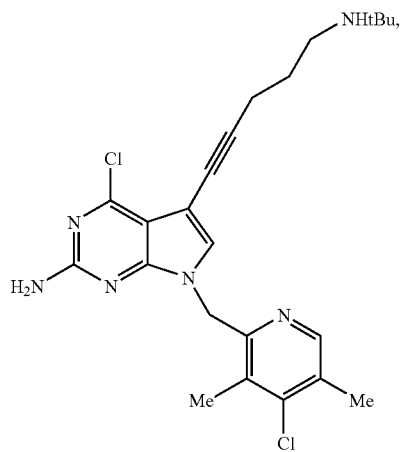
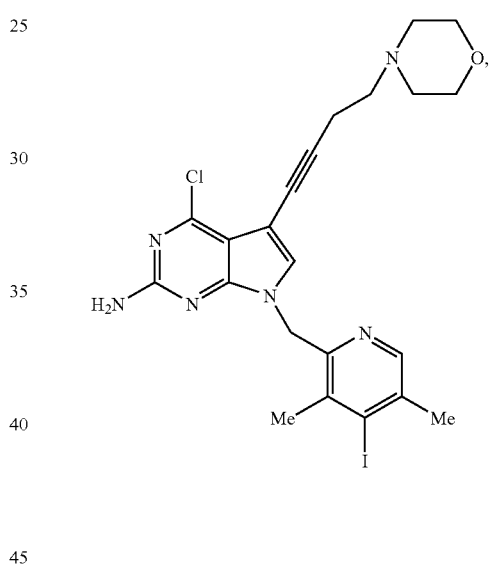
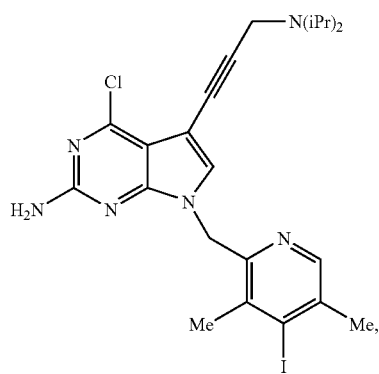
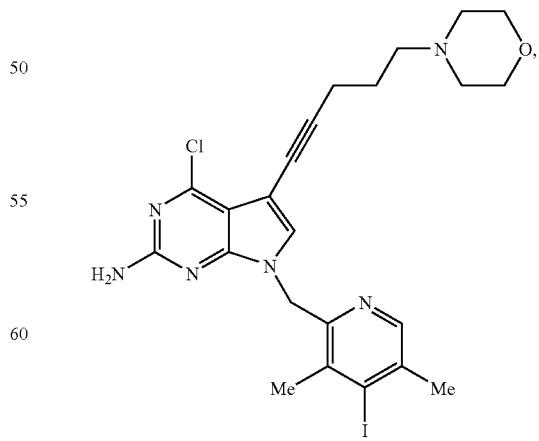

-continued
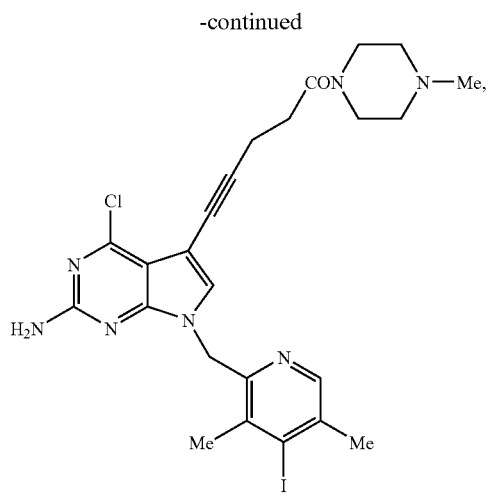
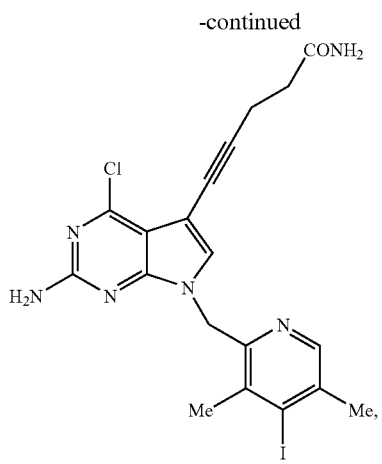
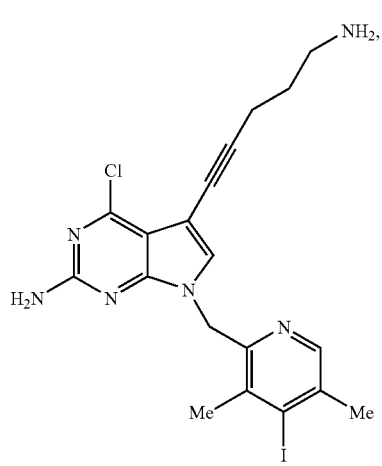
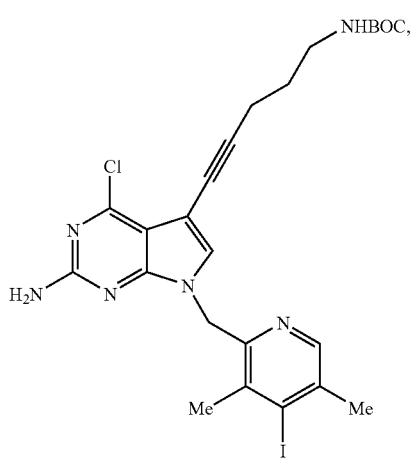
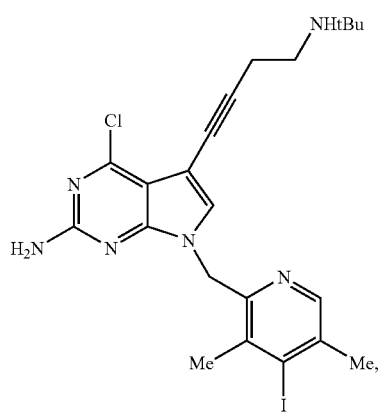
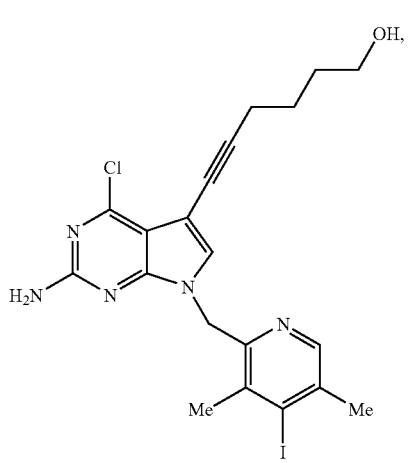

49
-continued
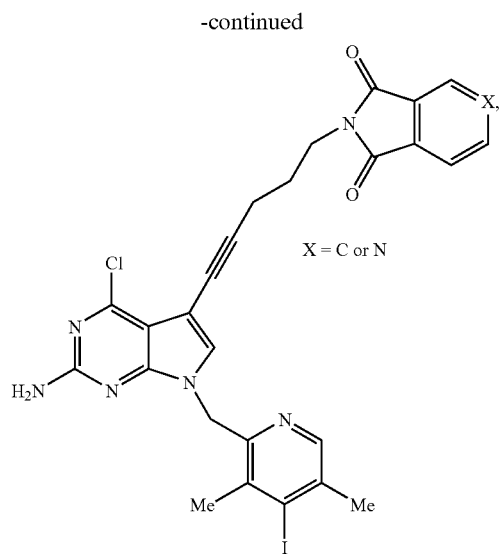
X = C or N
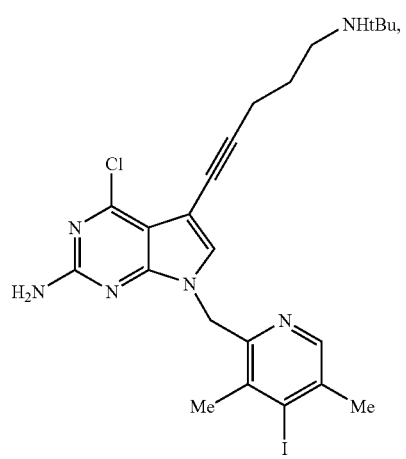
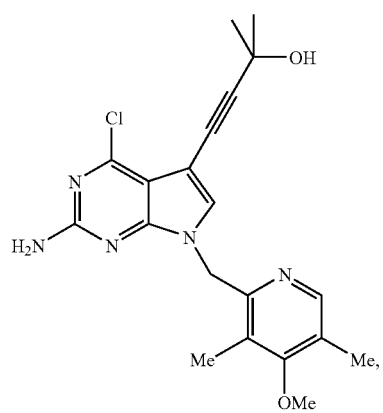
50
-continued
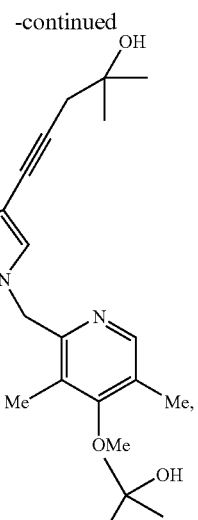
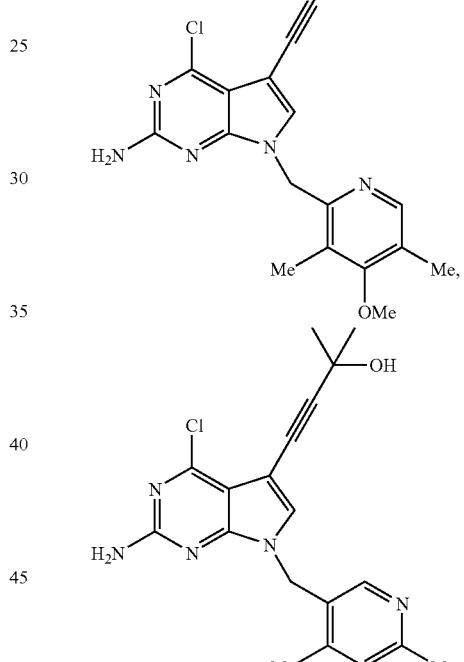
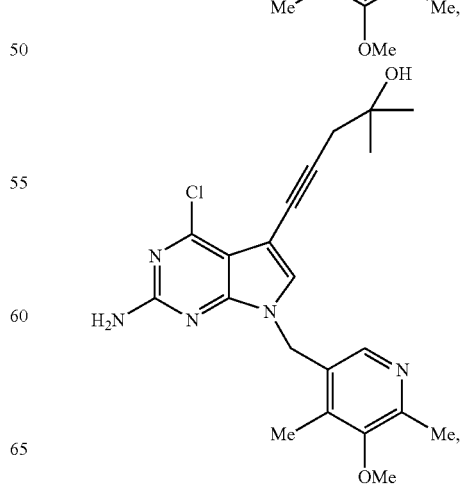

51
-continued
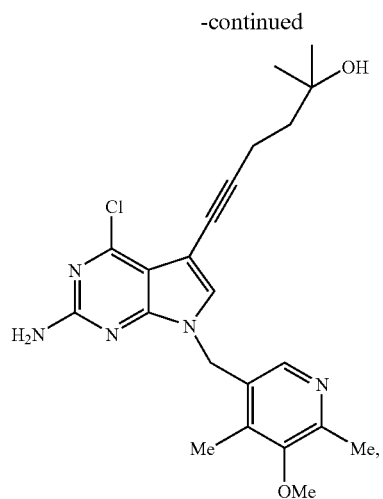
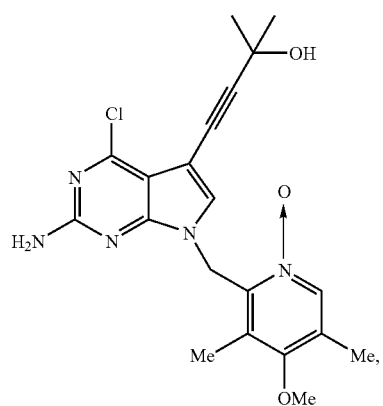
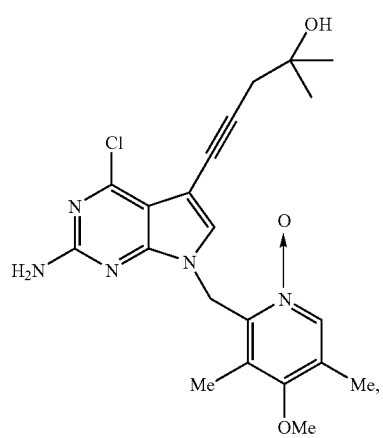
52
-continued
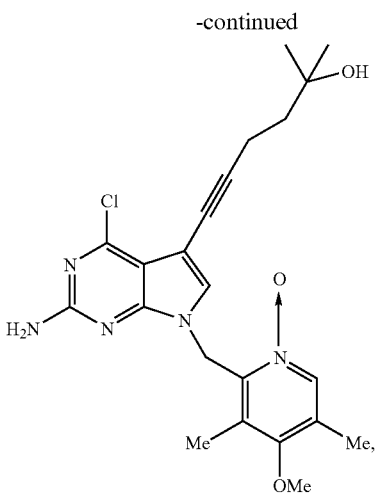
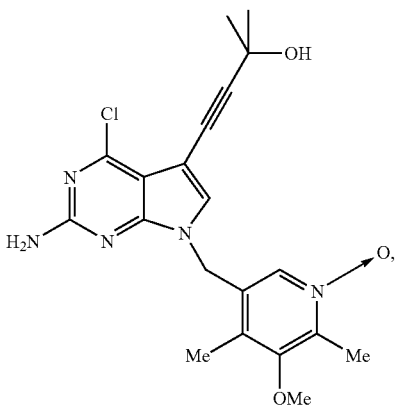
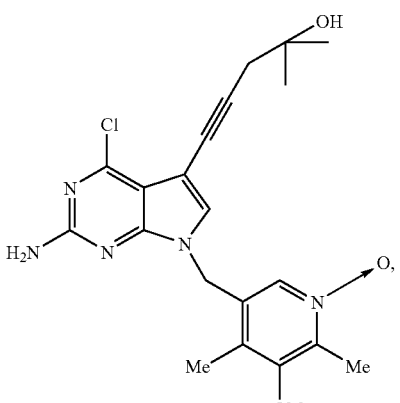

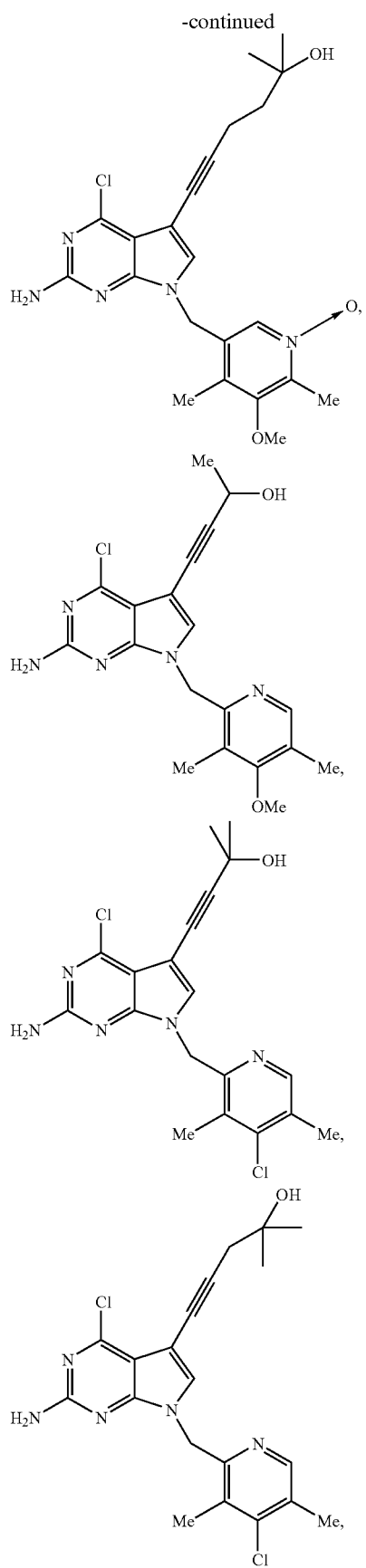
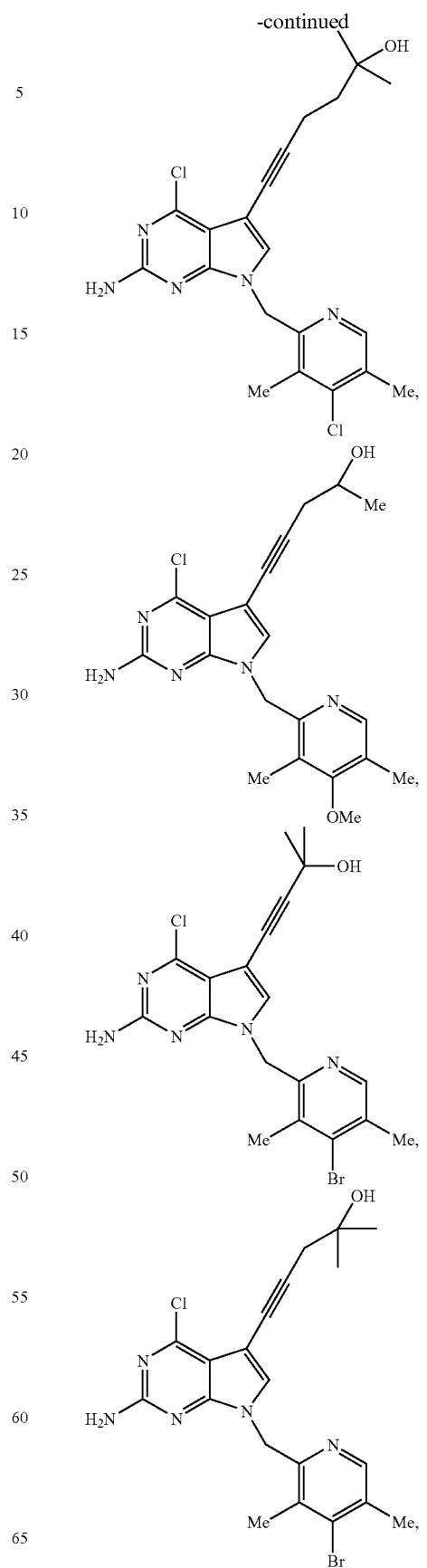

-continued
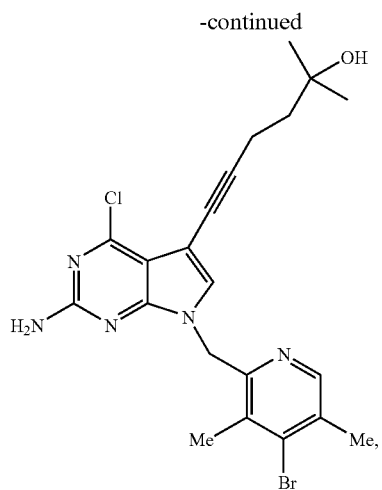
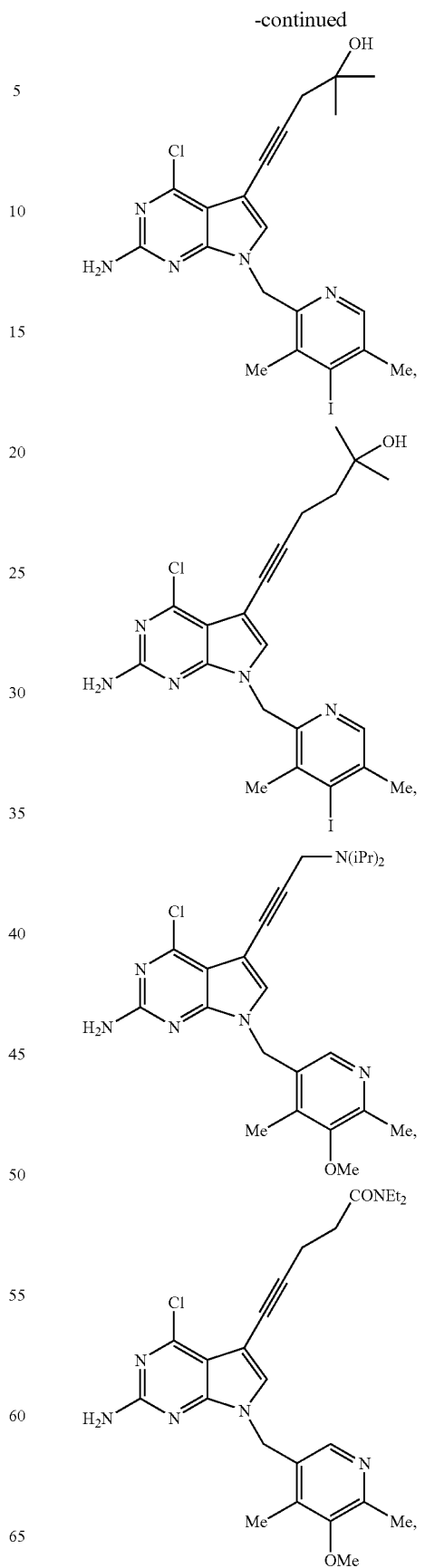

-continued
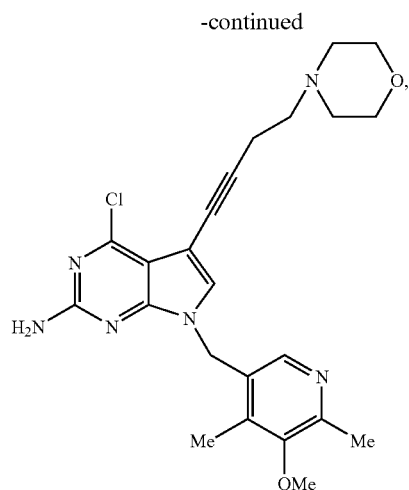
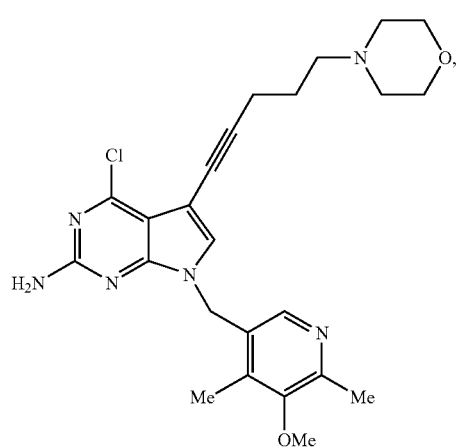
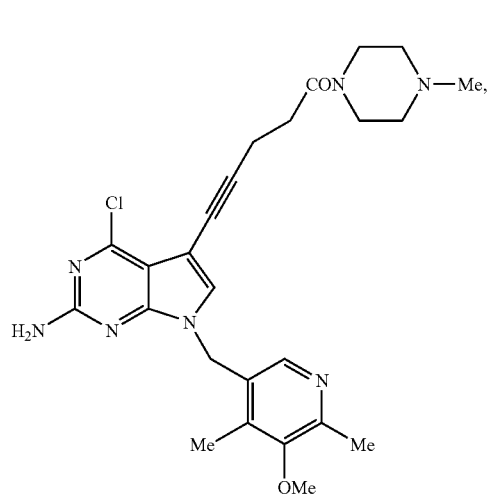
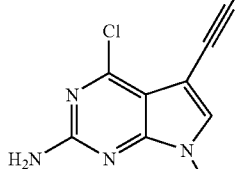
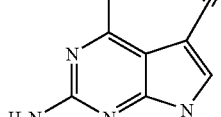
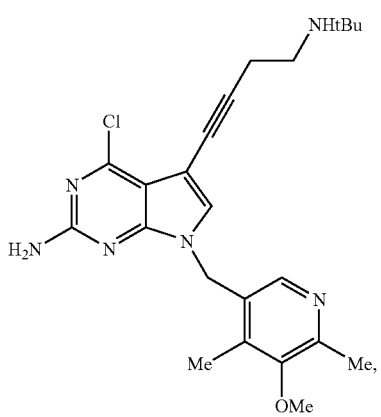
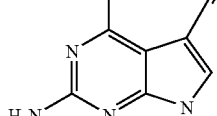
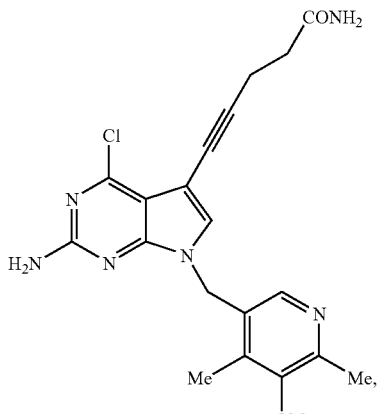
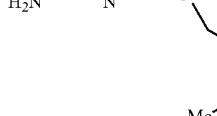

-continued
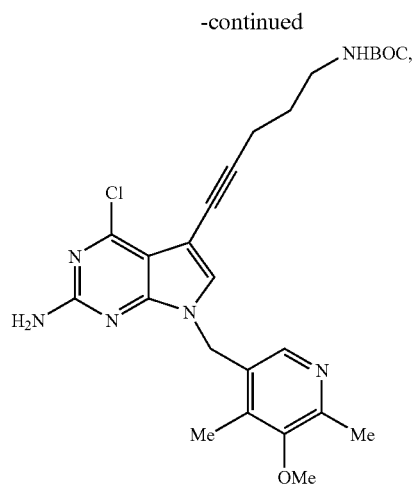
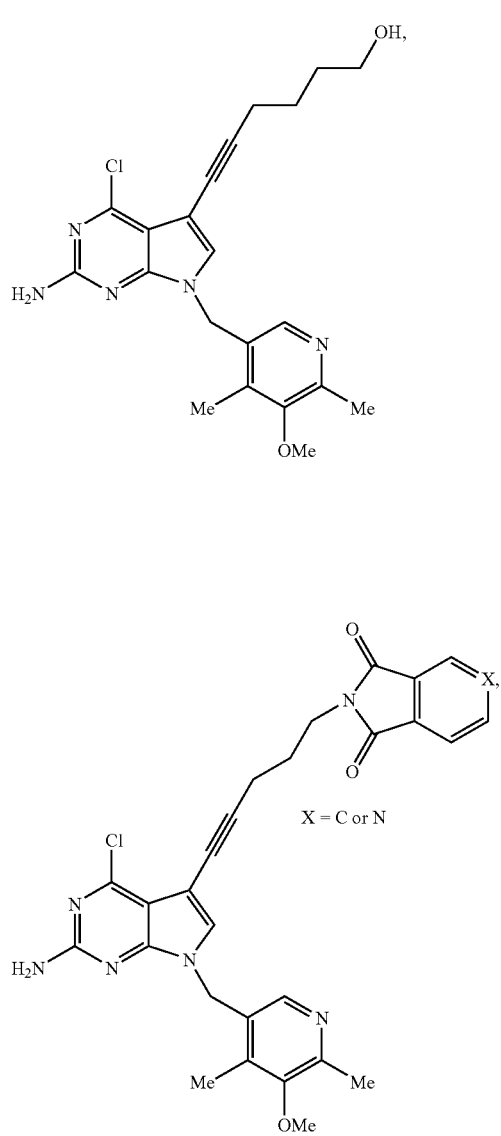
X = C or N
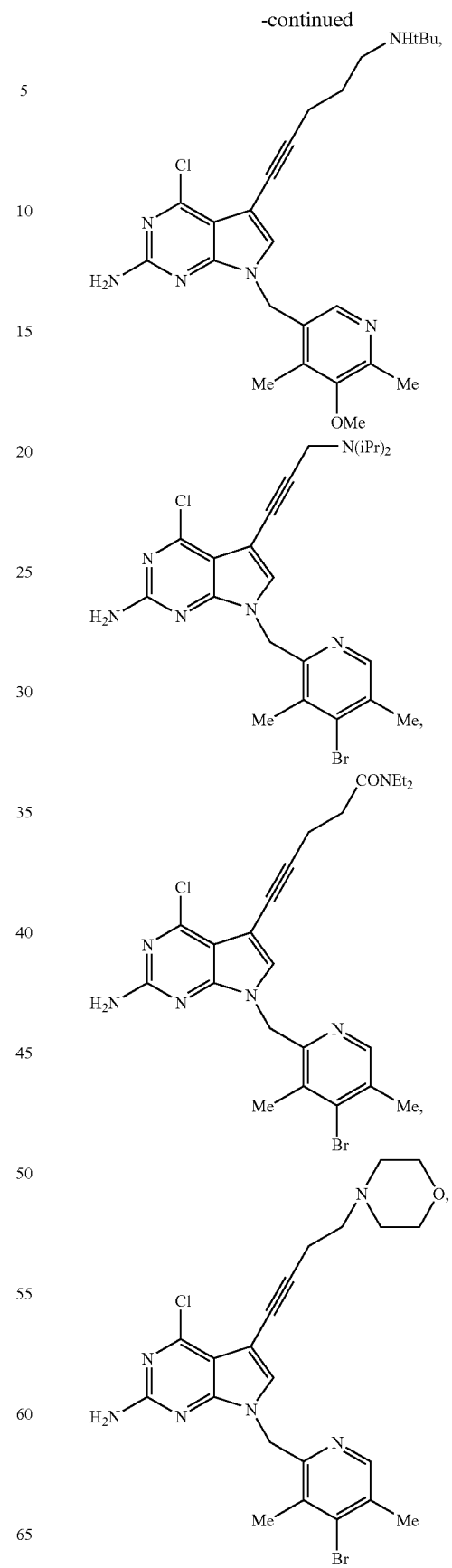

-continued
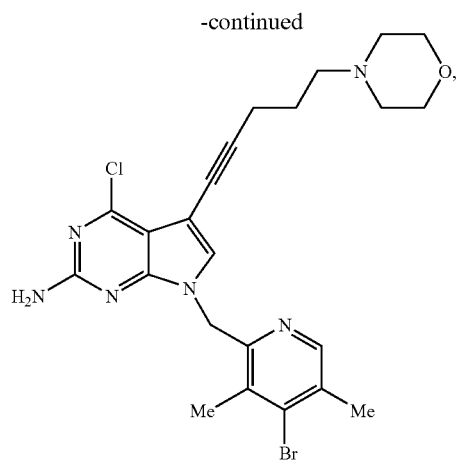
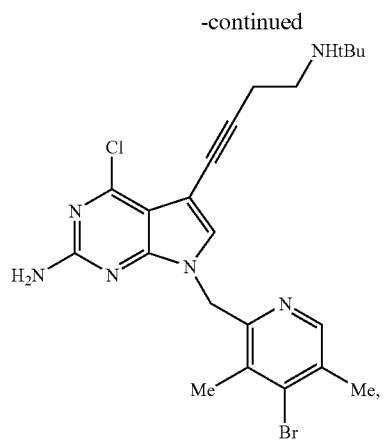
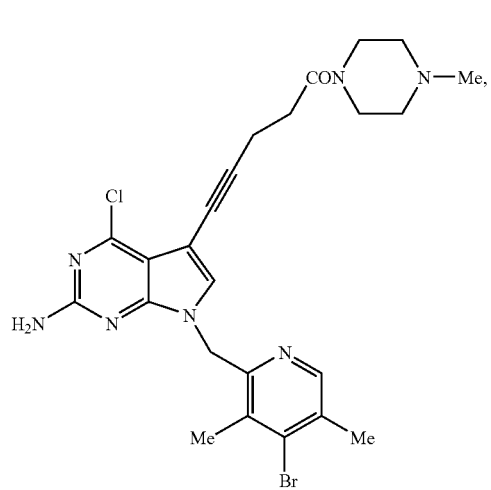
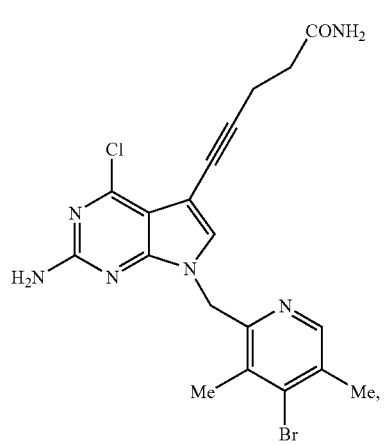
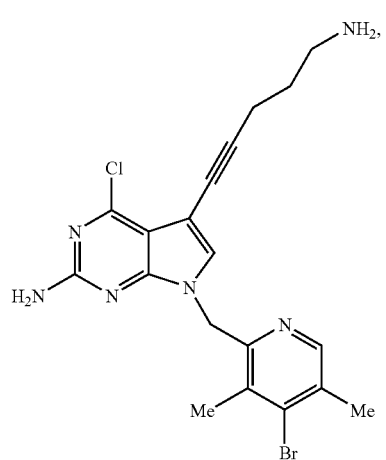
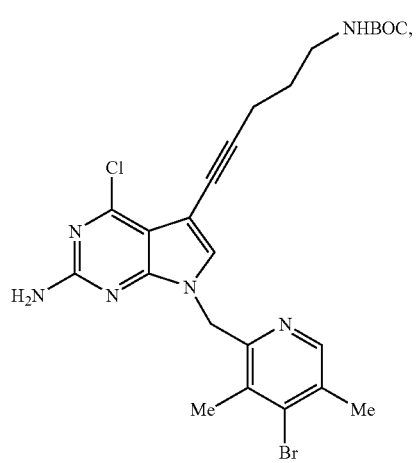

-continued
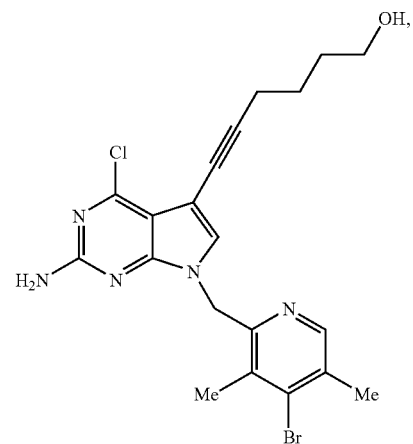
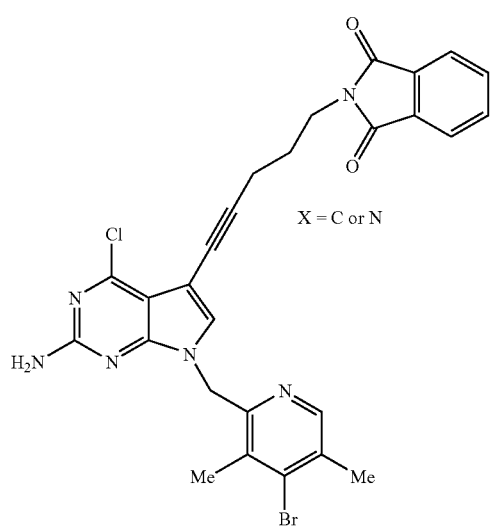
X = C or N
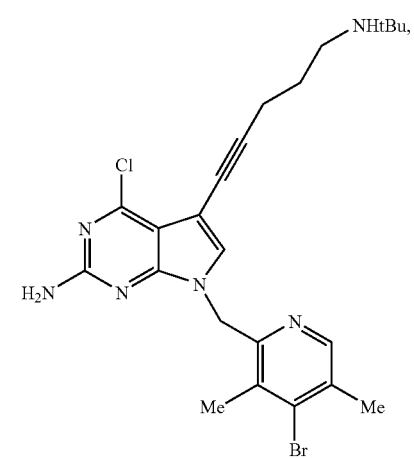
-continued
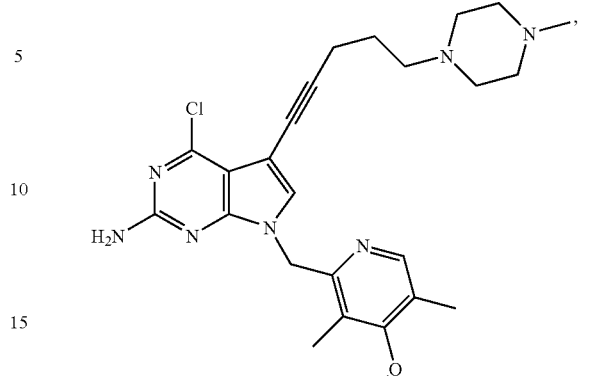
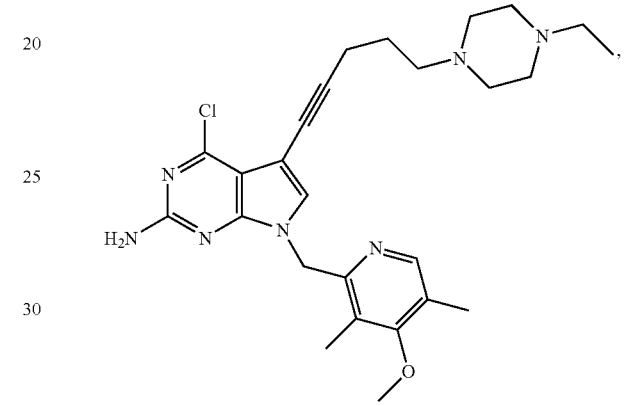
and
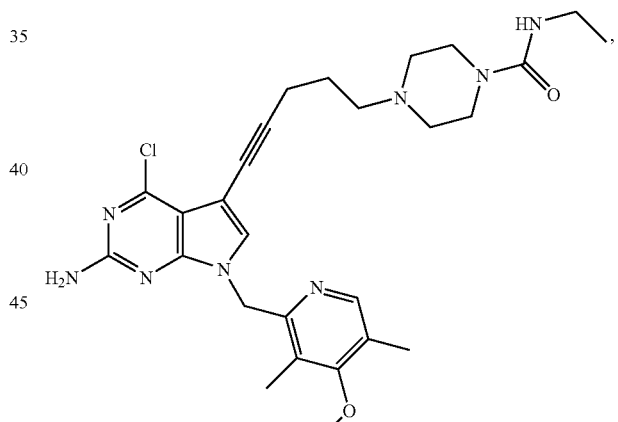
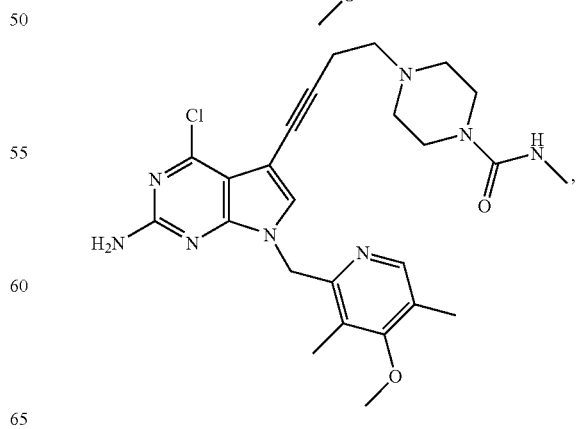

-continued
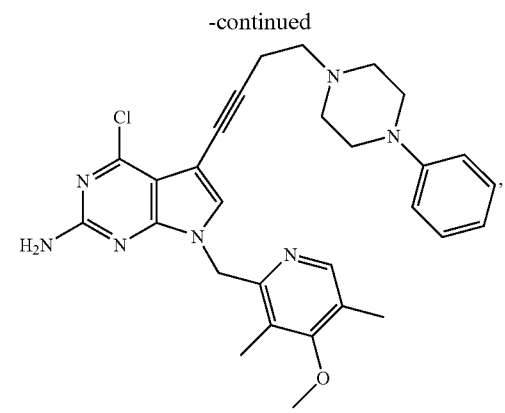
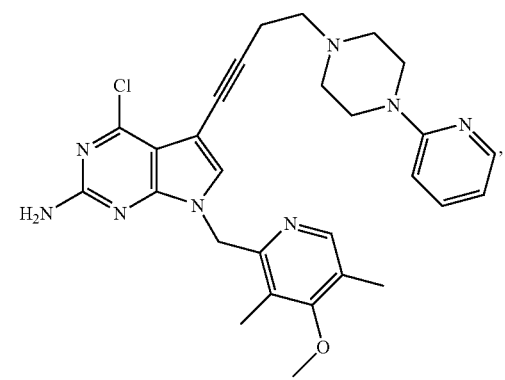
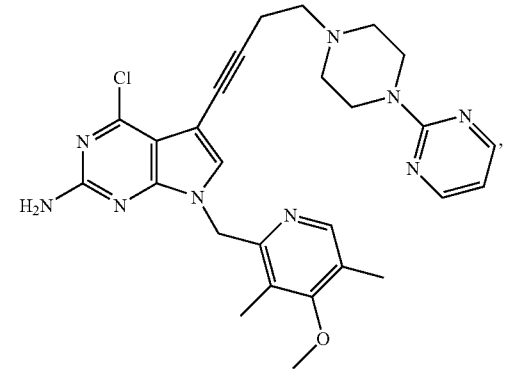
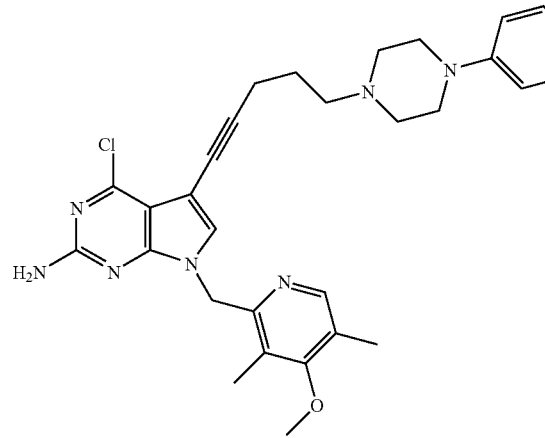
-continued
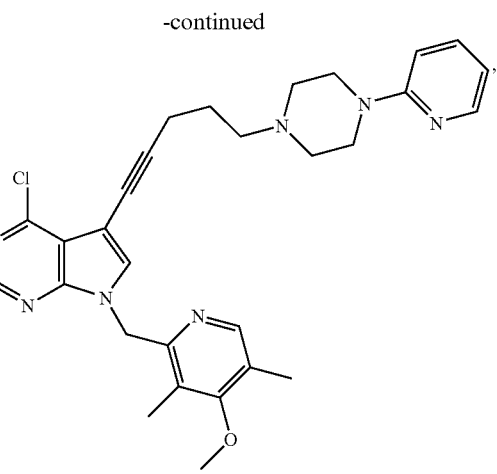
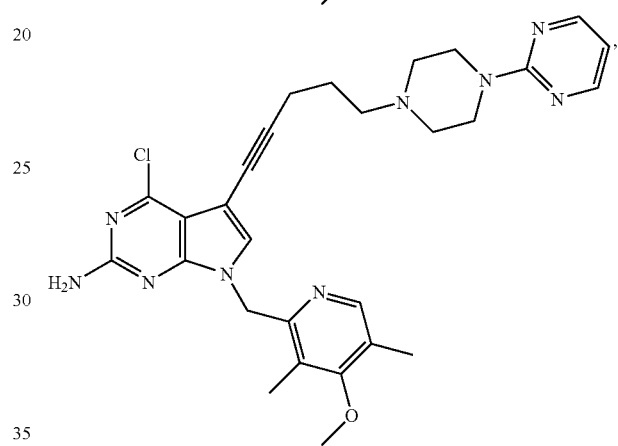
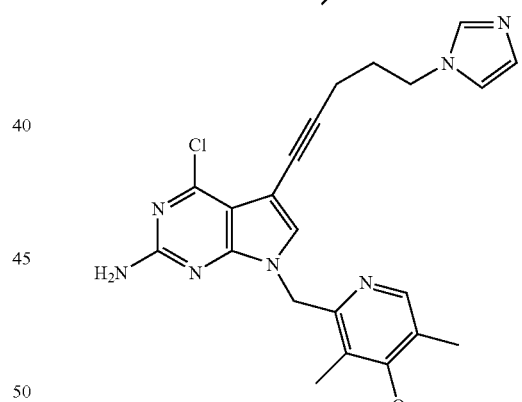
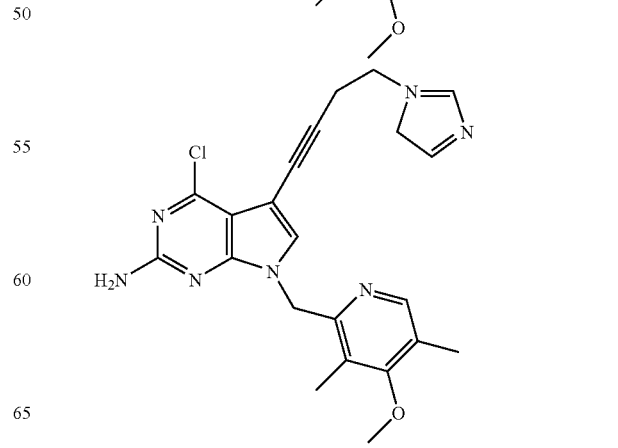

-continued
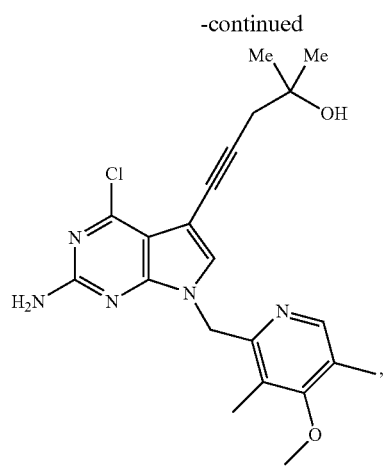
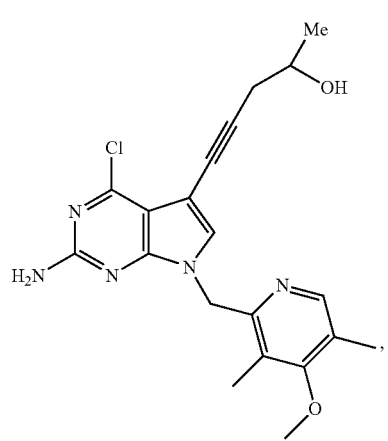
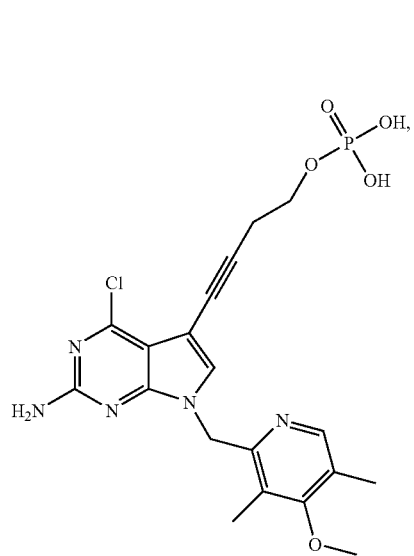
-continued
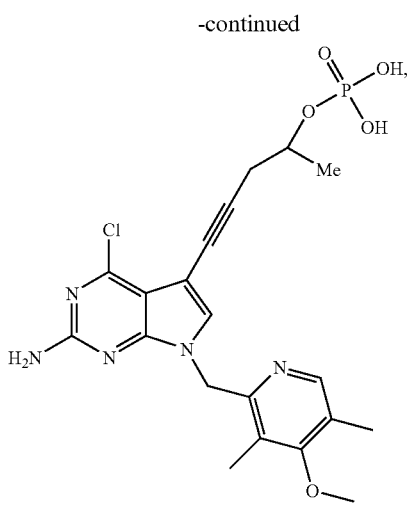
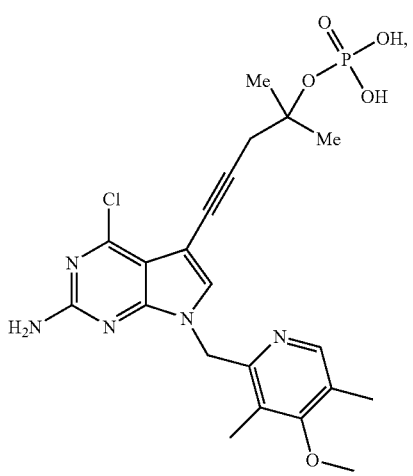
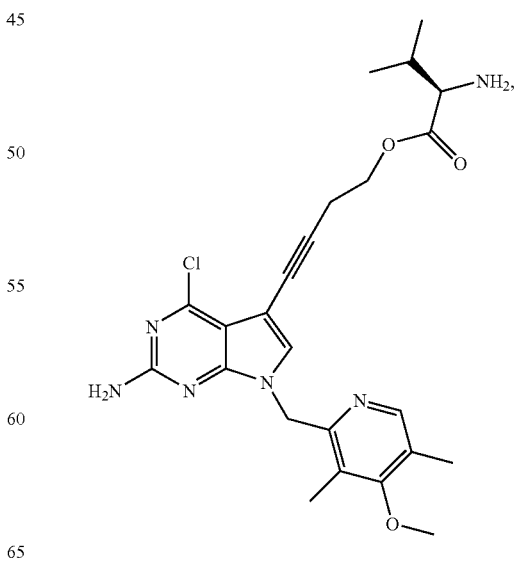

69
-continued
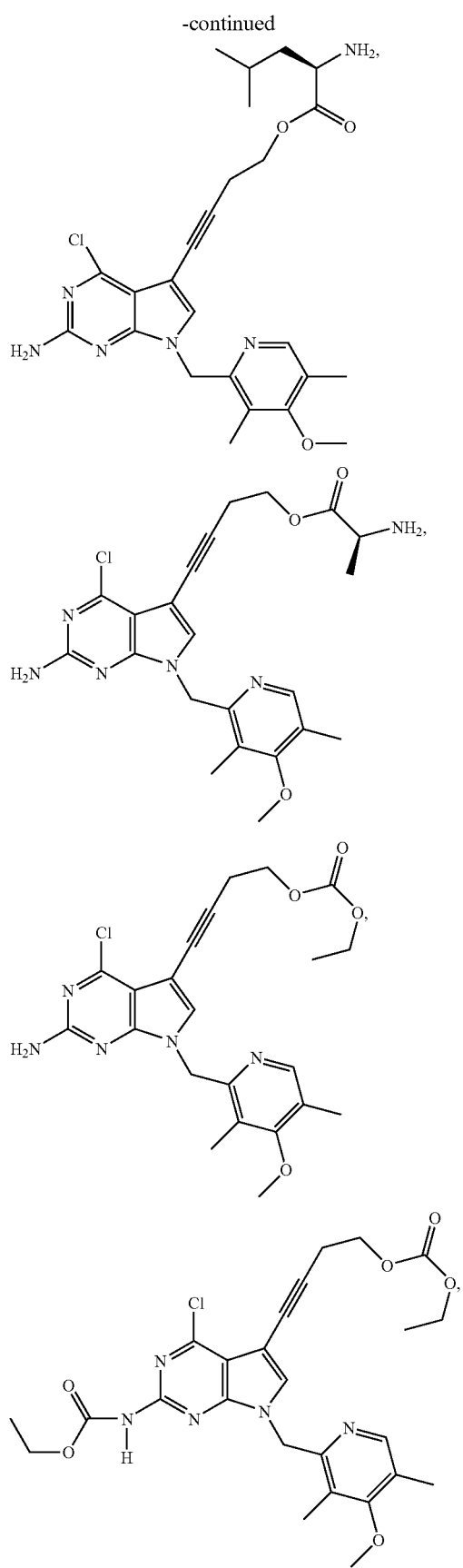
70
-continued
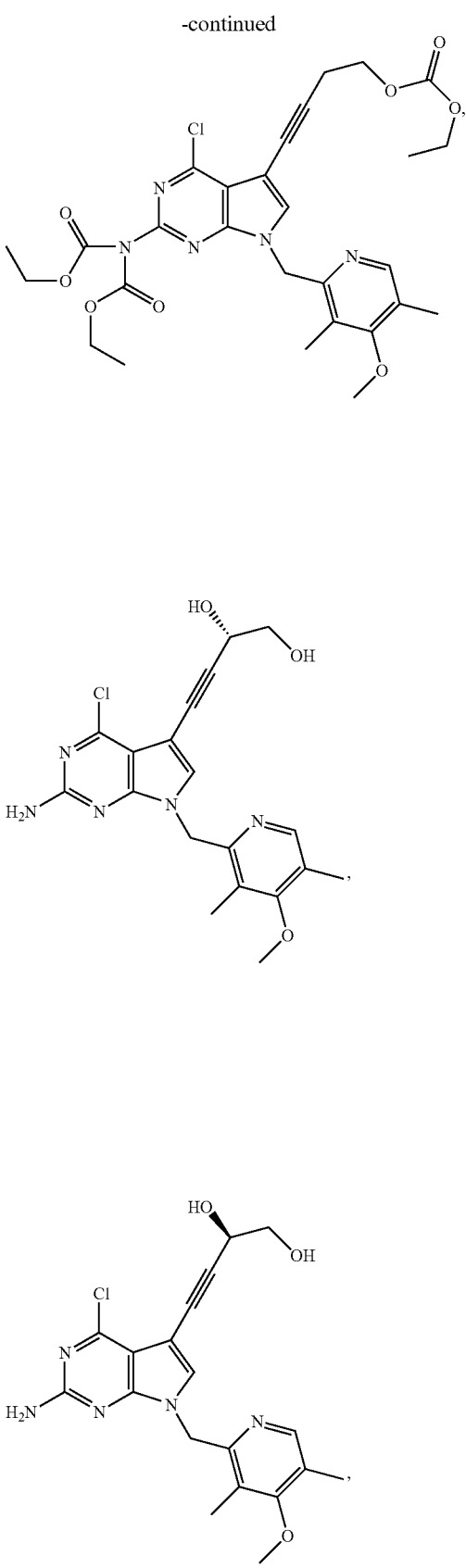

-continued

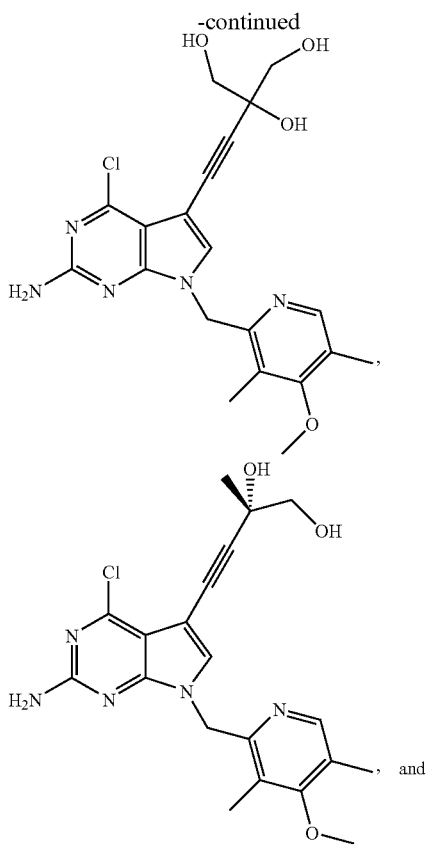

-continued

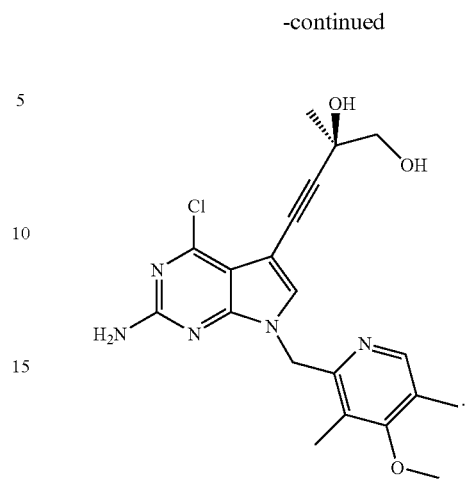

It should be understood that any of the above described embodiments of the invention can be combined in anyway where practical; those of ordinary skill in the art will appreciate the ways the various embodiments may be combined usefully within the spirit of the invention. A non-limiting list of compounds based on Formula I of the invention is exemplified in TABLE 1.

TABLE 1

Exemplary Compounds based on Formula I

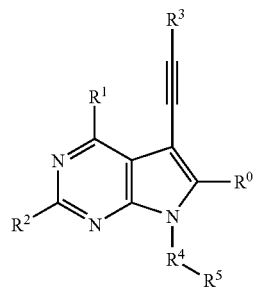

(I)

wherein $R^0$ is H, and $R^4$ is —$CH_2$—.

| No. | Ex | $R^1$ | $R^2$ | $R^3$ | $R^5$ |
|---|---|---|---|---|---|
| 1 |  | Cl | $NH_2$ | H | 3,4,5-Trimethoxyphenyl |
| 2 |  | Cl | $NH_2$ | H | 2-Chloro-3,4,5-trimethoxyphenyl |
| 3 |  | Cl | $NH_2$ | H | 2-Bromo-3,4,5-trimethoxyphenyl |
| 4 |  | Cl | $NH_2$ | H | 2-Iodo-3,4,5-trimethoxyphenyl |
| 5 |  | Cl | $NH_2$ | H | 2-Fluoro-3,4,5-trimethoxyphenyl |
| 6 |  | Cl | $NH_2$ | H | 3,4,5-Trimethylphenyl |
| 7 |  | Cl | $NH_2$ | H | 2-Chloro-3,4,5-trimethylphenyl |
| 8 |  | Cl | $NH_2$ | H | 2-Bromo-3,4,5-trimethylphenyl |
| 9 |  | Cl | $NH_2$ | H | 2-Iodo-3,4,5-trimethylphenyl |
| 10 |  | Cl | $NH_2$ | H | 2-Fluoro-3,4,5-trimethylphenyl |
| 11 |  | Cl | $NH_2$ | H | 3,5-Dimethoxy-4-methylphenyl |
| 12 |  | Cl | $NH_2$ | H | 2-Chloro-3,5-dimethoxy-4-methylphenyl |
| 13 |  | Cl | $NH_2$ | H | 2-Bromo-3,5-dimethoxy-4-methylphenyl |
| 14 |  | Cl | $NH_2$ | H | 2-Iodo-3,5-dimethoxy-4-methylphenyl |
| 15 |  | Cl | $NH_2$ | H | 2-Fluoro-3,5-dimethoxy-4-methylphenyl |
| 16 |  | Cl | $NH_2$ | 2-Py | 3,4,5-Trimethoxyphenyl |

TABLE 1-continued

Exemplary Compounds based on Formula I

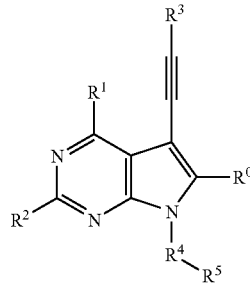

(I)

wherein $R^0$ is H, and $R^4$ is —CH$_2$—.

| No. | Ex | R$^1$ | R$^2$ | R$^3$ | R$^5$ |
|---|---|---|---|---|---|
| 17 | | Cl | NH$_2$ | 2-Py | 2-Chloro-3,4,5-trimethoxyphenyl |
| 18 | | Cl | NH$_2$ | 2-Py | 2-Bromo-3,4,5-trimethoxyphenyl |
| 19 | | Cl | NH$_2$ | 2-Py | 2-Iodo-3,4,5-trimethoxyphenyl |
| 20 | | Cl | NH$_2$ | 2-Py | 2-Fluoro-3,4,5-trimethoxyphenyl |
| 21 | | Cl | NH$_2$ | 2-Py | 3,4,5-Trimethylphenyl |
| 22 | | Cl | NH$_2$ | 2-Py | 2-Chloro-3,4,5-trimethylphenyl |
| 23 | | Cl | NH$_2$ | 2-Py | 2-Bromo-3,4,5-trimethylphenyl |
| 24 | | Cl | NH$_2$ | 2-Py | 2-Iodo-3,4,5-trimethylphenyl |
| 25 | | Cl | NH$_2$ | 2-Py | 2-Fluoro-3,4,5-trimethylphenyl |
| 26 | | Cl | NH$_2$ | 2-Py | 3,5-Dimethoxy-4-methylphenyl |
| 27 | | Cl | NH$_2$ | 2-Py | 2-Chloro-3,5-dimethoxy-4-methylphenyl |
| 28 | | Cl | NH$_2$ | 2-Py | 2-Bromo-3,5-dimethoxy-4-methylphenyl |
| 29 | | Cl | NH$_2$ | 2-Py | 2-Iodo-3,5-dimethoxy-4-methylphenyl |
| 30 | | Cl | NH$_2$ | 2-Py | 2-Fluoro-3,5-dimethoxy-4-methylphenyl |
| 31 | | Cl | NH$_2$ | 2-Py | 3,4,5-Trimethoxyphenyl |
| 32 | | Cl | NH$_2$ | 2-Py | 2-Chloro-3,4,5-trimethoxyphenyl |
| 33 | | Cl | NH$_2$ | 2-Py | 2-Bromo-3,4,5-trimethoxyphenyl |
| 34 | | Cl | NH$_2$ | 2-Py | 2-Iodo-3,4,5-trimethoxyphenyl |
| 35 | | Cl | NH$_2$ | 2-Py | 2-Fluoro-3,4,5-trimethoxyphenyl |
| 36 | | Cl | NH$_2$ | 2-Py | 3,4,5-Trimethylphenyl |
| 37 | | Cl | NH$_2$ | 2-Py | 2-Chloro-3,4,5-trimethylphenyl |
| 38 | | Cl | NH$_2$ | 2-Py | 2-Bromo-3,4,5-trimethylphenyl |
| 39 | | Cl | NH$_2$ | 2-Py | 2-Iodo-3,4,5-trimethylphenyl |
| 40 | | Cl | NH$_2$ | 2-Py | 2-Fluoro-3,4,5-trimethylphenyl |
| 41 | | Cl | NH$_2$ | Et | 3,5-Dimethoxy-4-methylphenyl |
| 42 | | Cl | NH$_2$ | Et | 2-Chloro-3,5-dimethoxy-4-methylphenyl |
| 43 | | Cl | NH$_2$ | Et | 2-Bromo-3,5-dimethoxy-4-methylphenyl |
| 44 | | Cl | NH$_2$ | Et | 2-Iodo-3,5-dimethoxy-4-methylphenyl |
| 45 | | Cl | NH$_2$ | Et | 2-Fluoro-3,5-dimethoxy-4-methylphenyl |
| 46 | | Cl | NH$_2$ | Me | 3,4,5-Trimethoxyphenyl |
| 47 | | Cl | NH$_2$ | Me | 2-Chloro-3,4,5-trimethoxyphenyl |
| 48 | | Cl | NH$_2$ | Me | 2-Bromo-3,4,5-trimethoxyphenyl |
| 49 | | Cl | NH$_2$ | Me | 2-Iodo-3,4,5-trimethoxyphenyl |
| 50 | | Cl | NH$_2$ | Me | 2-Fluoro-3,4,5-trimethoxyphenyl |
| 51 | | Cl | NH$_2$ | Me | 3,4,5-Trimethylphenyl |
| 52 | | Cl | NH$_2$ | Me | 2-Chloro-3,4,5-trimethylphenyl |
| 53 | | Cl | NH$_2$ | Me | 2-Bromo-3,4,5-trimethylphenyl |
| 54 | | Cl | NH$_2$ | Me | 2-Iodo-3,4,5-trimethylphenyl |
| 55 | | Cl | NH$_2$ | Me | 2-Fluoro-3,4,5-trimethylphenyl |
| 56 | | Cl | NH$_2$ | Me | 3,5-Dimethoxy-4-methylphenyl |
| 57 | | Cl | NH$_2$ | Me | 2-Chloro-3,5-dimethoxy-4-methylphenyl |
| 58 | | Cl | NH$_2$ | Me | 2-Bromo-3,5-dimethoxy-4-methylphenyl |
| 59 | | Cl | NH$_2$ | Me | 2-Iodo-3,5-dimethoxy-4-methylphenyl |
| 60 | | Cl | NH$_2$ | Me | 2-Fluoro-3,5-dimethoxy-4-methylphenyl |
| 61 | | Cl | NH$_2$ | Ph | 3,4,5-Trimethoxyphenyl |
| 62 | | Cl | NH$_2$ | Ph | 2-Chloro-3,4,5-trimethoxyphenyl |
| 63 | | Cl | NH$_2$ | Ph | 2-Bromo-3,4,5-trimethoxyphenyl |
| 64 | | Cl | NH$_2$ | Ph | 2-Iodo-3,4,5-trimethoxyphenyl |
| 65 | | Cl | NH$_2$ | Ph | 2-Fluoro-3,4,5-trimethoxyphenyl |
| 66 | | Cl | NH$_2$ | Ph | 3,4,5-Trimethylphenyl |
| 67 | | Cl | NH$_2$ | Ph | 2-Chloro-3,4,5-trimethylphenyl |
| 68 | | Cl | NH$_2$ | Ph | 2-Bromo-3,4,5-trimethylphenyl |
| 69 | | Cl | NH$_2$ | Ph | 2-Iodo-3,4,5-trimethylphenyl |
| 70 | | Cl | NH$_2$ | Ph | 2-Fluoro-3,4,5-trimethylphenyl |
| 71 | | Cl | NH$_2$ | Ph | 3,5-Dimethoxy-4-methylphenyl |
| 72 | | Cl | NH$_2$ | Ph | 2-Chloro-3,5-dimethoxy-4-methylphenyl |
| 73 | | Cl | NH$_2$ | Ph | 2-Bromo-3,5-dimethoxy-4-methylphenyl |
| 74 | | Cl | NH$_2$ | Ph | 2-Iodo-3,5-dimethoxy-4-methylphenyl |

TABLE 1-continued

Exemplary Compounds based on Formula I

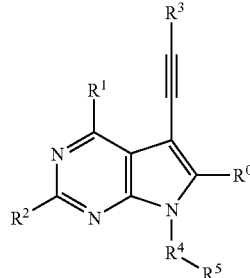

(I)

wherein $R^0$ is H, and $R^4$ is —$CH_2$—.

| No. | Ex | $R^1$ | $R^2$ | $R^3$ | $R^5$ |
|---|---|---|---|---|---|
| 75 | | Cl | $NH_2$ | Ph | 2-Fluoro-3,5-dimethoxy-4-methylphenyl |
| 76 | | Cl | $NH_2$ | $(CH_2)_2OH$ | 3,4,5-Trimethoxyphenyl |
| 77 | | Cl | $NH_2$ | $(CH_2)_2OH$ | 2-Chloro-3,4,5-trimethoxyphenyl |
| 78 | | Cl | $NH_2$ | $(CH_2)_2OH$ | 2-Bromo-3,4,5-trimethoxyphenyl |
| 79 | | Cl | $NH_2$ | $(CH_2)_2OH$ | 2-Iodo-3,4,5-trimethoxyphenyl |
| 80 | | Cl | $NH_2$ | $(CH_2)_2OH$ | 2-Fluoro-3,4,5-trimethoxyphenyl |
| 81 | | Cl | $NH_2$ | $(CH_2)_2OH$ | 3,4,5-Trimethylphenyl |
| 82 | | Cl | $NH_2$ | $(CH_2)_2OH$ | 2-Chloro-3,4,5-trimethylphenyl |
| 83 | | Cl | $NH_2$ | $(CH_2)_2OH$ | 2-Bromo-3,4,5-trimethylphenyl |
| 84 | | Cl | $NH_2$ | $(CH_2)_2OH$ | 2-Iodo-3,4,5-trimethylphenyl |
| 85 | | Cl | $NH_2$ | $(CH_2)_2OH$ | 2-Fluoro-3,4,5-trimethylphenyl |
| 86 | | Cl | $NH_2$ | $(CH_2)_2OH$ | 3,5-Dimethoxy-4-methylphenyl |
| 87 | | Cl | $NH_2$ | $(CH_2)_2OH$ | 2-Chloro-3,5-dimethoxy-4-methylphenyl |
| 88 | | Cl | $NH_2$ | $(CH_2)_2OH$ | 2-Bromo-3,5-dimethoxy-4-methylphenyl |
| 89 | | Cl | $NH_2$ | $(CH_2)_2OH$ | 2-Iodo-3,5-dimethoxy-4-methylphenyl |
| 90 | | Cl | $NH_2$ | $(CH_2)_2OH$ | 2-Fluoro-3,5-dimethoxy-4-methylphenyl |
| 91 | | Cl | $NH_2$ | 4-Py | 3,4,5-Trimethoxyphenyl |
| 92 | | Cl | $NH_2$ | 4-Py | 2-Chloro-3,4,5-trimethoxyphenyl |
| 93 | | Cl | $NH_2$ | 4-Py | 2-Bromo-3,4,5-trimethoxyphenyl |
| 94 | | Cl | $NH_2$ | 4-Py | 2-Iodo-3,4,5-trimethoxyphenyl |
| 95 | | Cl | $NH_2$ | 4-Py | 2-Fluoro-3,4,5-trimethoxyphenyl |
| 96 | | Cl | $NH_2$ | Ph | 3,4,5-Trimethylphenyl |
| 97 | | Cl | $NH_2$ | Ph | 2-Chloro-3,4,5-trimethylphenyl |
| 98 | | Cl | $NH_2$ | Ph | 2-Bromo-3,4,5-trimethylphenyl |
| 99 | | Cl | $NH_2$ | Ph | 2-Iodo-3,4,5-trimethylphenyl |
| 100 | | Cl | $NH_2$ | Ph | 2-Fluoro-3,4,5-trimethylphenyl |
| 101 | | Cl | $NH_2$ | Ph | 3,5-Dimethoxy-4-methylphenyl |
| 102 | | Cl | $NH_2$ | Ph | 2-Chloro-3,5-dimethoxy-4-methylphenyl |
| 103 | | Cl | $NH_2$ | Ph | 2-Bromo-3,5-dimethoxy-4-methylphenyl |
| 104 | | Cl | $NH_2$ | Ph | 2-Iodo-3,5-dimethoxy-4-methylphenyl |
| 105 | | Cl | $NH_2$ | Pr | 2-Fluoro-3,5-dimethoxy-4-methylphenyl |
| 106 | | Cl | $NH_2$ | Pr | 3,5-Dimethoxy-4-methylphenyl |
| 107 | | Cl | $NH_2$ | Pr | 2-Chloro-3,5-dimethoxy-4-methylphenyl |
| 108 | | Cl | $NH_2$ | Pr | 2-Bromo-3,5-dimethoxy-4-methylphenyl |
| 109 | | Cl | $NH_2$ | Pr | 2-Iodo-3,5-dimethoxy-4-methylphenyl |
| 110 | | Cl | $NH_2$ | Pr | 2-Fluoro-3,5-dimethoxy-4-methylphenyl |
| 111 | | Cl | $NH_2$ | Pr | 3,4,5-Trimethoxyphenyl |
| 112 | | Cl | $NH_2$ | Pr | 2-Chloro-3,4,5-trimethoxyphenyl |
| 113 | | Cl | $NH_2$ | Pr | 2-Bromo-3,4,5-trimethoxyphenyl |
| 114 | | Cl | $NH_2$ | Pr | 2-Iodo-3,4,5-trimethoxyphenyl |
| 115 | | Cl | $NH_2$ | Pr | 2-Fluoro-3,4,5-trimethoxyphenyl |
| 116 | | Cl | $NH_2$ | Pr | 3,4,5-Trimethylphenyl |
| 117 | | Cl | $NH_2$ | Pr | 2-Chloro-3,4,5-trimethylphenyl |
| 118 | | Cl | $NH_2$ | Pr | 2-Bromo-3,4,5-trimethylphenyl |
| 119 | | Cl | $NH_2$ | Pr | 2-Iodo-3,4,5-trimethylphenyl |
| 120 | | Cl | $NH_2$ | Pr | 2-Fluoro-3,4,5-trimethylphenyl |
| 121 | | Cl | $NH_2$ | Pr | 3,5-Dimethoxy-4-methylphenyl |
| 122 | | Cl | $NH_2$ | Pr | 2-Chloro-3,5-dimethoxy-4-methylphenyl |
| 123 | | Cl | $NH_2$ | Pr | 2-Bromo-3,5-dimethoxy-4-methylphenyl |
| 124 | | Cl | $NH_2$ | Pr | 2-Iodo-3,5-dimethoxy-4-methylphenyl |
| 125 | | Cl | $NH_2$ | Pr | 2-Fluoro-3,5-dimethoxy-4-methylphenyl |
| 126 | | Cl | $NH_2$ | $(CH_2)_3OH$ | 3,4,5-Trimethoxyphenyl |
| 127 | | Cl | $NH_2$ | $(CH_2)_3OH$ | 2-Chloro-3,4,5-trimethoxyphenyl |
| 128 | | Cl | $NH_2$ | $(CH_2)_3OH$ | 2-Bromo-3,4,5-trimethoxyphenyl |
| 129 | | Cl | $NH_2$ | $(CH_2)_3OH$ | 2-Iodo-3,4,5-trimethoxyphenyl |
| 130 | | Cl | $NH_2$ | $(CH_2)_3OH$ | 2-Fluoro-3,4,5-trimethoxyphenyl |
| 131 | | Cl | $NH_2$ | $(CH_2)_3OH$ | 3,4,5-Trimethylphenyl |
| 132 | | Cl | $NH_2$ | $(CH_2)_3OH$ | 2-Chloro-3,4,5-trimethylphenyl |

TABLE 1-continued

Exemplary Compounds based on Formula I

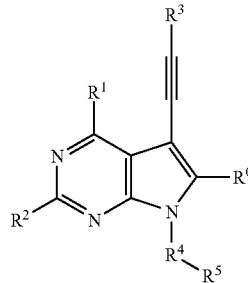

(I)

wherein $R^0$ is H, and $R^4$ is —$CH_2$—.

| No. | Ex | $R^1$ | $R^2$ | $R^3$ | $R^5$ |
|---|---|---|---|---|---|
| 133 | | Cl | $NH_2$ | $(CH_2)_3OH$ | 2-Bromo-3,4,5-trimethylphenyl |
| 134 | | Cl | $NH_2$ | $(CH_2)_3OH$ | 2-Iodo-3,4,5-trimethylphenyl |
| 135 | | Cl | $NH_2$ | $(CH_2)_3OH$ | 2-Fluoro-3,4,5-trimethylphenyl |
| 136 | | Cl | $NH_2$ | $(CH_2)_3OH$ | 3,5-Dimethoxy-4-methylphenyl |
| 137 | | Cl | $NH_2$ | $(CH_2)_3OH$ | 2-Chloro-3,5-dimethoxy-4-methylphenyl |
| 138 | | Cl | $NH_2$ | $(CH_2)_3OH$ | 2-Bromo-3,5-dimethoxy-4-methylphenyl |
| 139 | | Cl | $NH_2$ | $(CH_2)_3OH$ | 2-Iodo-3,5-dimethoxy-4-methylphenyl |
| 140 | | Cl | $NH_2$ | $(CH_2)_3OH$ | 2-Fluoro-3,5-dimethoxy-4-methylphenyl |
| 141 | | Cl | $NH_2$ | i-Bu | 3,4,5-Trimethoxyphenyl |
| 142 | | Cl | $NH_2$ | i-Bu | 2-Chloro-3,4,5-trimethoxyphenyl |
| 143 | | Cl | $NH_2$ | i-Bu | 2-Bromo-3,4,5-trimethoxyphenyl |
| 144 | | Cl | $NH_2$ | i-Bu | 2-Iodo-3,4,5-trimethoxyphenyl |
| 145 | | Cl | $NH_2$ | i-Bu | 2-Fluoro-3,4,5-trimethoxyphenyl |
| 146 | | Cl | $NH_2$ | i-Bu | 3,4,5-Trimethylphenyl |
| 147 | | Cl | $NH_2$ | i-Bu | 2-Chloro-3,4,5-trimethylphenyl |
| 148 | | Cl | $NH_2$ | i-Bu | 2-Bromo-3,4,5-trimethylphenyl |
| 149 | | Cl | $NH_2$ | i-Bu | 2-Iodo-3,4,5-trimethylphenyl |
| 150 | | Cl | $NH_2$ | i-Bu | 2-Fluoro-3,4,5-trimethylphenyl |
| 151 | | Cl | $NH_2$ | i-Bu | 3,5-Dimethoxy-4-methylphenyl |
| 152 | | Cl | $NH_2$ | i-Bu | 2-Chloro-3,5-dimethoxy-4-methylphenyl |
| 153 | | Cl | $NH_2$ | i-Bu | 2-Bromo-3,5-dimethoxy-4-methylphenyl |
| 154 | | Cl | $NH_2$ | i-Bu | 2-Iodo-3,5-dimethoxy-4-methylphenyl |
| 155 | | Cl | $NH_2$ | i-Bu | 2-Fluoro-3,5-dimethoxy-4-methylphenyl |
| 156 | | Cl | $NH_2$ | CN | 3,4,5-Trimethoxyphenyl |
| 157 | | Cl | $NH_2$ | CN | 2-Chloro-3,4,5-trimethoxyphenyl |
| 158 | | Cl | $NH_2$ | CN | 2-Bromo-3,4,5-trimethoxyphenyl |
| 159 | | Cl | $NH_2$ | CN | 2-Iodo-3,4,5-trimethoxyphenyl |
| 160 | | Cl | $NH_2$ | CN | 3,4,5-Trimethoxyphenyl |
| 161 | | Cl | $NH_2$ | CN | 2-Chloro-3,4,5-trimethoxyphenyl |
| 162 | | Cl | $NH_2$ | CN | 2-Bromo-3,4,5-trimethoxyphenyl |
| 163 | | Cl | $NH_2$ | CN | 2-Iodo-3,4,5-trimethoxyphenyl |
| 164 | | Cl | $NH_2$ | CN | 2-Fluoro-3,4,5-trimethoxyphenyl |
| 165 | | Cl | $NH_2$ | CN | 3,4,5-Trimethylphenyl |
| 166 | | Cl | $NH_2$ | CN | 2-Chloro-3,4,5-trimethylphenyl |
| 167 | | Cl | $NH_2$ | CN | 2-Bromo-3,4,5-trimethylphenyl |
| 168 | | Cl | $NH_2$ | CN | 2-Iodo-3,4,5-trimethylphenyl |
| 169 | | Cl | $NH_2$ | CN | 2-Fluoro-3,4,5-trimethylphenyl |
| 170 | | Cl | $NH_2$ | CN | 3,5-Dimethoxy-4-methylphenyl |
| 171 | | Cl | $NH_2$ | CN | 2-Chloro-3,5-dimethoxy-4-methylphenyl |
| 172 | | Cl | $NH_2$ | CN | 2-Bromo-3,5-dimethoxy-4-methylphenyl |
| 173 | | Cl | $NH_2$ | CN | 2-Iodo-3,5-dimethoxy-4-methylphenyl |
| 174 | | Cl | $NH_2$ | CN | 2-Fluoro-3,5-dimethoxy-4-methylphenyl |
| 175 | | Cl | $NH_2$ | $CH_2OH$ | 3,4,5-Trimethoxyphenyl |
| 176 | | Cl | $NH_2$ | $CH_2OH$ | 2-Chloro-3,4,5-trimethoxyphenyl |
| 177 | | Cl | $NH_2$ | $CH_2OH$ | 2-Bromo-3,4,5-trimethoxyphenyl |
| 178 | | Cl | $NH_2$ | $CH_2OH$ | 2-Iodo-3,4,5-trimethoxyphenyl |
| 179 | | Cl | $NH_2$ | $CH_2OH$ | 2-Fluoro-3,4,5-trimethoxyphenyl |
| 180 | | Cl | $NH_2$ | $CH_2OH$ | 3,4,5-Trimethylphenyl |
| 181 | | Cl | $NH_2$ | $CH_2OH$ | 2-Chloro-3,4,5-trimethylphenyl |
| 182 | | Cl | $NH_2$ | $CH_2OH$ | 2-Bromo-3,4,5-trimethylphenyl |
| 183 | | Cl | $NH_2$ | $CH_2OH$ | 2-Iodo-3,4,5-trimethylphenyl |
| 184 | | Cl | $NH_2$ | $CH_2OH$ | 2-Fluoro-3,4,5-trimethylphenyl |
| 185 | | Cl | $NH_2$ | $CH_2OH$ | 3,5-Dimethoxy-4-methylphenyl |
| 186 | | Cl | $NH_2$ | $CH_2OH$ | 2-Chloro-3,5-dimethoxy-4-methylphenyl |
| 187 | | Cl | $NH_2$ | $CH_2OH$ | 2-Bromo-3,5-dimethoxy-4-methylphenyl |
| 188 | | Cl | $NH_2$ | $CH_2OH$ | 2-Iodo-3,5-dimethoxy-4-methylphenyl |
| 189 | | Cl | $NH_2$ | $CH_2OH$ | 2-Fluoro-3,5-dimethoxy-4-methylphenyl |
| 190 | | Cl | $NH_2$ | i-Pr | 3,4,5-Trimethoxyphenyl |

TABLE 1-continued

Exemplary Compounds based on Formula I

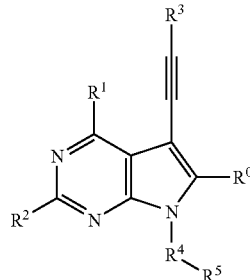

(I)

wherein R⁰ is H, and R⁴ is —CH₂—.

| No. | Ex | R¹ | R² | R³ | R⁵ |
|---|---|---|---|---|---|
| 191 |  | Cl | NH₂ | i-Pr | 2-Chloro-3,4,5-trimethoxyphenyl |
| 192 |  | Cl | NH₂ | i-Pr | 2-Bromo-3,4,5-trimethoxyphenyl |
| 193 |  | Cl | NH₂ | i-Pr | 2-Iodo-3,4,5-trimethoxyphenyl |
| 194 |  | Cl | NH₂ | i-Pr | 2-Fluoro-3,4,5-trimethoxyphenyl |
| 195 |  | Cl | NH₂ | i-Pr | 3,4,5-Trimethylphenyl |
| 196 |  | Cl | NH₂ | i-Pr | 2-Chloro-3,4,5-trimethylphenyl |
| 197 |  | Cl | NH₂ | i-Pr | 2-Bromo-3,4,5-trimethylphenyl |
| 198 |  | Cl | NH₂ | i-Pr | 2-Iodo-3,4,5-trimethylphenyl |
| 199 |  | Cl | NH₂ | i-Pr | 2-Fluoro-3,4,5-trimethylphenyl |
| 200 |  | Cl | NH₂ | i-Pr | 3,5-Dimethoxy-4-methylphenyl |
| 201 |  | Cl | NH₂ | i-Pr | 2-Chloro-3,5-dimethoxy-4-methylphenyl |
| 202 |  | Cl | NH₂ | i-Pr | 2-Bromo-3,5-dimethoxy-4-methylphenyl |
| 203 |  | Cl | NH₂ | i-Pr | 2-Iodo-3,5-dimethoxy-4-methylphenyl |
| 204 |  | Cl | NH₂ | i-Pr | 2-Fluoro-3,5-dimethoxy-4-methylphenyl |
| 205 |  | Cl | NH₂ | CO₂Et | 3,4,5-Trimethoxyphenyl |
| 206 |  | Cl | NH₂ | CO₂Et | 2-Chloro-3,4,5-trimethoxyphenyl |
| 207 |  | Cl | NH₂ | CO₂Et | 2-Bromo-3,4,5-trimethoxyphenyl |
| 208 |  | Cl | NH₂ | CO₂Et | 2-Iodo-3,4,5-trimethoxyphenyl |
| 209 |  | Cl | NH₂ | CO₂Et | 2-Fluoro-3,4,5-trimethoxyphenyl |
| 210 |  | Cl | NH₂ | CO₂Et | 3,4,5-Trimethylphenyl |
| 211 |  | Cl | NH₂ | CO₂Et | 2-Chloro-3,4,5-trimethylphenyl |
| 212 |  | Cl | NH₂ | CO₂Et | 2-Bromo-3,4,5-trimethylphenyl |
| 213 |  | Cl | NH₂ | CO₂Et | 2-Iodo-3,4,5-trimethylphenyl |
| 214 |  | Cl | NH₂ | CO₂Et | 2-Fluoro-3,4,5-trimethylphenyl |
| 215 |  | Cl | NH₂ | CO₂Et | 3,5-Dimethoxy-4-methylphenyl |
| 216 |  | Cl | NH₂ | CO₂Et | 2-Chloro-3,5-dimethoxy-4-methylphenyl |
| 217 |  | Cl | NH₂ | CO₂Et | 2-Bromo-3,5-dimethoxy-4-methylphenyl |
| 218 |  | Cl | NH₂ | CO₂Et | 2-Iodo-3,5-dimethoxy-4-methylphenyl |
| 219 |  | Cl | NH₂ | CO₂Et | 2-Fluoro-3,5-dimethoxy-4-methylphenyl |
| 220 |  | Cl | NH₂ | CH₂—NMe₂ | 3,4,5-Trimethoxyphenyl |
| 221 |  | Cl | NH₂ | CH₂—NMe₂ | 2-Chloro-3,4,5-trimethoxyphenyl |
| 222 |  | Cl | NH₂ | CH₂—NMe₂ | 2-Bromo-3,4,5-trimethoxyphenyl |
| 223 |  | Cl | NH₂ | CH₂—NMe₂ | 2-Iodo-3,4,5-trimethoxyphenyl |
| 224 |  | Cl | NH₂ | CH₂—NMe₂ | 2-Fluoro-3,4,5-trimethoxyphenyl |
| 225 |  | Cl | NH₂ | CH₂—NMe₂ | 3,4,5-Trimethylphenyl |
| 226 |  | Cl | NH₂ | CH₂—NMe₂ | 2-Chloro-3,4,5-trimethylphenyl |
| 227 |  | Cl | NH₂ | CH₂—NMe₂ | 2-Bromo-3,4,5-trimethylphenyl |
| 228 |  | Cl | NH₂ | CH₂—NMe₂ | 2-Iodo-3,4,5-trimethylphenyl |
| 229 |  | Cl | NH₂ | CH₂—NMe₂ | 2-Fluoro-3,4,5-trimethylphenyl |
| 230 |  | Cl | NH₂ | CH₂—NMe₂ | 3,5-Dimethoxy-4-methylphenyl |
| 231 |  | Cl | NH₂ | CH₂—NMe₂ | 2-Chloro-3,5-dimethoxy-4-methylphenyl |
| 232 |  | Cl | NH₂ | CH₂—NMe₂ | 2-Bromo-3,5-dimethoxy-4-methylphenyl |
| 233 |  | Cl | NH₂ | CH₂—NMe₂ | 2-Iodo-3,5-dimethoxy-4-methylphenyl |
| 234 |  | Cl | NH₂ | CH₂—NMe₂ | 2-Fluoro-3,5-dimethoxy-4-methylphenyl |
| 235 |  | Cl | NH₂ | 3-Py | 3,4,5-Trimethoxyphenyl |
| 236 |  | Cl | NH₂ | 3-Py | 2-Chloro-3,4,5-trimethoxyphenyl |
| 237 |  | Cl | NH₂ | 3-Py | 2-Bromo-3,4,5-trimethoxyphenyl |
| 238 |  | Cl | NH₂ | 3-Py | 2-Iodo-3,4,5-trimethoxyphenyl |
| 239 |  | Cl | NH₂ | 3-Py | 2-Fluoro-3,4,5-trimethoxyphenyl |
| 240 | 2 | Cl | NH₂ | (CH₂)₂OH | 3,5-Dimethyl-4-methoxypyridin-2-yl |
| 241 |  | Cl | NH₂ | (CH₂)₂OH | 3,5-Dimethyl-4-methoxy-1-oxypyridin-2-yl |
| 242 |  | Cl | NH₂ | (CH₂)₂OH | 6-Bromo-3,5-dimethyl-4-methoxypyridin-2-yl |
| 243 |  | Cl | NH₂ | (CH₂)₂OH | 6-Chloro-3,5-dimethyl-4-methoxypyridin-2-yl |
| 244 |  | Cl | NH₂ | (CH₂)₂OH | 3,5-Dimethyl-4-bromopyridin-2-yl |
| 245 |  | Cl | NH₂ | (CH₂)₂OH | 3,5-Dimethyl-4-bromo-1-oxypyridin-2-yl |
| 246 |  | Cl | NH₂ | (CH₂)₂OH | 3,5-Dimethyl-4-chloropyridin-2-yl |
| 247 |  | Cl | NH₂ | (CH₂)₂OH | 3,5-Dimethyl-4-chloro-1-oxypyridin-2-yl |
| 248 |  | Cl | NH₂ | (CH₂)₂OH | 3,5-Dimethyl-4-iodopyridin-2-yl |

TABLE 1-continued

Exemplary Compounds based on Formula I

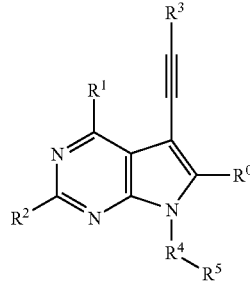

(I)

wherein $R^0$ is H, and $R^4$ is —$CH_2$—.

| No. | Ex | $R^1$ | $R^2$ | $R^3$ | $R^5$ |
|---|---|---|---|---|---|
| 249 | | Cl | $NH_2$ | $(CH_2)_2OH$ | 3,5-Dimethyl-4-iodo-1-oxypyridin-2-yl |
| 250 | | Cl | $NH_2$ | $(CH_2)_2OH$ | 3,5-Dimethyl-4-thiomethyl-pyridin-2-yl |
| 251 | | Cl | $NH_2$ | $(CH_2)_2OH$ | 3,5-Dimethyl-4-thiomethyl-1-oxypyridin-2-yl |
| 252 | | Cl | $NH_2$ | $(CH_2)_2OH$ | 3,4,5-Trimethyl-pyridin-2-yl |
| 253 | | Cl | $NH_2$ | $(CH_2)_2OH$ | 3,4,5-Trimethyl-1-oxypyridin-2-yl |
| 254 | | Cl | $NH_2$ | $(CH_2)_2OH$ | 4,5,6-Trimethoxypyridin-2-yl |
| 255 | | Cl | $NH_2$ | $(CH_2)_2OH$ | 4,5,6-Trimethoxy-1-oxypyridin-2-yl |
| 256 | | Cl | $NH_2$ | $(CH_2)_2OH$ | 3-Bromo-4,5,6-trimethoxypyridin-2-yl |
| 257 | | Cl | $NH_2$ | $(CH_2)_2OH$ | 3-Chloro-4,5,6-trimethoxypyridin-2-yl |
| 258 | | Cl | $NH_2$ | $(CH_2)_2OH$ | 3,4,5-Trimethoxy-pyridin-2-yl |
| 259 | | Cl | $NH_2$ | $(CH_2)_2OH$ | 3,4,5-Trimethoxy-1-oxypyridin-2-yl |
| 260 | | Cl | $NH_2$ | $(CH_2)_2OH$ | 3-Bromo-3,4,5-trimethoxy-pyridin-2-yl |
| 261 | | Cl | $NH_2$ | $(CH_2)_2OH$ | 3-Chloro-3,4,5-trimethoxy-pyridin-2-yl |
| 262 | | Cl | $NH_2$ | $(CH_2)_2OH$ | 4,5,6-Trimethyl-pyridin-2-yl |
| 263 | | Cl | $NH_2$ | $(CH_2)_2OH$ | 4,5,6-Trimethyl-1-oxypyridin-2-yl |
| 264 | | Cl | $NH_2$ | $(CH_2)_2OH$ | 4,6-Dimethyl-5-methoxy-pyridin-2-yl |
| 265 | | Cl | $NH_2$ | $(CH_2)_2OH$ | 4,6-Dimethyl-5-methoxypyridin-3-yl |
| 266 | | Cl | $NH_2$ | $(CH_2)_2OH$ | 4,6-Dimethyl-5-methoxy-1-oxypyridin-3-yl |
| 267 | | Cl | $NH_2$ | $(CH_2)_2OH$ | 4,6-Dimethyl-5-bromopyridin-3-yl |
| 268 | | Cl | $NH_2$ | $(CH_2)_2OH$ | 4,6-Dimethyl-5-chloropyridin-3-yl |
| 269 | | Cl | $NH_2$ | $(CH_2)_2OH$ | 5,6-Dimethyl-4-bromopyridin-3-yl |
| 270 | | Cl | $NH_2$ | $(CH_2)_2OH$ | 5,6-Dimethyl-4-chloropyridin-3-yl |
| 271 | | Cl | $NH_2$ | $(CH_2)_2OH$ | 2,6-Dimethyl-3-methoxypyridin-4-yl |
| 272 | | Cl | $NH_2$ | $(CH_2)_2OH$ | 2,6-Dimethyl-pyridin-4-yl |
| 273 | | Cl | $NH_2$ | $(CH_2)_2OH$ | 2,3,6-Trimethyl-pyridin-4-yl |
| 274 | | Cl | $NH_2$ | $(CH_2)_2OH$ | 2,3,6-Trimethoxy-pyridin-4-yl |
| 275 | | Cl | $NH_2$ | $(CH_2)_2OH$ | 2,6-Dimethyl-3-bromopyridin-4-yl |
| 276 | | Cl | $NH_2$ | $(CH_2)_2OH$ | 2,6-Dimethyl-3-chloropyridin-4-yl |
| 277 | | Cl | $NH_2$ | $(CH_2)_2OH$ | 2,6-Dimethyl-3-methoxy-1-oxy-pyridin-4-yl |
| 278 | | Cl | $NH_2$ | $(CH_2)_2OH$ | 2,6-Dimethyl-1-oxy-pyridin-4-yl |
| 279 | | Cl | $NH_2$ | $(CH_2)_2OH$ | 2,3,6-Trimethyl-1-oxy-pyridin-4-yl |
| 280 | | Cl | $NH_2$ | $(CH_2)_2OH$ | 2,3,6-Trimethoxy-1-oxy-pyridin-4-yl |
| 281 | | Cl | $NH_2$ | $(CH_2)_2OH$ | 2,6-Dimethyl-3-bromo 1-oxy-pyridin-4-yl |
| 282 | | Cl | $NH_2$ | $(CH_2)_2OH$ | 2,6-Dimethyl-3-chloro 1-oxy-pyridin-4-yl |
| 283 | | Cl | $NH_2$ | $(CH_2)_2OH$ | 4,6-Dimethyl-5-iodopyridin-3-yl |
| 284 | | Cl | $NH_2$ | $(CH_2)_2OH$ | 3,5-Dimethyl-4-aminopyridin-2-yl |
| 285 | | Cl | $NH_2$ | i-Pr | 3,5-Dimethyl-4-methoxypyridin-2-yl |
| 286 | | Cl | $NH_2$ | i-Pr | 3,5-Dimethyl-4-methoxy-1-oxypyridin-2-yl |
| 287 | | Cl | $NH_2$ | i-Pr | 6-Bromo-3,5-dimethyl-4-methoxypyridin-2-yl |
| 288 | | Cl | $NH_2$ | i-Pr | 6-Chloro-3,5-dimethyl-4-methoxypyridin-2-yl |
| 289 | | Cl | $NH_2$ | i-Pr | 3,5-Dimethyl-4-bromopyridin-2-yl |
| 290 | | Cl | $NH_2$ | i-Pr | 3,5-Dimethyl-4-bromo-1-oxypyridin-2-yl |
| 291 | | Cl | $NH_2$ | i-Pr | 3,5-Dimethyl-4-chloropyridin-2-yl |
| 292 | | Cl | $NH_2$ | i-Pr | 3,5-Dimethyl-4-chloro-1-oxypyridin-2-yl |
| 293 | | Cl | $NH_2$ | i-Pr | 3,5-Dimethyl-4-iodopyridin-2-yl |
| 294 | | Cl | $NH_2$ | i-Pr | 3,5-Dimethyl-4-iodo-1-oxypyridin-2-yl |
| 295 | | Cl | $NH_2$ | i-Pr | 3,5-Dimethyl-4-thiomethyl-pyridin-2-yl |
| 296 | | Cl | $NH_2$ | i-Pr | 3,5-Dimethyl-4-thiomethyl-1-oxypyridin-2-yl |
| 297 | | Cl | $NH_2$ | i-Pr | 3,4,5-Trimethyl-pyridin-2-yl |
| 298 | | Cl | $NH_2$ | i-Pr | 3,4,5-Trimethyl-1-oxypyridin-2-yl |
| 299 | | Cl | $NH_2$ | i-Pr | 4,5,6-Trimethoxypyridin-2-yl |
| 300 | | Cl | $NH_2$ | i-Pr | 4,5,6-Trimethoxy-1-oxypyridin-2-yl |
| 301 | | Cl | $NH_2$ | i-Pr | 3-Bromo-4,5,6-trimethoxypyridin-2-yl |
| 302 | | Cl | $NH_2$ | i-Pr | 3-Chloro-4,5,6-trimethoxypyridin-2-yl |
| 303 | | Cl | $NH_2$ | i-Pr | 3,4,5-Trimethoxy-pyridin-2-yl |
| 304 | | Cl | $NH_2$ | i-Pr | 3,4,5-Trimethoxy-1-oxypyridin-2-yl |
| 305 | | Cl | $NH_2$ | i-Pr | 3-Bromo-3,4,5-trimethoxy-pyridin-2-yl |
| 306 | | Cl | $NH_2$ | i-Pr | 3-Chloro-3,4,5-trimethoxy-pyridin-2-yl |

TABLE 1-continued

Exemplary Compounds based on Formula I

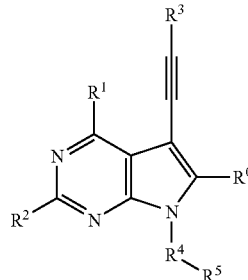

(I)

wherein $R^0$ is H, and $R^4$ is —CH$_2$—.

| No. | Ex | $R^1$ | $R^2$ | $R^3$ | $R^5$ |
|-----|----|-------|-------|-------|-------|
| 307 | | Cl | NH$_2$ | i-Pr | 4,5,6-Trimethyl-pyridin-2-yl |
| 308 | | Cl | NH$_2$ | i-Pr | 4,5,6-Trimethyl-1-oxypyridin-2-yl |
| 309 | | Cl | NH$_2$ | i-Pr | 4,6-Dimethyl-5-methoxy-pyridin-2-yl |
| 310 | | Cl | NH$_2$ | i-Pr | 4,6-Dimethyl-5-methoxypyridin-3-yl |
| 311 | | Cl | NH$_2$ | i-Pr | 4,6-Dimethyl-5-methoxy-1-oxypyridin-3-yl |
| 312 | | Cl | NH$_2$ | i-Pr | 4,6-Dimethyl-5-bromopyridin-3-yl |
| 313 | | Cl | NH$_2$ | i-Pr | 4,6-Dimethyl-5-chloropyridin-3-yl |
| 314 | | Cl | NH$_2$ | i-Pr | 5,6-Dimethyl-4-bromopyridin-3-yl |
| 315 | | Cl | NH$_2$ | i-Pr | 5,6-Dimethyl-4-chloropyridin-3-yl |
| 316 | | Cl | NH$_2$ | i-Pr | 2,6-Dimethyl-3-methoxypyridin-4-yl |
| 317 | | Cl | NH$_2$ | i-Pr | 2,6-Dimethyl-pyridin-4-yl |
| 318 | | Cl | NH$_2$ | i-Pr | 2,3,6-Trimethyl-pyridin-4-yl |
| 319 | | Cl | NH$_2$ | i-Pr | 2,3,6-Trimethoxy-pyridin-4-yl |
| 320 | | Cl | NH$_2$ | i-Pr | 2,6-Dimethyl-3-bromopyridin-4-yl |
| 321 | | Cl | NH$_2$ | i-Pr | 2,6-Dimethyl-3-chloropyridin-4-yl |
| 322 | | Cl | NH$_2$ | i-Pr | 2,6-Dimethyl-3-methoxy-1-oxy-pyridin-4-yl |
| 323 | | Cl | NH$_2$ | i-Pr | 2,6-Dimethyl-1-oxy-pyridin-4-yl |
| 324 | | Cl | NH$_2$ | i-Pr | 2,3,6-Trimethyl-1-oxy-pyridin-4-yl |
| 325 | | Cl | NH$_2$ | i-Pr | 2,3,6-Trimethoxy-1-oxy-pyridin-4-yl |
| 326 | | Cl | NH$_2$ | i-Pr | 2,6-Dimethyl-3-bromo1-oxy-pyridin-4-yl |
| 327 | | Cl | NH$_2$ | i-Pr | 2,6-Dimethyl-3-chloro1-oxy-pyridin-4-yl |
| 328 | | Cl | NH$_2$ | i-Pr | 4,6-Dimethyl-5-iodopyridin-3-yl |
| 329 | | Cl | NH$_2$ | i-Pr | 3,5-Dimethyl-4-aminopyridin-2-yl |
| 330 | 3 | Cl | NH$_2$ | (CH$_2$)$_3$OH | 3,5-Dimethyl-4-methoxypyridin-2-yl |
| 331 | | Cl | NH$_2$ | (CH$_2$)$_3$OH | 3,5-Dimethyl-4-methoxy-1-oxypyridin-2-yl |
| 332 | | Cl | NH$_2$ | (CH$_2$)$_3$OH | 3,5-Dimethyl-4-bromopyridin-2-yl |
| 333 | | Cl | NH$_2$ | (CH$_2$)$_3$OH | 3,5-Dimethyl-4-bromo-1-oxypyridin-2-yl |
| 334 | | Cl | NH$_2$ | (CH$_2$)$_3$OH | 3,5-Dimethyl-4-chloropyridin-2-yl |
| 335 | | Cl | NH$_2$ | (CH$_2$)$_3$OH | 3,5-Dimethyl-4-chloro-1-oxypyridin-2-yl |
| 336 | | Cl | NH$_2$ | (CH$_2$)$_3$OH | 3,5-Dimethyl-4-iodopyridin-2-yl |
| 337 | | Cl | NH$_2$ | (CH$_2$)$_3$OH | 3,5-Dimethyl-4-iodo-1-oxypyridin-2-yl |
| 338 | | Cl | NH$_2$ | (CH$_2$)$_3$OH | 3,5-Dimethyl-4-thiomethyl-pyridin-2-yl |
| 339 | | Cl | NH$_2$ | (CH$_2$)$_3$OH | 3,5-Dimethyl-4-thiomethyl-1-oxypyridin-2-yl |
| 340 | | Cl | NH$_2$ | (CH$_2$)$_3$OH | 3,4,5-Trimethyl-pyridin-2-yl |
| 341 | | Cl | NH$_2$ | (CH$_2$)$_3$OH | 3,4,5-Trimethyl-1-oxypyridin-2-yl |
| 342 | | Cl | NH$_2$ | (CH$_2$)$_3$OH | 4,5,6-Trimethoxypyridin-2-yl |
| 343 | | Cl | NH$_2$ | (CH$_2$)$_3$OH | 4,5,6-Trimethoxy-1-oxypyridin-2-yl |
| 344 | | Cl | NH$_2$ | (CH$_2$)$_3$OH | 3,4,5-Trimethoxy-pyridin-2-yl |
| 345 | | Cl | NH$_2$ | (CH$_2$)$_3$OH | 3,4,5-Trimethoxy-1-oxypyridin-2-yl |
| 346 | | Cl | NH$_2$ | (CH$_2$)$_3$OH | 4,5,6-Trimethyl-pyridin-2-yl |
| 347 | | Cl | NH$_2$ | (CH$_2$)$_3$OH | 4,5,6-Trimethyl-1-oxypyridin-2-yl |
| 348 | | Cl | NH$_2$ | (CH$_2$)$_3$OH | 4,6-Dimethyl-5-methoxy-pyridin-2-yl |
| 349 | | Cl | NH$_2$ | (CH$_2$)$_3$OH | 4,6-Dimethyl-5-methoxypyridin-3-yl |
| 350 | | Cl | NH$_2$ | (CH$_2$)$_3$OH | 4,6-Dimethyl-5-methoxy-1-oxypyridin-3-yl |
| 351 | | Cl | NH$_2$ | (CH$_2$)$_3$OH | 4,6-Dimethyl-5-bromopyridin-3-yl |
| 352 | | Cl | NH$_2$ | (CH$_2$)$_3$OH | 4,6-Dimethyl-5-chloropyridin-3-yl |
| 353 | | Cl | NH$_2$ | (CH$_2$)$_3$OH | 5,6-Dimethyl-4-bromopyridin-3-yl |
| 354 | | Cl | NH$_2$ | (CH$_2$)$_3$OH | 5,6-Dimethyl-4-chloropyridin-3-yl |
| 355 | | Cl | NH$_2$ | (CH$_2$)$_3$OH | 2,6-Dimethyl-3-methoxypyridin-4-yl |
| 356 | | Cl | NH$_2$ | (CH$_2$)$_3$OH | 2,6-Dimethyl-pyridin-4-yl |
| 357 | | Cl | NH$_2$ | (CH$_2$)$_3$OH | 2,3,6-Trimethyl-pyridin-4-yl |
| 358 | | Cl | NH$_2$ | (CH$_2$)$_3$OH | 2,3,6-Trimethoxy-pyridin-4-yl |
| 359 | | Cl | NH$_2$ | (CH$_2$)$_3$OH | 2,6-Dimethyl-3-bromopyridin-4-yl |
| 360 | | Cl | NH$_2$ | (CH$_2$)$_3$OH | 2,6-Dimethyl-3-chloropyridin-4-yl |
| 361 | | Cl | NH$_2$ | (CH$_2$)$_3$OH | 4,6-Dimethyl-5-iodopyridin-3-yl |
| 362 | | Cl | NH$_2$ | (CH$_2$)$_3$OH | 3,5-Dimethyl-4-aminopyridin-2-yl |
| 363 | 1 | Cl | NH$_2$ | CH$_2$OH | 3,5-Dimethyl-4-methoxypyridin-2-yl |
| 364 | | Cl | NH$_2$ | CH$_2$OH | 3,5-Dimethyl-4-methoxy-1-oxypyridin-2-yl |

TABLE 1-continued

Exemplary Compounds based on Formula I

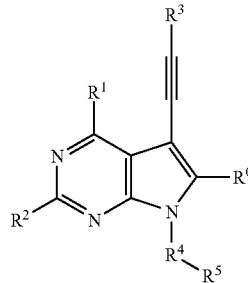

(I)

wherein $R^0$ is H, and $R^4$ is —CH$_2$—.

| No. | Ex | R$^1$ | R$^2$ | R$^3$ | R$^5$ |
|---|---|---|---|---|---|
| 365 | | Cl | NH$_2$ | CH$_2$OH | 3,5-Dimethyl-4-bromopyridin-2-yl |
| 366 | | Cl | NH$_2$ | CH$_2$OH | 3,5-Dimethyl-4-bromo-1-oxypyridin-2-yl |
| 367 | | Cl | NH$_2$ | CH$_2$OH | 3,5-Dimethyl-4-chloropyridin-2-yl |
| 368 | | Cl | NH$_2$ | CH$_2$OH | 3,5-Dimethyl-4-chloro-1-oxypyridin-2-yl |
| 369 | | Cl | NH$_2$ | CH$_2$OH | 3,5-Dimethyl-4-iodopyridin-2-yl |
| 370 | | Cl | NH$_2$ | CH$_2$OH | 3,5-Dimethyl-4-iodo-1-oxypyridin-2-yl |
| 371 | | Cl | NH$_2$ | CH$_2$OH | 3,5-Dimethyl-4-thiomethyl-pyridin-2-yl |
| 372 | | Cl | NH$_2$ | CH$_2$OH | 3,5-Dimethyl-4-thiomethyl-1-oxypyridin-2-yl |
| 373 | | Cl | NH$_2$ | CH$_2$OH | 3,4,5-Trimethyl-pyridin-2-yl |
| 374 | | Cl | NH$_2$ | CH$_2$OH | 3,4,5-Trimethyl-1-oxypyridin-2-yl |
| 375 | | Cl | NH$_2$ | CH$_2$OH | 4,5,6-Trimethoxypyridin-2-yl |
| 376 | | Cl | NH$_2$ | CH$_2$OH | 4,5,6-Trimethoxy-1-oxypyridin-2-yl |
| 377 | | Cl | NH$_2$ | CH$_2$OH | 3,4,5-Trimethoxy-pyridin-2-yl |
| 378 | | Cl | NH$_2$ | CH$_2$OH | 3,4,5-Trimethoxy-1-oxypyridin-2-yl |
| 379 | | Cl | NH$_2$ | CH$_2$OH | 4,5,6-Trimethyl-pyridin-2-yl |
| 380 | | Cl | NH$_2$ | CH$_2$OH | 4,5,6-Trimethyl-1-oxypyridin-2-yl |
| 381 | | Cl | NH$_2$ | CH$_2$OH | 4,6-Dimethyl-5-methoxy-pyridin-2-yl |
| 382 | | Cl | NH$_2$ | CH$_2$OH | 4,6-Dimethyl-5-methoxypyridin-3-yl |
| 383 | | Cl | NH$_2$ | CH$_2$OH | 4,6-Dimethyl-5-methoxy-1-oxypyridin-3-yl |
| 384 | | Cl | NH$_2$ | CH$_2$OH | 4,6-Dimethyl-5-bromopyridin-3-yl |
| 385 | | Cl | NH$_2$ | CH$_2$OH | 4,6-Dimethyl-5-chloropyridin-3-yl |
| 386 | | Cl | NH$_2$ | CH$_2$OH | 5,6-Dimethyl-4-bromopyridin-3-yl |
| 387 | | Cl | NH$_2$ | CH$_2$OH | 5,6-Dimethyl-4-chloropyridin-3-yl |
| 388 | | Cl | NH$_2$ | CH$_2$OH | 2,6-Dimethyl-3-methoxypyridin-4-yl |
| 389 | | Cl | NH$_2$ | CH$_2$OH | 2,6-Dimethyl-pyridin-4-yl |
| 390 | | Cl | NH$_2$ | CH$_2$OH | 2,3,6-Trimethyl-pyridin-4-yl |
| 391 | | Cl | NH$_2$ | CH$_2$OH | 2,3,6-Trimethoxy-pyridin-4-yl |
| 392 | | Cl | NH$_2$ | CH$_2$OH | 2,6-Dimethyl-3-bromopyridin-4-yl |
| 393 | | Cl | NH$_2$ | CH$_2$OH | 2,6-Dimethyl-3-chloropyridin-4-yl |
| 394 | | Cl | NH$_2$ | CH$_2$OH | 4,6-Dimethyl-5-iodopyridin-3-yl |
| 395 | | Cl | NH$_2$ | CH$_2$OH | 3,5-Dimethyl-4-aminopyridin-2-yl |
| 396 | 6 | Cl | NH$_2$ | 2-Py | 3,5-Dimethyl-4-methoxypyridin-2-yl |
| 397 | | Cl | NH$_2$ | 2-Py | 3,5-Dimethyl-4-methoxy-1-oxypyridin-2-yl |
| 398 | | Cl | NH$_2$ | 2-Py | 3,5-Dimethyl-4-bromopyridin-2-yl |
| 399 | | Cl | NH$_2$ | 2-Py | 3,5-Dimethyl-4-bromo-1-oxypyridin-2-yl |
| 400 | | Cl | NH$_2$ | 2-Py | 3,5-Dimethyl-4-chloropyridin-2-yl |
| 401 | | Cl | NH$_2$ | 2-Py | 3,5-Dimethyl-4-chloro-1-oxypyridin-2-yl |
| 402 | | Cl | NH$_2$ | 2-Py | 3,5-Dimethyl-4-iodopyridin-2-yl |
| 403 | | Cl | NH$_2$ | 2-Py | 3,5-Dimethyl-4-iodo-1-oxypyridin-2-yl |
| 404 | | Cl | NH$_2$ | 2-Py | 3,5-Dimethyl-4-thiomethyl-pyridin-2-yl |
| 405 | | Cl | NH$_2$ | 2-Py | 3,5-Dimethyl-4-thiomethyl-1-oxypyridin-2-yl |
| 406 | | Cl | NH$_2$ | 2-Py | 3,4,5-Trimethyl-pyridin-2-yl |
| 407 | | Cl | NH$_2$ | 2-Py | 3,4,5-Trimethyl-1-oxypyridin-2-yl |
| 408 | | Cl | NH$_2$ | 2-Py | 4,5,6-Trimethoxypyridin-2-yl |
| 409 | | Cl | NH$_2$ | 2-Py | 4,5,6-Trimethoxy-1-oxypyridin-2-yl |
| 410 | | Cl | NH$_2$ | 2-Py | 3,4,5-Trimethoxy-pyridin-2-yl |
| 411 | | Cl | NH$_2$ | 2-Py | 3,4,5-Trimethoxy-1-oxypyridin-2-yl |
| 412 | | Cl | NH$_2$ | 2-Py | 4,5,6-Trimethyl-pyridin-2-yl |
| 413 | | Cl | NH$_2$ | 2-Py | 4,5,6-Trimethyl-1-oxypyridin-2-yl |
| 414 | | Cl | NH$_2$ | 2-Py | 4,6-Dimethyl-5-methoxy-pyridin-2-yl |
| 415 | | Cl | NH$_2$ | 2-Py | 4,6-Dimethyl-5-methoxypyridin-3-yl |
| 416 | | Cl | NH$_2$ | 2-Py | 4,6-Dimethyl-5-methoxy-1-oxypyridin-3-yl |
| 417 | | Cl | NH$_2$ | 2-Py | 4,6-Dimethyl-5-bromopyridin-3-yl |
| 418 | | Cl | NH$_2$ | 2-Py | 4,6-Dimethyl-5-chloropyridin-3-yl |
| 419 | | Cl | NH$_2$ | 2-Py | 5,6-Dimethyl-4-bromopyridin-3-yl |
| 420 | | Cl | NH$_2$ | 2-Py | 5,6-Dimethyl-4-chloropyridin-3-yl |
| 421 | | Cl | NH$_2$ | 2-Py | 2,6-Dimethyl-3-methoxypyridin-4-yl |
| 422 | | Cl | NH$_2$ | 2-Py | 2,6-Dimethyl-pyridin-4-yl |

TABLE 1-continued

Exemplary Compounds based on Formula I

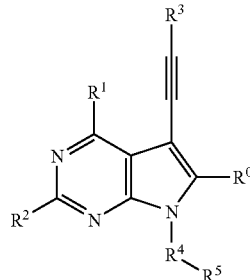

(I)

wherein $R^0$ is H, and $R^4$ is —CH$_2$—.

| No. | Ex | $R^1$ | $R^2$ | $R^3$ | $R^5$ |
|---|---|---|---|---|---|
| 423 | | Cl | NH$_2$ | 2-Py | 2,3,6-Trimethyl-pyridin-4-yl |
| 424 | | Cl | NH$_2$ | 2-Py | 2,3,6-Trimethoxy-pyridin-4-yl |
| 425 | | Cl | NH$_2$ | 2-Py | 2,6-Dimethyl-3-bromopyridin-4-yl |
| 426 | | Cl | NH$_2$ | 2-Py | 2,6-Dimethyl-3-chloropyridin-4-yl |
| 427 | | Cl | NH$_2$ | 2-Py | 4,6-Dimethyl-5-iodopyridin-3-yl |
| 428 | | Cl | NH$_2$ | 2-Py | 3,5-Dimethyl-4-aminopyridin-2-yl |
| 429 | | Cl | NH$_2$ | Ph | 3,5-Dimethyl-4-methoxypyridin-2-yl |
| 430 | | Cl | NH$_2$ | Ph | 3,5-Dimethyl-4-methoxy-1-oxypyridin-2-yl |
| 431 | | Cl | NH$_2$ | Ph | 3,5-Dimethyl-4-bromopyridin-2-yl |
| 432 | | Cl | NH$_2$ | Ph | 3,5-Dimethyl-4-bromo-1-oxypyridin-2-yl |
| 433 | | Cl | NH$_2$ | Ph | 3,5-Dimethyl-4-chloropyridin-2-yl |
| 434 | | Cl | NH$_2$ | Ph | 3,5-Dimethyl-4-chloro-1-oxypyridin-2-yl |
| 435 | | Cl | NH$_2$ | Ph | 3,5-Dimethyl-4-iodopyridin-2-yl |
| 436 | | Cl | NH$_2$ | Ph | 3,5-Dimethyl-4-iodo-1-oxypyridin-2-yl |
| 437 | | Cl | NH$_2$ | Ph | 3,5-Dimethyl-4-thiomethylpyridin-2-yl |
| 438 | | Cl | NH$_2$ | Ph | 3,5-Dimethyl-4-thiomethyl-1-oxypyridin-2-yl |
| 439 | | Cl | NH$_2$ | Ph | 3,4,5-Trimethyl-pyridin-2-yl |
| 440 | | Cl | NH$_2$ | Ph | 3,4,5-Trimethyl-1-oxypyridin-2-yl |
| 441 | | Cl | NH$_2$ | Ph | 4,5,6-Trimethoxypyridin-2-yl |
| 442 | | Cl | NH$_2$ | Ph | 4,5,6-Trimethoxy-1-oxypyridin-2-yl |
| 443 | | Cl | NH$_2$ | Ph | 3,4,5-Trimethoxy-pyridin-2-yl |
| 444 | | Cl | NH$_2$ | Ph | 3,4,5-Trimethoxy-1-oxypyridin-2-yl |
| 445 | | Cl | NH$_2$ | Ph | 4,5,6-Trimethyl-pyridin-2-yl |
| 446 | | Cl | NH$_2$ | Ph | 4,5,6-Trimethyl-1-oxypyridin-2-yl |
| 447 | | Cl | NH$_2$ | Ph | 4,6-Dimethyl-5-methoxy-pyridin-2-yl |
| 448 | | Cl | NH$_2$ | Ph | 4,6-Dimethyl-5-methoxypyridin-3-yl |
| 449 | | Cl | NH$_2$ | Ph | 4,6-Dimethyl-5-methoxy-1-oxypyridin-3-yl |
| 450 | | Cl | NH$_2$ | Ph | 4,6-Dimethyl-5-bromopyridin-3-yl |
| 451 | | Cl | NH$_2$ | Ph | 4,6-Dimethyl-5-chloropyridin-3-yl |
| 452 | | Cl | NH$_2$ | Ph | 5,6-Dimethyl-4-bromopyridin-3-yl |
| 453 | | Cl | NH$_2$ | Ph | 5,6-Dimethyl-4-chloropyridin-3-yl |
| 454 | | Cl | NH$_2$ | Ph | 2,6-Dimethyl-3-methoxypyridin-4-yl |
| 455 | | Cl | NH$_2$ | Ph | 2,6-Dimethyl-pyridin-4-yl |
| 456 | | Cl | NH$_2$ | Ph | 2,3,6-Trimethyl-pyridin-4-yl |
| 457 | | Cl | NH$_2$ | Ph | 2,3,6-Trimethoxy-pyridin-4-yl |
| 458 | | Cl | NH$_2$ | Ph | 2,6-Dimethyl-3-bromopyridin-4-yl |
| 459 | | Cl | NH$_2$ | Ph | 2,6-Dimethyl-3-chloropyridin-4-yl |
| 460 | | Cl | NH$_2$ | Ph | 4,6-Dimethyl-5-iodopyridin-3-yl |
| 461 | | Cl | NH$_2$ | Ph | 3,5-Dimethyl-4-aminopyridin-2-yl |
| 462 | | Cl | NH$_2$ | 3-Py | 3,5-Dimethyl-4-methoxypyridin-2-yl |
| 463 | | Cl | NH$_2$ | 3-Py | 3,5-Dimethyl-4-methoxy-1-oxypyridin-2-yl |
| 464 | | Cl | NH$_2$ | 3-Py | 3,5-Dimethyl-4-bromopyridin-2-yl |
| 465 | | Cl | NH$_2$ | 3-Py | 3,5-Dimethyl-4-bromo-1-oxypyridin-2-yl |
| 466 | | Cl | NH$_2$ | 3-Py | 3,5-Dimethyl-4-chloropyridin-2-yl |
| 467 | | Cl | NH$_2$ | 3-Py | 3,5-Dimethyl-4-chloro-1-oxypyridin-2-yl |
| 468 | | Cl | NH$_2$ | 3-Py | 3,5-Dimethyl-4-iodopyridin-2-yl |
| 469 | | Cl | NH$_2$ | 3-Py | 3,5-Dimethyl-4-iodo-1-oxypyridin-2-yl |
| 470 | | Cl | NH$_2$ | 3-Py | 3,5-Dimethyl-4-thiomethylpyridin-2-yl |
| 471 | | Cl | NH$_2$ | 3-Py | 3,5-Dimethyl-4-thiomethyl-1-oxypyridin-2-yl |
| 472 | | Cl | NH$_2$ | 3-Py | 3,4,5-Trimethyl-pyridin-2-yl |
| 473 | | Cl | NH$_2$ | 3-Py | 3,4,5-Trimethyl-1-oxypyridin-2-yl |
| 474 | | Cl | NH$_2$ | 3-Py | 4,5,6-Trimethoxypyridin-2-yl |
| 475 | | Cl | NH$_2$ | 3-Py | 4,5,6-Trimethoxy-1-oxypyridin-2-yl |
| 476 | | Cl | NH$_2$ | 3-Py | 3,4,5-Trimethoxy-pyridin-2-yl |
| 477 | | Cl | NH$_2$ | 3-Py | 3,4,5-Trimethoxy-1-oxypyridin-2-yl |
| 478 | | Cl | NH$_2$ | 3-Py | 4,5,6-Trimethyl-pyridin-2-yl |
| 479 | | Cl | NH$_2$ | 3-Py | 4,5,6-Trimethyl-1-oxypyridin-2-yl |
| 480 | | Cl | NH$_2$ | 3-Py | 4,6-Dimethyl-5-methoxy-pyridin-2-yl |

TABLE 1-continued

Exemplary Compounds based on Formula I

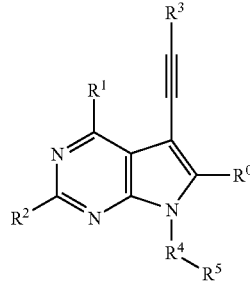

(I)

wherein $R^0$ is H, and $R^4$ is —CH$_2$—.

| No. | Ex | $R^1$ | $R^2$ | $R^3$ | $R^5$ |
|---|---|---|---|---|---|
| 481 | | Cl | NH$_2$ | 3-Py | 4,6-Dimethyl-5-methoxypyridin-3-yl |
| 482 | | Cl | NH$_2$ | 3-Py | 4,6-Dimethyl-5-methoxy-1-oxypyridin-3-yl |
| 483 | | Cl | NH$_2$ | 3-Py | 4,6-Dimethyl-5-bromopyridin-3-yl |
| 484 | | Cl | NH$_2$ | 3-Py | 4,6-Dimethyl-5-chloropyridin-3-yl |
| 485 | | Cl | NH$_2$ | 3-Py | 5,6-Dimethyl-4-bromopyridin-3-yl |
| 486 | | Cl | NH$_2$ | 3-Py | 5,6-Dimethyl-4-chloropyridin-3-yl |
| 487 | | Cl | NH$_2$ | 3-Py | 2,6-Dimethyl-3-methoxypyridin-4-yl |
| 488 | | Cl | NH$_2$ | 3-Py | 2,6-Dimethyl-pyridin-4-yl |
| 489 | | Cl | NH$_2$ | 3-Py | 2,3,6-Trimethyl-pyridin-4-yl |
| 490 | | Cl | NH$_2$ | 3-Py | 2,3,6-Trimethoxy-pyridin-4-yl |
| 491 | | Cl | NH$_2$ | 3-Py | 2,6-Dimethyl-3-bromopyridin-4-yl |
| 492 | | Cl | NH$_2$ | 3-Py | 2,6-Dimethyl-3-chloropyridin-4-yl |
| 493 | | Cl | NH$_2$ | 3-Py | 4,6-Dimethyl-5-iodopyridin-3-yl |
| 494 | | Cl | NH$_2$ | 3-Py | 3,5-Dimethyl-4-aminopyridin-2-yl |
| 495 | | Cl | NH$_2$ | CH$_2$—NMe$_2$ | 3,5-Dimethyl-4-methoxypyridin-2-yl |
| 496 | | Cl | NH$_2$ | CH$_2$—NMe$_2$ | 3,5-Dimethyl-4-methoxy-1-oxypyridin-2-yl |
| 497 | | Cl | NH$_2$ | CH$_2$—NMe$_2$ | 3,5-Dimethyl-4-bromopyridin-2-yl |
| 498 | | Cl | NH$_2$ | CH$_2$—NMe$_2$ | 3,5-Dimethyl-4-bromo-1-oxypyridin-2-yl |
| 499 | | Cl | NH$_2$ | CH$_2$—NMe$_2$ | 3,5-Dimethyl-4-chloropyridin-2-yl |
| 500 | | Cl | NH$_2$ | CH$_2$—NMe$_2$ | 3,5-Dimethyl-4-chloro-1-oxypyridin-2-yl |
| 501 | | Cl | NH$_2$ | CH$_2$—NMe$_2$ | 3,5-Dimethyl-4-iodopyridin-2-yl |
| 502 | | Cl | NH$_2$ | CH$_2$—NMe$_2$ | 3,5-Dimethyl-4-iodo-1-oxypyridin-2-yl |
| 503 | | Cl | NH$_2$ | CH$_2$—NMe$_2$ | 3,5-Dimethyl-4-thiomethyl-pyridin-2-yl |
| 504 | | Cl | NH$_2$ | CH$_2$—NMe$_2$ | 3,5-Dimethyl-4-thiomethyl-1-oxypyridin-2-yl |
| 505 | | Cl | NH$_2$ | CH$_2$—NMe$_2$ | 3,4,5-Trimethyl-pyridin-2-yl |
| 506 | | Cl | NH$_2$ | CH$_2$—NMe$_2$ | 3,4,5-Trimethyl-1-oxypyridin-2-yl |
| 507 | | Cl | NH$_2$ | CH$_2$—NMe$_2$ | 4,5,6-Trimethoxypyridin-2-yl |
| 508 | | Cl | NH$_2$ | CH$_2$—NMe$_2$ | 4,5,6-Trimethoxy-1-oxypyridin-2-yl |
| 509 | | Cl | NH$_2$ | CH$_2$—NMe$_2$ | 3,4,5-Trimethoxy-pyridin-2-yl |
| 510 | | Cl | NH$_2$ | CH$_2$—NMe$_2$ | 3,4,5-Trimethoxy-1-oxypyridin-2-yl |
| 511 | | Cl | NH$_2$ | CH$_2$—NMe$_2$ | 4,5,6-Trimethyl-pyridin-2-yl |
| 512 | | Cl | NH$_2$ | CH$_2$—NMe$_2$ | 4,5,6-Trimethyl-1-oxypyridin-2-yl |
| 513 | | Cl | NH$_2$ | CH$_2$—NMe$_2$ | 4,6-Dimethyl-5-methoxy-pyridin-2-yl |
| 514 | | Cl | NH$_2$ | CH$_2$—NMe$_2$ | 4,6-Dimethyl-5-methoxypyridin-3-yl |
| 515 | | Cl | NH$_2$ | CH$_2$—NMe$_2$ | 4,6-Dimethyl-5-methoxy-1-oxypyridin-3-yl |
| 516 | | Cl | NH$_2$ | CH$_2$—NMe$_2$ | 4,6-Dimethyl-5-bromopyridin-3-yl |
| 517 | | Cl | NH$_2$ | CH$_2$—NMe$_2$ | 4,6-Dimethyl-5-chloropyridin-3-yl |
| 518 | | Cl | NH$_2$ | CH$_2$—NMe$_2$ | 5,6-Dimethyl-4-bromopyridin-3-yl |
| 519 | | Cl | NH$_2$ | CH$_2$—NMe$_2$ | 5,6-Dimethyl-4-chloropyridin-3-yl |
| 520 | | Cl | NH$_2$ | CH$_2$—NMe$_2$ | 2,6-Dimethyl-3-methoxypyridin-4-yl |
| 521 | | Cl | NH$_2$ | CH$_2$—NMe$_2$ | 2,6-Dimethyl-pyridin-4-yl |
| 522 | | Cl | NH$_2$ | CH$_2$—NMe$_2$ | 2,3,6-Trimethyl-pyridin-4-yl |
| 523 | | Cl | NH$_2$ | CH$_2$—NMe$_2$ | 2,3,6-Trimethoxy-pyridin-4-yl |
| 524 | | Cl | NH$_2$ | CH$_2$—NMe$_2$ | 2,6-Dimethyl-3-bromopyridin-4-yl |
| 525 | | Cl | NH$_2$ | CH$_2$—NMe$_2$ | 2,6-Dimethyl-3-chloropyridin-4-yl |
| 526 | | Cl | NH$_2$ | CH$_2$—NMe$_2$ | 4,6-Dimethyl-5-iodopyridin-3-yl |
| 527 | | Cl | NH$_2$ | CH$_2$—NMe$_2$ | 3,5-Dimethyl-4-aminopyridin-2-yl |
| 528 | | Cl | NH$_2$ | H | 3,5-Dimethyl-4-methoxypyridin-2-yl |
| 529 | | Cl | NH$_2$ | H | 3,5-Dimethyl-4-methoxy-1-oxypyridin-2-yl |
| 530 | | Cl | NH$_2$ | H | 3,5-Dimethyl-4-bromopyridin-2-yl |
| 531 | | Cl | NH$_2$ | H | 3,5-Dimethyl-4-bromo-1-oxypyridin-2-yl |
| 532 | | Cl | NH$_2$ | H | 3,5-Dimethyl-4-chloropyridin-2-yl |
| 533 | | Cl | NH$_2$ | H | 3,5-Dimethyl-4-chloro-1-oxypyridin-2-yl |
| 534 | | Cl | NH$_2$ | H | 3,5-Dimethyl-4-iodopyridin-2-yl |
| 535 | | Cl | NH$_2$ | H | 3,5-Dimethyl-4-iodo-1-oxypyridin-2-yl |
| 536 | | Cl | NH$_2$ | H | 3,5-Dimethyl-4-thiomethyl-pyridin-2-yl |
| 537 | | Cl | NH$_2$ | H | 3,5-Dimethyl-4-thiomethyl-1-oxypyridin-2-yl |
| 538 | | Cl | NH$_2$ | H | 3,4,5-Trimethyl-pyridin-2-yl |

TABLE 1-continued

Exemplary Compounds based on Formula I

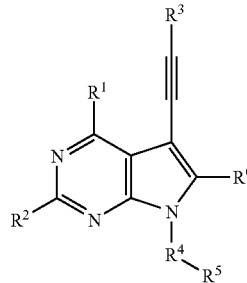

(I)

wherein R⁰ is H, and R⁴ is —CH₂—.

| No. | Ex | R¹ | R² | R³ | R⁵ |
|---|---|---|---|---|---|
| 539 | | Cl | NH₂ | H | 3,4,5-Trimethyl-1-oxypyridin-2-yl |
| 540 | | Cl | NH₂ | H | 4,5,6-Trimethoxypyridin-2-yl |
| 541 | | Cl | NH₂ | H | 4,5,6-Trimethoxy-1-oxypyridin-2-yl |
| 542 | | Cl | NH₂ | H | 3,4,5-Trimethoxy-pyridin-2-yl |
| 543 | | Cl | NH₂ | H | 3,4,5-Trimethoxy-1-oxypyridin-2-yl |
| 544 | | Cl | NH₂ | H | 4,5,6-Trimethyl-pyridin-2-yl |
| 545 | | Cl | NH₂ | H | 4,5,6-Trimethyl-1-oxypyridin-2-yl |
| 546 | | Cl | NH₂ | H | 4,6-Dimethyl-5-methoxy-pyridin-2-yl |
| 547 | | Cl | NH₂ | H | 4,6-Dimethyl-5-methoxypyridin-3-yl |
| 548 | | Cl | NH₂ | H | 4,6-Dimethyl-5-methoxy-1-oxypyridin-3-yl |
| 549 | | Cl | NH₂ | H | 4,6-Dimethyl-5-bromopyridin-3-yl |
| 550 | | Cl | NH₂ | H | 4,6-Dimethyl-5-chloropyridin-3-yl |
| 551 | | Cl | NH₂ | H | 5,6-Dimethyl-4-bromopyridin-3-yl |
| 552 | | Cl | NH₂ | H | 5,6-Dimethyl-4-chloropyridin-3-yl |
| 553 | | Cl | NH₂ | H | 2,6-Dimethyl-3-methoxypyridin-4-yl |
| 554 | | Cl | NH₂ | H | 2,6-Dimethyl-pyridin-4-yl |
| 555 | | Cl | NH₂ | H | 2,3,6-Trimethyl-pyridin-4-yl |
| 556 | | Cl | NH₂ | H | 2,3,6-Trimethoxy-pyridin-4-yl |
| 557 | | Cl | NH₂ | H | 2,6-Dimethyl-3-bromopyridin-4-yl |
| 558 | | Cl | NH₂ | H | 2,6-Dimethyl-3-chloropyridin-4-yl |
| 559 | | Cl | NH₂ | H | 3,5-Dimethyl-4-aminopyridin-2-yl |
| 560 | | Cl | NH₂ | Me | 3,5-Dimethyl-4-methoxypyridin-2-yl |
| 561 | | Cl | NH₂ | Me | 3,5-Dimethyl-4-methoxy-1-oxypyridin-2-yl |
| 562 | | Cl | NH₂ | Me | 3,5-Dimethyl-4-bromopyridin-2-yl |
| 563 | | Cl | NH₂ | Me | 3,5-Dimethyl-4-bromo-1-oxypyridin-2-yl |
| 564 | | Cl | NH₂ | Me | 3,5-Dimethyl-4-chloropyridin-2-yl |
| 565 | | Cl | NH₂ | Me | 3,5-Dimethyl-4-chloro-1-oxypyridin-2-yl |
| 566 | | Cl | NH₂ | Me | 3,5-Dimethyl-4-iodopyridin-2-yl |
| 567 | | Cl | NH₂ | Me | 3,5-Dimethyl-4-iodo-1-oxypyridin-2-yl |
| 568 | | Cl | NH₂ | Me | 3,5-Dimethyl-4-thiomethyl-pyridin-2-yl |
| 569 | | Cl | NH₂ | Me | 3,5-Dimethyl-4-thiomethyl-1-oxypyridin-2-yl |
| 570 | | Cl | NH₂ | Me | 3,4,5-Trimethyl-pyridin-2-yl |
| 571 | | Cl | NH₂ | Me | 3,4,5-Trimethyl-1-oxypyridin-2-yl |
| 572 | | Cl | NH₂ | Me | 4,6-Dimethyl-5-methoxypyridin-3-yl |
| 573 | | Cl | NH₂ | Me | 4,6-Dimethyl-5-methoxy-1-oxypyridin-3-yl |
| 574 | | Cl | NH₂ | Me | 3,5-Dimethyl-4-aminopyridin-2-yl |
| 575 | | Cl | NH₂ | Et | 3,5-Dimethyl-4-methoxypyridin-2-yl |
| 576 | | Cl | NH₂ | Et | 3,5-Dimethyl-4-methoxy-1-oxypyridin-2-yl |
| 577 | | Cl | NH₂ | Et | 3,5-Dimethyl-4-bromopyridin-2-yl |
| 578 | | Cl | NH₂ | Et | 3,5-Dimethyl-4-bromo-1-oxypyridin-2-yl |
| 579 | | Cl | NH₂ | Et | 3,5-Dimethyl-4-chloropyridin-2-yl |
| 580 | | Cl | NH₂ | Et | 3,5-Dimethyl-4-chloro-1-oxypyridin-2-yl |
| 581 | | Cl | NH₂ | Et | 3,5-Dimethyl-4-iodopyridin-2-yl |
| 582 | | Cl | NH₂ | Et | 3,5-Dimethyl-4-iodo-1-oxypyridin-2-yl |
| 583 | | Cl | NH₂ | Et | 3,5-Dimethyl-4-thiomethyl-pyridin-2-yl |
| 584 | | Cl | NH₂ | Et | 3,5-Dimethyl-4-thiomethyl-1-oxypyridin-2-yl |
| 585 | | Cl | NH₂ | Et | 3,4,5-Trimethyl-pyridin-2-yl |
| 586 | | Cl | NH₂ | Et | 3,4,5-Trimethyl-1-oxypyridin-2-yl |
| 587 | | Cl | NH₂ | Et | 4,6-Dimethyl-5-methoxypyridin-3-yl |
| 588 | | Cl | NH₂ | Et | 4,6-Dimethyl-5-methoxy-1-oxypyridin-3-yl |
| 589 | | Cl | NH₂ | Et | 3,5-Dimethyl-4-aminopyridin-2-yl |
| 590 | | Cl | NH₂ | CO₂Et | 3,5-Dimethyl-4-methoxypyridin-2-yl |
| 591 | | Cl | NH₂ | CO₂Et | 3,5-Dimethyl-4-methoxy-1-oxypyridin-2-yl |
| 592 | | Cl | NH₂ | CO₂Et | 3,5-Dimethyl-4-bromopyridin-2-yl |
| 593 | | Cl | NH₂ | CO₂Et | 3,5-Dimethyl-4-bromo-1-oxypyridin-2-yl |
| 594 | | Cl | NH₂ | CO₂Et | 3,5-Dimethyl-4-chloropyridin-2-yl |
| 595 | | Cl | NH₂ | CO₂Et | 3,5-Dimethyl-4-chloro-1-oxypyridin-2-yl |
| 596 | | Cl | NH₂ | CO₂Et | 3,5-Dimethyl-4-iodopyridin-2-yl |

TABLE 1-continued

Exemplary Compounds based on Formula I

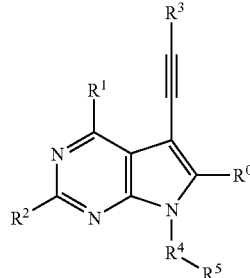

(I)

wherein $R^0$ is H, and $R^4$ is —CH$_2$—.

| No. | Ex | $R^1$ | $R^2$ | $R^3$ | $R^5$ |
|---|---|---|---|---|---|
| 597 | | Cl | NH$_2$ | CO$_2$Et | 3,5-Dimethyl-4-iodo-1-oxypyridin-2-yl |
| 598 | | Cl | NH$_2$ | CO$_2$Et | 3,5-Dimethyl-4-thiomethyl-pyridin-2-yl |
| 599 | | Cl | NH$_2$ | CO$_2$Et | 3,5-Dimethyl-4-thiomethyl-1-oxypyridin-2-yl |
| 600 | | Cl | NH$_2$ | CO$_2$Et | 3,4,5-Trimethyl-pyridin-2-yl |
| 601 | | Cl | NH$_2$ | CO$_2$Et | 3,4,5-Trimethyl-1-oxypyridin-2-yl |
| 602 | | Cl | NH$_2$ | CO$_2$Et | 4,6-Dimethyl-5-methoxypyridin-3-yl |
| 603 | | Cl | NH$_2$ | CO$_2$Et | 4,6-Dimethyl-5-methoxy-1-oxypyridin-3-yl |
| 604 | | Cl | NH$_2$ | CO$_2$Et | 3,5-Dimethyl-4-aminopyridin-2-yl |
| 605 | | Cl | NH$_2$ | CN | 3,5-Dimethyl-4-methoxypyridin-2-yl |
| 606 | | Cl | NH$_2$ | CN | 3,5-Dimethyl-4-methoxy-1-oxypyridin-2-yl |
| 607 | | Cl | NH$_2$ | CN | 3,5-Dimethyl-4-bromopyridin-2-yl |
| 608 | | Cl | NH$_2$ | CN | 3,5-Dimethyl-4-bromo-1-oxypyridin-2-yl |
| 609 | | Cl | NH$_2$ | CN | 3,5-Dimethyl-4-chloropyridin-2-yl |
| 610 | | Cl | NH$_2$ | CN | 3,5-Dimethyl-4-chloro-1-oxypyridin-2-yl |
| 611 | | Cl | NH$_2$ | CN | 3,5-Dimethyl-4-iodopyridin-2-yl |
| 612 | | Cl | NH$_2$ | CN | 3,5-Dimethyl-4-iodo-1-oxypyridin-2-yl |
| 613 | | Cl | NH$_2$ | CN | 3,5-Dimethyl-4-thiomethyl-pyridin-2-yl |
| 614 | | Cl | NH$_2$ | CN | 3,5-Dimethyl-4-thiomethyl-1-oxypyridin-2-yl |
| 615 | | Cl | NH$_2$ | CN | 3,4,5-Trimethyl-pyridin-2-yl |
| 616 | | Cl | NH$_2$ | CN | 3,4,5-Trimethyl-1-oxypyridin-2-yl |
| 617 | | Cl | NH$_2$ | CN | 4,6-Dimethyl-5-methoxypyridin-3-yl |
| 618 | | Cl | NH$_2$ | CN | 4,6-Dimethyl-5-methoxy-1-oxypyridin-3-yl |
| 619 | | Cl | NH$_2$ | CN | 3,5-Dimethyl-4-aminopyridin-2-yl |
| 620 | | Cl | NH$_2$ | CMe$_2$OH | 3,5-Dimethyl-4-methoxypyridin-2-yl |
| 621 | | Cl | NH$_2$ | CMe$_2$OH | 3,5-Dimethyl-4-methoxy-1-oxypyridin-2-yl |
| 622 | | Cl | NH$_2$ | CMe$_2$OH | 3,5-Dimethyl-4-bromopyridin-2-yl |
| 623 | | Cl | NH$_2$ | CMe$_2$OH | 3,5-Dimethyl-4-bromo-1-oxypyridin-2-yl |
| 624 | | Cl | NH$_2$ | CMe$_2$OH | 3,5-Dimethyl-4-chloropyridin-2-yl |
| 625 | | Cl | NH$_2$ | CMe$_2$OH | 3,5-Dimethyl-4-chloro-1-oxypyridin-2-yl |
| 626 | | Cl | NH$_2$ | CMe$_2$OH | 3,5-Dimethyl-4-iodopyridin-2-yl |
| 627 | | Cl | NH$_2$ | CMe$_2$OH | 3,5-Dimethyl-4-iodo-1-oxypyridin-2-yl |
| 628 | | Cl | NH$_2$ | CMe$_2$OH | 3,5-Dimethyl-4-thiomethyl-pyridin-2-yl |
| 629 | | Cl | NH$_2$ | CMe$_2$OH | 3,5-Dimethyl-4-thiomethyl-1-oxypyridin-2-yl |
| 630 | | Cl | NH$_2$ | CMe$_2$OH | 3,4,5-Trimethyl-pyridin-2-yl |
| 631 | | Cl | NH$_2$ | CMe$_2$OH | 3,4,5-Trimethyl-1-oxypyridin-2-yl |
| 632 | | Cl | NH$_2$ | CMe$_2$OH | 4,6-Dimethyl-5-methoxypyridin-3-yl |
| 633 | | Cl | NH$_2$ | CMe$_2$OH | 4,6-Dimethyl-5-methoxy-1-oxypyridin-3-yl |
| 634 | | Cl | NH$_2$ | CMe$_2$OH | 3,5-Dimethyl-4-aminopyridin-2-yl |
| 635 | | Cl | NH$_2$ | CH$_2$CMe$_2$OH | 3,5-Dimethyl-4-methoxypyridin-2-yl |
| 636 | | Cl | NH$_2$ | CH$_2$CMe$_2$OH | 3,5-Dimethyl-4-methoxy-1-oxypyridin-2-yl |
| 637 | | Cl | NH$_2$ | CH$_2$CMe$_2$OH | 3,5-Dimethyl-4-bromopyridin-2-yl |
| 638 | | Cl | NH$_2$ | CH$_2$CMe$_2$OH | 3,5-Dimethyl-4-bromo-1-oxypyridin-2-yl |
| 639 | | Cl | NH$_2$ | CH$_2$CMe$_2$OH | 3,5-Dimethyl-4-chloropyridin-2-yl |
| 640 | | Cl | NH$_2$ | CH$_2$CMe$_2$OH | 3,5-Dimethyl-4-chloro-1-oxypyridin-2-yl |
| 641 | | Cl | NH$_2$ | CH$_2$CMe$_2$OH | 3,5-Dimethyl-4-iodopyridin-2-yl |
| 642 | | Cl | NH$_2$ | CH$_2$CMe$_2$OH | 3,5-Dimethyl-4-iodo-1-oxypyridin-2-yl |
| 643 | | Cl | NH$_2$ | CH$_2$CMe$_2$OH | 3,5-Dimethyl-4-thiomethyl-pyridin-2-yl |
| 644 | | Cl | NH$_2$ | CH$_2$CMe$_2$OH | 3,5-Dimethyl-4-thiomethyl-1-oxypyridin-2-yl |
| 645 | | Cl | NH$_2$ | CH$_2$CMe$_2$OH | 3,4,5-Trimethyl-pyridin-2-yl |
| 646 | | Cl | NH$_2$ | CH$_2$CMe$_2$OH | 3,4,5-Trimethyl-1-oxypyridin-2-yl |
| 647 | | Cl | NH$_2$ | CH$_2$CMe$_2$OH | 4,6-Dimethyl-5-methoxypyridin-3-yl |
| 648 | | Cl | NH$_2$ | CH$_2$CMe$_2$OH | 4,6-Dimethyl-5-methoxy-1-oxypyridin-3-yl |
| 649 | | Cl | NH$_2$ | CH$_2$CH$_2$CMe$_2$OH | 3,5-Dimethyl-4-methoxypyridin-2-yl |
| 650 | | Cl | NH$_2$ | CH$_2$CH$_2$CMe$_2$OH | 3,5-Dimethyl-4-methoxy-1-oxypyridin-2-yl |
| 651 | | Cl | NH$_2$ | CH$_2$CH$_2$CMe$_2$OH | 3,5-Dimethyl-4-bromopyridin-2-yl |
| 652 | | Cl | NH$_2$ | CH$_2$CH$_2$CMe$_2$OH | 3,5-Dimethyl-4-bromo-1-oxypyridin-2-yl |
| 653 | | Cl | NH$_2$ | CH$_2$CH$_2$CMe$_2$OH | 3,5-Dimethyl-4-chloropyridin-2-yl |
| 654 | | Cl | NH$_2$ | CH$_2$CH$_2$CMe$_2$OH | 3,5-Dimethyl-4-chloro-1-oxypyridin-2-yl |

TABLE 1-continued

Exemplary Compounds based on Formula I

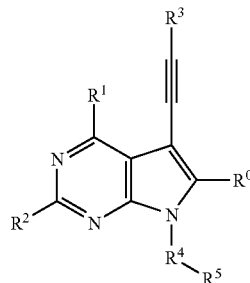

(I)

wherein $R^0$ is H, and $R^4$ is —$CH_2$—.

| No. | Ex | $R^1$ | $R^2$ | $R^3$ | $R^5$ |
|---|---|---|---|---|---|
| 655 | | Cl | $NH_2$ | $CH_2CH_2CMe_2OH$ | 3,5-Dimethyl-4-iodopyridin-2-yl |
| 656 | | Cl | $NH_2$ | $CH_2CH_2CMe_2OH$ | 3,5-Dimethyl-4-iodo-1-oxypyridin-2-yl |
| 657 | | Cl | $NH_2$ | $CH_2CH_2CMe_2OH$ | 3,5-Dimethyl-4-thiomethyl-pyridin-2-yl |
| 658 | | Cl | $NH_2$ | $CH_2CH_2CMe_2OH$ | 3,5-Dimethyl-4-thiomethyl-1-oxypyridin-2-yl |
| 659 | | Cl | $NH_2$ | $CH_2CH_2CMe_2OH$ | 3,4,5-Trimethyl-pyridin-2-yl |
| 660 | | Cl | $NH_2$ | $CH_2CH_2CMe_2OH$ | 3,4,5-Trimethyl-1-oxypyridin-2-yl |
| 661 | | Cl | $NH_2$ | $CH_2CH_2CMe_2OH$ | 4,6-Dimethyl-5-methoxypyridin-3-yl |
| 662 | | Cl | $NH_2$ | $CH_2CH_2CMe_2OH$ | 4,6-Dimethyl-5-methoxy-1-oxypyridin-3-yl |
| 663 | | Cl | $NH_2$ | —$CH_2$—N(morpholino) | 3,5-Dimethyl-4-methoxypyridin-2-yl |
| 664 | | Cl | $NH_2$ | —$CH_2$—N(morpholino) | 3,5-Dimethyl-4-methoxy-1-oxypyridin-2-yl |
| 665 | | Cl | $NH_2$ | —$CH_2$—N(morpholino) | 3,5-Dimethyl-4-bromopyridin-2-yl |
| 666 | | Cl | $NH_2$ | —$CH_2$—N(morpholino) | 3,5-Dimethyl-4-bromo-1-oxypyridin-2-yl |
| 667 | | Cl | $NH_2$ | —$CH_2$—N(morpholino) | 3,5-Dimethyl-4-chloropyridin-2-yl |
| 668 | | Cl | $NH_2$ | —$CH_2$—N(morpholino) | 3,5-Dimethyl-4-chloro-1-oxypyridin-2-yl |
| 669 | | Cl | $NH_2$ | —$CH_2$—N(morpholino) | 3,5-Dimethyl-4-iodopyridin-2-yl |
| 670 | | Cl | $NH_2$ | —$CH_2$—N(morpholino) | 3,5-Dimethyl-4-iodo-1-oxypyridin-2-yl |
| 671 | | Cl | $NH_2$ | —$CH_2$—N(morpholino) | 3,5-Dimethyl-4-thiomethyl-pyridin-2-yl |
| 672 | | Cl | $NH_2$ | —$CH_2$—N(morpholino) | 3,5-Dimethyl-4-thiomethyl-1-oxypyridin-2-yl |

TABLE 1-continued

Exemplary Compounds based on Formula I

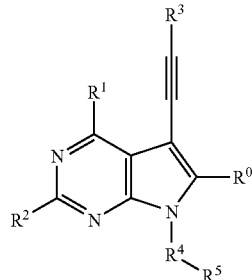
(I)

wherein $R^0$ is H, and $R^4$ is —$CH_2$—.

| No. | Ex | $R^1$ | $R^2$ | $R^3$ | $R^5$ |
|---|---|---|---|---|---|
| 673 | | Cl | $NH_2$ | —$CH_2$—N(morpholine) | 3,4,5-Trimethyl-pyridin-2-yl |
| 674 | | Cl | $NH_2$ | —$CH_2$—N(morpholine) | 3,4,5-Trimethyl-1-oxypyridin-2-yl |
| 675 | | Cl | $NH_2$ | —$CH_2$—N(morpholine) | 4,6-Dimethyl-5-methoxypyridin-3-yl |
| 676 | | Cl | $NH_2$ | —$CH_2$—N(morpholine) | 4,6-Dimethyl-5-methoxy-1-oxypyridin-3-yl |
| 677 | | Cl | $NH_2$ | —$CH_2$—N(morpholine) | 3,5-Dimethyl-4-aminopyridin-2-yl |
| 678 | 18 | Cl | $NH_2$ | —$CH_2CH_2$—N(morpholine) | 3,5-Dimethyl-4-methoxypyridin-2-yl |
| 679 | | Cl | $NH_2$ | —$CH_2CH_2$—N(morpholine) | 3,5-Dimethyl-4-methoxy-1-oxypyridin-2-yl |
| 680 | | Cl | $NH_2$ | —$CH_2CH_2$—N(morpholine) | 3,5-Dimethyl-4-bromopyridin-2-yl |
| 681 | | Cl | $NH_2$ | —$CH_2CH_2$—N(morpholine) | 3,5-Dimethyl-4-bromo-1-oxypyridin-2-yl |
| 682 | | Cl | $NH_2$ | —$CH_2CH_2$—N(morpholine) | 3,5-Dimethyl-4-chloropyridin-2-yl |
| 683 | | Cl | $NH_2$ | —$CH_2CH_2$—N(morpholine) | 3,5-Dimethyl-4-chloro-1-oxypyridin-2-yl |
| 684 | | Cl | $NH_2$ | —$CH_2CH_2$—N(morpholine) | 3,5-Dimethyl-4-iodopyridin-2-yl |

TABLE 1-continued

Exemplary Compounds based on Formula I

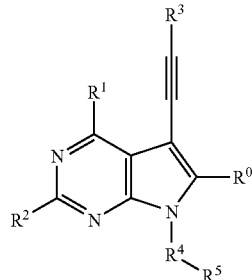
(I)

wherein $R^0$ is H, and $R^4$ is —CH$_2$—.

| No. | Ex | $R^1$ | $R^2$ | $R^3$ | $R^5$ |
|---|---|---|---|---|---|
| 685 | | Cl | NH$_2$ | —CH$_2$CH$_2$—N(morpholino) | 3,5-Dimethyl-4-iodo-1-oxypyridin-2-yl |
| 686 | | Cl | NH$_2$ | —CH$_2$CH$_2$—N(morpholino) | 3,5-Dimethyl-4-thiomethyl-pyridin-2-yl |
| 687 | | Cl | NH$_2$ | —CH$_2$CH$_2$—N(morpholino) | 3,5-Dimethyl-4-thiomethyl-1-oxypyridin-2-yl |
| 688 | | Cl | NH$_2$ | —CH$_2$CH$_2$—N(morpholino) | 3,4,5-Trimethyl-pyridin-2-yl |
| 689 | | Cl | NH$_2$ | —CH$_2$CH$_2$—N(morpholino) | 3,4,5-Trimethyl-1-oxypyridin-2-yl |
| 690 | | Cl | NH$_2$ | —CH$_2$CH$_2$—N(morpholino) | 4,6-Dimethyl-5-methoxypyridin-3-yl |
| 691 | | Cl | NH$_2$ | —CH$_2$CH$_2$—N(morpholino) | 4,6-Dimethyl-5-methoxy-1-oxypyridin-3-yl |
| 692 | 19 | Cl | NH$_2$ | —CH$_2$CH$_2$CH$_2$—N(morpholino) | 3,5-Dimethyl-4-methoxypyridin-2-yl |
| 693 | | Cl | NH$_2$ | —CH$_2$CH$_2$CH$_2$—N(morpholino) | 3,5-Dimethyl-4-methoxy-1-oxypyridin-2-yl |
| 694 | | Cl | NH$_2$ | —CH$_2$CH$_2$CH$_2$—N(morpholino) | 3,5-Dimethyl-4-bromopyridin-2-yl |
| 695 | | Cl | NH$_2$ | —CH$_2$CH$_2$CH$_2$—N(morpholino) | 3,5-Dimethyl-4-bromo-1-oxypyridin-2-yl |
| 696 | | Cl | NH$_2$ | —CH$_2$CH$_2$CH$_2$—N(morpholino) | 3,5-Dimethyl-4-chloropyridin-2-yl |

TABLE 1-continued

Exemplary Compounds based on Formula I

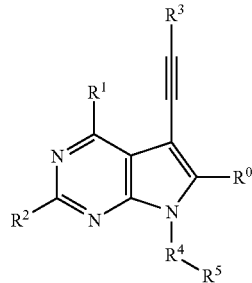
(I)

wherein R⁰ is H, and R⁴ is —CH₂—.

| No. | Ex | R¹ | R² | R³ | R⁵ |
|---|---|---|---|---|---|
| 697 | | Cl | NH₂ | —CH₂CH₂CH₂—N(morpholine) | 3,5-Dimethyl-4-chloro-1-oxypyridin-2-yl |
| 698 | | Cl | NH₂ | —CH₂CH₂CH₂—N(morpholine) | 3,5-Dimethyl-4-iodopyridin-2-yl |
| 699 | | Cl | NH₂ | —CH₂CH₂CH₂—N(morpholine) | 3,5-Dimethyl-4-iodo-1-oxypyridin-2-yl |
| 700 | | Cl | NH₂ | —CH₂CH₂CH₂—N(morpholine) | 3,5-Dimethyl-4-thiomethyl-pyridin-2-yl |
| 701 | | Cl | NH₂ | —CH₂CH₂CH₂—N(morpholine) | 3,5-Dimethyl-4-thiomethyl-1-oxypyridin-2-yl |
| 702 | | Cl | NH₂ | —CH₂CH₂CH₂—N(morpholine) | 3,4,5-Trimethyl-pyridin-2-yl |
| 703 | | Cl | NH₂ | —CH₂CH₂CH₂—N(morpholine) | 3,4,5-Trimethyl-1-oxypyridin-2-yl |
| 704 | | Cl | NH₂ | —CH₂CH₂CH₂—N(morpholine) | 4,6-Dimethyl-5-methoxypyridin-3-yl |
| 705 | | Cl | NH₂ | —CH₂CH₂CH₂—N(morpholine) | 4,6-Dimethyl-5-methoxy-1-oxypyridin-3-yl |
| 706 | | Cl | NH₂ | —CH₂—N(morpholine) | 3,4,5-Trimethoxyphenyl |
| 707 | | Cl | NH₂ | —CH₂—N(morpholine) | 2-Chloro-3,4,5-trimethoxyphenyl |
| 708 | | Cl | NH₂ | —CH₂—N(morpholine) | 2-Bromo-3,4,5-trimethoxyphenyl |

TABLE 1-continued

Exemplary Compounds based on Formula I

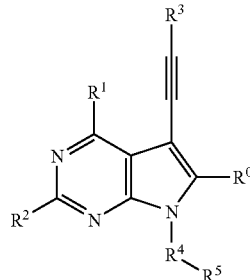

(I)

wherein R⁰ is H, and R⁴ is —CH₂—.

| No. | Ex | R¹ | R² | R³ | R⁵ |
|---|---|---|---|---|---|
| 709 | | Cl | $NH_2$ | —CH₂—N(morpholine) | 3,5-Dimethyl-4-methoxyphenyl |
| 710 | | Cl | $NH_2$ | —CH₂—N(morpholine) | 2-Chloro-3,5-Dimethyl-4-methoxyphenyl |
| 711 | | Cl | $NH_2$ | —CH₂—N(morpholine) | 2-Bromo-3,5-Dimethyl-4-methoxyphenyl |
| 712 | | Cl | $NH_2$ | —CH₂CH₂—N(morpholine) | 3,4,5-Trimethoxyphenyl |
| 713 | | Cl | $NH_2$ | —CH₂CH₂—N(morpholine) | 2-Chloro-3,4,5-trimethoxyphenyl |
| 714 | | Cl | $NH_2$ | —CH₂CH₂—N(morpholine) | 2-Bromo-3,4,5-trimethoxyphenyl |
| 715 | | Cl | $NH_2$ | —CH₂CH₂—N(morpholine) | 3,5-Dimethyl-4-methoxyphenyl |
| 716 | | Cl | $NH_2$ | —CH₂CH₂—N(morpholine) | 2-Chloro-3,5-Dimethyl-4-methoxyphenyl |
| 717 | | Cl | $NH_2$ | —CH₂CH₂—N(morpholine) | 2-Bromo-3,5-Dimethyl-4-methoxyphenyl |
| 718 | | Cl | $NH_2$ | $(CH_2)_2C(O)NMe_2$ | 3,5-Dimethyl-4-methoxypyridin-2-yl |
| 719 | | Cl | $NH_2$ | $(CH_2)_2C(O)NMe_2$ | 3,5-Dimethyl-4-methoxy-1-oxypyridin-2-yl |
| 720 | | Cl | $NH_2$ | $(CH_2)_2C(O)NMe_2$ | 3,5-Dimethyl-4-bromopyridin-2-yl |
| 721 | | Cl | $NH_2$ | $(CH_2)_2C(O)NMe_2$ | 3,5-Dimethyl-4-bromo-1-oxypyridin-2-yl |
| 722 | | Cl | $NH_2$ | $(CH_2)_2C(O)NMe_2$ | 3,5-Dimethyl-4-chloropyridin-2-yl |
| 723 | | Cl | $NH_2$ | $(CH_2)_2C(O)NMe_2$ | 3,5-Dimethyl-4-chloro-1-oxypyridin-2-yl |
| 724 | | Cl | $NH_2$ | $(CH_2)_2C(O)NMe_2$ | 3,5-Dimethyl-4-iodopyridin-2-yl |
| 725 | | Cl | $NH_2$ | $(CH_2)_2C(O)NMe_2$ | 3,5-Dimethyl-4-iodo-1-oxypyridin-2-yl |
| 726 | | Cl | $NH_2$ | $(CH_2)_2C(O)NMe_2$ | 3,5-Dimethyl-4-thiomethyl-pyridin-2-yl |
| 727 | | Cl | $NH_2$ | $(CH_2)_2C(O)NMe_2$ | 3,5-Dimethyl-4-thiomethyl-1-oxypyridin-2-yl |
| 728 | | Cl | $NH_2$ | $(CH_2)_2C(O)NMe_2$ | 3,4,5-Trimethyl-pyridin-2-yl |
| 729 | | Cl | $NH_2$ | $(CH_2)_2C(O)NMe_2$ | 3,4,5-Trimethyl-1-oxypyridin-2-yl |
| 730 | | Cl | $NH_2$ | $(CH_2)_2C(O)NMe_2$ | 4,6-Dimethyl-5-methoxypyridin-3-yl |
| 731 | | Cl | $NH_2$ | $(CH_2)_2C(O)NMe_2$ | 4,6-Dimethyl-5-methoxy-1-oxypyridin-3-yl |

TABLE 1-continued

Exemplary Compounds based on Formula I

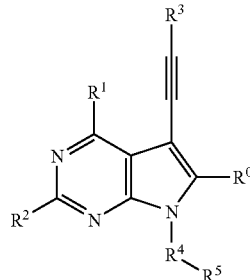

(I)

wherein $R^0$ is H, and $R^4$ is —$CH_2$—.

| No. | Ex | $R^1$ | $R^2$ | $R^3$ | $R^5$ |
|---|---|---|---|---|---|
| 732 | 11 | Cl | $NH_2$ | —$CH_2CH_2C(O)$—N⟨piperazine⟩N—Me | 3,5-Dimethyl-4-methoxypyridin-2-yl |
| 733 |  | Cl | $NH_2$ | —$CH_2CH_2C(O)$—N⟨piperazine⟩N—Me | 3,5-Dimethyl-4-methoxy-1-oxypyridin-2-yl |
| 734 |  | Cl | $NH_2$ | —$CH_2CH_2C(O)$—N⟨piperazine⟩N—Me | 3,5-Dimethyl-4-bromopyridin-2-yl |
| 735 |  | Cl | $NH_2$ | —$CH_2CH_2C(O)$—N⟨piperazine⟩N—Me | 3,5-Dimethyl-4-bromo-1-oxypyridin-2-yl |
| 736 |  | Cl | $NH_2$ | —$CH_2CH_2C(O)$—N⟨piperazine⟩N—Me | 3,5-Dimethyl-4-chloropyridin-2-yl |
| 737 |  | Cl | $NH_2$ | —$CH_2CH_2C(O)$—N⟨piperazine⟩N—Me | 3,5-Dimethyl-4-chloro-1-oxypyridin-2-yl |
| 738 |  | Cl | $NH_2$ | —$CH_2CH_2C(O)$—N⟨piperazine⟩N—Me | 3,5-Dimethyl-4-iodopyridin-2-yl |
| 739 |  | Cl | $NH_2$ | —$CH_2CH_2C(O)$—N⟨piperazine⟩N—Me | 3,5-Dimethyl-4-iodo-1-oxypyridin-2-yl |
| 740 |  | Cl | $NH_2$ | —$CH_2CH_2C(O)$—N⟨piperazine⟩N—Me | 3,5-Dimethyl-4-thiomethyl-pyridin-2-yl |
| 741 |  | Cl | $NH_2$ | —$CH_2CH_2C(O)$—N⟨piperazine⟩N—Me | 3,5-Dimethyl-4-thiomethyl-1-oxypyridin-2-yl |
| 742 |  | Cl | $NH_2$ | —$CH_2CH_2C(O)$—N⟨piperazine⟩N—Me | 3,4,5-Trimethyl-pyridin-2-yl |
| 743 |  | Cl | $NH_2$ | —$CH_2CH_2C(O)$—N⟨piperazine⟩N—Me | 3,4,5-Trimethyl-1-oxypyridin-2-yl |

TABLE 1-continued

Exemplary Compounds based on Formula I

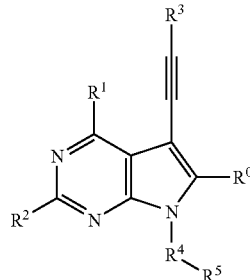

(I)

wherein R⁰ is H, and R⁴ is —CH₂—.

| No. | Ex | R¹ | R² | R³ | R⁵ |
|---|---|---|---|---|---|
| 744 | | Cl | NH$_2$ | —CH$_2$CH$_2$C(O)—N(piperazine)N—Me | 4,6-Dimethyl-5-methoxypyridin-3-yl |
| 745 | | Cl | NH$_2$ | —CH$_2$CH$_2$C(O)—N(piperazine)N—Me | 4,6-Dimethyl-5-methoxy-1-oxypyridin-3-yl |
| 746 | 12 | Cl | NH$_2$ | (CH$_2$)$_2$CONH$_2$ | 3,5-Dimethyl-4-methoxypyridin-2-yl |
| 747 | | Cl | NH$_2$ | (CH$_2$)$_2$CONH$_2$ | 3,5-Dimethyl-4-methoxy-1-oxypyridin-2-yl |
| 748 | | Cl | NH$_2$ | (CH$_2$)$_2$CONH$_2$ | 3,5-Dimethyl-4-bromopyridin-2-yl |
| 749 | | Cl | NH$_2$ | (CH$_2$)$_2$CONH$_2$ | 3,5-Dimethyl-4-bromo-1-oxypyridin-2-yl |
| 750 | | Cl | NH$_2$ | (CH$_2$)$_2$CONH$_2$ | 3,5-Dimethyl-4-chloropyridin-2-yl |
| 751 | | Cl | NH$_2$ | (CH$_2$)$_2$CONH$_2$ | 3,5-Dimethyl-4-chloro-1-oxypyridin-2-yl |
| 752 | | Cl | NH$_2$ | (CH$_2$)$_2$CONH$_2$ | 3,5-Dimethyl-4-iodopyridin-2-yl |
| 753 | | Cl | NH$_2$ | (CH$_2$)$_2$CONHBOC | 3,5-Dimethyl-4-methoxypyridin-2-yl |
| 754 | | Cl | NH$_2$ | (CH$_2$)$_2$CONHBOC | 3,5-Dimethyl-4-methoxy-1-oxypyridin-2-yl |
| 755 | | Cl | NH$_2$ | (CH$_2$)$_2$CONHBOC | 6-Bromo-3,5-dimethyl-4-methoxypyridin-2-yl |
| 756 | | Cl | NH$_2$ | (CH$_2$)$_2$CONHBOC | 6-Chloro-3,5-dimethyl-4-methoxypyridin-2-yl |
| 757 | | Cl | NH$_2$ | (CH$_2$)$_2$CONHBOC | 3,5-Dimethyl-4-bromopyridin-2-yl |
| 758 | | Cl | NH$_2$ | (CH$_2$)$_2$CONHBOC | 3,5-Dimethyl-4-bromo-1-oxypyridin-2-yl |
| 759 | | Cl | NH$_2$ | (CH$_2$)$_2$CONHBOC | 3,5-Dimethyl-4-chloropyridin-2-yl |
| 760 | | Cl | NH$_2$ | (CH$_2$)$_2$CONHBOC | 3,5-Dimethyl-4-chloro-1-oxypyridin-2-yl |
| 761 | | Cl | NH$_2$ | (CH$_2$)$_2$CONHBOC | 3,5-Dimethyl-4-iodopyridin-2-yl |
| 762 | | Cl | NH$_2$ | (CH$_2$)$_2$CONHBOC | 3,5-Dimethyl-4-iodo-1-oxypyridin-2-yl |
| 763 | | Cl | NH$_2$ | (CH$_2$)$_2$CONHBOC | 3,5-Dimethyl-4-thiomethyl-pyridin-2-yl |
| 764 | | Cl | NH$_2$ | (CH$_2$)$_2$CONHBOC | 3,5-Dimethyl-4-thiomethyl-1-oxypyridin-2-yl |
| 765 | | Cl | NH$_2$ | (CH$_2$)$_2$CONHBOC | 3,4,5-Trimethyl-pyridin-2-yl |
| 766 | | Cl | NH$_2$ | (CH$_2$)$_2$CONHBOC | 3,4,5-Trimethyl-1-oxypyridin-2-yl |
| 767 | | Cl | NH$_2$ | (CH$_2$)$_2$CONHBOC | 4,5,6-Trimethoxypyridin-2-yl |
| 768 | | Cl | NH$_2$ | (CH$_2$)$_2$CONHBOC | 4,5,6-Trimethoxy-1-oxypyridin-2-yl |
| 769 | | Cl | NH$_2$ | (CH$_2$)$_2$CONHBOC | 3-Bromo-4,5,6-trimethoxypyridin-2-yl |
| 770 | | Cl | NH$_2$ | (CH$_2$)$_2$CONHBOC | 3-Chloro-4,5,6-trimethoxypyridin-2-yl |
| 771 | | Cl | NH$_2$ | (CH$_2$)$_2$CONHBOC | 3,4,5-Trimethoxy-pyridin-2-yl |
| 772 | | Cl | NH$_2$ | (CH$_2$)$_2$CONHBOC | 3,4,5-Trimethoxy-1-oxypyridin-2-yl |
| 773 | | Cl | NH$_2$ | (CH$_2$)$_2$CONHBOC | 3-Bromo-3,4,5-trimethoxy-pyridin-2-yl |
| 774 | | Cl | NH$_2$ | (CH$_2$)$_2$CONHBOC | 3-Chloro-3,4,5-trimethoxy-pyridin-2-yl |
| 775 | | Cl | NH$_2$ | (CH$_2$)$_2$CONHBOC | 4,5,6-Trimethyl-pyridin-2-yl |
| 776 | | Cl | NH$_2$ | (CH$_2$)$_2$CONHBOC | 4,5,6-Trimethyl-1-oxypyridin-2-yl |
| 777 | | Cl | NH$_2$ | (CH$_2$)$_2$CONHBOC | 4,6-Dimethyl-5-methoxy-pyridin-2-yl |
| 778 | | Cl | NH$_2$ | (CH$_2$)$_2$CONHBOC | 4,6-Dimethyl-5-methoxypyridin-3-yl |
| 779 | | Cl | NH$_2$ | (CH$_2$)$_2$CONHBOC | 4,6-Dimethyl-5-methoxy-1-oxypyridin-3-yl |
| 780 | | Cl | NH$_2$ | (CH$_2$)$_2$CONHBOC | 4,6-Dimethyl-5-bromopyridin-3-yl |
| 781 | | Cl | NH$_2$ | (CH$_2$)$_2$CONHBOC | 4,6-Dimethyl-5-chloropyridin-3-yl |
| 782 | | Cl | NH$_2$ | (CH$_2$)$_2$CONHBOC | 5,6-Dimethyl-4-bromopyridin-3-yl |
| 783 | | Cl | NH$_2$ | (CH$_2$)$_2$CONHBOC | 5,6-Dimethyl-4-chloropyridin-3-yl |
| 784 | | Cl | NH$_2$ | (CH$_2$)$_2$CONHBOC | 2,6-Dimethyl-3-methoxypyridin-4-yl |
| 785 | | Cl | NH$_2$ | (CH$_2$)$_2$CONHBOC | 2,6-Dimethyl-pyridin-4-yl |
| 786 | | Cl | NH$_2$ | (CH$_2$)$_2$CONHBOC | 2,3,6-Trimethyl-pyridin-4-yl |
| 787 | | Cl | NH$_2$ | (CH$_2$)$_2$CONHBOC | 2,3,6-Trimethoxy-pyridin-4-yl |
| 788 | | Cl | NH$_2$ | (CH$_2$)$_2$CONHBOC | 2,6-Dimethyl-3-bromopyridin-4-yl |
| 789 | | Cl | NH$_2$ | (CH$_2$)$_2$CONHBOC | 2,6-Dimethyl-3-chloropyridin-4-yl |
| 790 | | Cl | NH$_2$ | (CH$_2$)$_2$CONHBOC | 2,6-Dimethyl-3-methoxy-1-oxy-pyridin-4-yl |
| 791 | | Cl | NH$_2$ | (CH$_2$)$_2$CONHBOC | 2,6-Dimethyl-1-oxy-pyridin-4-yl |
| 792 | | Cl | NH$_2$ | (CH$_2$)$_2$CONHBOC | 2,3,6-Trimethyl-1-oxy-pyridin-4-yl |

TABLE 1-continued

Exemplary Compounds based on Formula I

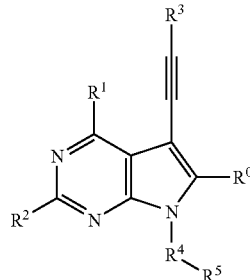

(I)

wherein R⁰ is H, and R⁴ is —CH₂—.

| No. | Ex | R¹ | R² | R³ | R⁵ |
|---|---|---|---|---|---|
| 793 | | Cl | NH₂ | (CH₂)₂CONHBOC | 2,3,6-Trimethoxy-1-oxy-pyridin-4-yl |
| 794 | | Cl | NH₂ | (CH₂)₂CONHBOC | 2,6-Dimethyl-3-bromo1-oxy-pyridin-4-yl |
| 795 | | Cl | NH₂ | (CH₂)₂CONHBOC | 2,6-Dimethyl-3-chloro1-oxy-pyridin-4-yl |
| 796 | | Cl | NH₂ | (CH₂)₂CONHBOC | 4,6-Dimethyl-5-iodopyridin-3-yl |
| 797 | | Cl | NH₂ | (CH₂)₂CONHBOC | 3,5-Dimethyl-4-aminopyridin-2-yl |
| 798 | | Cl | NH₂ | —CH₂CH₂—N(phthalimide) | 3,5-Dimethyl-4-methoxypyridin-2-yl |
| 799 | | Cl | NH₂ | —CH₂CH₂—N(phthalimide) | 3,5-Dimethyl-4-methoxy-1-oxypyridin-2-yl |
| 800 | | Cl | NH₂ | —CH₂CH₂—N(phthalimide) | 6-Bromo-3,5-dimethyl-4-methoxypyridin-2-yl |
| 801 | | Cl | NH₂ | —CH₂CH₂—N(phthalimide) | 6-Chloro-3,5-dimethyl-4-methoxypyridin-2-yl |
| 802 | | Cl | NH₂ | —CH₂CH₂—N(phthalimide) | 3,5-Dimethyl-4-bromopyridin-2-yl |
| 803 | | Cl | NH₂ | —CH₂CH₂—N(phthalimide) | 3,5-Dimethyl-4-bromo-1-oxypyridin-2-yl |

TABLE 1-continued

Exemplary Compounds based on Formula I

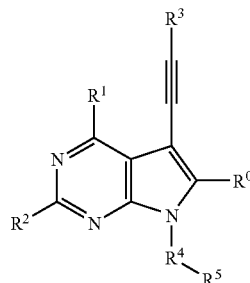

wherein $R^0$ is H, and $R^4$ is —$CH_2$—.

| No. | Ex | $R^1$ | $R^2$ | $R^3$ | $R^5$ |
|---|---|---|---|---|---|
| 804 | | Cl | $NH_2$ | —CH₂CH₂—N(phthalimide) | 3,5-Dimethyl-4-chloropyridin-2-yl |
| 805 | | Cl | $NH_2$ | —CH₂CH₂—N(phthalimide) | 3,5-Dimethyl-4-chloro-1-oxypyridin-2-yl |
| 806 | | Cl | $NH_2$ | —CH₂CH₂—N(phthalimide) | 3,5-Dimethyl-4-iodopyridin-2-yl |
| 807 | | Cl | $NH_2$ | —CH₂CH₂—N(phthalimide) | 3,5-Dimethyl-4-iodo-1-oxypyridin-2-yl |
| 808 | | Cl | $NH_2$ | —CH₂CH₂—N(phthalimide) | 3,5-Dimethyl-4-thiomethyl-pyridin-2-yl |
| 809 | | Cl | $NH_2$ | —CH₂CH₂—N(phthalimide) | 3,5-Dimethyl-4-thiomethyl-1-oxypyridin-2-yl |

TABLE 1-continued

Exemplary Compounds based on Formula I

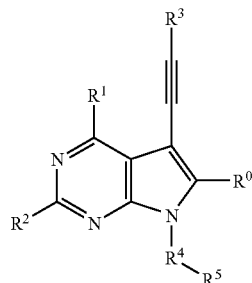

wherein $R^0$ is H, and $R^4$ is —$CH_2$—.

| No. | Ex | $R^1$ | $R^2$ | $R^3$ | $R^5$ |
|---|---|---|---|---|---|
| 810 | | Cl | $NH_2$ | —$CH_2CH_2$—phthalimide | 3,4,5-Trimethyl-pyridin-2-yl |
| 811 | | Cl | $NH_2$ | —$CH_2CH_2$—phthalimide | 3,4,5-Trimethyl-1-oxypyridin-2-yl |
| 812 | | Cl | $NH_2$ | —$CH_2CH_2$—phthalimide | 4,5,6-Trimethoxypyridin-2-yl |
| 813 | | Cl | $NH_2$ | —$CH_2CH_2$—phthalimide | 4,5,6-Trimethoxy-1-oxypyridin-2-yl |
| 814 | | Cl | $NH_2$ | —$CH_2CH_2$—phthalimide | 3-Bromo-4,5,6-trimethoxypyridin-2-yl |
| 815 | | Cl | $NH_2$ | —$CH_2CH_2$—phthalimide | 3-Chloro-4,5,6-trimethoxypyridin-2-yl |

TABLE 1-continued

Exemplary Compounds based on Formula I

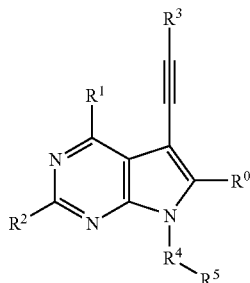

wherein $R^0$ is H, and $R^4$ is —$CH_2$—.

| No. | Ex | $R^1$ | $R^2$ | $R^3$ | $R^5$ |
|---|---|---|---|---|---|
| 816 | | Cl | $NH_2$ | —$CH_2CH_2$—N(phthalimide) | 3,4,5-Trimethoxy-pyridin-2-yl |
| 817 | | Cl | $NH_2$ | —$CH_2CH_2$—N(phthalimide) | 3,4,5-Trimethoxy-1-oxypyridin-2-yl |
| 818 | | Cl | $NH_2$ | —$CH_2CH_2$—N(phthalimide) | 3-Bromo-3,4,5-trimethoxy-pyridin-2-yl |
| 819 | | Cl | $NH_2$ | —$CH_2CH_2$—N(phthalimide) | 3-Chloro-3,4,5-trimethoxy-pyridin-2-yl |
| 820 | | Cl | $NH_2$ | —$CH_2CH_2$—N(phthalimide) | 4,5,6-Trimethyl-pyridin-2-yl |
| 821 | | Cl | $NH_2$ | —$CH_2CH_2$—N(phthalimide) | 4,5,6-Trimethyl-1-oxypyridin-2-yl |

TABLE 1-continued

Exemplary Compounds based on Formula I

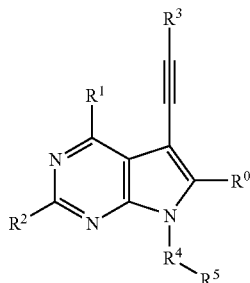

(I)

wherein $R^0$ is H, and $R^4$ is $-CH_2-$.

| No. | Ex | $R^1$ | $R^2$ | $R^3$ | $R^5$ |
|---|---|---|---|---|---|
| 822 | | Cl | $NH_2$ | —CH₂CH₂—N(phthalimide) | 4,6-Dimethyl-5-methoxy-pyridin-2-yl |
| 823 | | Cl | $NH_2$ | —CH₂CH₂—N(phthalimide) | 4,6-Dimethyl-5-methoxypyridin-3-yl |
| 824 | | Cl | $NH_2$ | —CH₂CH₂—N(phthalimide) | 4,6-Dimethyl-5-methoxy-1-oxypyridin-3-yl |
| 825 | | Cl | $NH_2$ | —CH₂CH₂—N(phthalimide) | 4,6-Dimethyl-5-bromopyridin-3-yl |
| 826 | | Cl | $NH_2$ | —CH₂CH₂—N(phthalimide) | 4,6-Dimethyl-5-chloropyridin-3-yl |
| 827 | | Cl | $NH_2$ | —CH₂CH₂—N(phthalimide) | 5,6-Dimethyl-4-bromopyridin-3-yl |

TABLE 1-continued

Exemplary Compounds based on Formula I

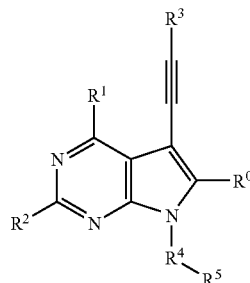

wherein $R^0$ is H, and $R^4$ is —$CH_2$—.

| No. | Ex | $R^1$ | $R^2$ | $R^3$ | $R^5$ |
|---|---|---|---|---|---|
| 828 | | Cl | $NH_2$ | —$CH_2CH_2$—phthalimide | 5,6-Dimethyl-4-chloropyridin-3-yl |
| 829 | | Cl | $NH_2$ | —$CH_2CH_2$—phthalimide | 2,6-Dimethyl-3-methoxypyridin-4-yl |
| 830 | | Cl | $NH_2$ | —$CH_2CH_2$—phthalimide | 2,6-Dimethyl-pyridin-4-yl |
| 831 | | Cl | $NH_2$ | —$CH_2CH_2$—phthalimide | 2,3,6-Trimethyl-pyridin-4-yl |
| 832 | | Cl | $NH_2$ | —$CH_2CH_2$—phthalimide | 2,3,6-Trimethoxy-pyridin-4-yl |
| 833 | | Cl | $NH_2$ | —$CH_2CH_2$—phthalimide | 2,6-Dimethyl-3-bromopyridin-4-yl |

TABLE 1-continued

Exemplary Compounds based on Formula I

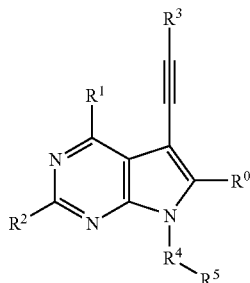

(I)

wherein $R^0$ is H, and $R^4$ is —$CH_2$—.

| No. | Ex | $R^1$ | $R^2$ | $R^3$ | $R^5$ |
|---|---|---|---|---|---|
| 834 | | Cl | $NH_2$ | —CH₂CH₂—N(phthalimido) | 2,6-Dimethyl-3-chloropyridin-4-yl |
| 835 | | Cl | $NH_2$ | —CH₂CH₂—N(phthalimido) | 2,6-Dimethyl-3-methoxy-1-oxypyridin-4-yl |
| 836 | | Cl | $NH_2$ | —CH₂CH₂—N(phthalimido) | 2,6-Dimethyl-1-oxy-pyridin-4-yl |
| 837 | | Cl | $NH_2$ | —CH₂CH₂—N(phthalimido) | 2,3,6-Trimethyl-1-oxypyridin-4-yl |
| 838 | | Cl | $NH_2$ | —CH₂CH₂—N(phthalimido) | 2,3,6-Trimethoxy-1-oxypyridin-4-yl |
| 839 | | Cl | $NH_2$ | —CH₂CH₂—N(phthalimido) | 2,6-Dimethyl-3-bromo1-oxypyridin-4-yl |

TABLE 1-continued

Exemplary Compounds based on Formula I

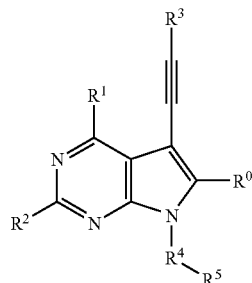

wherein $R^0$ is H, and $R^4$ is —$CH_2$—.

| No. | Ex | $R^1$ | $R^2$ | $R^3$ | $R^5$ |
|---|---|---|---|---|---|
| 840 | | Cl | $NH_2$ | —CH$_2$CH$_2$—phthalimide | 2,6-Dimethyl-3-chloro1-oxypyridin-4-yl |
| 841 | | Cl | $NH_2$ | —CH$_2$CH$_2$—phthalimide | 4,6-Dimethyl-5-iodopyridin-3-yl |
| 842 | | Cl | $NH_2$ | —CH$_2$CH$_2$—phthalimide | 3,5-Dimethyl-4-aminopyridin-2-yl |
| 843 | | Cl | $NH_2$ | —CH$_2$—phthalimide | 3,5-Dimethyl-4-methoxypyridin-2-yl |
| 844 | | Cl | $NH_2$ | —CH$_2$—phthalimide | 3,5-Dimethyl-4-methoxy-1-oxypyridin-2-yl |
| 845 | | Cl | $NH_2$ | —CH$_2$—phthalimide | 6-Bromo-3,5-dimethyl-4-methoxypyridin-2-yl |

TABLE 1-continued

Exemplary Compounds based on Formula I

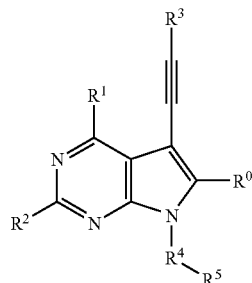

wherein $R^0$ is H, and $R^4$ is —CH$_2$—.

| No. | Ex | $R^1$ | $R^2$ | $R^3$ | $R^5$ |
|---|---|---|---|---|---|
| 846 | | Cl | NH$_2$ | —CH$_2$—N(phthalimide) | 6-Chloro-3,5-dimethyl-4-methoxypyridin-2-yl |
| 847 | | Cl | NH$_2$ | —CH$_2$—N(phthalimide) | 3,5-Dimethyl-4-bromopyridin-2-yl |
| 848 | | Cl | NH$_2$ | —CH$_2$—N(phthalimide) | 3,5-Dimethyl-4-bromo-1-oxypyridin-2-yl |
| 849 | | Cl | NH$_2$ | —CH$_2$—N(phthalimide) | 3,5-Dimethyl-4-chloropyridin-2-yl |
| 850 | | Cl | NH$_2$ | —CH$_2$—N(phthalimide) | 3,5-Dimethyl-4-chloro-1-oxypyridin-2-yl |
| 851 | | Cl | NH$_2$ | —CH$_2$—N(phthalimide) | 3,5-Dimethyl-4-iodopyridin-2-yl |

TABLE 1-continued

Exemplary Compounds based on Formula I

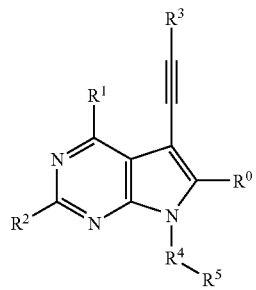

wherein $R^0$ is H, and $R^4$ is —$CH_2$—.

| No. | Ex | $R^1$ | $R^2$ | $R^3$ | $R^5$ |
|---|---|---|---|---|---|
| 852 | | Cl | $NH_2$ | —$CH_2$—phthalimide | 3,5-Dimethyl-4-iodo-1-oxypyridin-2-yl |
| 853 | | Cl | $NH_2$ | —$CH_2$—phthalimide | 3,5-Dimethyl-4-thiomethyl-pyridin-2-yl |
| 854 | | Cl | $NH_2$ | —$CH_2$—phthalimide | 3,5-Dimethyl-4-thiomethyl-1-oxypyridin-2-yl |
| 855 | | Cl | $NH_2$ | —$CH_2$—phthalimide | 3,4,5-Trimethyl-pyridin-2-yl |
| 856 | | Cl | $NH_2$ | —$CH_2$—phthalimide | 3,4,5-Trimethyl-1-oxypyridin-2-yl |
| 857 | | Cl | $NH_2$ | —$CH_2$—phthalimide | 4,5,6-Trimethoxypyridin-2-yl |

TABLE 1-continued

Exemplary Compounds based on Formula I

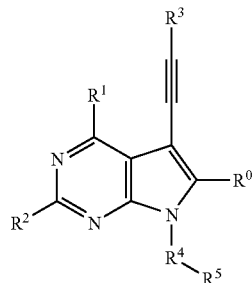

(I)

wherein R⁰ is H, and R⁴ is —CH₂—.

| No. | Ex | R¹ | R² | R³ | R⁵ |
|---|---|---|---|---|---|
| 858 | | Cl | NH₂ | —CH₂—N(phthalimide) | 4,5,6-Trimethoxy-1-oxypyridin-2-yl |
| 859 | | Cl | NH₂ | —CH₂—N(phthalimide) | 3-Bromo-4,5,6-trimethoxypyridin-2-yl |
| 860 | | Cl | NH₂ | —CH₂—N(phthalimide) | 3-Chloro-4,5,6-trimethoxypyridin-2-yl |
| 861 | | Cl | NH₂ | —CH₂—N(phthalimide) | 4,6-Dimethyl-5-methoxypyridin-3-yl |
| 862 | | Cl | NH₂ | —CH₂—N(phthalimide) | 4,6-Dimethyl-5-methoxy-1-oxypyridin-3-yl |
| 863 | | Br | NH₂ | (CH₂)OH | 3,5-Dimethyl-4-methoxypyridin-2-yl |
| 864 | | Br | NH₂ | (CH₂)₂OH | 3,5-Dimethyl-4-methoxypyridin-2-yl |
| 865 | | Br | NH₂ | (CH₂)₃OH | 3,5-Dimethyl-4-methoxypyridin-2-yl |
| 866 | | Br | NH₂ | —CH₂—N(morpholino) | 3,5-Dimethyl-4-methoxypyridin-2-yl |
| 867 | | Br | NH₂ | —CH₂CH₂—N(morpholino) | 3,5-Dimethyl-4-methoxypyridin-2-yl |

TABLE 1-continued

Exemplary Compounds based on Formula I

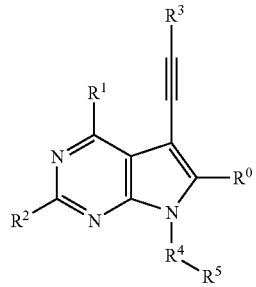

(I)

wherein $R^0$ is H, and $R^4$ is —CH$_2$—.

| No. | Ex | $R^1$ | $R^2$ | $R^3$ | $R^5$ |
|---|---|---|---|---|---|
| 868 | | Br | NH$_2$ | —CH$_2$CH$_2$CH$_2$—N(morpholino) | 3,5-Dimethyl-4-methoxypyridin-2-yl |
| 869 | | Br | NH$_2$ | (CH$_2$)OH | 3,5-Dimethyl-4-iodopyridin-2-yl |
| 870 | | Br | NH$_2$ | (CH$_2$)$_2$OH | 3,5-Dimethyl-4-iodopyridin-2-yl |
| 871 | | Br | NH$_2$ | (CH$_2$)$_3$OH | 3,5-Dimethyl-4-iodopyridin-2-yl |
| 872 | | Br | NH$_2$ | —CH$_2$—N(morpholino) | 3,5-Dimethyl-4-iodopyridin-2-yl |
| 873 | | Br | NH$_2$ | —CH$_2$CH$_2$—N(morpholino) | 3,5-Dimethyl-4-iodopyridin-2-yl |
| 874 | | Br | NH$_2$ | —CH$_2$CH$_2$CH$_2$—N(morpholino) | 3,5-Dimethyl-4-iodopyridin-2-yl |
| 875 | | Cl | NH$_2$ | —CH$_2$—N(phthalimido) | 3,5-Dimethyl-4-methoxypyridin-2-yl |
| 876 | | Cl | NH$_2$ | —CH$_2$CH$_2$CH$_2$—N(morpholino) | 2-Chloro-4,5-dimethoxylphenyl |
| 877 | | Cl | NH$_2$ | —CH$_2$CH$_2$CH$_2$—N(morpholino) | 2-Nitro-4,5-dimethoxylphenyl |
| 878 | | Cl | NH$_2$ | —CH$_2$CH$_2$CH$_2$—N(morpholino) | 3,4-Dichlorophenyl |
| 879 | | Cl | NH$_2$ | —CH$_2$CH$_2$CH$_2$—N(morpholino) | 3,5-Dimethoxylphenyl |
| 880 | | Cl | NH$_2$ | —CH$_2$CH$_2$CH$_2$—N(morpholino) | 2,5-Dimethoxylphenyl |

TABLE 1-continued

Exemplary Compounds based on Formula I

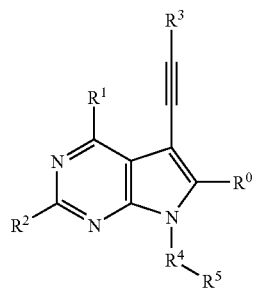
(I)

wherein $R^0$ is H, and $R^4$ is —$CH_2$—.

| No. | Ex | $R^1$ | $R^2$ | $R^3$ | $R^5$ |
|---|---|---|---|---|---|
| 881 | | Cl | $NH_2$ | —$CH_2CH_2CH_2$—N(morpholine) | 3,5-Dimethoxyphenyl |
| 882 | | Cl | $NH_2$ | —$CH_2CH_2CH_2$—N(morpholine) | 3-Methoxyphenyl |
| 883 | | Cl | $NH_2$ | —$CH_2CH_2CH_2$—N(morpholine) | 4-Methoxyphenyl |
| 884 | | Cl | —NH-C(O)-C(CH$_3$)$_3$ | $(CH_2)_2OH$ | 3,5-Dimethyl-4-iodopyridin-2-yl |
| 885 | | Cl | —NH-C(O)-C(CH$_3$)$_3$ | $(CH_2)_3OH$ | 3,5-Dimethyl-4-iodopyridin-2-yl |
| 886 | | Cl | —NH-C(O)-C(CH$_3$)$_3$ | —$CH_2CH_2$—N(morpholine) | 3,5-Dimethyl-4-iodopyridin-2-yl |
| 887 | | Cl | —NH-C(O)-C(CH$_3$)$_3$ | —$CH_2CH_2CH_2$—N(morpholine) | 3,5-Dimethyl-4-iodopyridin-2-yl |
| 888 | | Cl | —NH-C(O)-C(CH$_3$)$_3$ | $(CH_2)OH$ | 3,5-Dimethyl-4-methoxypyridin-2-yl |
| 889 | | Cl | —NH-C(O)-C(CH$_3$)$_3$ | $(CH_2)_2OH$ | 3,5-Dimethyl-4-methoxypyridin-2-yl |

TABLE 1-continued

Exemplary Compounds based on Formula I

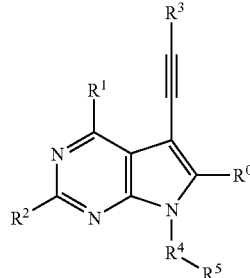

(I)

wherein $R^0$ is H, and $R^4$ is —$CH_2$—.

| No. | Ex | $R^1$ | $R^2$ | $R^3$ | $R^5$ |
|---|---|---|---|---|---|
| 890 | | Cl | ![pivaloylamino] | $(CH_2)_3OH$ | 3,5-Dimethyl-4-methoxypyridin-2-yl |
| 891 | | Cl | ![pivaloylamino] | —$CH_2$—morpholino | 3,5-Dimethyl-4-methoxypyridin-2-yl |
| 892 | | Cl | ![pivaloylamino] | —$CH_2CH_2$—morpholino | 3,5-Dimethyl-4-methoxypyridin-2-yl |
| 893 | | Cl | ![pivaloylamino] | —$CH_2CH_2CH_2$—morpholino | 3,5-Dimethyl-4-methoxypyridin-2-yl |
| 894 | 4 | Cl | $NH_2$ | $CH_2N(i\text{-}Bu)_2$ | 3,5-Dimethyl-4-methoxypyridin-2-yl |
| 895 | 5 | Cl | $NH_2$ | $CH_2N(i\text{-}Bu)_2$ | 3,5-Dimethyl-4-methoxypyridin-2-yl |
| 896 | 7 | Cl | $NH_2$ | $(CH_2)_4OH$ | 3,5-Dimethyl-4-methoxypyridin-2-yl |
| 897 | 8 | Cl | $NH_2$ | $Si(CH_3)_3$ | 3,5-Dimethyl-4-methoxypyridin-2-yl |
| 898 | 9 | Cl | $NH_2$ | $(CH_2)_2CO_2H$ | 3,5-Dimethyl-4-methoxypyridin-2-yl |
| 899 | 10 | Cl | $NH_2$ | $(CH_2)_2CON(Et)_2$ | 3,5-Dimethyl-4-methoxypyridin-2-yl |
| 900 | 13 | Cl | $NH_2$ | $CH_2NHCOOtBu$ | 3,5-Dimethyl-4-methoxypyridin-2-yl |
| 901 | 14 | Cl | $NH_2$ | $CH_2NH_2$ | 3,5-Dimethyl-4-methoxypyridin-2-yl |
| 902 | | Cl | $NH_2$ | $CH_2NH_2$ | 3,5-Dimethyl-4-methoxy-1-oxypyridin-2-yl |
| 903 | | Cl | $NH_2$ | $CH_2NH_2$ | 3,5-Dimethyl-4-bromopyridin-2-yl |
| 904 | | Cl | $NH_2$ | $CH_2NH_2$ | 3,5-Dimethyl-4-bromo-1-oxypyridin-2-yl |
| 905 | | Cl | $NH_2$ | $CH_2NH_2$ | 3,5-Dimethyl-4-chloropyridin-2-yl |
| 906 | | Cl | $NH_2$ | $CH_2NH_2$ | 3,5-Dimethyl-4-chloro-1-oxypyridin-2-yl |
| 907 | | Cl | $NH_2$ | $CH_2NH_2$ | 3,5-Dimethyl-4-iodopyridin-2-yl |
| 908 | | Cl | $NH_2$ | $CH_2NH_2$ | 3,5-Dimethyl-4-iodo-1-oxypyridin-2-yl |
| 909 | | Cl | $NH_2$ | $CH_2NH_2$ | 3,5-Dimethyl-4-thiomethyl-pyridin-2-yl |
| 910 | | Cl | $NH_2$ | $CH_2NH_2$ | 3,5-Dimethyl-4-thiomethyl-1-oxypyridin-2-yl |
| 911 | | Cl | $NH_2$ | $CH_2NH_2$ | 3,4,5-Trimethyl-pyridin-2-yl |
| 912 | | Cl | $NH_2$ | $CH_2NH_2$ | 3,4,5-Trimethyl-1-oxypyridin-2-yl |
| 913 | | Cl | $NH_2$ | $CH_2NH_2$ | 4,5,6-Trimethoxypyridin-2-yl |
| 914 | | Cl | $NH_2$ | $CH_2NH_2$ | 4,5,6-Trimethoxy-1-oxypyridin-2-yl |
| 915 | | Cl | $NH_2$ | $CH_2NH_2$ | 3,4,5-Trimethoxy-pyridin-2-yl |
| 916 | | Cl | $NH_2$ | $CH_2NH_2$ | 3,4,5-Trimethoxy-1-oxypyridin-2-yl |
| 917 | | Cl | $NH_2$ | $CH_2NH_2$ | 4,5,6-Trimethyl-pyridin-2-yl |
| 918 | | Cl | $NH_2$ | $CH_2NH_2$ | 4,5,6-Trimethyl-1-oxypyridin-2-yl |
| 919 | | Cl | $NH_2$ | $CH_2NH_2$ | 4,6-Dimethyl-5-methoxy-pyridin-2-yl |
| 920 | | Cl | $NH_2$ | $CH_2NH_2$ | 4,6-Dimethyl-5-methoxypyridin-3-yl |
| 921 | | Cl | $NH_2$ | $CH_2NH_2$ | 4,6-Dimethyl-5-methoxy-1-oxypyridin-3-yl |
| 922 | | Cl | $NH_2$ | $CH_2NH_2$ | 4,6-Dimethyl-5-bromopyridin-3-yl |
| 923 | | Cl | $NH_2$ | $CH_2NH_2$ | 4,6-Dimethyl-5-chloropyridin-3-yl |
| 924 | | Cl | $NH_2$ | $CH_2NH_2$ | 5,6-Dimethyl-4-bromopyridin-3-yl |

TABLE 1-continued

Exemplary Compounds based on Formula I

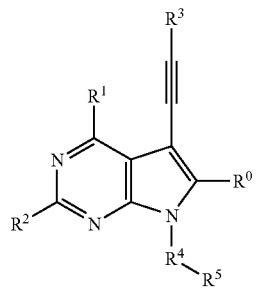

(I)

wherein $R^0$ is H, and $R^4$ is —$CH_2$—.

| No. | Ex | $R^1$ | $R^2$ | $R^3$ | $R^5$ |
|---|---|---|---|---|---|
| 925 | | Cl | $NH_2$ | $CH_2NH_2$ | 5,6-Dimethyl-4-chloropyridin-3-yl |
| 926 | | Cl | $NH_2$ | $CH_2NH_2$ | 2,6-Dimethyl-3-methoxypyridin-4-yl |
| 927 | | Cl | $NH_2$ | $CH_2NH_2$ | 2,6-Dimethyl-pyridin-4-yl |
| 928 | | Cl | $NH_2$ | $CH_2NH_2$ | 2,3,6-Trimethyl-pyridin-4-yl |
| 929 | | Cl | $NH_2$ | $CH_2NH_2$ | 2,3,6-Trimethoxy-pyridin-4-yl |
| 930 | | Cl | $NH_2$ | $CH_2NH_2$ | 2,6-Dimethyl-3-bromopyridin-4-yl |
| 931 | | Cl | $NH_2$ | $CH_2NH_2$ | 2,6-Dimethyl-3-chloropyridin-4-yl |
| 932 | | Cl | $NH_2$ | $CH_2NH_2$ | 4,6-Dimethyl-5-iodopyridin-3-yl |
| 933 | | Cl | $NH_2$ | $CH_2NH_2$ | 3,5-Dimethyl-4-aminopyridin-2-yl |
| 934 | 15 | Cl | $NH_2$ | $(CH_2)_3NHCOOtBu$ | 3,5-Dimethyl-4-methoxypyridin-2-yl |
| 935 | 16 | Cl | $NH_2$ | $(CH_2)_3NH_2$ | 3,5-Dimethyl-4-methoxypyridin-2-yl |
| 936 | 17 | Cl | $NH_2$ | —$CH_2CH_2CH_2$—N(phthalimide) | 3,5-Dimethyl-4-methoxypyridin-2-yl |
| 937 | 20 | Cl | $NH_2$ | $(CH_2)_2NHtBu$ | 3,5-Dimethyl-4-methoxypyridin-2-yl |
| 938 | 21 | Cl | $NH_2$ | $(CH_2)_2NHtBu$ | 3,5-Dimethyl-4-methoxypyridin-2-yl |
| 939 | 22 | Cl | $NH_2$ | $CH_2OCOCH_2NMe_2$ | 3,5-Dimethyl-4-methoxypyridin-2-yl |
| 940 | | Cl | $NH_2$ | $CH_2CH(OH)CH_3$ | 3,5-Dimethyl-4-methoxypyridin-2-yl |
| 941 | | Cl | $NH_2$ | $CH_2C(O)CH_3$ | 3,5-Dimethyl-4-methoxypyridin-2-yl | wherein each abbreviation has its usual meaning, which would be known to one of skill in the chemical arts, i.e. Me = methyl; Et = ethyl; Pr = propyl; i-Pr = iso-propyl; Bu = butyl; i-Bu = iso-butyl; tBu = tert-butyl; Ph = phenyl; BOC = tert-butoxycarbonyl; 2-Py = 2-pyridyl; 3-Py = 3-pyridyl; 4-Py = 4-pyridyl.

Selected compounds in TABLE 1 are compounds 2, 3, 4, 7, 8, 12, 13, 17, 18, 22, 23, 27, 28, 32, 33, 38, 42, 43, 47, 48, 52, 53, 57, 58, 62, 63, 67, 68, 72, 73, 77, 78, 82, 83, 87, 88, 92, 93, 102, 103, 107, 108, 112, 113, 117, 118, 122, 123, 127, 128, 132, 133, 137, 138, 147, 148, 152, 153, 157, 158, 161, 162, 166, 167, 171, 172, 176, 177, 181, 182, 186, 187, 191, 192, 196, 197, 201, 202, 206, 207, 211, 212, 216, 217, 221, 222, 226, 227, 231, 232, 236, 237, 240, 241, 244, 246, 248, 265, 266, 285, 289, 291, 293, 310, 311, 330, 331, 332, 334, 349, 350, 363, 364, 365, 367, 369, 382, 383, 396, 397, 398, 400, 402, 415, 416, 429, 430, 431, 433, 435, 448, 449, 462, 463, 464, 466, 468, 481, 482, 495, 496, 497, 499, 501, 514, 515, 528, 529, 530, 532, 534, 547, 548, 560, 561, 652, 566, 587, 588, 590, 591, 592, 594, 596, 602, 603, 620, 621, 622, 624, 626, 632, 633, 635, 636, 637, 639, 641, 661, 662, 663, 664, 665, 667, 669, 675, 676, 678, 679, 680, 682, 684, 690, 691, 692, 693, 694, 696, 698, 704, 705, 707, 708, 710, 711, 713, 714, 716, 717, 718, 719, 720, 722, 730, 731, 732, 733, 734, 736, 738, 744, 745, 746, 747, 748, 750, 752, 753, 754, 757, 759, 761, 778, 779, 782, 783, 784, 798, 799, 802, 804, 806, 823, 824, 843, 844, 847, 849, 851, 861, 862, 863, 864, 865, 866, 867, 868, 869, 870, 875, 894, 895, 896, 899, 900, 901, 903, 905, 907, 920, 921, 934, 935, 936, 937, 938, 939, 940, and 941. Further selected compounds are 77, 78, 82, 83, 87, 88, 92, 93, 240, 241, 248, 265, 285, 293, 310, 330, 349, 382, 396, 415, 429, 448, 462, 481, 495, 514, 528, 560, 587, 602, 620, 632, 635, 661, 663, 675, 678, 690, 692, 704, 718, 730, 732, 744, 746, 753, 778, 798, 823, 863, 864, 865, 866, 867, 868, 869, 875, 894, 895, 896, 899, 900, 901, 903, 905, 920, 934, 935, 936, 940, and 941.

Compounds of the invention exhibit improved HSP90 inhibiting activities over some pyrrolo[2,3-d]pyrimidine compounds of Formula II:

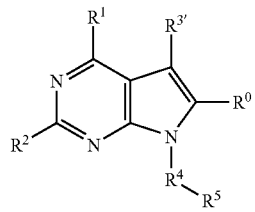
(II)

wherein R³' is not alkynyl, which were disclosed in U.S. patent application Ser. No. 10/945,851 and PCT Application US04/31248. The pyrrolopyrimidine compounds specified in the EXAMPLE sections of the above patent applications carry either no substituent or a substituted alkyl group. Compound 0, one of the embodiments of the compounds of Formula II, carries no substitutents on the C-5 position (ie R³'=H) and it has an IC$_{50}$=98 nM as measured by a Her-2 degradation assay (described in EXAMPLE section below). A simple alkyl or a substituted alkyl at C-5 (ie R³'=alkyl or substituted alkyl) can only bring two-fold additional activity. Conversely, if C-5 is alkyne substituted, the potency increases approximately 10-20 fold. (See, Series A: compounds A, B, C and D below).

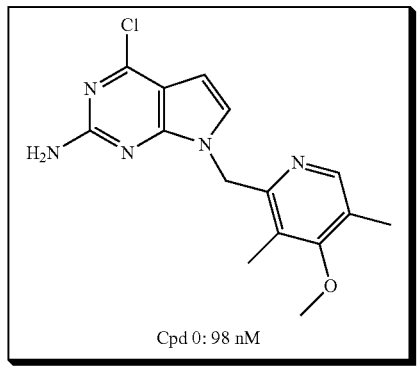

Cpd 0: 98 nM

Series A: Non-Alkynes

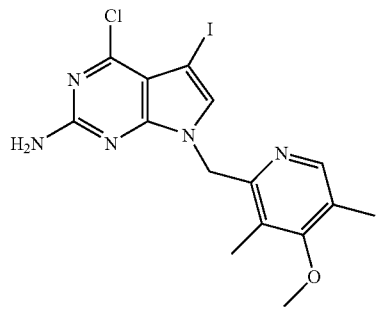

Cpd A: 50 nM

-continued

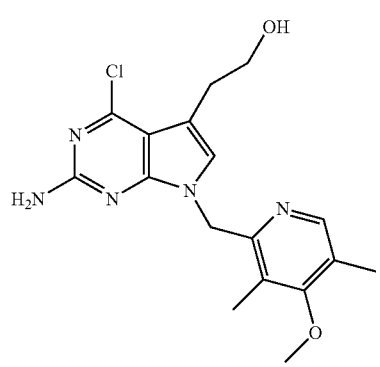

Cpd B: 70 nM

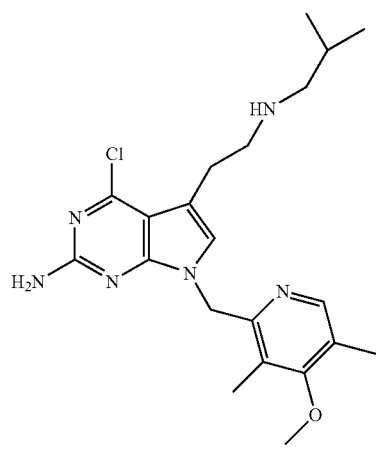

Cpd C: 100 nM

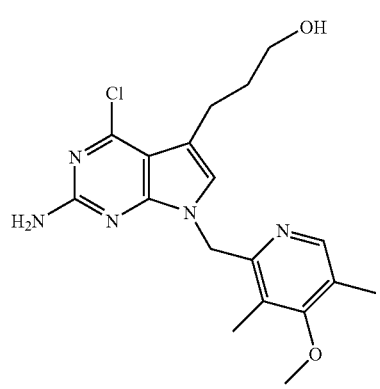

Cpd D: 38 nM

Series B: Alkynes

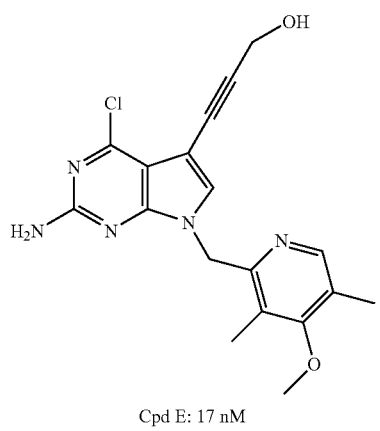

Cpd E: 17 nM

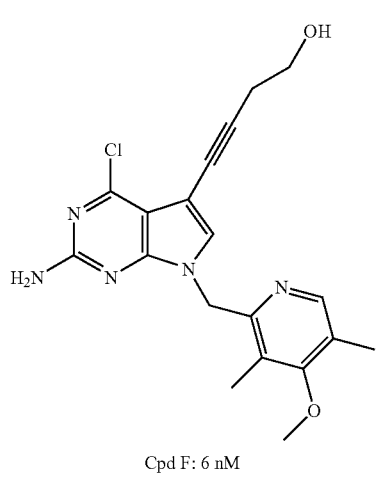

Cpd F: 6 nM

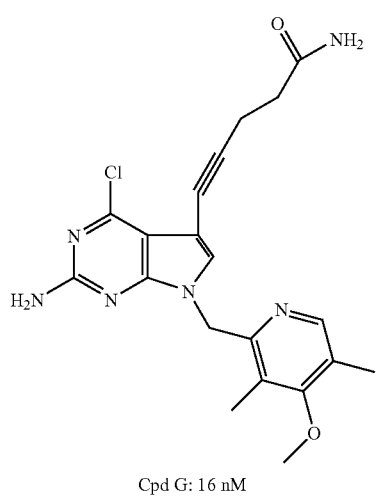

Cpd G: 16 nM

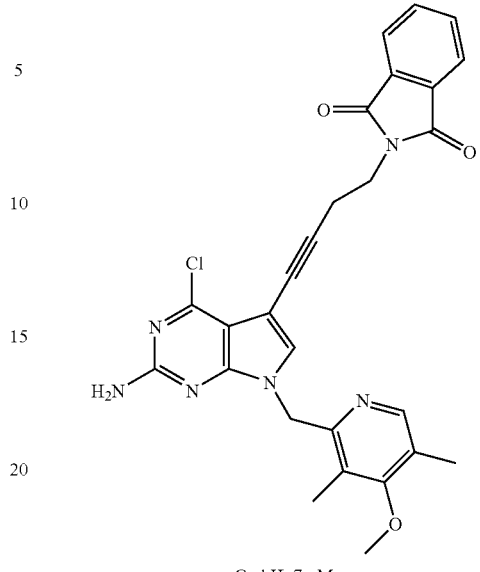

Cpd H: 7 nM

For example, the alkynyl substutuents at the C-5 position (see Series B: Cpds E, F, G and H), showed an potency range of 6-17 nM an improvement of at least tenfold over the parent Compound 0. Further, when two compounds having exactly the same structure, except for the presence of a triple vs. single bond, e.g. comparing Compound D to Compound E, Compound E which has a propargylic alcohol substituted on C-5 has an $IC_{50}$=17 nM, while Compound D which has a propanol substituent on C-5 has an $IC_{50}$=38 nM, a two-fold improvement. The difference in potency index beween alkynes and non-alkynes measured by a secondary assay is also striking. The secondary assay measures the efficiency of killing tumor cells. For a given compound, the the potency index is defined as:

Index=$EC_{50}$(compound)/$EC_{50}$(control)

where the control is 17-AAG (17-allyl-17-desmethoxy-geldanamycin). $EC_{50}$ is defined as the amount of compound added to effect a 50% reduction in viable cell number. Selected compounds were tested on cells of MCF7 and BT474 breast tumor cell lines. The assay shows that Compound 0 is over 10 times less active than 17-AAG. The best non-alkyne substituted analogs are 6 to >50 times less potent than 17-AAG. In contrast, the alkyne substituted analogs can be more potent than 17-AAG (see Cpd. H)—a record in the field of HSP90 inhibitors, or nearly as active, with an index between 0.7-6. TABLE 2 summarized the result of the assay.

TABLE 2

Potency Index against Tumor Cells from MCF 7 and BT474 Cell Lines

| Compound | Subsitutent @ C-5 | MCF7 Index (µM) | BT474 Index (µM) |
|---|---|---|---|
| 0 | none | 0.4 | 0.3 |
| A | non-alkyne | 0.2 | 1.0 |
| B | non-alkyne | 0.08 | 0.3 |
| C | non-alkyne | 0.6 | 0.3 |
| D | non-alkyne | 0.23 | 1.0 |
| E | alkyne | 0.13 | 0.02 |
| F | alkyne | 0.006 | 0.13 |

TABLE 2-continued

Potency Index against Tumor Cells from MCF 7 and BT474 Cell Lines

| Compound | Subsitutent @ C-5 | MCF7 Index (μM) | BT474 Index (μM) |
|---|---|---|---|
| G | alkyne | 0.03 | 0.02 |
| H | alkyne | 0.01 | 0.1 |

Synthesis of the Compounds of the Invention

The compounds of the present invention may be prepared from 5-halo-pyrolo[2,3-d]pyrimidines according to Scheme A below. The preparation of the starting material, N-(4-chloro-5-iodo-7H-pyrrolo[2,3-d]pyrimidin-2-yl)pivalamide, wherein PG is the pivaloyl protecting group and X=I, has been reported in Seela, F. *Synthesis* 2004, 8, 1203 and references therein.

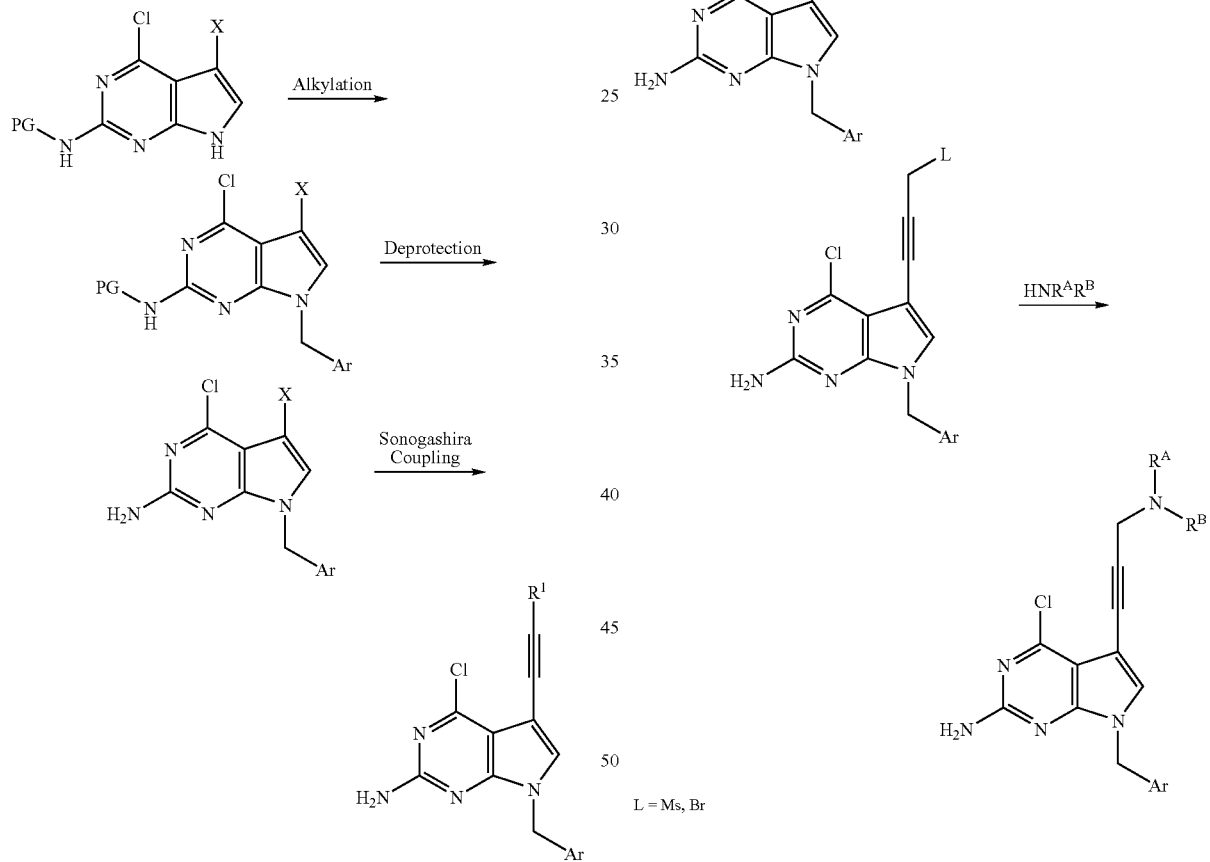

PG = Protecting Group
X = Halogen
Ar = aryl or heteroayl

Treatment of N-(4-chloro-5-iodo-7H-pyrrolo[2,3-d]pyrimidin-2-yl)pivalamide with the appropriate alkylating agent in a polar solvent (e.g. DMF, DMSO, NMP), in the presence of a base (e.g. $K_2CO_3$, $C_2CO_3$, NaH, NaOH, t-BuOH) affords the N(7)-alkylated adduct. The alkylation is typically run at 20-60° C. for 0.5-24 h.

Cleavage of the $NH_2$ protecting group gives the 2-amino derivative. If the protecting group is a pivaloyl group, it can be cleaved with $ZnCl_2$. The depivaloylation is typically run in EtOH, with 1-10 vol % of water, at 50-85° C., for 2-24 h. Zinc (II) chloride can be substituted with other Lewis acids, such as $ZnI_2$ or CuCl which, however, may not give yields as high.

Sonogasira coupling of 4-chloro-7-alkyl-5-halo-7H-pyrrolo[2,3-d]pyrimidin-2-amine with an alkyne of Formula $HC\equiv C-R^1$ gives the desired alkyne. Typical reaction conditions require $Pd(PPh_3)_4$/CuI as catalytic system, $Et_3N$ as base, and DCM or DMF as solvent. The reactions are typically run at 20-50° C. for 0.5 to 24 h. However, a variety of alternative catalytic systems/base/conditons can be used (see Liang, B. et. al., *J. Org. Chem.* 2005, 70, 391 and references therein).

The R group can be further manipulated if necessary, as illustrated below:

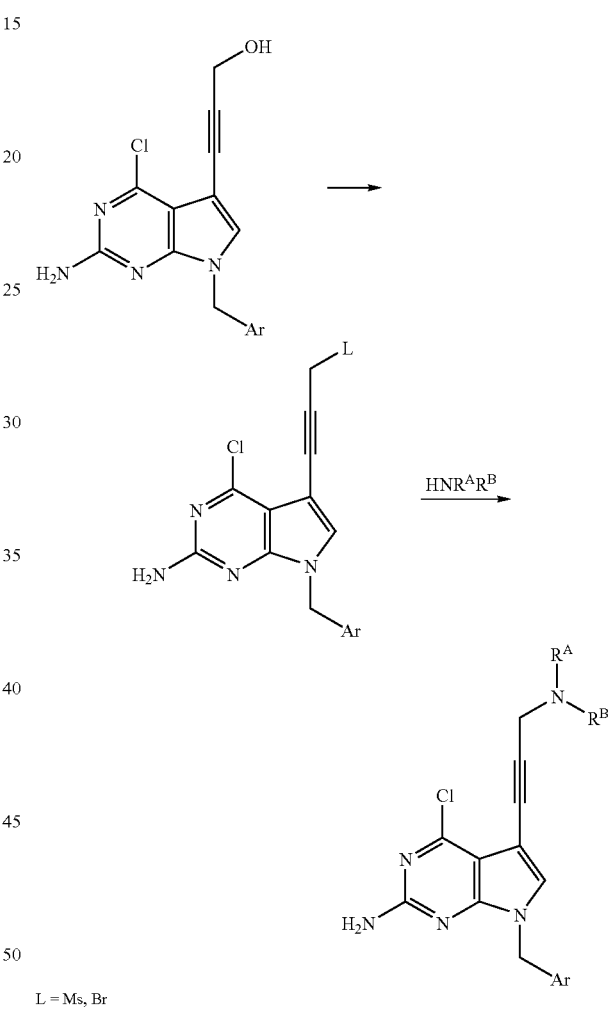

L = Ms, Br

For illustration purposes, the propargylic alcohol can be converted to the mesylate or bromide using methods well known in the art. The mesyl or bromide group can then be displaced by nucleophiles such as amines. Care must be taken to avoid the unwanted nucleophilic substitution of the 4-Cl atom.

The sequence of these steps can be performed in a different order than the one indicated on the Scheme, as for instance (i) alkylation, (ii), Sonogashira coupling, and (iii) deprotection.

Pharmaceutical Compositions, Medicaments, Dosaging and Modes of Administration The present invention is also directed to the use of alkynyl pyrrolo[2,3-D]pyrimidine compounds of Formula I and their related analogs, and their polymorphs, solvates, esters, tautomers, diastereomers, enantiomers, pharmaceutically acceptable salts and prod rugs thereof. In some embodiments, the compounds are used for the treatment or prevention of diseases that are HSP90-dependent. In some embodiments, the compounds are used in the manufacture of a medicament. In other embodiments, the compounds are used in the manufacture of a medicament for the therapeutic and/or prophylactic treatment of diseases and conditions that are HSP90-dependent. Examples of such diseases and conditions include disorders such as inflammatory diseases, infections, autoimmune disorders, stroke, ischemia, cardiac disorder, neurological disorders, fibrogenic disorders, proliferative disorders, tumors, leukemias, chronic lymphocytic leukemia, acquired immunodeficiency syndrome, neoplasms, cancers, carcinomas, metabolic diseases, and malignant disease. The fibrogenic disorders include but are not limited to scleroderma, polymyositis, systemic lupus, rheumatoid arthritis, liver cirrhosis, keloid formation, interstitial nephritis and pulmonary fibrosis.

The present invention features pharmaceutical compositions and medicaments comprising the compound of Formula I, or a polymorph, solvate, ester, tautomer, enantiomer, diastereomer, pharmaceutically acceptable salt thereof, or prodrug thereof, of any of the preceding aspects and embodiments and one or more pharmaceutical excipients. Those of ordinary skill in the art are familiar with formulation and administration techniques that can be employed with the compounds and methods of the invention, e.g., as discussed in Goodman and Gilman, *The Pharmacological Basis of Therapeutics* (10th edition); Pergamon; and *Remington's, Pharmaceutical Sciences* (20th edition), Mack Publishing Co., Easton, Pa.

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration. For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue. Still further, the compounds or compositions of the invention can be delivered in a vesicle, e.g., a liposome (see, for example, Langer, *Science* 1990, 249, 1527-1533; Treat et al., *Liposomes in the Therapy of Infectious Disease and Cancer*, Lopez-Bernstein and Fidler, Ed., Liss, N.Y., pp. 353-365, 1989).

The compounds and pharmaceutical compositions used in the methods of the present invention can also be delivered in a controlled release system. In one embodiment, a pump may be used (see, Sefton, 1987, CRC Crit. Ref. Biomed. Eng. 14:201; Buchwald et al. *Surgery*, 1980 88, 507; Saudek et al. *N. Engl. J. Med.* 1989, 321, (574). Additionally, a controlled release system can be placed in proximity of the therapeutic target. (See, Goodson, *Medical Applications of Controlled Release*, 1984, Vol. 2, pp. 115-138).

The pharmaceutical compositions used in the methods of the instant invention can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropyl-cellulose, or a time delay material such as ethyl cellulose, or cellulose acetate butyrate may be employed as appropriate.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The compounds and pharmaceutical compositions used in the methods of the instant invention may also be in the form of an oil-in-water emulsion. The oily phase may be a vegetable oil, for example olive oil or arachis oil, or a mineral oil, for example liquid paraffin, or mixtures of these. Suitable emulsifying agents may be naturally-occurring phosphatides, for example soybean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution may then be introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol. For topical use, creams, ointments, jellies, solutions or suspensions, etc., containing a compound or composition of the invention can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods, compounds and compositions of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin. Examples of antineoplastic agents that can be used in combination with the compounds and methods of the present invention include, in general, and as appropriate, alkylating agents, anti-metabolites, epidophyllotoxins, an antineoplastic enzyme, a topoisomerase inhibitor, procarbazine, mitoxantrone, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolide, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When a compound or composition of the invention is administered into a human subject, the daily dosage will normally be determined by the prescribing physician with the dosage generally varying according to the age, weight, and response of the individual patient, as well as the severity of the patient's symptoms. In one exemplary application, a suitable amount of compound is administered to a mammal undergoing treatment for cancer, for example, breast cancer. Administration typically occurs in an amount of between about 0.01 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 1000 mg of compound, and preferably includes, e.g., from about 1 mg to about 1000 mg. The quantity of active compound in a unit dose of preparation may be varied or adjusted from about 0.1 mg to 1000 mg, preferably from about 1 mg to 300 mg, more preferably 10 mg to 200 mg, according to the particular application. The amount administered will vary depending on the particular $IC_{50}$ value of the compound used and the judgment of the attending clinician taking into consideration factors such as health, weight, and age. In combinational applications in which the compound is not the sole active ingredient, it may be possible to administer lesser amounts of compound and still have therapeutic or prophylactic effect.

Preferably, the pharmaceutical preparation is in unit dosage form. In such form, the preparation is subdivided into unit doses containing appropriate quantities of the active component, e.g., an effective amount to achieve the desired purpose. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds and compositions of the present invention used in the methods of the present invention, and if applicable other chemotherapeutic agents and/or radiation therapy, will be regulated according to the judgment of the attending clinician (physician) considering such factors as age, condition and size of the patient as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the compounds of the invention need not be administered in the same pharmaceutical composition as a chemotherapeutic agent, and may, because of different physical and chemical characteristics, be administered by a different route. For example, the compounds/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound (and where appropriate, chemotherapeutic agent and/or radiation) will depend upon the diagnosis of the attending physicians and their judgment of the condition of the patient and the appropriate treatment protocol.

The compounds/compositions of the invention (and where appropriate chemotherapeutic agent and/or radiation) may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound/composition. In combinational applications and uses, the compound/composition and the chemotherapeutic agent and/or radiation need not be administered simultaneously or essentially simultaneously, and the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete.

Thus, in accordance with experience and knowledge, the practicing physician can modify each protocol for the administration of a compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Assays for Determining HSP90 Binding and Downstream Effect

A variety of in vitro and in vivo assays are available to test the effect of the alkynyl pyrrolo[2,3-d]pyrimidine compounds of the invention on HSP90. HSP90 competitive binding assays and functional assays can be performed as known in the art by substituting in the compounds of the invention. Chiosis et al. *Chemistry & Biology* 2001, 8, 289-299, describe some of the known ways in which this can be done. For example, competition binding assays using, e.g., geldanamycin or 17-AAG as a competitive binding inhibitor of HSP90 can be used to determine relative HSP90 affinity of the compounds of the invention by immobilizing the compound of interest or other competitive inhibitor on a gel or solid matrix, preincubating HSP90 with the other inhibitor, passing the preincubated mix over the gel or matrix, and then measuring the amount of HSP90 that retains or does not retain on the gel or matrix.

Downstream effects can also be evaluated based on the known effect of HSP90 inhibition on function and stability of various steroid receptors and signaling proteins including, e.g., Raf1 and Her2. Compounds of the present invention induce dose-dependent degradation of these molecules, which can be measured using standard techniques. Inhibition of HSP90 also results in up-regulation of HSP90 and related chaperone proteins that can similarly be measured. Antiproliferative activity on various cancer cell lines can also be measured, as can morphological and functional differentiation related to HSP90 inhibition.

Many different types of methods are known in the art for determining protein concentrations and measuring or predicting the level of proteins within cells and in fluid samples. Indirect techniques include nucleic acid hybridization and amplification using, e.g., polymerase chain reaction (PCR). These techniques are known to the person of skill and are discussed, e.g., in Sambrook, Fritsch & Maniatis *Molecular Cloning: A Laboratory Manual*, 2nd ed., Cold Spring Harbor Laboratory, Cold Spring Harbor, N.Y., 1989; Ausubel, et al. *Current Protocols in Molecular Biology*, John Wiley & Sons, NY, 1994, and, as specifically applied to the quantification, detection, and relative activity of HER2/Neu in patient samples, e.g., in U.S. Pat. Nos. 4,699,877, 4,918,162, 4,968,603, and 5,846,749. A brief discussion of two generic techniques that can be used follows.

The determination of whether cells overexpress or contain elevated levels of Her2 can be determined using well known antibody techniques such as immunoblotting, radioimmunoassays, western blotting, immunoprecipitation, enzyme-linked immunosorbant assays (ELISA), and derivative techniques that make use of antibodies directed against Her2. As an example, Her2 expression in breast cancer cells can be determined with the use of an immunohistochemical assay, such as the Dako Hercep™ test (Dako Corp., Carpinteria, Calif.). The Hercep™ test is an antibody staining assay designed to detect Her2 overexpression in tumor tissue specimens. This particular assay grades Her2 expression into four levels: 0, 1, 2, and 3, with level 3 representing the highest level of Her2 expression. Accurate quantitation can be enhanced by employing an Automated Cellular Imaging System (ACIS) as described, e.g., by Press, M. et al. *Modern Pathology* 2000, 13, 225A.

Antibodies, polyclonal or monoclonal, can be purchased from a variety of commercial suppliers, or may be manufactured using well-known methods, e.g., as described in Harlow et al. *Antibodies: A Laboratory Manual*, 2nd ed; Cold Spring Harbor Laboratory, Cold Spring Harbor, N.Y., 1988.

Her2 overexpression can also be determined at the nucleic acid level since there is a reported high correlation between overexpression of the Her2 protein and amplification of the gene that codes for it. One way to test this is by using RT-PCR. The genomic and cDNA sequences for Her2 are known. Specific DNA primers can be generated using standard, well-known techniques, and can then be used to amplify template already present in the cell. An example of this is described in Kurokawa, H. et al. *Cancer Res.* 2000, 60, 5887-5894. PCR can be standardized such that quantitative differences are observed as between normal and abnormal cells, e.g., cancerous and noncancerous cells. Well known methods employing, e.g., densitometry, can be used to quantitate and/or compare nucleic acid levels amplified using PCR.

Similarly, fluorescent in situ hybridization (FISH) assays and other assays can be used, e.g., Northern and/or Southern blotting. These rely on nucleic acid hybridization between the Her2 gene or mRNA and a corresponding nucleic acid probe that can be designed in the same or a similar way as for PCR primers, above. See, e.g., Mitchell M S, and Press M. F. *Oncol., Suppl.* 1999, 12, 108-116. For FISH, this nucleic acid probe can be conjugated to a fluorescent molecule, e.g., fluorescein and/or rhodamine, that preferably does not interfere with hybridization, and which fluorescence can later be measured following hybridization. See, e.g., Kurokawa, H et al, *Cancer Res.* 2000, 60, 5887-5894 (describing a specific nucleic acid probe having sequence 5'-FAM-NucleicAcid-TAMRA-p-3' sequence). ACIS-based approaches as described above can be employed to make the assay more quantitative (de la Torre-Bueno, J., et al. *Modern Pathology* 2000, 13, 221A).

Immuno and nucleic acid detection can also be directed against proteins other than HSP90 and HER2, which proteins are nevertheless affected in response to HSP90 inhibition. The following examples are offered by way of illustration only and are not intended to be limiting of the full scope and spirit of the invention.

EXAMPLES

Materials and Methods

The chemical reagents used to create the novel products of the invention below are all available commercially, e.g., from Aldrich Chemical Co., Milwaukee, Wis., USA. Otherwise their preparation is facile and known to one of ordinary skill in the art, or it is referenced or described herein.

The final compounds were usually purified by preparative TLC (silica gel 60 Å, Whatman Partisil PK6F) or flash chromatography (silica gel 60 Å, EMD Chemicals) using EtOAc/hexane or MeOH/$CH_2Cl_2$ as eluents. Rf's were measured using silica gel TLC plates (silica gel 60 Å, EMD Chemicals). Analytical HPLC chromatograms were obtained using a C18 column (Agilent Zorbax 300SB-C18; 5 microns; 4.6 mm×150 mm). A gradient was applied between solvent A (0.1% TFA in $H_2O$) and solvent B (0.5% TFA in $CH_3CN$) increasing the proportion of A linearly from 5% (t=0) to 100% (t=7.00 min), with a constant flow rate of 1 mL/min. The samples were diluted to typically 0.1-1 mg/mL in MeOH or $CH_3CN$ and the injection volumes were typically 10 μL. The column was not heated, and UV detection was effected at 254 nm. $^1$H-NMR spectra were recorded on a Bruker Avance 400 MHz spectrometer.

The chemical names were generated using the Beilstein Autonom 2.1 software.

General Procedures

General Procedure A: Sonogashira Coupling.

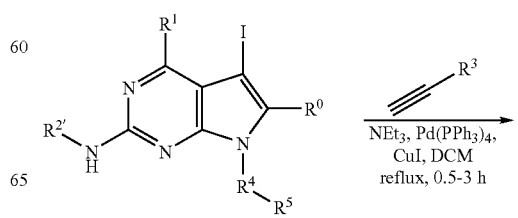

-continued

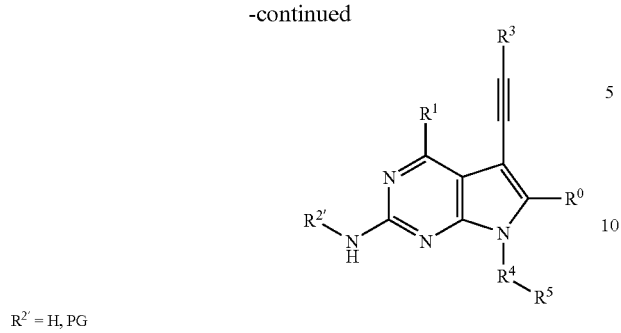

R²' = H, PG

A mixture of the appropriate 5-iodo-pyrrolo[2,3-d]pyrimidine, alkyne (2-5 equiv.), Et₃N (2-5 equiv.), Pd(PPh₃)₄ (0.01-0.05 equiv.), and CuI (0.05-0.30 equiv.) in DCM (5 mL/mmol of starting iodide) was heated to reflux for 0.5-3 h. The reaction mixture was washed with sat. sq. NaHCO₃ and brine, dried (Na₂SO₄), concentrated. Flash chromatography (EtOAc/DCM/Et₃N 15:74:1, gradually adding MeOH (0-7 vol %)) gave the desired 5-alkynyl-pyrrolo[2,3-d]pyrimidine in typically 20-70% yield.

General Procedure B: ZnCl₂-mediated Deprotection.

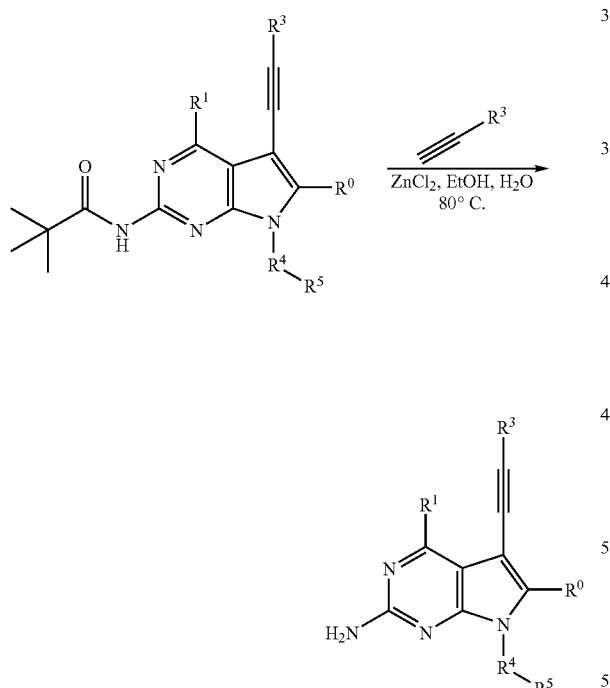

PG = PIV

A suspension of 2-(pivaloylamino)-pyrrolo[2,3-d]pyrimidine and ZnCl₂ (3-20 equiv.) in wet EtOH (5 vol % water) was heated to 80° C., and monitored by HPLC. When the reaction reached completion, DCM was added, and the organic layer was washed with sat. aq. NaHCO₃ and brine. Drying (Na₂SO₄) and concentration afforded the desired 2-aminopyrrolo[2,3-d]pyrimidine.

Example 1

3-[2-Amino-4-chloro-7-(4-methoxy-3,5-dimethyl-pyridin-2-ylmethyl)-7H-pyrrolo[2,3-d]pyrimidin-5-yl]-prop-2-yn-1-ol

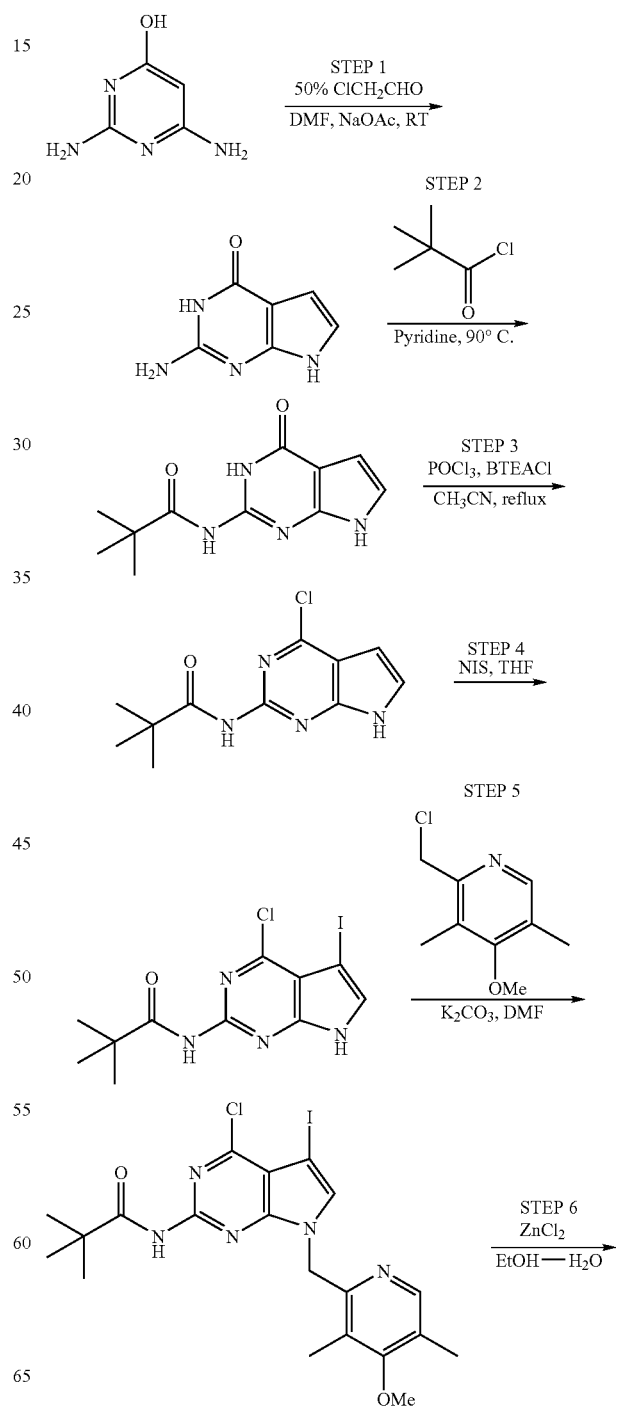

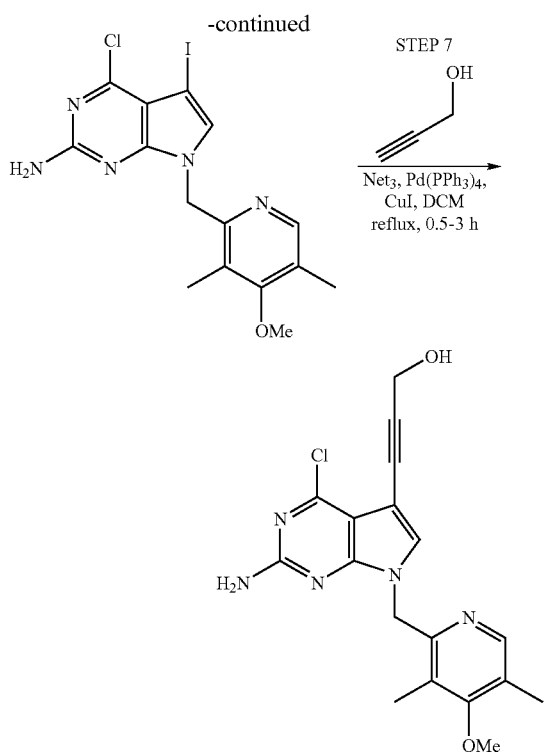

See Shih, C. et al. *Heterocycles*, 1993, 35, 825 and U.S. Pat. No. 5,196,424.

Step 1.
2-Amino-3,7-dihydro-pyrrolo[2,3-d]pyrimidin-4-one

A mixture of 2,4-diamino-6-hydroxypyrimidine (300 g, 2.37 mol), chloroacetaldehyde (50% aq. solution, 382 g, 2.43 mol, 303 mL, 1.02 eq.), sodium acetate (195 g, 2.37 mol), DMF (2.5 L), and water (360 mL) was stirred mechanically at rt for 2 days. The resulting solid was collected by filtration, and washed with water (50 mL×3). The mother liquor was concentrated to give additional material which was washed with water (50 mL×3). The combined solid materials were recrystallized from MeOH to give the title compound as a white powder (186 g, 52% yield, HPLC purity: 100%). $t_R$: 2.21 min. $^1$H-NMR (DMSO-d$_6$) δ 11.00 (br. s, 1H), 10.33 (br. s, 1H), 6.63 (q, 1H), 6.21 (q, 1H), 6.12 (br. s, 2H).

Step 2. 2,2-Dimethyl-N-(4-oxo-4,7-dihydro-3H-pyrrolo[2,3-d]pyrimidin-2-yl)-propionamide A solution of 2-amino-3,7-dihydro-pyrrolo[2,3-d]pyrimidin-4-one (186 g, 1.23 mol) in pyridine (2 L) was treated with trimethylacetyl chloride (475 g, 3.94 mol, 485 mL, 3.2 eq) at 90° C. for 2 h, to give a mixture of N(2)-monoacylated and N(2), N(7)-bisacylated material. The solvent was evaporated and the residue was taken up in aqueous ammonia (37% NH$_3$, 310 mL) and MeOH (2 L), and stirred at rt for 30 min, to selectively cleave the N(7)-pivaloyl group. The solid was collected by filtration, washed with water (500 mL×5), and dried on high vacuum to give the title compound as a solid (193 g). Concentration of the mother liquor provided additional solid material, which was collected, washed with water (50 mL×5), and dried (77 g). The combined yield was 93% (HPLC purity 98.6% ). $t_R$: 4.57 min. $^1$H-NMR (DMSO-d$_6$) δ 12.00, (br. s, 1H), 7.40 (br. s, 1H), 6.96 (q, 1H), 6.40 (q, 1H), 1.24 (s, 9H).

Step 3. N-(4-Chloro-7H-pyrrolo[2,3-d]pyrimidin-2-yl)-2,2-dimethyl-propionamide

A mixture of 2,2-dimethyl-N-(4-oxo-4,7-dihydro-3H-pyrrolo[2,3-d]pyrimidin-2-yl)-propionamide (210 g, 0.90 mol), POCl$_3$ (828 g, 5.40 mol, 503 mL, 6.0 eq), benzyltriethylammonium chloride (411 g, 1.80 mol), N,N-dimethylaniline (220 g, 231 mL, 1.80 mol), and acetonitrile (2.0 L) was heated to reflux for 40-60 min, monitoring with HPLC. The solvent was evaporated on a rotary evaporator, and the residue was carefully (caution: exothermic and corrosive) and slowly added to ice water (16 L). The pH was adjsuted to 7 with solid NaOH, and the resulting precipitate was collected by filtration. Drying afforded the title compound (159 g, 70% yield 70%, HPLC purity 100%). $t_R$: 5.37 min. $^1$H-NMR (DMSO-d$_6$) δ 12.35 (br. s, 1H), 10.06 (br. s, 1H), 7.54 (q, 1H), 6.52 (q, 1H), 1.25 (s, 9H).

Step 4. N-(4-Chloro-5-iodo-7H-pyrrolo[2,3-d]pyrimidin-2-yl)-2,2-dimethyl-propionamide A solution of N-(4-chloro-7H-pyrrolo[2,3-d]pyrimidin-2-yl)-2,2-dimethyl-propionamide (101 g, 0.40 mol) in anhydrous THF (2 L) was treated with N-iodosuccinimide (98.9 g, 0.44 mol, 1.1 eq.) under N$_2$ atmosphere at rt for 40 min. The solvent was evaporated, and the residue was taken up in CH$_2$Cl$_2$ (1.5 L), and washed with Na$_2$SO$_3$ (500 mL×3) and brine (300 mL×3). Evaporated and recrystallizion from MeOH gave the title product as a white powder (122 g, 81% yield, HPLC purity: 98.2%). $t_R$: 6.19 min. $^1$H-NMR (DMSO-d$_6$) δ 12.65 (br.s, 1H), 10.11 (br. s, 1H), 7.76 (d, 1H), 1.24 (s, 9H).

Step 5. N-[4-Chloro-5-iodo-7-(4-methoxy-3,5-dimethyl-pyridin-2-ylmethyl)-7H-pyrrolo[2,3-d]pyrimidin-2-yl]-2,2-dimethyl-propionamide A mixture of N-(4-chloro-5-iodo-7H-pyrrolo[2,3-d]pyrimidin-2-yl)-2,2-dimethyl-propionamide (37.8 g, 0.1 mol), 2-chloromethyl-4-methoxy-3,5-dimethyl-pyridine hydrochloride (23.1 g, 0.104 mol), finely powdered K$_2$CO$_3$, (41.5 g, 0.3 mol, 3.0 eq.), and anhydrous DMF (200 mL) was stirred at rt overnight. The solvent was evaporated, and the residue taken up in CH$_2$Cl$_2$ (500 mL), washed with brine (200 mL×3), evaporated, and recrystallized from MeOH to give the title product as a white powder (42.0 g, 80% yield; HPLC purity 98%). $t_R$: 6.49 min. $^1$H-NMR (DMSO-d$_6$) δ 10.16 (br. s, 1H), 8.04 (s, 1H), 7.72 (s, 1H), 5.46 (s, 2H), 3.73 (s, 3H), 2.33 (s, 3H), 2.15 (s, 3H), 1.21 (s, 9H).

Step 6. 4-Chloro-5-iodo-7-(4-methoxy-3,5-dimethyl-pyridin-2-ylmethyl)-7H-pyrrolo[2,3-d]pyrimidin-2-ylamine A mixture of N-[4-chloro-5-iodo-7-(4-methoxy-3,5-dimethyl-pyridin-2-ylmethyl)-7H-pyrrolo[2,3-d]pyrimidin-2-yl]-2,2-dimethyl-propionamide (1.0 g, 1.89 mmol), ZnCl$_2$ (1.29 g, 9.47 mol, 5.0 eq.), and EtOH/H$_2$O solution (25 mL, volumetric ratio 100:5) was stirred at 80° C. overnight. The reaction mixture poured into water, and the solid was collected by filtration, washed with water (10 mL×3), and recrystallized from MeOH to give the title product (0.67 g, 85% yield; HPLC purity 98%). $t_R$: 5.39 min. $^1$H-NMR (DMSO-d$_6$) δ 8.07 (s, 1H), 7.28 (s, 1H), 6.75 (br. s, 2H), 5.29 (s, 2H), 3.73 (s, 3H), 2.26 (s, 3H), 2.17 (s, 3H).

Step 7. 3-[2-Amino-4-chloro-7-(4-methoxy-3,5-dimethyl-pyridin-2-ylmethyl)-7H-pyrrolo[2,3-d]pyrimidin-5-yl]-prop-2-yn-1-ol The title compound was prepared by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see example 1) with propargylic alcohol according to the General Procedure A. $t_R$: 4.42 min. $^1$H-NMR (DMSO-d$_6$) δ 8.04 (s, 1H), 7.32 (s, 1H), 6.71 (br. s, 2H), 5.27 (s, 2H), 5.22 (t,1H), 4.26 (d, 1H), 3.71 (s, 3H), 2.24 (s, 3H), 2.14 (s, 3H).

Example 2

4-[2-Amino-4-chloro-7-(4-methoxy-3,5-dimethyl-pyridin-2-ylmethyl)-7H-pyrrolo[2,3-d]pyrimidin-5-yl]-but-3-yn-1-ol

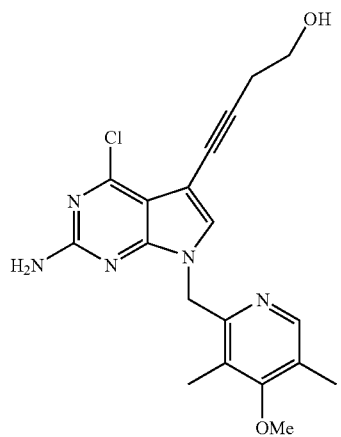

The title compound was prepared by Sonogashira coupling of 4-chloro-5-iodo-7-(4-methoxy-3,5-dimethyl-pyridin-2-ylmethyl)-7H-pyrrolo[2,3-d]pyrimidin-2-ylamine (see Example 1) with 3-butyn-1-ol according to the General Procedure A. $t_R$: 4.54 min. $^1$H-NMR (DMSO-d$_6$) δ 8.04 (s, 1H), 7.22 (s, 1H), 6.69 (br.s., 2H), 5.25 (s, 2H), 4.82 (d, 1H), 3.70 (s, 3H), 3.55 (q, 2H), 2.49 (t, 2H), 2.23 (s, 3H), 2.14 (s, 3H).

Example 3

5-[2-Amino-4-chloro-7-(4-methoxy-3,5-dimethyl-pyridin-2-ylmethyl)-7H-pyrrolo[2,3-d]pyrimidin-5-yl]-pent-4-yn-1-ol

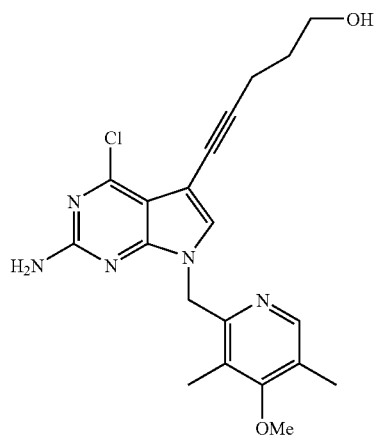

The title compound was prepared by Sonogashira coupling of 4-chloro-5-iodo-7-(4-methoxy-3,5-dimethyl-pyridin-2-ylmethyl)-7H-pyrrolo[2,3-d]pyrimidin-2-ylamine (see Example 1) with 4-pentyn-1-ol according to the General Procedure A. $t_R$: 4.71 min. $^1$H-NMR (DMSO-d$_6$) δ 8.04 (s, 1H), 7.22 (s, 1H), 6.69 (br. s, 2H), 5.25 (s, 2H), 4.48 (d, 1H), 3.71 (s, 3H), 3.50 (q, 2H), 2.42 (t, 2H), 2.23 (s, 3H), 2.14 (s, 3H), 1.65 (5, 2H).

Example 4

4-Chloro-5-(3-diisobutylamino-prop-1-ynyl)-7-(4-methoxy-3,5-dimethyl-pyridin-2-ylmethyl)-7H-pyrrolo[2,3-d]pyrimidin-2-ylamine

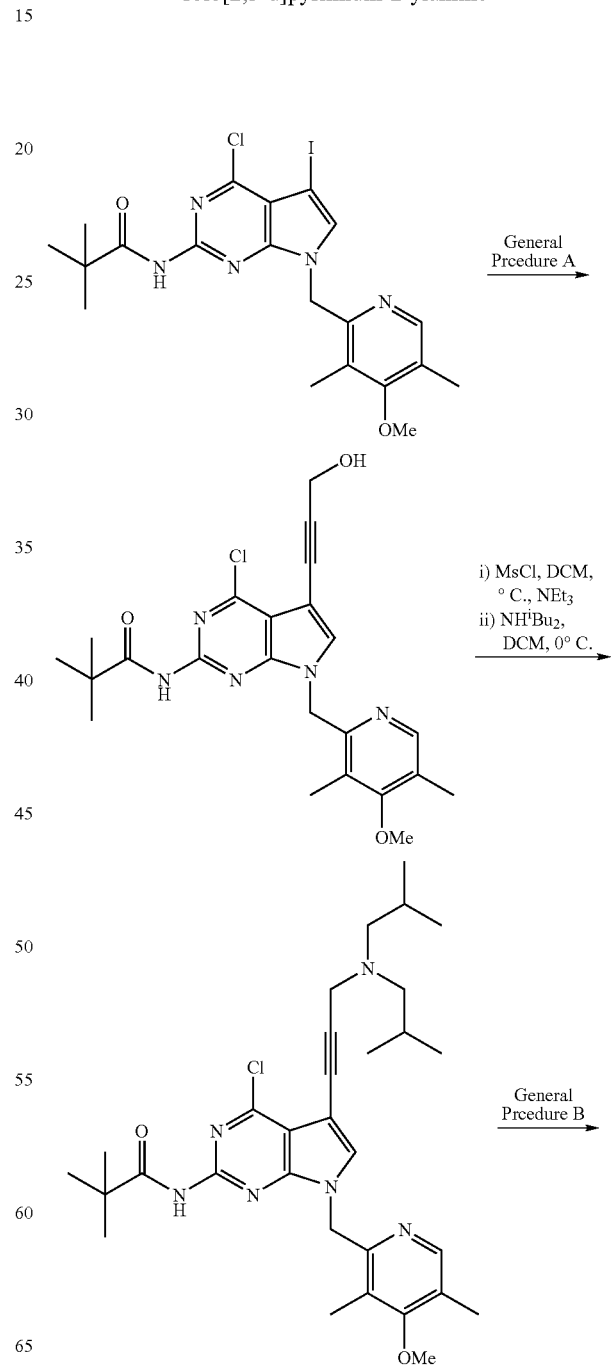

-continued

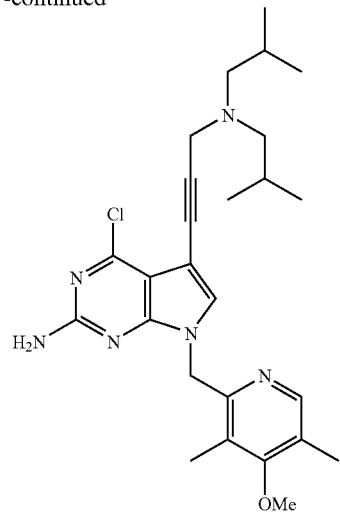

Step 1. N-[4-Chloro-5-(3-hydroxy-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide The title compound was prepared by Sonogashira coupling of N-[4-chloro-5-iodo-7-(4-methoxy-3,5-dimethyl-pyridin-2-ylmethyl)-7H-pyrrolo[2,3-d]pyrimidin-2-yl]-2,2-dimethyl-propionamide (see Example 1) with propargylic alcohol according to the General Procedure A. $t_R$: 5.58 min. $^1$H-NMR (DMSO-$d_6$): δ 10.15 (br. s, 1H), 8.04 (s, 1H), 7.80 (s, 1H), 5.48 (s, 2H), 5.31 (t, 1H), 4.33 (d, 2H), 3.74 (s, 3H), 2.33 (s, 3H), 2.15 (s, 3H), 1.21 (s, 9H).

Step 2. N-[4-Chloro-5-(3-diisobutylamino-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide A solution of N-[4-chloro-5-(3-hydroxy-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide (9.0 g, 19.7 mmol) and Et$_3$N (2 mL) in DCM (50 mL) was treated with MsCl (15.3 mL, 19.7 mmol) at 0° C. for 20 min and evaporated to give a yellow solid, containg mostly the desired mesylate (10.7 g). An aliquot of this solid (106.8 mg, 0.2 mmol) was treated with diisobutylamine (25.9 mg, 24.8 µL) in DCM (2 mL) at 0° C. for 10 h, and then at 25° C. for 3 days. Evaporation and prepartive plate chromatography gave the title compound.

Step 3. 4-Chloro-5-(3-diisobutylamino-prop-1-ynyl)-7-(4-methoxy-3,5-dimethyl-pyridin-2-ylmethyl)-7H-pyrrolo[2,3-d]pyrimidin-2-ylamine The title compound was prepared by cleaving the pivaloyl protecting group of N-[4-chloro-5-(3-diisobutylamino-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide with ZnCl$_2$ according to the General Procedure B. $t_R$: 5.23 min. $^1$H-NMR (CDCl$_3$) δ 8.23 (s, 1H), 7.08 (s, 1H), 5.31 (s, 2H), 4.99 (s, 1H), 3.76 (s, 3H), 3.56 (s, 2H), 2.29 (s, 3H), 2.27 (d, 4H), 2.21 (s, 3H), 1.74 (m, 2H), 0.90 (d, 12H).

Example 5

4-Chloro-5-(3-diisopropylamino-prop-1-ynyl)-7-(4-methoxy-3,5-dimethyl-pyridin-2-ylmethyl)-7H-pyrrolo[2,3-d]pyrimidin-2-ylamine

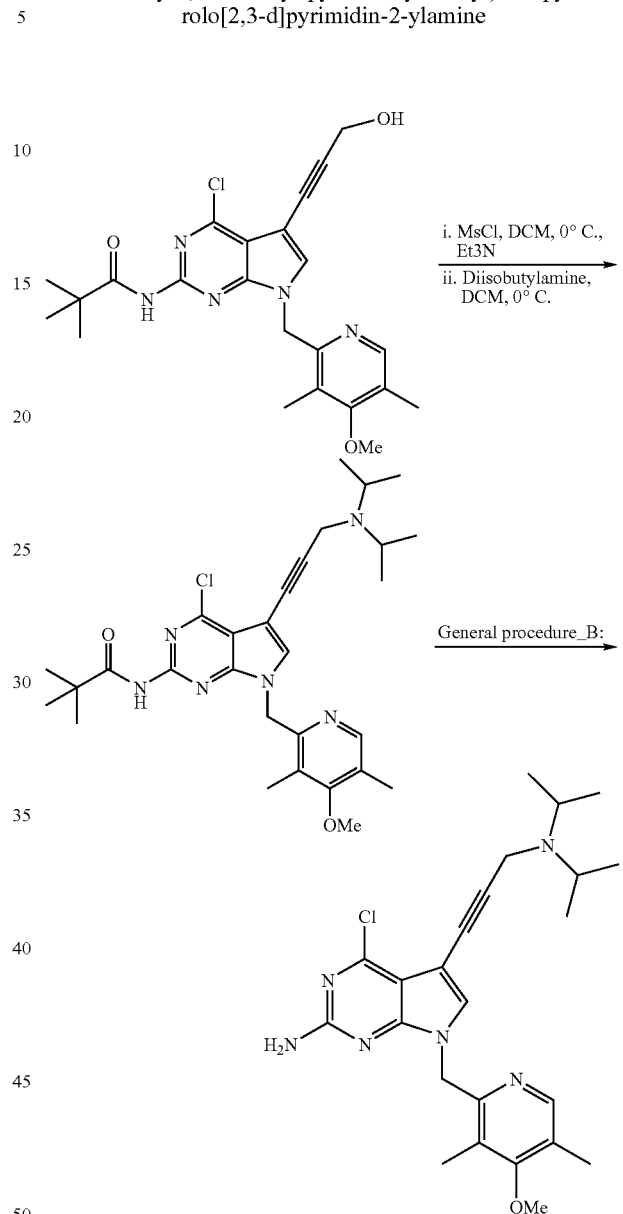

Step 1. N-[4-Chloro-5-(3-diisopropylamino-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide A solution of N-[4-chloro-5-(3-hydroxy-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide (9.0 g, 19.7 mmol) and Et$_3$N (2 mL) in DCM (50 mL) was treated with MsCl (15.3 mL, 19.7 mmol) at 0° C. for 20 min and evaporated to give a yellow solid, containg mostly the desired mesylate (10.7 g). An aliquot of this solid (106.8 mg, 0.2 mmol) was treated with diisopropylamine (20.3 mg, 28.1 µL) in DCM (2 mL) at 0° C. for 10 h, and then at 25° C. for 3 days. Evaporation and prepartive plate chromatography gave the title compound.

Step 2. 4-Chloro-5-(3-diisopropylamino-prop-1-ynyl)-7-(4-methoxy-3,5-dimethyl-pyridin-2-ylmethyl)-7H-pyrrolo[2,3-d]pyrimidin-2-ylamine The title compound was prepared by cleaving the pivaloyl protecting group of N-[4-chloro-5-(3-diisopropylamino-prop-1-ynyl)-7-(4-methoxy-3,5-dimethyl-pyridin-2-ylmethyl)-7H-pyrrolo[2,3-d]pyrimidin-2-yl]-2,2-dimethyl-propionamide with ZnCl$_2$ according to the General Procedure B. $t_R$: 4.71 min. $^1$H-NMR (CDCl$_3$) δ 8.24 (s, 1H), 7.05 (s, 1H), 5.30 (s, 2H), 4.96 (s, 1H), 3.76 (s, 3H), 3.68 (s, 2H), 3.27 (7, 2H), 2.27 (s, 2H), 2.20 (s, 2H), 1.15 (d, 12H).

Example 6

4-Chloro-7-(4-methoxy-3,5-dimethyl-pyridin-2-ylmethyl)-5-pyridin-2-ylethynyl-7H-pyrrolo[2,3-d]pyrimidin-2-ylamine

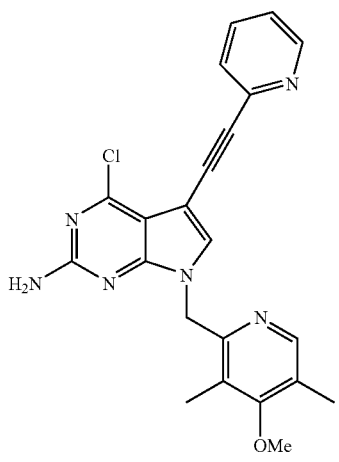

The title compound was prepared by Sonogashira coupling of 4-chloro-5-iodo-7-(4-methoxy-3,5-dimethyl-pyridin-2-ylmethyl)-7H-pyrrolo[2,3-d]pyrimidin-2-ylamine (see Example 1) with 2-ethynylpyridine according to the General Procedure A. $t_R$: 4.65 min. $^1$H-NMR (DMSO-d$_6$) δ 8.59 (s, 1H), 8.07 (s, 1H), 7.82 (td, 1H), 7.62 (s, 1H), 7.56 (d, 1H), 7.36 (td, 1H), 6.84 (br. s, 2H), 5.36 (s, 2H), 3.74 (s, 3H), 2.28 (s, 3H), 2.17 (s, 3H).

Example 7

6-[2-Amino-4-chloro-7-(4-methoxy-3,5-dimethyl-pyridin-2-ylmethyl)-7H-pyrrolo[2,3-d]pyrimidin-5-yl]-hex-5-yn-1-ol The title compound was prepared by Sonogashira coupling of 4-chloro-5-iodo-7-(4-methoxy-3,5-dimethyl-pyridin-2-ylmethyl)-7H-pyrrolo[2,3-d]pyrimidin-2-ylamine (see Example 1) with 5-hexyn-1-ol according to the General Procedure A. $t_R$: 4.92 min. $^1$H-NMR (DMSO-d$_6$) δ 8.04 (s, 1H), 7.22 (s, 1H), 6.69 (br. s, 2H), 5.25 (s, 2H), 4.39 (t, 1H), 3.70 (s, 3H), 3.40 (q, 2H), 2.39 (t, 2H), 2.23 (s, 3H), 2.14 (s, 3H), 1.55 (m, 4H).

Example 8

4-Chloro-7-(4-methoxy-3,5-dimethyl-pyridin-2-ylmethyl)-5-trimethylsilanylethynyl-7H-pyrrolo[2,3-d]pyrimidin-2-ylamine -continued

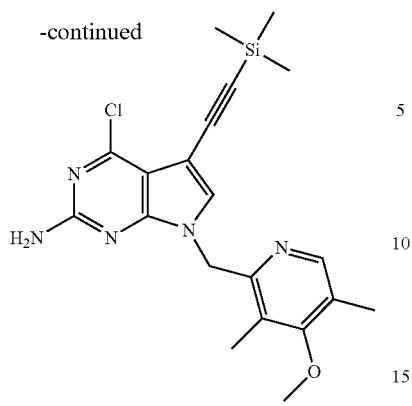

Step 1: N-[4-Chloro-7-(4-methoxy-3,5-dimethyl-pyridin-2-ylmethyl)-5-trimethylsilanylethynyl-7H-pyrrolo[2,3-d]pyrimidin-2-yl]-2,2-dimethyl-propionamide The title compound was prepared by Sonogashira coupling of N-[4-chloro-5-iodo-7-(4-methoxy-3,5-dimethyl-pyridin-2-ylmethyl)-7H-pyrrolo[2,3-d]pyrimidin-2-yl]-2,2-dimethyl-propionamide (see Example 1) with ethynyl-trimethyl-silane according to the General Procedure A. $t_R$=7.48 min. $^1$H NMR (CDCl$_3$) δ 8.18 (s, 2H), 7.38 (s, 1H), 5.49 (s, 2H), 3.74 (s, 3H), 2.24 (s, 6H), 1.35 (s, 9H), 0.24 (s, 9H).

Step 2: 4-Chloro-7-(4-methoxy-3,5-dimethyl-pyridin-2-ylmethyl)-5-trimethylsilanylethynyl-7H-pyrrolo[2,3-d]pyrimidin-2-ylamine The title compound was prepared by cleaving the pivaloyl protecting group of N-[4-chloro-7-(4-methoxy-3,5-dimethyl-pyridin-2-ylmethyl)-5-trimethylsilanylethynyl-7H-pyrrolo[2,3-d]pyrimidin-2-yl]-2,2-dimethyl-propionamide with ZnCl$_2$ according to the General Procedure B. $t_R$=6.56 min. $^1$H NMR (CDCl$_3$) δ 8.22 (s, 1H), 7.11 (s, 1H), 5.30 (s, 2H), 5.09 (s, 2H), 3.75 (s, 3H), 2.26 (s, 3H), 2.18 (s, 3H), 0.24 (s, 9H).

Example 9

5-[2-Amino-4-chloro-7-(4-methoxy-3,5-dimethyl-pyridin-2-ylmethyl)-7H-pyrrolo[2,3-d]pyrimidin-5-yl]-pent-4-ynoic acid

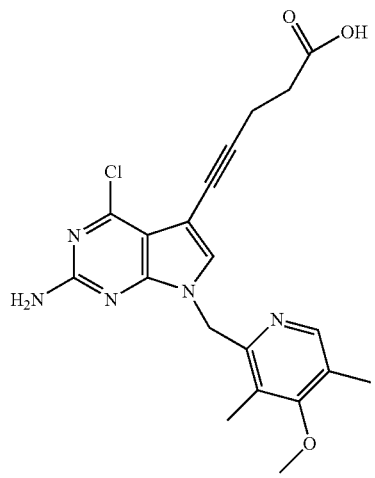

The title compound was prepared by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with 4-pentynoic acid according to the General Procedure A. $t_R$=4.73 min. $^1$H NMR (DMSO-d$_6$) δ 12.2 (s, 1H), 8.15 (s, 1H), 7.28 (s, 1H), 6.80 (s, 2H), 5.33 (s, 2H), 3.73 (s, 3H), 3.31 (br. s, 2H), 2362 (br. t, 2H), 2.27 (s, 3H), 2.17 (s, 3H).

Example 10

5-[2-Amino-4-chloro-7-(4-methoxy-3,5-dimethyl-pyridin-2-ylmethyl)-7H-pyrrolo[2,3-d]pyrimidin-5-yl]-pent-4-ynoic acid diethylamide

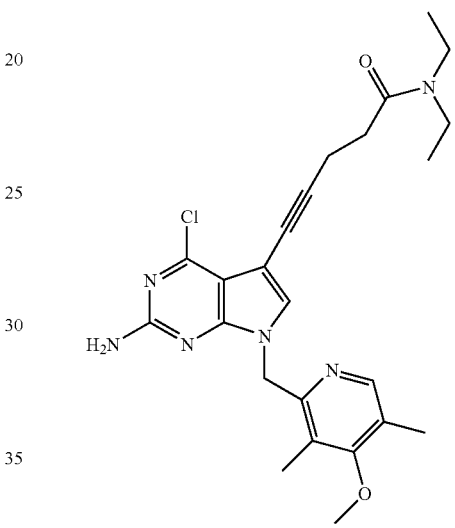

A mixture of 5-[2-amino-4-chloro-7-(4-methoxy-3,5-dimethyl-pyridin-2-ylmethyl)-7H-pyrrolo[2,3-d]pyrimidin-5-yl]-pent-4-ynoic acid (see previous example, 25 mg), Et$_2$NH (100 μL), EDCI (87 mg), HOBt (50 mg), and DMF (1 mL) was stirred at rt for 16 h. Preparative plate chromatography (EtOAc/hexane 2:1) gave the title compound. $t_R$=5.33 min. $^1$H NMR (CDCl$_3$) δ 8.23 (s, 1H), 7.01 (s, 1H), 5.32 (s, 2H), 4.98 (s, 2H), 3.76 (s, 3H), 3.42 (q, 2H), 3.33 (q, 2H), 2.78 (dd, 2H), 2.64 (dd, 2H), 2.27 (s, 3H), 2.18 (s, 3H), 1.20 (t, 3H), 1.13 (t, 3H).

Example 11

5-[2-Amino-4-chloro-7-(4-methoxy-3,5-dimethyl-pyridin-2-ylmethyl)-7H-pyrrolo[2,3-d]pyrimidin-5-yl]-1-(4-methyl-piperazin-1-yl)-pent-4-yn-1-one

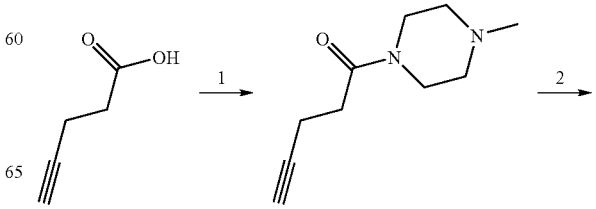

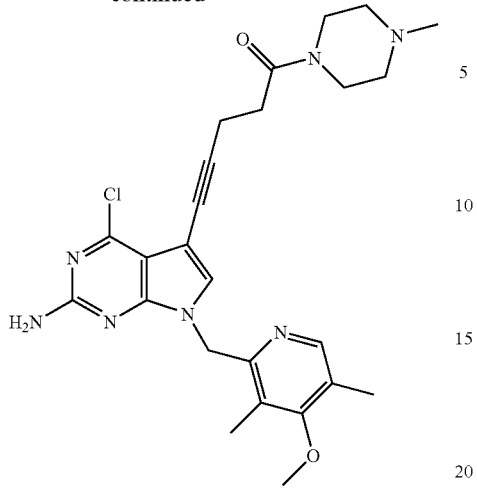
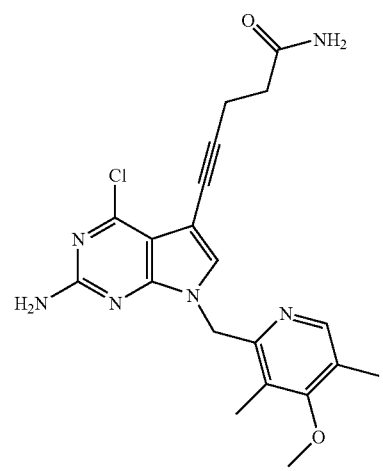

Step 1: 1-(4-Methyl-piperazin-1-yl)-pent-4-yn-1-one

A solution of 4-pentynoic acid (519 mg, 5.29 mmol) and Et₃N (737 μL, 5.29 mmol) in DCM (10 mL) was treated with ethyl chloroformate (504 μL, 5.29 mmol) at rt for 15 min. Then N-methyl-piperazine (588 μL, 5.29 mmol) was added, and stirring was prolonged for 45 min. Work-up (sat. aq. NaHCO₃) and concentration gave the title compound as a colorless oil. ¹H NMR (CDCl₃) δ 3.63 (t, 2H), 3.48 (t, 2H), 2.55 (m, 4H), 2.38 (quint., 4H), 2.30 (s, 3H).

Step 2: 5-[2-Amino-4-chloro-7-(4-methoxy-3,5-dimethyl-pyridin-2-ylmethyl)-7H-pyrrolo[2,3-d]pyrimidin-5-yl]-1-(4-methyl-piperazin-1-yl)-pent-4-yn-1-one The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with 1-(4-Methyl-piperazin-1-yl)-pent-4-yn-1-one according to the General Procedure A. $t_R$=4.16 min. ¹H NMR (CDCl₃) δ 8.22 (s, 1H), 7.00 (s, 1H), 5.30 (s, 2H), 5.14 (s, 2H), 3.74 (s, 3H), 3.64 (t, 2H), 3.50 (t, 2H), 2.76 (dd, 2H), 2.64 (dd, 2H), 2.29 (s, 3H), 2.24 (s, 3H), 2.18 (s, 3H).

Example 12

5-[2-Amino-4-chloro-7-(4-methoxy-3,5-dimethyl-pyridin-2-ylmethyl)-7H-pyrrolo[2,3-d]pyrimidin-5-yl]-pent-4-ynoic acid amide

Step 1: Pent-4-ynoic acid amide

A solution of 4-pentynoic acid (517 mg, 5.29 mmol) and Et₃N (737 μL, 5.29 mmol) in DCM (10 mL) was treated with ethyl chloroformate (504 μL, 5.29 mmol) at rt for 15 min. Then NH₃ (7M in MeOH, 1 mL, 7 mmol) was added, and stirring was prolonged for 5 min. Work-up (sat. aq. NaHCO₃) and concentration gave the title compound as a colorless solid. ¹H NMR (CDCl₃) δ 6.03 (s, 1H), 5.86 (s, 1H), 2.55 (m, 2H), 2.46 (m, 2H), 2.02 (t, 1H).

Step 2: 5-[2-Amino-4-chloro-7-(4-methoxy-3,5-dimethyl-pyridin-2-ylmethyl)-7H-pyrrolo[2,3-d]pyrimidin-5-yl]-pent-4-ynoic acid amide The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with pent-4-ynoic acid amide according to the general procedure A. $t_R$=4.35 min. ¹H NMR (DMSO-d₆) δ 8.07 (s, 1H), 7.36 (s, 1H), 7.23 (s, 1H), 6.87 (s, 1H), 6.71 (s, 2H), 5.28 (s, 2H), 3.72 (s, 3H), 2.59 (t, 2H), 2.34 (t, 2H), 2.25 (s, 3H), 2.16 (s, 3H).

Example 13

{3-[2-Amino-4-chloro-7-(4-methoxy-3,5-dimethyl-pyridin-2-ylmethyl)-7H-pyrrolo[2,3-d]pyrimidin-5-yl]-prop-2-ynyl}-carbamic acid tert-butyl ester

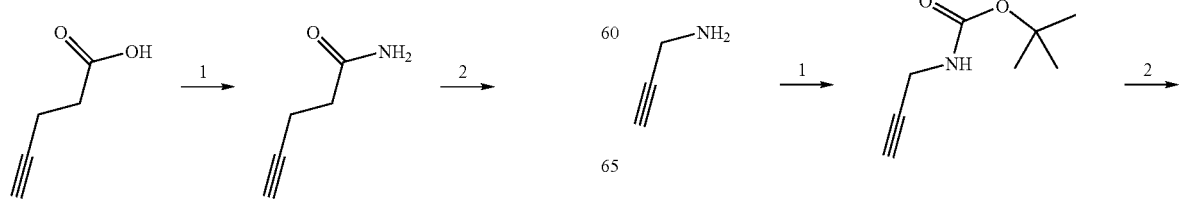

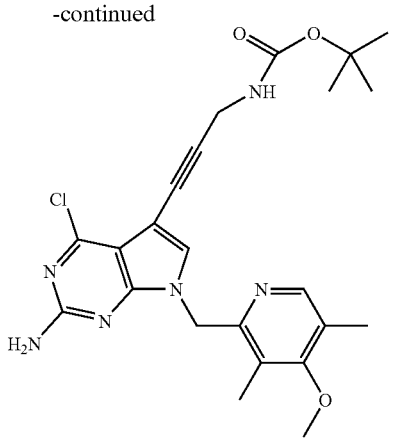

Step 1: Prop-2-ynyl-carbamic acid tert-butyl ester

A solution of propargylamine (1 g, 18 mmol) in DCM (10 mL) was treated with (BOC)$_2$O (4.0 g, 18 mmol) at rt for 3 h. Evaporation gave the title compound as an oil. $^1$H NMR (CDCl$_3$) δ 4.80 (s, 1H), 3.93 (s, 2H), 2.23 (t, 1H), 1.47 (s, 9H).

Step 2: {3-[2-Amino-4-chloro-7-(4-methoxy-3,5-dimethyl-pyridin-2-ylmethyl)-7H-pyrrolo[2,3-d]pyrimidin-5-yl]-prop-2-ynyl}-carbamic acid tert-butyl ester The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with prop-2-ynyl-carbamic acid tert-butyl ester according to the General Procedure A. $t_R$=5.91 min. $^1$H NMR (CDCl$_3$) δ 8.20 (s, 1H), 7.05 (s, 1H), 5.36 (s, 2H), 5.31 (s, 2H), 4.82 (s, 1H), 4.16 (s, 2H), 3.76 (s, 3H), 2.26 (s, 3H), 2.24 (s, 3H), 1.47 (s, 9H).

Example 14

5-(3-Amino-prop-1-ynyl)-4-chloro-7-(4-methoxy-3,5-dimethyl-pyridin-2-ylmethyl)-7H-pyrrolo[2,3-d]pyrimidin-2-ylamine

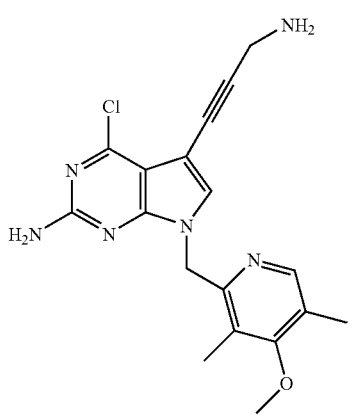

A solution of {3-[2-Amino-4-chloro-7-(4-methoxy-3,5-dimethyl-pyridin-2-ylmethyl)-7H-pyrrolo[2,3-d]pyrimidin-5-yl]-prop-2-ynyl}-carbamic acid tert-butyl ester (see previous example, 22 mg) in DCM (3 mL) was treated with TFA (0.6 mL) at rt for 15 min. Evaporation, work-up (DCM/sat. aq. NaHCO$_3$), drying (Na$_2$SO$_4$), and evaporation gave the title compound as an oil. $t_R$=3.85 min. $^1$H NMR (CDCl$_3$) δ 8.24 (s, 1H), 7.06 (s, 1H), 5.32 (s, 2H), 5.02 (s, 2H), 3.75 (s, 3H), 2.27 (s, 3H), 2.20 (s, 3H).

Example 15

{5-[2-Amino-4-chloro-7-(4-methoxy-3,5-dimethyl-pyridin-2-ylmethyl)-7H-pyrrolo[2,3-d]pyrimidin-5-yl]-pent-4-ynyl}-carbamic acid tert-butyl ester

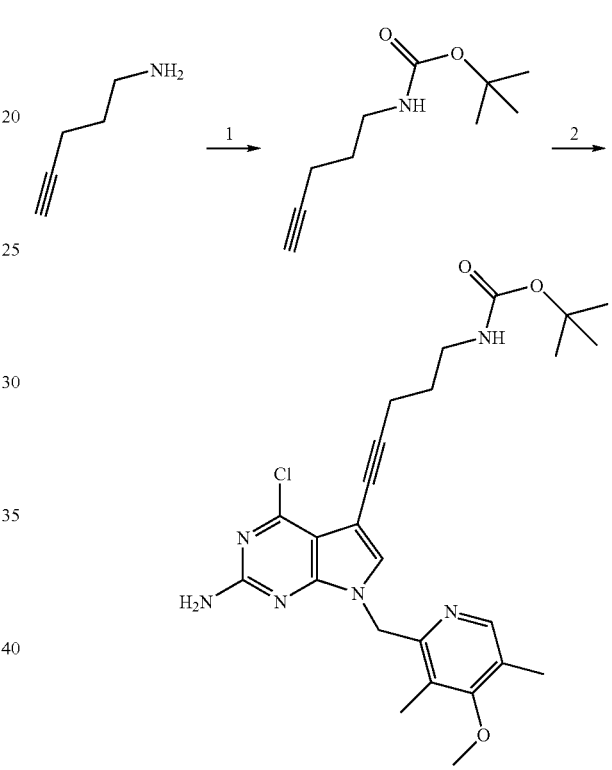

Step 1: Pent-4-ynyl-carbamic acid tert-butyl ester

A solution of pent-4-ynylamine (480 mg; Li, Y. et al. J. Am. Chem. Soc. 1996, 118, 9295) in DCM (5 mL) was treated with (BOC)$_2$O at rt for 15 min. Evaporation gave the title compound as a colorless oil. $^1$H NMR (CDCl$_3$) δ 4.68 (s, 1H), 3.24 (q, 2H), 2.25 (td, 2H), 1.97 (t, 1H), 1.70 (quint., 2H), 1.45 (s, 9H).

Step 2: {5-[2-Amino-4-chloro-7-(4-methoxy-3,5-dimethyl-pyridin-2-ylmethyl)-7H-pyrrolo[2,3-d]pyrimidin-5-yl]-pent-4-ynyl}-carbamic acid tert-butyl ester The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with pent-4-ynyl-carbamic acid tert-butyl ester according to the General Procedure A. $t_R$=5.96 min. $^1$H NMR (CDCl$_3$) δ 8.23 (s, 1H), 7.02 (s, 1H), 5.30 (s, 2H), 5.07 (s, 2H), 4.80 (br. t, 1H), 3.75 (s, 3H), 3.30 (q, 2H), 2.48 (t, 2H), 2.26 (s, 3H), 2.19 (s, 3H), 1.80 (quint., 2H), 1.43 (s, 9H).

Example 16

5-(5-Amino-pent-1-ynyl)-4-chloro-7-(4-methoxy-3,5-dimethyl-pyridin-2-ylmethyl)-7H-pyrrolo[2,3-d]pyrimidin-2-ylamine

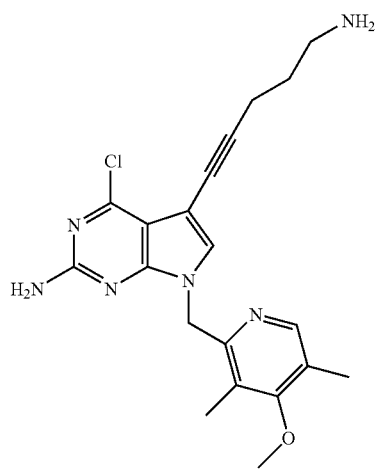

A solution of {5-[2-amino-4-chloro-7-(4-methoxy-3,5-dimethyl-pyridin-2-ylmethyl)-7H-pyrrolo[2,3-d]pyrimidin-5-yl]-pent-4-ynyl}-carbamic acid tert-butyl ester (see previous example, 33 mg) in DCM (1.0 mL) was treated with TFA (0.2 mL) at rt for 10 min. The reaction mixture was concentrated, taken in water (1.5 mL), washed with EtOAc (1.5 mL), made alkaline with sat. aq. NH$_4$OH (0.5 mL), and back-extracted into EtOAc (25 mL). Washing (NH$_4$OH 1M), drying (Na$_2$SO$_4$) and concetration affroded the title compound. $t_R$=4.37 min. $^1$H NMR (CDCl$_3$) δ 8.15 (s, 1H), 6.97 (s, 1H), 5.25 (s, 2H), 3.72 (s, 3H), 2.94 (m, 2H), 2.48 (t, 2H), 2.23 (s, 3H), 2.16 (s, 3H), 1.80 (quint., 2H).

Example 17

2-{5-[2-Amino-4-chloro-7-(4-methoxy-3,5-dimethyl-pyridin-2-ylmethyl)-7H-pyrrolo[2,3-d]pyrimidin-5-yl]-pent-4-ynyl}-isoindole-1,3-dione

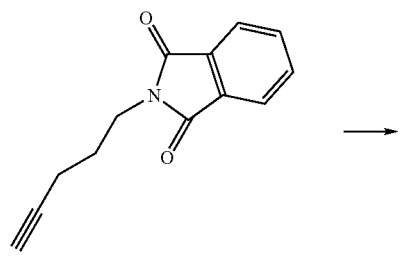

-continued

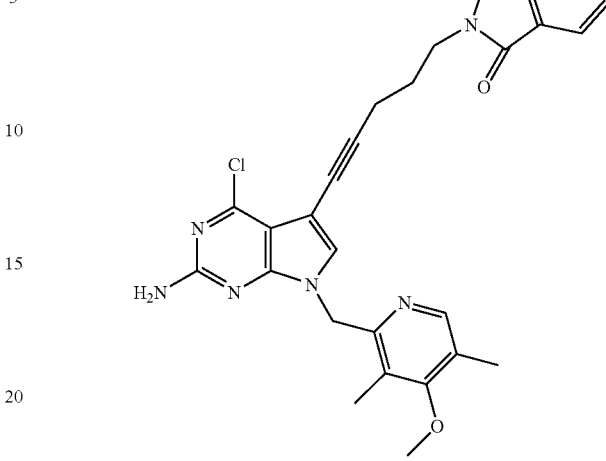

The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with 2-pent-4-ynyl-isoindole-1,3-dione (Li, Y. et al. J. Am. Chem. Soc. 1996, 118, 9295) according to the General Procedure A. $t_R$=6.08 min. $^1$H NMR (CDCl$_3$) δ 8.17 (s, 1H), 7.75 (dd, 2H), 7.58 (dd, 2H), 6.85 (s, 1H), 5.22 (s, 2H), 3.81 (t, 2H), 3.72 (s, 3H), 2.46 (t, 2H), 2.23 (s, 3H), 2.14 (s, 3H), 1.95 (quint., 2H).

Example 18

4-Chloro-7-(4-methoxy-3,5-dimethyl-pyridin-2-ylmethyl)-5-(4-morpholin-4-yl-but-1-ynyl)-7H-pyrrolo[2,3-d]pyrimidin-2-ylamine

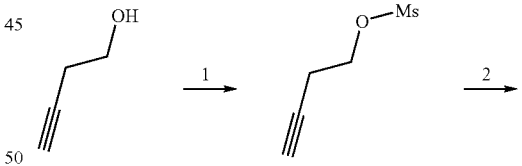

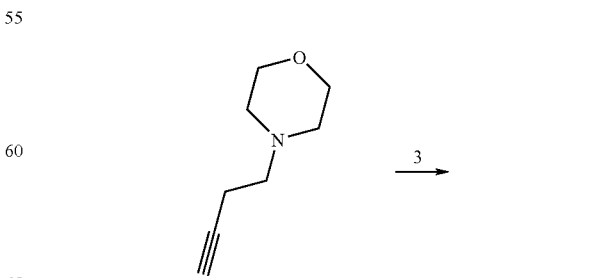

-continued

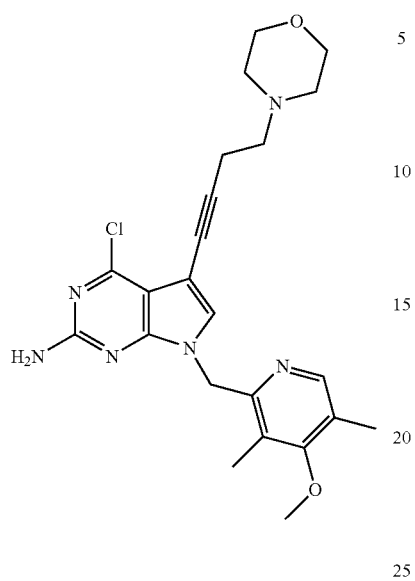

Step 1: Methanesulfonic acid but-3-ynyl ester

A solution of 3-but-1-ynol (5.62 g, 80.2 mmoL) and Et₃N (14.5 mL, 104 mmol) in DCM (40 mL) was treated with MsCl (7.48 mL, 96.2 mmol) at 0° C. for 10 min. Work-up (water; sat. aq. NaHCO₃), drying (Na₂SO₄), and concetration gave the title compound as a pale orange oil. ¹H NMR (CDCl₃) δ 4.32 (t, 2H), 3.07 (s, 3H), 2.67 (td, 2H), 2.09 (t, 2H).

Step 2: 4-But-3-ynyl-morpholine

A mixture of methanesulfonic acid but-3-ynyl ester (10.1 g, 68 mmol) and morpholine (12.5 mL, 143 mmol) was heated to 100° C. for 1 h. The mixture was diluted with Et₂O (50 mL) and filtered. The solid residue was discarded, and the mother liquor extracted with 3N HCl. The aqueous layer was basified with NaOH, and back-extracted into EtOAc. Drying (Na₂SO₄), concentration, and distillation (short-path, b.p.=130° C. at ~5 mm Hg) gave the title compound as a colorless oil. ¹H NMR (CDCl₃) δ 3.72 (t, 4H), 2.60 (t, 2H), 2.48 (t, 4H), 2.39 (td, 2H), 2.00 (t, 1H).

Step 3: 4-Chloro-7-(4-methoxy-3,5-dimethyl-pyridin-2-ylmethyl)-5-(4-morpholin-4-yl-but-1-ynyl)-7H-pyrrolo[2,3-d]pyrimidin-2-ylamine The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with 4-but-3-ynyl-morpholine according to the General Procedure A. t_R=4.12 min. ¹H NMR (CDCl₃) δ 8.33 (s, 1H), 6.96 (s, 1H), 5.26 (s, 2H), 5.12 (s, 2H), 3.76 (s, 3H), 3.72 (t, 4H), 2.67 (m, 2H), 2.60 (m, 2H), 2.52 (t, 4H), 2.25 (s, 3H), 2.20 (s, 3H).

Example 19

4-Chloro-7-(4-methoxy-3,5-dimethyl-pyridin-2-ylmethyl)-5-(5-morpholin-4-yl-pent-1-ynyl)-7H-pyrrolo[2,3-d]pyrimidin-2-ylamine

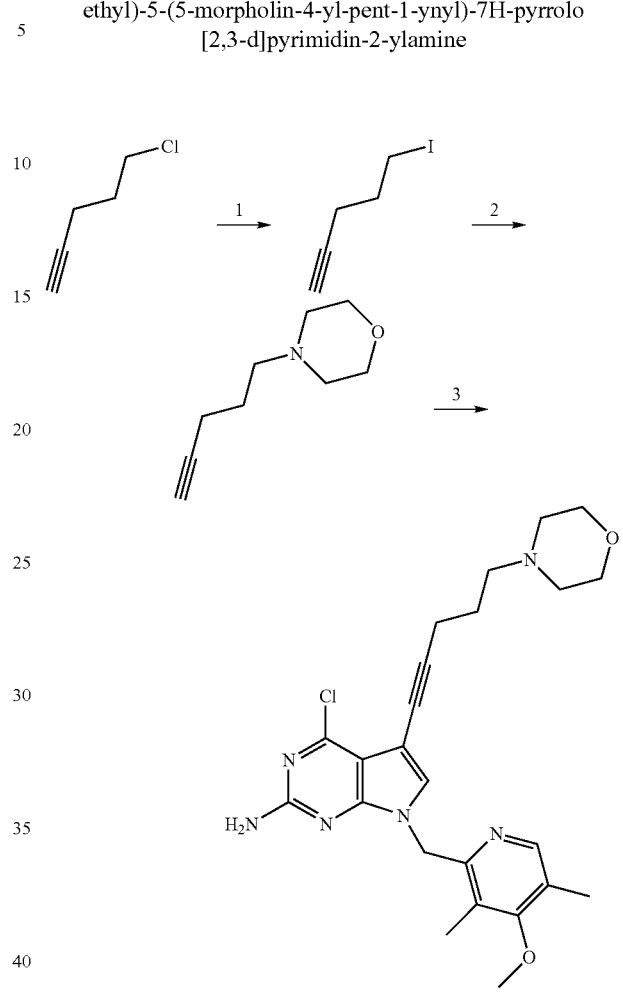

Step 1: 5-Iodo-pent-1-yne

A mixture of 5-chloro-pent-1-yne (5.0 mL, 47 mmol), NaI (9.7 g, 65 mmol) and acetone (20 mL) was heated to reflux for 15 h. Additional NaI (9.7 g, 65 mmol) was added, and the refluxed was prolonged for 24 h. After filtration and concentration, the residue was dissolved in hexane and washed with water and aq. Na₂S₂O₃. Drying (Na₂SO₄) and conncetration afforded the title compound. ¹H NMR (CDCl₃) δ 3.33 (t, 2H), 2.36 (td, 2H), 2.03 (quint., 2H), 2.01 (t, 1H).

Step 2: 4-Pent-4-ynyl-morpholine

A mixture of 5-iodo-pent-1-yne (2.40 g, 12.3 mmol) and morpholine (2.70 g, 30.9 mmol) was heated to 80° C. for 15 min. The mixture was diluted with Et₂O and filtered. The solid residue was discarded, and the mother liquor was extracted with 3N HCl. The aqueous layer was made basic with NaOH, and back-extracted into EtOAc. Drying (Na₂SO₄), and concentration gave the title compound as a pale orange oil. ¹H NMR (CDCl₃) δ 3.67 (t, 4H), 2.39 (m, 6H), 2.21 (td, 2H), 1.93 (t, 1H), 1.67 (quint., 2H).

Step 3: 4-Chloro-7-(4-methoxy-3,5-dimethyl-pyridin-2-ylmethyl)-5-(5-morpholin-4-yl-pent-1-ynyl)-7H-pyrrolo[2,3-d]pyrimidin-2-ylamine The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with 4-pent-4-ynyl-morpholine according to the general procedure A. $t_R$=4.26 min. $^1$H NMR (CDCl$_3$) δ 8.21 (s, 1H), 7.00 (s, 1H), 5.29 (s, 2H), 5.13 (s, 2H), 3.74 (s, 3H), 3.71 (t, 4H), 2.51-2.45 (m, 8H), 2.25 (s, 3H), 2.18 (s, 3H), 1.78 (quint., 2H).

Example 20

5-(4-tert-Butylamino-but-1-ynyl)-4-chloro-7-(4-methoxy-3,5-dimethyl-pyridin-2-ylmethyl)-7H-pyrrolo[2,3-d]pyrimidin-2-ylamine

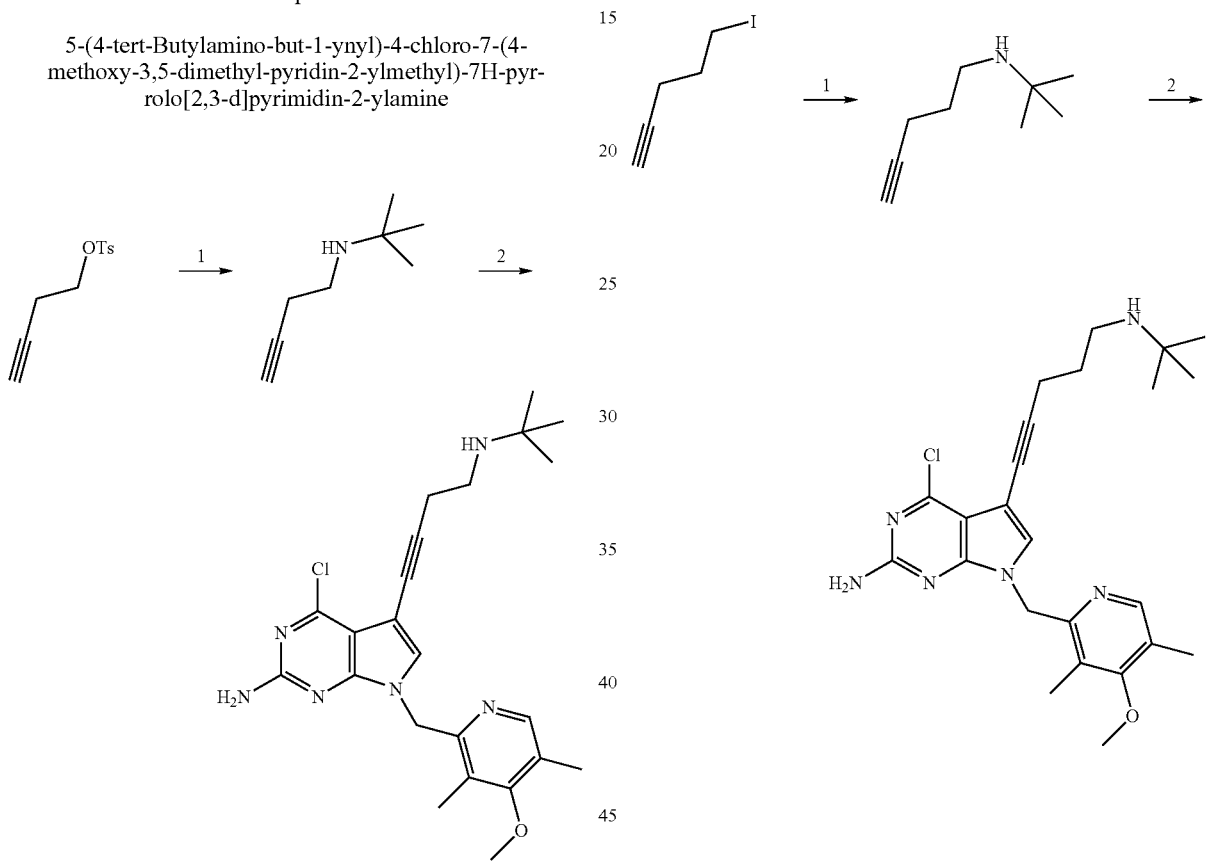

Step 1: tert-Butyl-but-3-ynyl-amine

A solution of toluene-4-sulfonic acid but-3-ynyl ester (1.57 g, 7.1 mmol) in tert-BuNH$_2$ (3.54 g. 48 mmol) was heated to reflux for 18 h. The reaction mixture was diluted with Et$_2$O (20 mL), filtered, and concentrated to afford the title product. $^1$H NMR (CDCl$_3$) δ 2.74 (t, 2H), 2.38 (td, 2H), 2.00 (t, 1H), 1.12 (s, 9H).

Step 2: 5-(4-tert-Butylamino-but-1-ynyl)-4-chloro-7-(4-methoxy-3,5-dimethyl-pyridin-2-ylmethyl)-7H-pyrrolo[2,3-d]pyrimidin-2-ylamine The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with tert-butyl-but-3-ynyl-amine according to the General Procedure A. $t_R$=4.38 min. $^1$H NMR (CDCl$_3$) δ 8.21 (s, 1H), 7.03 (s, 1H), 5.29 (s, 2H), 5.10 (s, 2H), 3.74 (s, 3H), 2.81 (t, 2H), 2.62 (t, 2H), 2.25 (s, 3H), 2.18 (s, 3H), 1.13 (s, 9H).

Example 21

5-(5-tert-Butylamino-pent-1-ynyl)-4-chloro-7-(4-methoxy-3,5-dimethyl-pyridin-2-ylmethyl)-7H-pyrrolo[2,3-d]pyrimidin-2-ylamine

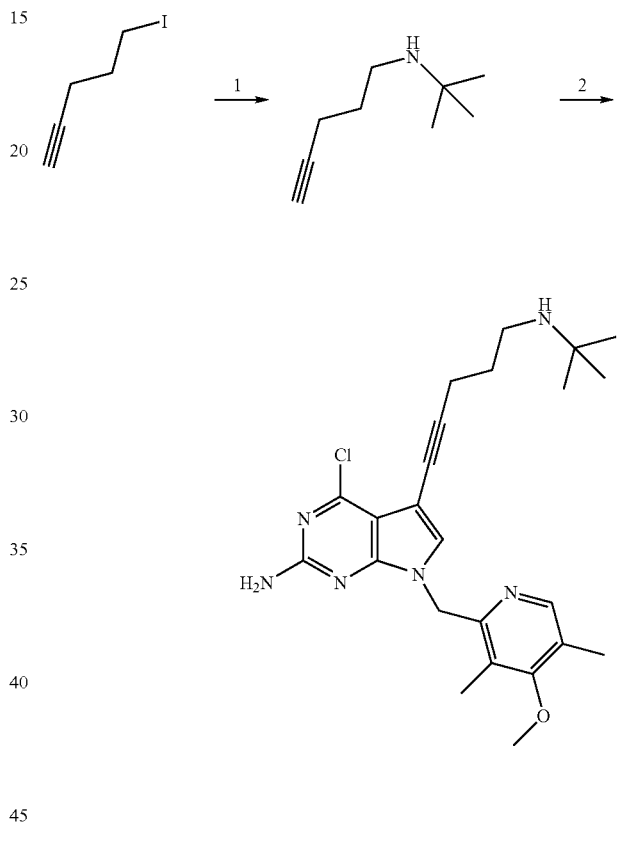

Step 1: tert-Butyl-pent-4-ynyl-amine

A solution of 5-iodo-pent-1-yne (1.0 g, 5.2 mmol) in tert-BuNH$_2$ (2.0 g. 27 mmol) was heated to reflux for 4 h, evaporated, diluted with Et$_2$O, filtered, and concentrated to afford the title compound. $^1$H NMR (CDCl$_3$) δ 2.67 (t, 2H), 2.27 (td, 2H), 1.96 (t, 1H), 1.70 (quint., 2H), 1.11 (s, 9H).

Step 2: 5-(5-tert-Butylamino-pent-1-ynyl)-4-chloro-7-(4-methoxy-3,5-dimethyl-pyridin-2-ylmethyl)-7H-pyrrolo[2,3-d]pyrimidin-2-ylamine The title compound was obtained by Sonogashira coupling of 4-Chloro-5-iodo-7-(4-methoxy-3,5-dimethyl-pyridin-2-ylmethyl)-7H-pyrrolo[2,3-d]pyrimidin-2-ylamine (see Example 1) with tert-butyl-pent-4-ynyl-amine according to the General Procedure A. $t_R$=4.51 min. $^1$H NMR (CDCl$_3$) δ 8.23 (s, 1H), 7.02 (s, 1H), 5.30 (s, 2H), 5.00 (s, 2H), 3.75 (s, 3H), 2.74 (t, 2H), 2.50 (t, 2H), 2.27 (s, 3H), 2.19 (s, 3H), 1.76 (quint., 2H), 1.12 (s, 9H).

Example 22

Dimethylamino-acetic acid 3-[2-amino-4-chloro-7-(4-methoxy-3,5-dimethyl-pyridin-2-ylmethyl)-7H-pyrrolo[2,3-d]pyrimidin-5-yl]-prop-2-ynyl ester

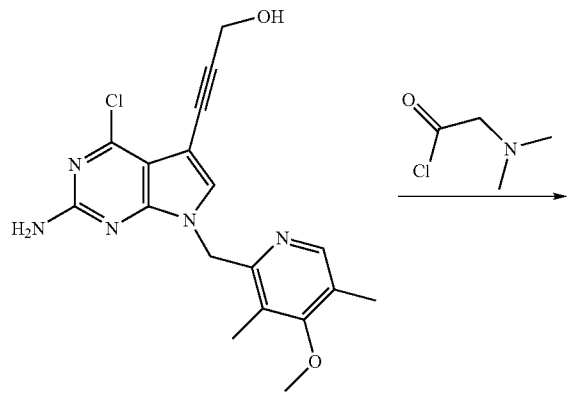

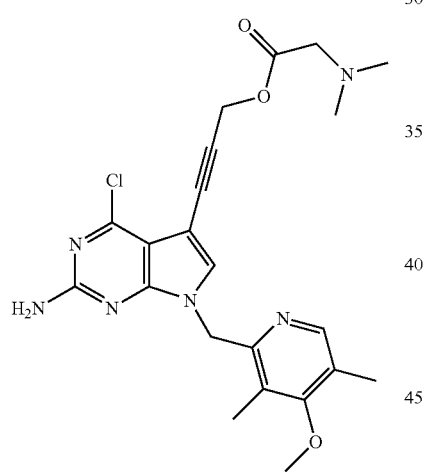

A solution of 3-[2-amino-4-chloro-7-(4-methoxy-3,5-dimethyl-pyridin-2-ylmethyl)-7H-pyrrolo[2,3-d]pyrimidin-5-yl]-prop-2-yn-1-ol (see example 1, 177 mg, 0.48 mmol) in anhydrous pyridine (3 mL) was treated with N,N-dimethylamino-acetyl chloride hydrochloride (113 mg, 0.72 mmol) at rt for 30 min. Addition of toluene (10 mL) caused the formation of a sticky pellet. The toluene solution was discarded, and the pellet was partitioned between water and DCM. The DCM layer was concentrated, and purifed by flash chromatography (EtOAc/DCM/Et$_3$N 33:66:1, gradually adding MeOH (0-2%)) to afford the title compound. t$_R$=4.51 min. $^1$H NMR (CDCl$_3$) δ 8.23 (s, 1H), 7.14 (s, 1H), 5.31 (s, 2H), 5.00 (s, 2H), 4.98 (s, 2H), 3.76 (s, 3H), 3.25 (s, 2H), 2.38 (s, 6H), 2.28 (s, 3H), 2.20 (s, 3H).

Example 23

5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol

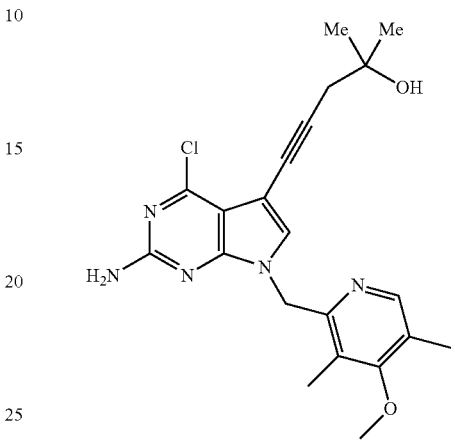

Sonogashira coupling of 4-chloro-5-iodo-7-((4-methoxy-3,5-dimethylpyridin-2-yl)methyl)-7H-pyrrolo[2,3-d]pyrimidin-2-amine with 2-methylpent-4-yn-2-ol (H. Zhang et al., *Tetrahedron Lett.* 1999, 40, 7851) according to the general procedure A gave the title compound, as a solid. Mp=163-165° C. HPLC Rt=4.98 min.

Example 24

4-chloro-7-((4-methoxy-3,5-dimethylpyridin-2-yl)methyl)-5-(5-(4-methylpiperazin-1-yl)pent-1-ynyl)-7H-pyrrolo[2,3-d]pyrimidin-2-amine

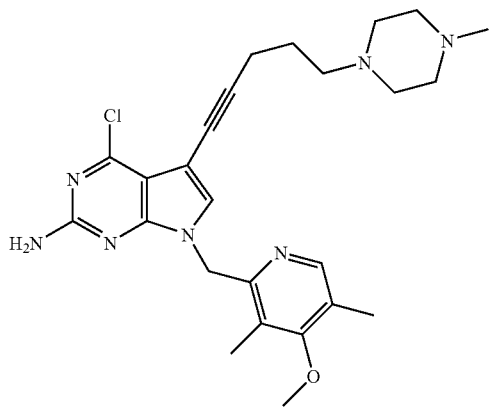

Step 1: 1-methyl-4-(pent-4-ynyl)piperazine

A mixture of pent-4-ynyl methanesulfonate (887 mg) and N-methyl piperazine (607 μL) was heated to 80° C. for 4.5 h, diluted with 1,2-dichloroethane (5 mL) and heated to 70° C.

for 18 h. Saturated aq. NaHCO₃ was added (10 mL) and the mixture was extracted with DCM (3×40 mL), dried over Na₂SO₄, and concentrated to afford 1-methyl-4-(pent-4-ynyl)piperazine (0.23 g).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-methyl-4-pent-4-ynyl)piperazine, according to the general procedure A gave the title compound, as a solid. Mp=160.1-162.3° C. HPLC Rt=4.08 min.

Example 25

4-chloro-5-(5-(4-ethylpiperazin-1-yl)pent-1-ynyl)-7-((4-methoxy-3,5-dimethylpyridin-2-yl)methyl)-7H-pyrrolo[2,3-d]pyrimidin-2-amine

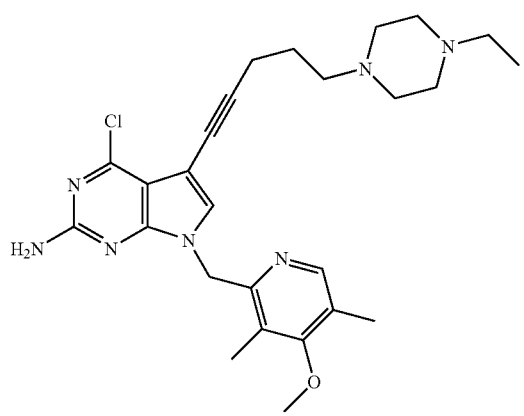

Step 1: 1-ethyl-4-(pent-4-ynyl)piperazine

A mixture of pent-4-ynyl methanesulfonate (849 mg) and N-methyl piperazine (665 µL) was heated to 80° C. for 3 h, diluted with 1,2-dichloroethane (5 mL) and heated to 70° C. for 18 h. Saturated aq. NaHCO₃ was added (10 mL) and the mixture was extracted with DCM (1×40 mL), dried over Na₂SO₄, and concentrated to afford 0.56 g of 1-ethyl-4-(pent-4-ynyl)piperazine.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-ethyl-4-(pent-4-ynyl)piperazine, according to the general procedure A gave the title compound, as a solid. Mp=142.3-144.1° C. HPLC Rt=4.11 min.

Example 26

4-chloro-7-((4-methoxy-3,5-dimethylpyridin-2-yl)methyl)-5-(4-(4-methylpiperazin-1-yl)but-1-ynyl)-7H-pyrrolo[2,3-d]pyrimidin-2-amine

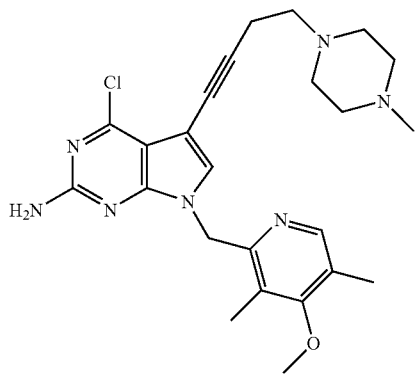

Step 1: 1-(but-3-ynyl)-4-methylpiperazine

A mixture of but-3-ynyl 4-methylbenzenesulfonate (972 mg) and N-methyl piperazine (482 µL) was heated to 80 C. for 4.5 h, diluted with 1,2-dichloroethane (5 mL) and heated to 70° C. for 18 h. Saturated aq. NaHCO₃ was added (10 mL) and the mixture was extracted with DCM (3×40 mL), and concentrated to afford 0.70 g of 1-(but-3-ynyl)-4-methylpiperazine as a 3:2 mixture of tosylate salt and free base.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(but-3-ynyl)-4-methylpiperazine according to the general procedure A gave the title compound, as an oil. HPLC Rt=4.05 min.

Example 27

4-(5-(2-amino-4-chloro-7-((4-methoxy-3,5-dimethylpyridin-2-yl)methyl)-7H-pyrrolo[2,3-d]pyrimidin-5-yl)pent-4-ynyl)-N-methylpiperazine-1-carboxamide

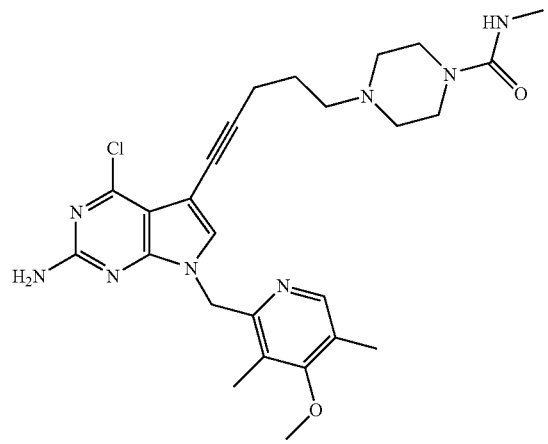

Step 1: 1-(pent-4-ynyl)piperazine

A solution of pent-4-ynyl methanesulfonate (19.55 g) and piperazine (41.5 g) in EtOH (80 mL) was heated to reflux for 1 h, and evaporated. The residue was taken in NaOH 2M (70 mL) and extracted with Et$_2$O (70 mL). Evaporation gave 1-(pent-4-ynyl)piperazine (4.4 g).

Step 2: 4-nitrophenyl 4-(pent-4-ynyl)piperazine-1-carboxylate

A solution of 1-(pent-4-ynyl)piperazine (2.2 g) and Et$_3$N (22 mL) in 1,2-dichloroethane (22 mL) was treated with p-nitrophenyl chloroformate (2.9 g) at rt for 10 min. Work-up and silica gel chromatography (DCM:EtOAc 1:3→0:3) gave 4-nitrophenyl 4-(pent-4-ynyl)piperazine-1-carboxylate as a yellow oil (2.96 g).

Step 3: N-methyl-4-(pent-4-ynyl)piperazine-1-carboxamide

A solution of 4-nitrophenyl 4-(pent-4-ynyl)piperazine-1-carboxylate (1.37 g) in THF (10 mL) was treated with 40% aq. MeNH$_2$ (10 mL) at 70 C for 2 h. The mixture was concentrated and diluted with conc. NH$_4$OH (5 mL) and water (15 mL). Extraction (DCM, 80 mL) and concentration gave N-methyl-4-(pent-4-ynyl)piperazine-1-carboxamide (0.659 g).

Step 4

Sonogashira coupling of 4-chloro-5-iodo-7-((4-methoxy-3,5-dimethylpyridin-2-yl)methyl)-7H-pyrrolo[2,3-d]pyrimidin-2-amine with N-methyl-4-(pent-4-ynyl)piperazine-1-carboxamide according to the general procedure A gave the title compound, as a solid. Mp=191.2-193.2° C. HPLC Rt=4.24 min.

Example 28

4-(5-(2-amino-4-chloro-7-((4-methoxy-3,5-dimethylpyridin-2-yl)methyl)-7H-pyrrolo[2,3-d]pyrimidin-5-yl)pent-4-ynyl)-N-ethylpiperazine-1-carboxamide

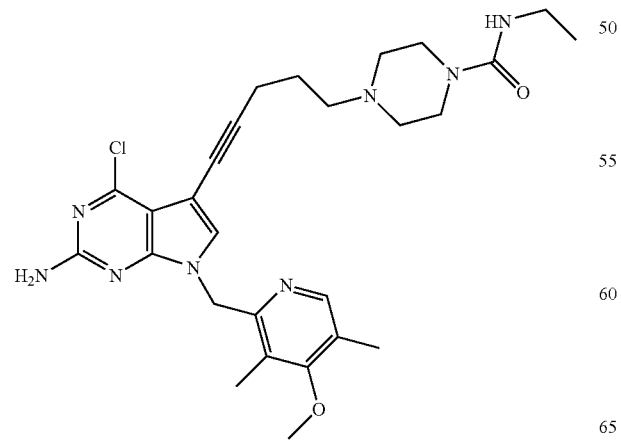

Step 1: N-ethyl-4-(pent-4-ynyl)piperazine-1-carboxamide

A solution of 1-(pent-4-ynyl)piperazine (1.08) in DCM (5 mL) was treated with ethyl isocyanate (0.56 mL) at rt for 2 h, and evaporated to yield N-ethyl-4-(pent-4-ynyl)piperazine-1-carboxamide.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with N-ethyl-4-(pent-4-ynyl)piperazine-1-carboxamide according to the general procedure A gave the title compound, as a solid. Mp=200.5-203.3° C. HPLC Rt=4.35 min.

Example 29

4-chloro-7-((4-methoxy-3,5-dimethylpyridin-2-yl)methyl)-5-(4-(4-phenylpiperazin-1-yl)but-1-ynyl)-7H-pyrrolo[2,3-d]pyrimidin-2-amine

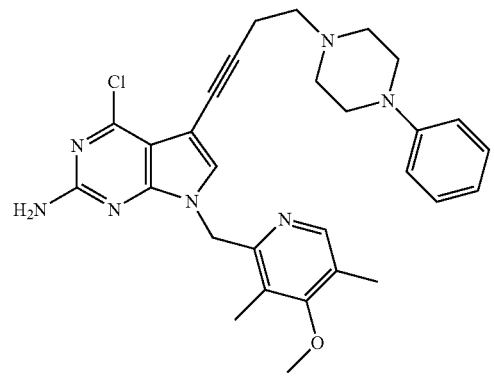

Step 1: 1-(but-3-ynyl)-4-phenylpiperazine

A solution of but-3-ynyl 4-methylbenzenesulfonate (1.72 g), N-phenyl piperazine (1.17 mL) and diisoproylethylamine (1.45 mL) in 1,2-dichloroethane (5 mL) was heated to reflux overnight. The mixture was concentrated, diluted with sat. aq. NaHCO$_3$ (5 mL) and extracted with DCM (2×50 mL). Drying (Na$_2$SO$_4$) and silica gel flash chromatography (3% Et$_3$N in EtOAc) afforded 1-(but-3-ynyl)-4-phenylpiperazine (0.76 g)

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(but-3-ynyl)-4-phenylpiperazine according to the general procedure A gave the title compound, as a solid. HPLC Rt=4.97 min.

Example 30

4-chloro-7-((4-methoxy-3,5-dimethylpyridin-2-yl)methyl)-5-(4-(4-(pyridin-2-yl)piperazin-1-yl)but-1-ynyl)-7H-pyrrolo[2,3-d]pyrimidin-2-amine

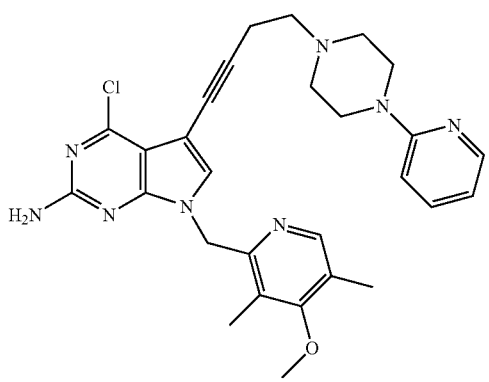

Step 1: 1-(but-3-ynyl)-4-(pyridin-2-yl)piperazine

A solution of but-3-ynyl 4-methylbenzenesulfonate (1.27 g), 1-(pyridin-2-yl)piperazine (1.17 g) and diisoproylethylamine (1.37 mL) in 1,2-dichloroethane (7 mL) was heated to reflux overnight. The mixture was concentrated, diluted with sat. aq. NaHCO₃ (5 mL) and extracted with DCM (2×50 mL). Drying (Na₂SO₄) and silica gel flash chromatography (EtOAc/hexane 1:1→1:0) afforded 1-(but-3-ynyl)-4-(pyridin-2-yl)piperazine (0.59 g)

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(but-3-ynyl)-4-(pyridin-2-yl)piperazine according to the general procedure A gave the title compound, as a solid. HPLC Rt=4.09 min.

Example 31

4-chloro-7-((4-methoxy-3,5-dimethylpyridin-2-yl)methyl)-5-(4-(4-(pyrimidin-2-yl)piperazin-1-yl)but-1-ynyl)-7H-pyrrolo[2,3-d]pyrimidin-2-amine

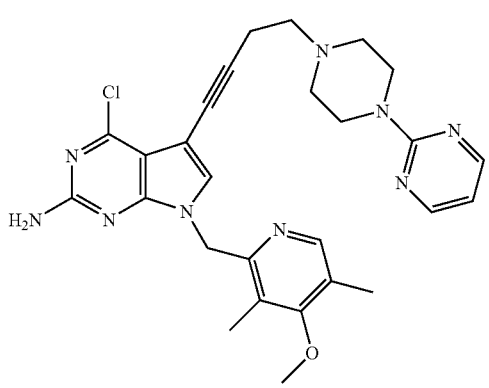

Step 1: 2-(4-(but-3-ynyl)piperazin-1-yl)pyrimidine

A solution of but-3-ynyl 4-methylbenzenesulfonate (1.14 g), 2-(piperazin-1-yl)pyrimidine (1.06 g) and diisoproylethylamine (1.24 mL) in 1,2-dichloroethane (6 mL) was heated to reflux overnight. The mixture was concentrated, diluted with sat. aq. NaHCO₃ (5 mL) and extracted with DCM (2×50 mL). Drying (Na₂SO₄) and silica gel flash chromatography (EtOAc/hexane 1:1→1:0) afforded 2-(4-(but-3-ynyl)piperazin-1-yl)pyrimidine (0.60 g).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 2-(4-(but-3-ynyl)piperazin-1-yl)pyrimidine according to the general procedure A gave the title compound, as a solid. HPLC Rt=4.50 min.

Example 32

4-chloro-7-((4-methoxy-3,5-dimethylpyridin-2-yl)methyl)-5-(5-(4-phenylpiperazin-1-yl)pent-1-ynyl)-7H-pyrrolo[2,3-d]pyrimidin-2-amine

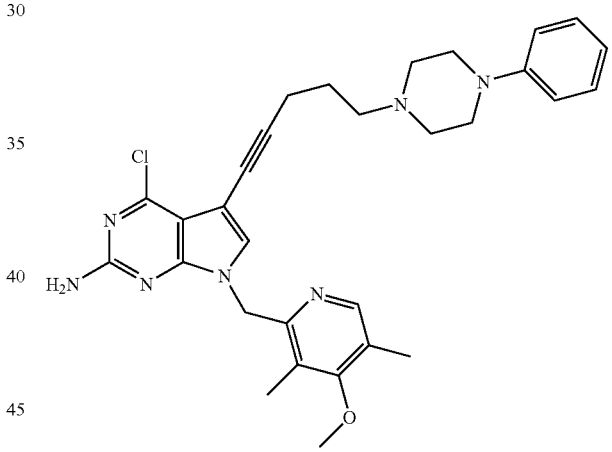

Step 1: 1-(pent-4-ynyl)-4-phenylpiperazine

A solution of pent-4-ynyl methanesulfonate (1.05 g), N-phenyl piperazine (1.02 g) and diisoproylethylamine (1.2 mL) in THF (5 mL) was heated to reflux overnight. The mixture was concentrated, diluted with aq. NaOH 2M (10 mL) and extracted with DCM (2×50 mL). Drying (Na₂SO₄) and silica gel flash chromatography (EtOAc/hexane 2:1→2:0) afforded 1-(pent-4-ynyl)-4-phenylpiperazine (1.03 g).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(pent-4-ynyl)-4-phenylpiperazine according to the general procedure A gave the title compound, as a solid. HPLC Rt=5.08 min.

Example 33

4-chloro-7-((4-methoxy-3,5-dimethylpyridin-2-yl)methyl)-5-(5-(4-(pyridin-2-yl)piperazin-1-yl)pent-1-ynyl)-7H-pyrrolo[2,3-d]pyrimidin-2-amine

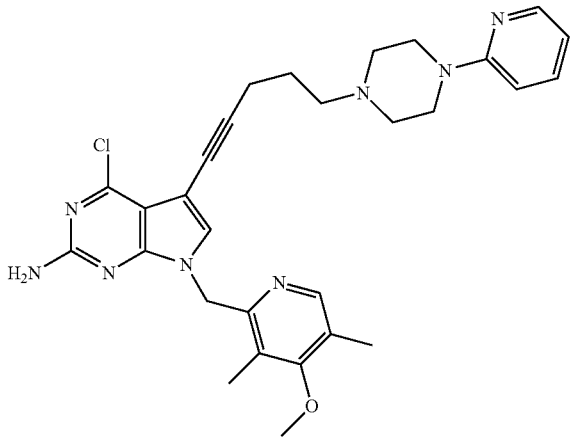

Step 1: 1-(pent-4-ynyl)-4-(pyridin-2-yl)piperazine

A solution of pent-4-ynyl methanesulfonate (1.05 g), 1-(pyridin-2-yl)piperazine (1.02 g) and diisoproylethylamine (1.2 mL) in THF (5 mL) was heated to reflux overnight. The mixture was concentrated, diluted with aq. NaOH 2M (10 mL) and extracted with DCM (2×50 mL). Drying (Na₂SO₄) and silica gel flash chromatography (EtOAc/hexane 2:1→2:0) afforded 1-(pent-4-ynyl)-4-(pyridin-2-yl)piperazine (1.02 g).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(pent-4-ynyl)-4-(pyridin-2-yl)piperazine according to the general procedure A gave the title compound, as a solid. HPLC Rt=4.23 min.

Example 34

4-chloro-7-((4-methoxy-3,5-dimethylpyridin-2-yl)methyl)-5-(5-(4-(pyrimidin-2-yl)piperazin-1-yl)pent-1-ynyl)-7H-pyrrolo[2,3-d]pyrimidin-2-amine

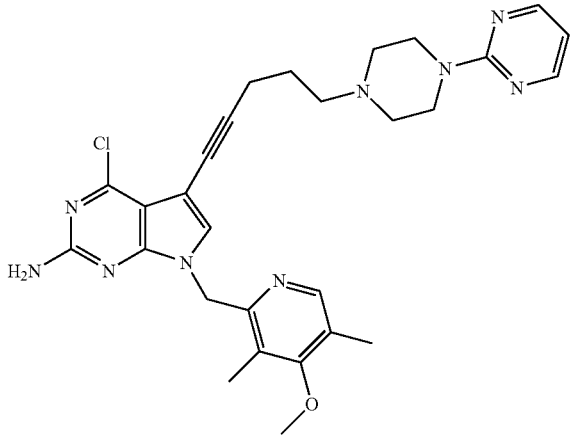

Step 1: 2-(4-(pent-4-ynyl)piperazin-1-yl)pyrimidine

A solution of pent-4-ynyl methanesulfonate (1.05 g), 2-(piperazin-1-yl)pyrimidine (1.02 g) and diisoproylethylamine (1.2 mL) in THF (5 mL) was heated to reflux overnight. The mixture was concentrated, diluted with aq. NaOH 2M (10 mL) and extracted with DCM (2×50 mL). Drying (Na₂SO₄) and silica gel flash chromatography (EtOAc/hexane 2:1→2:0) afforded 2-(4-(pent-4-ynyl)piperazin-1-yl)pyrimidine (0.95 g).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 2-(4-(pent-4-ynyl)piperazin-1-yl)pyrimidine according to the general procedure A gave the title compound, as a solid. HPLC Rt=4.61 min.

Example 35

5-(5-(1H-imidazol-1-yl)pent-1-ynyl)-4-chloro-7-((4-methoxy-3,5-dimethylpyridin-2-yl)methyl)-7H-pyrrolo[2,3-d]pyrimidin-2-amine

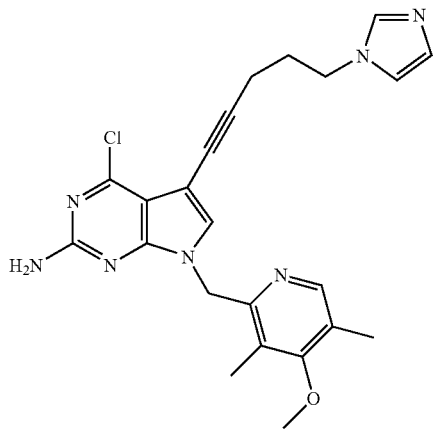

Step 1: 1-(pent-4-ynyl)-1H-imidazole

A mixture of pent-4-ynyl methanesulfonate (1.06 g), imidazole (534 mg) and K₂CO₃ (3.66 g) in 2-butanone (11 mL) was heated to reflux overnight. Work-up (DCM, H₂O), drying (Na₂SO₄) and concentration gave 1-(pent-4-ynyl)-1H-imidazole (472 mg).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(pent-4-ynyl)-1H-imidazole according to the general procedure A gave the title compound, as a solid. HPLC Rt=4.40 min.

Example 36

4-(2-amino-4-chloro-7-((4-methoxy-3,5-dimethylpyridin-2-yl)methyl)-7H-pyrrolo[2,3-d]pyrimidin-5-yl)but-3-ynyl ethyl carbonate

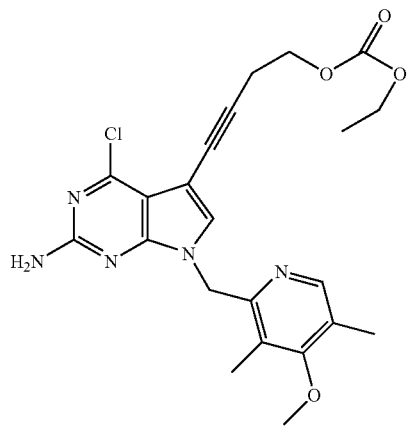

A solution of 4-[2-Amino-4-chloro-7-(4-methoxy-3,5-dimethyl-pyridin-2-ylmethyl)-7H-pyrrolo[2,3-d]pyrimidin-5-yl]-but-3-yn-1-ol (see example 2) (1.53 g) and NaH (95%, 0.38 g) in anhydrous DMA (25 mL) was treated with ethyl chloroformate (1.5 mL) at 0-23° C. for 0.5 h. Work-up and preparative HPLC gave the title compound. HPLC Rt=5.65 min.

Example 37

Ethyl-4-chloro-5-(4-(ethoxycarbonyloxy)but-1-ynyl)-7-((4-methoxy-3,5-dimethylpyridin-2-yl)methyl)-7H-pyrrolo[2,3-d]pyrimidin-2-ylcarbamate

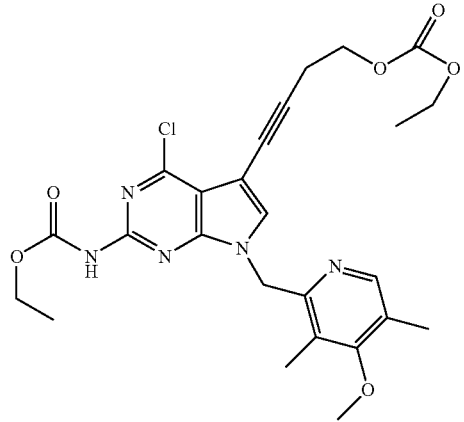

A suspension of 4-[2-Amino-4-chloro-7-(4-methoxy-3,5-dimethyl-pyridin-2-ylmethyl)-7H-pyrrolo[2,3-d]pyrimidin-5-yl]-but-3-yn-1-ol (see example 2) (0.73 g) in anhydrous pyridine (5 mL) and DCM (25 mL) was treated with ethyl chloroformate (1 mL) at rt for 30 min. The mixture was cooled to 0° C., treated with addition EtOCOCl (1 mL), and the temperature was allowed to slowly reach rt overnight. The reaction mixture was diluted with DCM (30 mL) and washed sequentially with H₂O, NH₄OH 1M, and brine. The DCM was evaporated, but not the residual pyridine, Addition of MeOH (20 mL) induced crystallization of the product, as white needles. HPLC Rt=6.28 min.

Example 38

4-(4-(2-amino-4-chloro-7-((4-methoxy-3,5-dimethylpyridin-2-yl)methyl)-7H-pyrrolo[2,3-d]pyrimidin-5-yl)but-3-ynyl)-N-methylpiperazine-1-carboxamide

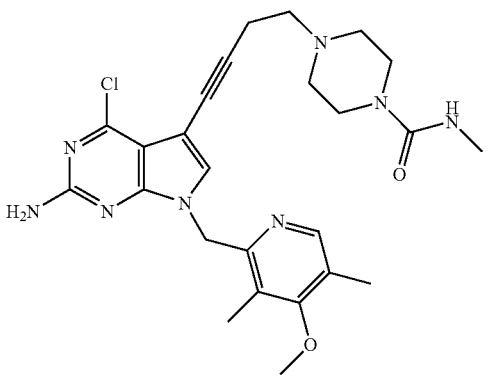

Step 1: 1-(but-3-ynyl)piperazine

A solution of but-3-ynyl 4-methylbenzenesulfonate (2.0 mL) and piperazine (2.0 g) in EtOH (6 mL) was heated to reflux for 30 min. The mixture was concentrated, diluted with NaOH 2 M (8 mL) and extracted with Et₂O (50 mL). Evaporation of the organic layer gave a 2:1 mixture of mono and bis-alkylated piperazine (450 mg) which was discarded. The aqueous layer was further extracted with DCM (100 mL) to give of 1-(but-3-ynyl)piperazine (640 mg).

Step 2: 4-(but-3-ynyl)-N-methylpiperazine-1-carboxamide

A solution of 1-(but-3-ynyl)piperazine (445 mg) in THF (4 mL) was treated with 4-nitrophenyl carbonochloridate (649 mg) at rt for 5 min. A precipitate formed immediately, and the suspension was treated with Et₃N (0.45 mL) to ensure complete reaction. The suspension was diluted wiht H₂O (2 mL), MeOH (2 mL) and 40% aq. MeNH₂ (4.0 mL) and stirred at rt for 3 days. Extraction with DCM (50 mL), washing (NaOH 2M), drying (Na₂SO₄) and concentration gave 4-(but-3-ynyl)-N-methylpiperazine-1-carboxamide (370 mg).

Step 3

Sonogashira coupling of 4-chloro-5-iodo-7-((4-methoxy-3,5-dimethylpyridin-2-yl)methyl)-7H-pyrrolo[2,3-d]pyrimidin-2-amine with 4-(but-3-ynyl)-N-methylpiperazine-1-carboxamide according to the general procedure A gave the title compound, as a solid. HPLC Rt=4.10 min

Example 39

5-(4-(1H-imidazol-1-yl)but-1-ynyl)-4-chloro-7-((4-methoxy-3,5-dimethylpyridin-2-yl)methyl)-7H-pyrrolo[2,3-d]pyrimidin-2-amine

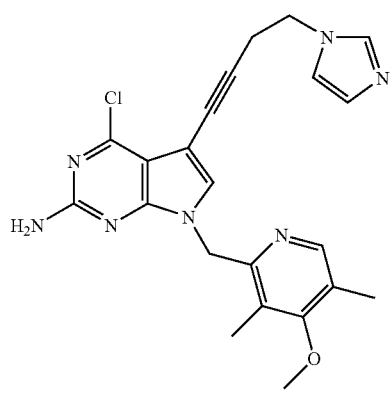

Step 1: 1-(but-3-ynyl)-1H-imidazole

A mixture of but-3-ynyl 4-methylbenzenesulfonate (1.04 g), imidazole (573 mg) and $K_2CO_3$ (3.88 g) in 2-butanone (10 mL) was heated to reflux overnight. Work-up (DCM, $H_2O$), drying ($Na_2SO_4$) and concentration gave 1-(but-3-ynyl)-1H-imidazole (501 mg).

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with 1-(but-3-ynyl)-1H-imidazole according to the general procedure A gave the title compound., as a solid. HPLC Rt=4.21 min.

Example 40

(S)-4-(2-amino-4-chloro-7-((4-methoxy-3,5-dimethylpyridin-2-yl)methyl)-7H-pyrrolo[2,3-d]pyrimidin-5-yl)but-3-ynyl 2-aminopropanoate

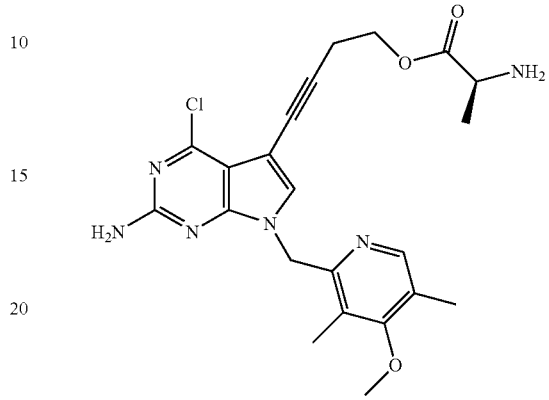

A solution of 4-[2-Amino-4-chloro-7-(4-methoxy-3,5-dimethyl-pyridin-2-ylmethyl)-7H-pyrrolo[2,3-d]pyrimidin-5-yl]-but-3-yn-1-ol (see example 2) (51.7 mg), N-Boc alanine (53.3 mg), DMAP (33.7 mg), and EDCI (54.9 mg) in anhyrous DMA (4 mL) was stirred at rt overnight. Work-up (EtOAc; $H_2O$) gave the crude Boc-protected intermediate. A solution of this intermediate (40 mg) in DCM (1.0 mL) was treated with TFA (0.2 mL) at rt for 5 min, and evaporated. The material was dissolved in MeOH (1 ml) and water (10 mL), and washed with $Et_2O$ (10 mL). The organic layer was discarded. The aqueous layer was brought to pH >7 with sat. aq. $NaHCO_3$ and back-extracted with DCM. The title compound was isolates as a solid. HPLC Rt=4.37 min.

Example 41

(R)-4-(2-amino-4-chloro-7-((4-methoxy-3,5-dimethylpyridin-2-yl)methyl)-7H-pyrrolo[2,3-d]pyrimidin-5-yl)but-3-ynyl 2-amino-3-methylbutanoate

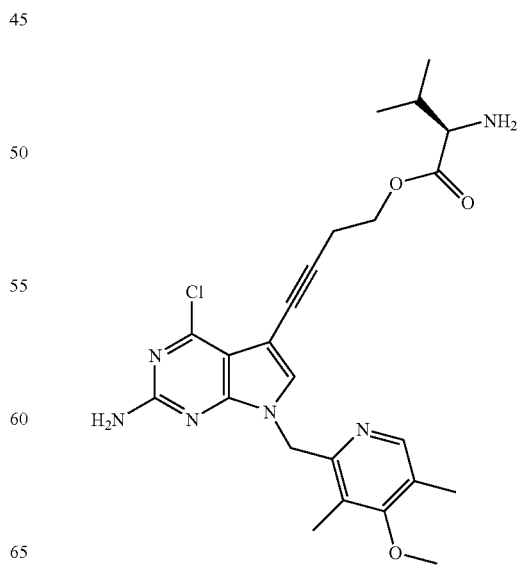

This compound was obtained by the same procedure as used for example 40, using N-Boc valine in place of N-Boc alanine, to give the title compound as a solid. HPLC Rt=4.58 min.

Example 42

(R)-4-(2-amino-4-chloro-7-((4-methoxy-3,5-dimethylpyridin-2-yl)methyl)-7H-pyrrolo[2,3-d]pyrimidin-5-yl)but-3-ynyl 2-amino-4-methylpentanoate

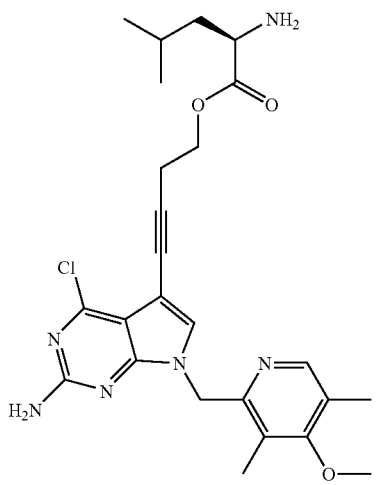

This compound was obtained by the same procedure as used for example 40, using N-Boc isoleucine in place of N-Boc valine, to give the title compound as a solid. HPLC Rt=4.76 min.

Example 43

4-(2-amino-4-chloro-7-((4-methoxy-3,5-dimethylpyridin-2-yl)methyl)-7H-pyrrolo[2,3-d]pyrimidin-5-yl)but-3-ynyl di-tert-butyl phosphate

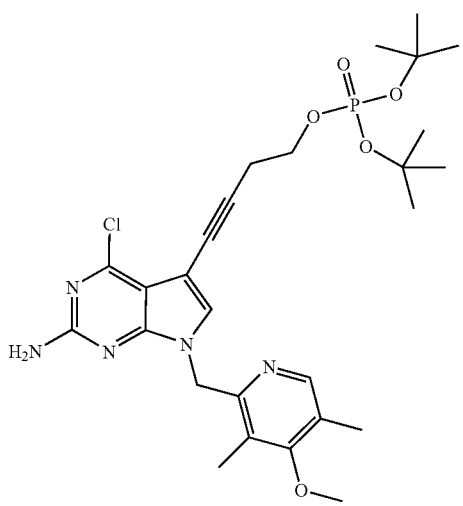

A solution of 4-[2-Amino-4-chloro-7-(4-methoxy-3,5-dimethyl-pyridin-2-ylmethyl)-7H-pyrrolo[2,3-d]pyrimidin-5-yl]-but-3-yn-1-ol (see example 2) (4.0 g) and 1-H-tetrazole (0.45 M in acetonitrile, 70 mL) in THF (160 mL) was treated with di-tert-butyl diisopropylphosphoramidite (16.4 mL) at rt for 2 h. The solution was cooled to 0° C. and treated with 30% aqueous H₂O₂ (11 mL) for 30 mm. Work-up (EtOAc, aq. NaHCO₃) and reverse-phase preparative HPLC gave the title compound, as a solid. HPLC Rt=6.13 mm.

Example 44

4-(2-amino-4-chloro-7-((4-methoxy-3,5-dimethylpyridin-2-yl)methyl)-7H-pyrrolo[2,3-d]pyrimidin-5-yl)but-3-ynyl dihydrogen phosphate

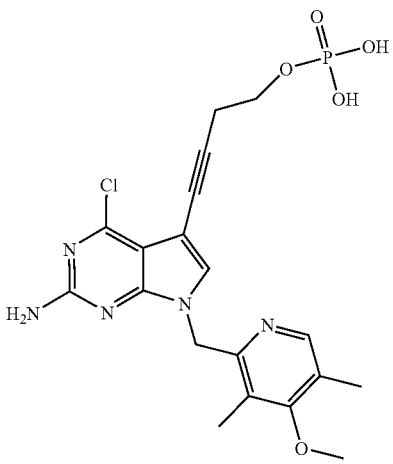

A solution of 4-(2-amino-4-chloro-7-((4-methoxy-3 5-dimethylpyridin-2-yl)methyl)-7H-pyrrolo[2,3-d]pyrimidin-5-yl)but-3-ynyl di-tert-butyl phosphate (see example 43) in DCM ( ) was treated with TFA ( ) at rt for x h. Evaporation gave the title compound as a TFA salt (5 g). The crude was dissolved in a mixture of Et₃N (0.7 mL and MeOH (60 mL), loaded on Dowex 50Wx2-400 (20 g, pre-washed with MeOH), and the resin was washed with MeOH (200 mL) to remove the excess TFA. The desired phosphate was released from the resin with Et₃N:MeOH 1:10 (200 mL) The solution was concentrated to give the phosphate as an oily triethylamine salt (2.75 g). Crystallization was induced with EtOH (60 mL). The mixture was left at rt for 1.5 h and at −20° C. overnight to give a first crop of crystals (0.64 g). The mixture was concentrated and the crystallization procedure was repeated to give a second crop (0.74 g). The combined triethylamine salts (1274 mg) were dissolved in MeOH (50 mL) with the help of Et₃N (326 μL) and treated with a 1.0 M solution of NaGH in MeOH (4.68 mL). Evaporation and drying on high vacuum overnight gave the title compound as a solid sodium salt. HPLC Rt=4.21 mm.

Example 45

2-((2-amino-4-chloro-5-(4-hydroxybut-1-ynyl)-7H-pyrrolo[2,3-d]pyrimidin-7-yl)methyl)-4-methoxy-3,5-dimethylpyridine 1-oxide

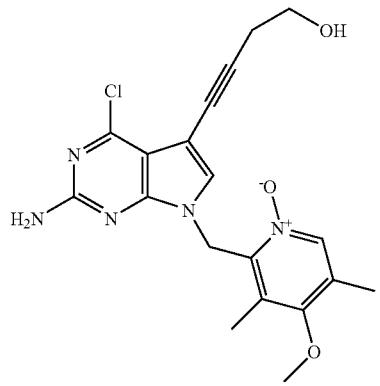

Step 1: 2-((4-chloro-5-iodo-2-pivalamido-7H-pyrrolo[2,3-d]pyrimidin-7-yl)methyl)-4-methoxy-3,5-dimethylpyridine 1-oxide A mixture of N-(4-chloro-5-iodo-7H-pyrrolo[2,3-d]pyrimidin-2-yl)pivalamide (235 mg), 2-(chloromethyl)-4-methoxy-3,5-dimethylpyridine 1-oxide (129 mg), and $K_2CO_3$ (413 mg) in DMF (6.0 mL) was stirred at rt for 3 days, and diluted with water. The precipitate was collected by filtration and washed with IPA to give 2-((4-chloro-5-iodo-2-pivalamido-7H-pyrrolo[2,3-d]pyrimidin-7-yl)methyl)-4-methoxy-3,5-dimethylpyridine 1-oxide (124 mg).

Solid. HPLC Rt=6.73 min

Step 2: 2-((4-chloro-5-(4-hydroxybut-1-ynyl)-2-pivalamido-7H-pyrrolo[2,3-d]pyrimidin-7-yl)methyl)-4-methoxy-3,5-dimethylpyridine 1-oxide Sonogashira coupling of 2-((4-chloro-5-iodo-2-pivalamido-7H-pyrrolo[2,3-d]pyrimidin-7-yl)methyl)-4-methoxy-3,5-dimethylpyridine 1-oxide (335 mg) with but-3-yn-1-ol (200 μL) according to the general procedure A gave crude 2-((4-chloro-5-(4-hydroxybut-1-ynyl)-2-pivalamido-7H-pyrrolo[2,3-d]pyrimidin-7-yl)methyl)-4-methoxy-3,5-dimethylpyridine 1-oxide (291 mg).

Solid. HPLC Rt=5.82 min.

Step 3

Crude 2-((4-chloro-5-(4-hydroxybut-1-ynyl)-2-pivalamido-7H-pyrrolo[2,3-d]pyrimidin-7-yl)methyl)-4-methoxy-3,5-dimethylpyridine 1-oxide (291 mg) was dissolved in 10 mL EtOH. An aliquot of this solution (2 mL) was further diluted with EtOH (5 mL) and treated with $ZnCl_2$ (103 mg) at 120° C. for 20 min in a microwave oven. Reverse-phase preparative HPLC gave the title compound (2.2 mg), as a solid. HPLC Rt=4.88 min.

Example 46

5-(but-3-en-1-ynyl)-4-chloro-7-((4-methoxy-3,5-dimethylpyridin-2-yl)methyl)-7H-pyrrolo[2,3-d]pyrimidin-2-amine

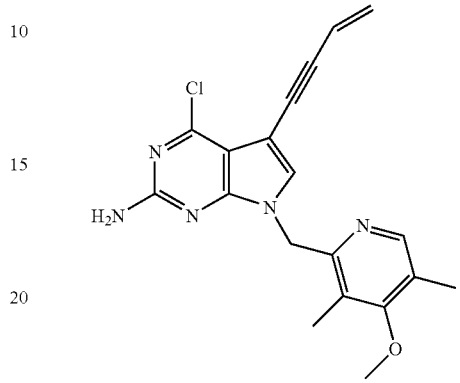

A mixture of 4-(2-amino-4-chloro-7-((4-methoxy-3,5-dimethylpyridin-2-yl)methyl)-7H-pyrrolo[2,3-d]pyrimidin-5-yl)but-3-ynyl 4-methylbenzenesulfonate (516 mg) and CsF (2.0 g) in DMF (7.0 mL) was heated to 70° C. for 1 h. Work-up and flash chromatogrpahy (1→3% MeOH in DCM) gave the title compound (280 mg), as a pale yellow oil. HPLC Rt=5.90 min.

Example 47

5-(2-amino-4-chloro-7-((4-methoxy-3,5-dimethylpyridin-2-yl)methyl)-7H-pyrrolo[2,3-d]pyrimidin-5-yl)pent-4-ynyl methanesulfonate

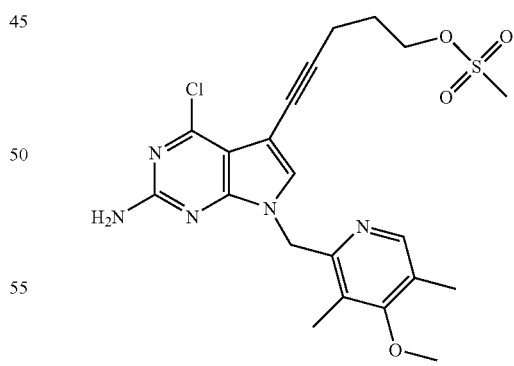

Sonogashira coupling of 4-chloro-5-iodo-7-((4-methoxy-3,5-dimethylpyridin-2-yl)methyl)-7H-pyrrolo[2,3-d]pyrimidin-2-amine with pent-4-ynyl methanesulfonate according to the general procedure A gave the title compound, as a solid. HPLC Rt=5.31 mm.

Example 48

4-chloro-5-(5-fluoropent-1-ynyl)-7-((4-methoxy-3,5-dimethylpyridin-2-yl)methyl)-7H-pyrrolo[2,3-d]pyrimidin-2-amine

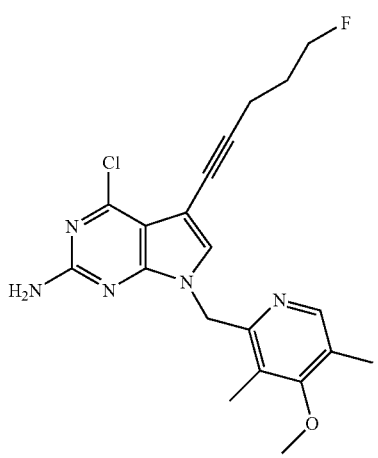

A solution of KF (77.8 mg), Kryptofix 222 (Aldrich, 839 mg) and water (10 mL) was evaporated to dryness, and dried first azeotropically with anh. $CH_3CN$ (3×20 mL), then on high vacuum at 50° C. overnight. The solid was redissolved in anhydrous acetonitrile (13 mL) to give a 0.1 M fluoride solution. Treatement of 5-(2-amino-4-chloro-7-((4-methoxy-3,5-dimethylpyridin-2-yl)methyl)-7H-pyrrolo[2,3-d]pyrimidin-5-yl)pent-4-ynyl methanesulfonate (see example 47) (42 mg) with this solution (3 mL) at 60-70° C. for 2 h, work-up and reverse-phase preparative HPLC gave the title compound, as an oil. HPLC Rt=5.88 min.

Example 49

(S)-4-(2-amino-4-chloro-7-((4-methoxy-3,5-dimethylpyridin-2-yl)methyl)-7H-pyrrolo[2,3-d]pyrimidin-5-yl)but-3-yne-1,2-diol

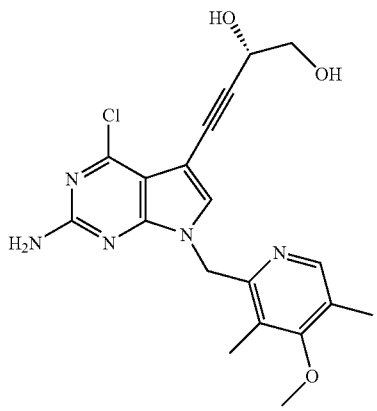

Treatment of 5-(but-3-en-1-ynyl)-4-chloro-7-((4-methoxy-3,5-dimethylpyridin-2-yl)methyl)-7H-pyrrolo[2,3-d]pyrimidin-2-amine (see example 46) (35 mg) with AD-mix-α (Aldrich, 540 mg) in t-BuOH:THF:water 1:1:1 (6 mL) at rt overnight, followed by work-up and reverse-phase preparative HPLC gave the title compound (10 mg), as a solid. HPLC Rt=4.13 min

Example 50

(R)-4-(2-amino-4-chloro-7-((4-methoxy-3,5-dimethylpyridin-2-yl)methyl)-7H-pyrrolo[2,3-d]pyrimidin-5-yl)but-3-yne-1,2-diol

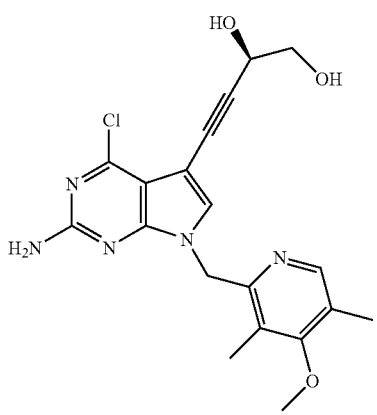

Treatment of 5-(but-3-en-1-ynyl)-4-chloro-7-((4-methoxy-3,5-dimethylpyridin-2-yl)methyl)-7H-pyrrolo[2,3-d]pyrimidin-2-amine (see example 46) (35 mg) with AD-mix-β (Aldrich, 540 mg) in t-BuOH:THF:water 1:1:1 (6 mL) at rt overnight, followed by work-up and reverse-phase preparative HPLC gave the title compound (10 mg), as a solid. HPLC Rt=4.13 min

Example 51

4-chloro-7-((4-methoxy-3,5-dimethylpyridin-2-yl)methyl)-5-(3-methylbut-3-en-1-ynyl)-7H-pyrrolo[2,3-d]pyrimidin-2-amine

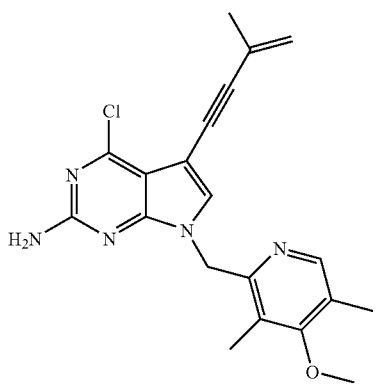

Sonogashira coupling of 4-chloro-5-iodo-7-((4-methoxy-3,5-dimethylpyridin-2-yl)methyl)-7H-pyrrolo[2,3-d]pyrimidin-2-amine with 2-methylbut-1-en-3-yne according to the general procedure A gave the title compound, as a solid. HPLC Rt=6.00 min.

Example 52

(S)-4-(2-amino-4-chloro-7-((4-methoxy-3,5-dimethylpyridin-2-yl)methyl)-7H-pyrrolo[2,3-d]pyrimidin-5-yl)-2-methylbut-3-yne-1,2-diol

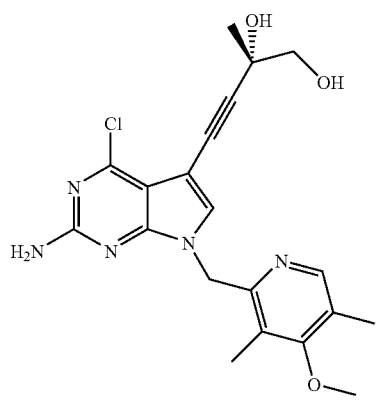

Treatment of 4-chloro-7-((4-methoxy-3,5-dimethylpyridin-2-yl)methyl)-5-(3-methylbut-3-en-1-ynyl)-7H-pyrrolo[2,3-d]pyrimidin-2-amine (see example 51) (263 mg) with AD-mix-α (Aldrich, 1.41 g) in t-BuOH:water 1:1: (7 mL) at rt for 3 days, followed by quench (NaHSO₃, 1.6 g), work-up, and preparative HPLC gave the title compound (69 mg), as a solid. HPLC Rt=4.36 min

Example 53

(R)-4-(2-amino-4-chloro-7-((4-methoxy-3,5-dimethylpyridin-2-yl)methyl)-7H-pyrrolo[2,3-d]pyrimidin-5-yl)-2-methylbut-3-yne-1,2-diol

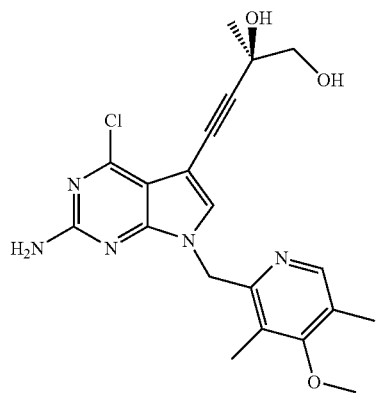

Treatment of 4-chloro-7-((4-methoxy-3,5-dimethylpyridin-2-yl)methyl)-5-(3-methylbut-3-en-1-ynyl)-7H-pyrrolo[2,3-d]pyrimidin-2-amine (see example 51) (357 mg) with AD-mix-β (Aldrich, 1.57 g) in t-BuOH:water 1:1: (10 mL) at rt for 18 h, followed by quench (NaHSO₃, 1.2 g), work-up, and silica gel flash chromatography (1→10% MeOH inDCM) gave the title compound (61 mg) and recovered starting material (263 mg).
Solid. HPLC Rt=4.36 min.

Example 54

(R)-((S)-4-(2-amino-4-chloro-7-((4-methoxy-3,5-dimethylpyridin-2-yl)methyl)-7H-pyrrolo[2,3-d]pyrimidin-5-yl)-2-hydroxy-2-methylbut-3-ynyl) 3,3,3-trifluoro-2-methoxy-2-phenylpropanoate

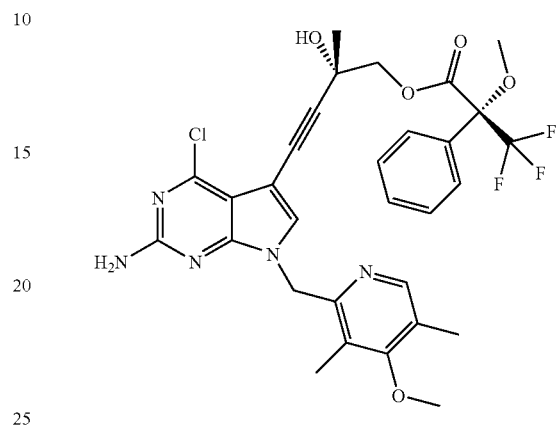

A mixture of (S)-4-(2-amino-4-chloro-7-((4-methoxy-3,5-dimethylpyridin-2-yl)methyl)-7H-pyrrolo[2,3-d]pyrimidin-5-yl)-2-methylbut-3-yne-1,2-diol (see example 52) (18 mg), (S)-(+)-α-methoxy-alpha-(trifluoromethyl)phenylacetyl chloride (45 μL), and Et₃N (50 μL) in THF (3.0 mL) was heated to 70° C. for 2 h, and then to 40° C. overnight. Preparative TLC (EtOAc/DCM 25:65) gave the title compound, as a solid. HPLC Rt=6.45 min.

Example 55

(R)-((R)-4-(2-amino-4-chloro-7-((4-methoxy-3,5-dimethylpyridin-2-yl)methyl)-7H-pyrrolo[2,3-d]pyrimidin-5-yl)-2-hydroxy-2-methylbut-3-ynyl) 3,3,3-trifluoro-2-methoxy-2-phenylpropanoate

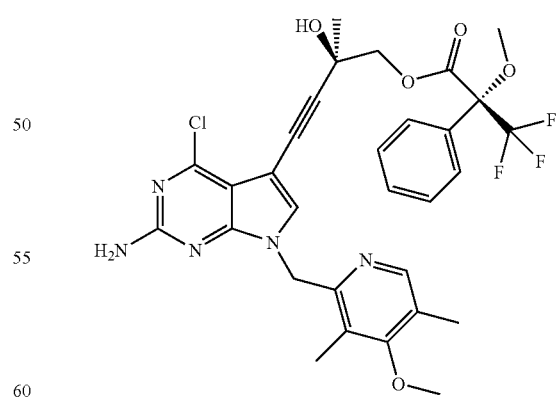

A mixture of (R)-4-(2-amino-4-chloro-7-((4-methoxy-3,5-dimethylpyridin-2-yl)methyl)-7H-pyrrolo[2,3-d]pyrimidin-5-yl)-2-methylbut-3-yne-1,2-diol (see example 53) (22 mg), (S)-(+)-α-methoxy-alpha-(trifluoromethyl)phenylacetyl chloride (45 μL), and Et3N (50 μL) in THF (3.0 mL)

was heated to 40° C. overnight. Preparative TLC (EtOAc/DCM 25:65) gave the title compound, as a solid. HPLC Rt=6.44 min.

Example 56

2-((2-amino-4-chloro-7-((4-methoxy-3,5-dimethylpyridin-2-yl)methyl)-7H-pyrrolo[2,3-d]pyrimidin-5-yl)ethynyl)-2-hydroxypropane-1,3-diyl diacetate

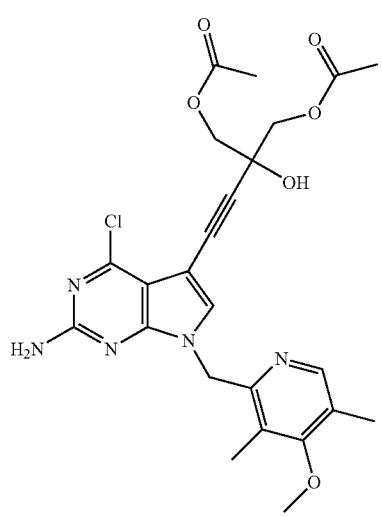

Step 1: 2-ethynyl-2-hydroxypropane-1,3-diyl diacetate

An ethynylmagnesium bromide solution (0.5 M in THF) was cooled to −78° C. under nitrogen. A solution of 1,3-diacetoxyacetone (0.5 g) in THF (3.0 mL) was added, and the resulting mixture was stirred for 30 min at −78° C., then at 0° C. for 5 min, quenched with 1.0 N aq. HCl (3 mL) and extracted in EtOAc. Evaporation gave crude 2-ethynyl-2-hydroxypropane-1,3-diyl diacetate, contaminated with about 50 mol % of 1,3-dacetoxyacetone. The crude material was used without further purification.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with crude 2-ethynyl-2-hydroxypropane-1,3-diyl diacetate according to the general procedure A gave the title compound, as an oil. HPLC Rt=4.89 min.

Example 57

2-((2-amino-4-chloro-7-((4-methoxy-3,5-dimethylpyridin-2-yl)methyl)-7H-pyrrolo[2,3-d]pyrimidin-5-yl)ethynyl)propane-1,2,3-triol

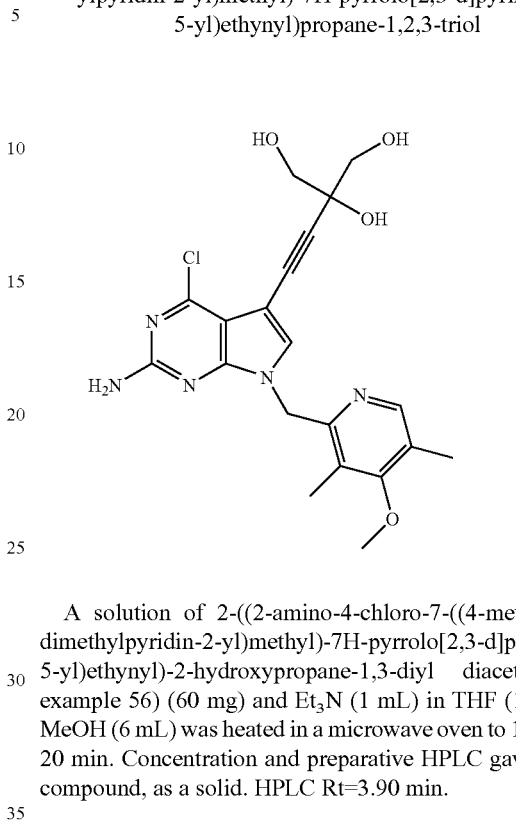

A solution of 2-((2-amino-4-chloro-7-((4-methoxy-3,5-dimethylpyridin-2-yl)methyl)-7H-pyrrolo[2,3-d]pyrimidin-5-yl)ethynyl)-2-hydroxypropane-1,3-diyl diacetate (see example 56) (60 mg) and Et$_3$N (1 mL) in THF (1 mL) and MeOH (6 mL) was heated in a microwave oven to 150° C. for 20 min. Concentration and preparative HPLC gave the title compound, as a solid. HPLC Rt=3.90 min.

Example 58

4-(2-amino-4-chloro-7-((4-methoxy-3,5-dimethylpyridin-2-yl)methyl)-7H-pyrrolo[2,3-d]pyrimidin-5-yl)-2-methylbut-3-yn-2-ol

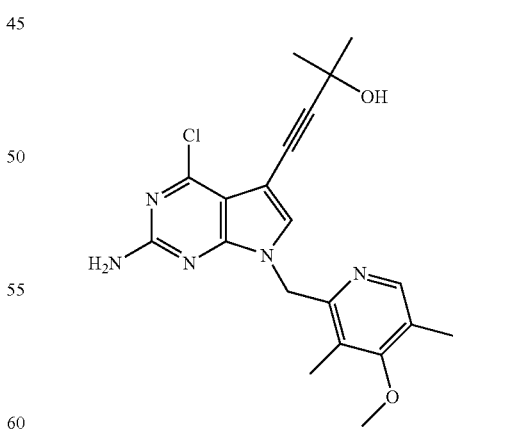

Sonogashira coupling of 4-chloro-5-iodo-7-((4-methoxy-3,5-dimethylpyridin-2-yl)methyl)-7H-pyrrolo[2,3-d]pyrimidin-2-amine with 2-methylbut-3-yn-2-ol according to the general procedure A gave the title compound, as a solid. HPLC Rt=4.81 min.

Example 59

5-(2-amino-4-chloro-7-((4-methoxy-3,5-dimethylpyridin-2-yl)methyl)-7H-pyrrolo[2,3-d]pyrimidin-5-yl)pent-4-yn-2-ol

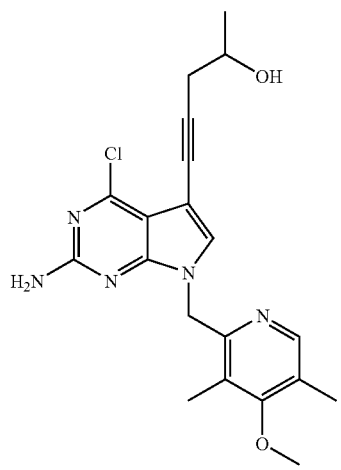

Sonogashira coupling of 4-chloro-5-iodo-7-((4-methoxy-3,5-dimethylpyridin-2-yl)methyl)-7H-pyrrolo[2,3-d]pyrimidin-2-amine with pent-4-yn-2-ol according to the general procedure A gave the title compound, as a solid. HPLC Rt=4.29 mm

Example 60

4-(2-amino-4-chloro-7-((4-methoxy-3,5-dimethylpyridin-2-yl)methyl)-7H-pyrrolo[2,3-d]pyrimidin-5-yl)but-3-ynyl acetate

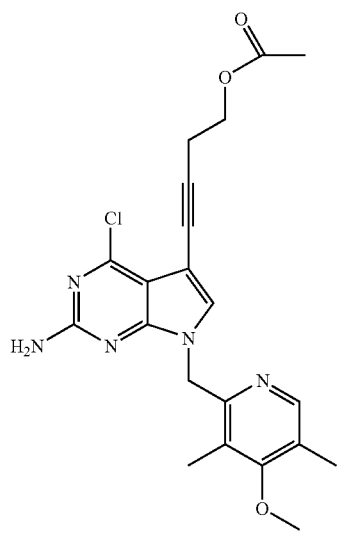

Step 1: But-3-ynyl acetate

A solution of but-3-yn-1-ol (3.0 mL) and Et₃N (6.6 mL) in 1,2-dichloroethane (10 mL) was treated with AcCl (3.1 mL) with caution (very exothermic). Work-up gave but-3-ynyl acetate.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with but-3-ynyl acetate according to the general procedure A gave the title compound, as a solid. HPLC Rt=5.31 mm.

Example 61

4-(2-amino-4-chloro-7-((4-methoxy-3,5-dimethylpyridin-2-yl)methyl)-7H-pyrrolo[2,3-d]pyrimidin-5-yl)but-3-ynyl sulfamate

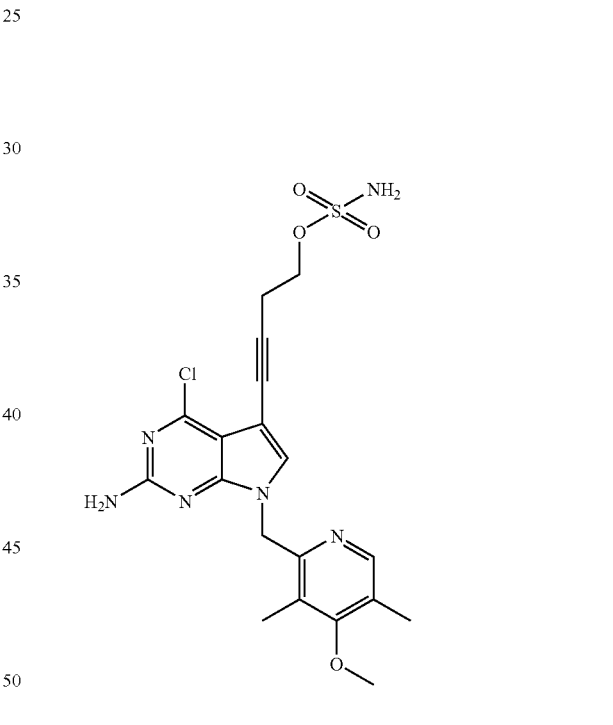

A mixture of formic acid (0.463 g) and N,N-dimethylacetamide (1 drop) was added to a solution of chlorosulfonyl isocyanate (1.31 g) in DCM (9 mL), and heated to reflux for 3 h. The resulting solution was added to a solution of 4-[2-Amino-4-chloro-7-(4-methoxy-3,5-dimethyl-pyridin-2-yl-methyl)-7H-pyrrolo[2,3-d]pyrimidin-5-yl]-but-3-yn-1-ol (see example 2) (200 mg) in DMA (10 mL) and stirred at rt for 30 mm. Work-up and reverse-phase preparative HPLC gave the title compound, as a solid. HPLC Rt=4.96 mm.

Example 62

5-(2-amino-4-chloro-7-((4-methoxy-3,5-dimethylpyridin-2-yl)methyl)-7H-pyrrolo[2,3-d]pyrimidin-5-yl)pent-4-ynyl sulfamate

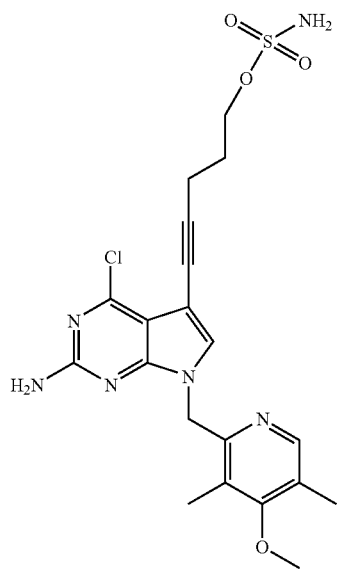

The title compound was obtained by the same procedure as in example 61, carrying out the reaction on 5-[2-Amino-4-chloro-7-(4-methoxy-3,5-dimethyl-pyridin-2-ylmethyl)-7H-pyrrolo[2,3-d]pyrimidin-5-yl]-pent-4-yn-1-ol (see example 2). Solid. HPLC Rt=4.77 mm.

Example 63

4-(2-amino-4-chloro-7-((4-methoxy-3,5-dimethylpyridin-2-yl)methyl)-7H-pyrrolo[2,3-d]pyrimidin-5-yl)but-3-ynyl hydrogen sulfate

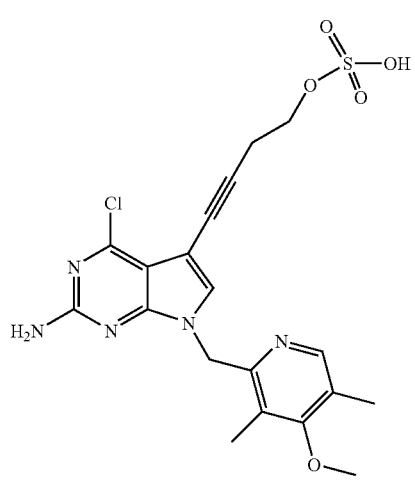

Step 1: But-3-ynyl hydrogen sulfate, pyridine salt

But-3-yn-1-ol (2.1 g) in DCM (20 mL) was treated with sulfur trioxide-pyridine complex (4.77 g) overnight. The solid was filtered off and the reaction mixture was concentrated and used without further purification.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with the pyridine salt of but-3-ynyl hydrogen sulfate according to the general procedure A gave the title compound. Solid. HPLC Rt=4.24 mm.

Example 64

4-(2-amino-4-chloro-7-((4-methoxy-3,5-dimethylpyridin-2-yl)methyl)-7H-pyrrolo[2,3-d]pyrimidin-5-yl)but-3-ynyl bis(2,2,2-trichloroethyl) phosphate

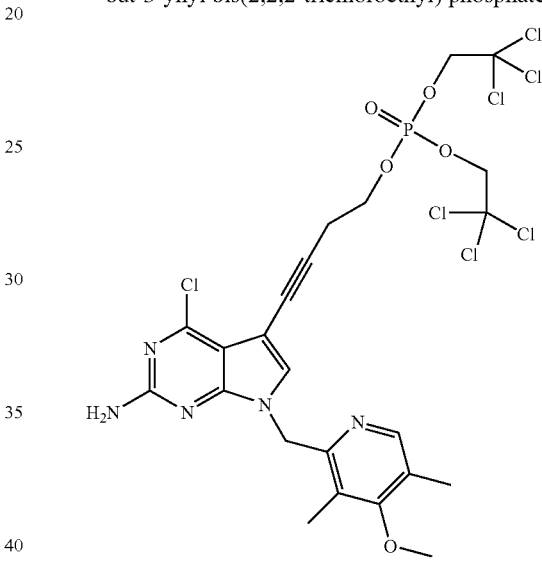

Step 1: But3-ynyl bis(2,2,2-trichloroethyl) phosphate

A solution of but-3-yn-1-ol (0.413 g) in DCE (20 mL) was treated with Et$_3$N (2 mL) and bis(2,2,2-trichloroethyl)phosphorochloride (2.27 g) at 50° C. overnight. Work-up gave crude but-3-ynyl bis(2,2,2-trichloroethyl) phosphate as an oil that was used without further purification.

Step 2

Sonogashira coupling of 4-chloro-5-iodo-7-((4-methoxy-3,5-dimethylpyridin-2-yl)methyl)-7H-pyrrolo[2,3-d]pyrimidin-2-amine with but-3-ynyl bis(2,2,2-trichioroethyl) phosphate according to the general procedure I gave the title compound.
Solid. HPLC Rt=6.69 mm.

Example 65 rHSP90 Competitive Binding Assay

Five microgram of purified rHSP90 protein (Stressgen, BC, Canada, #SPP-770) in phosphate buffered saline (PBS) was coated on 96 well plates by incubating overnight at 4° C. Unbound protein was removed and the coated wells were washed twice with 200 µL PBS. DMSO controls (considered as untreated samples) or test compounds were then added at 100-30-10-3-1-0.3 µM dilutions (in PBS), the plates mixed for 30 seconds on the plate shaker, and then incubated for 60 min. at 37° C. The wells were washed twice with 200 µL PBS, and 10 µM biotinylated-geldanamycin (biotin-GM) was added and incubated for 60 min. at 37° C. The wells were washed again twice with 200 µL PBS, before the addition of 20 µg/mL streptavidin-phycoerythrin (streptavidin-PE) (Molecular Probes, Eugene, Oreg.) and incubation for 60 min. at 37° C. The wells were washed again twice with 200 µL PBS. Relative fluorescence units (RFU) was measured using a SpectraMax Gemini XS Spectrofluorometer (Molecular Devices, Sunnyvale, Calif.) with an excitation at 485 nm and emission at 580 nm; data was acquired using SOFTmax®PRO software (Molecular Devices Corporation, Sunnyvale, Calif.). The background was defined as the RFU generated from wells that were not coated with HSP90 but were treated with the biotin-GM and streptavidin-PE. The background measurements were subtracted from each sample treated with biotin-GM and streptavidin-PE measurements before other computation. Percent inhibition of binding for each sample was calculated from the background subtracted values as follows:

% binding inhibition=[(RFU untreated−RFU treated)/ RFU untreated]×100.

Example 66

Cell Lysate Binding Assay

MCF7 breast carcinoma cell lysates were prepared by douncing in lysing buffer (20 mM HEPES, pH 7.3, 1 mM EDTA, 5 mM MgCl$_2$, 100 mM KCl), and then incubated with or without test compound for 30 mins at 4° C., followed by incubation with biotin-GM linked to BioMag™ streptavidin magnetic beads (Qiagen) for 1 hr at 4° C. The tubes were placed on a magnetic rack, and the unbound supernatant removed. The magnetic beads were washed three times in lysis buffer and boiled for 5 mins at 95° C. in SDS-PAGE sample buffer. Samples were analyzed on SDS protein gels, and Western Blots were done for rHSP90. Bands in the Western Blots were quantitated using the Bio-rad Fluor-S Multi-Imager, and the % inhibition of binding of rHSP90 to the biotin-GM was calculated. The lysate binding ability of selected compounds of the invention based on the above assay is summarized in Table 3. The IC$_{50}$ reported is the concentration of test compound needed to achieve 50% inhibition of the biotin-GM binding to rHSP90 in the MCF7 cell lysates.

Example 67

Her2 Degradation Assay

Many cancers are associated with the over expression Her2 protein. It has been shown that compounds able to diminish Her2 levels show good promise as anti-cancer agents. Thus a good in vitro assay for identifying compounds of the present invention, which are likely to demonstrate anti-cancer activity, is the Her2 degradation assay, as described below:

MCF7 breast carcinoma cells (ATCC) were grown in Dulbecco's modified Eagle's medium (DMEM) containing 10% fetal bovine serum (FBS) and 10 mM HEPES, and plated in 24 well plates (50% confluent). Twenty-four hrs later (cells are 65-70% confluent), test compounds were added and incubated overnight for 16 h. For the less potent compounds, the amounts added were &&&100 µM, 30 µM, 10 µM and 1 µM, and for more potent compounds, the amounts added were 1 µM, 0.3 µM, 0.1 µM, 0.03 µM, 0.01 µM and 0.003 µM. The wells were washed with 1 mL phosphate buffered saline (PBS), and 200 µL trypsin was added to each well. After trypsinization was complete, 50 µL of FBS was added to each well. Then 200 µL cells were transferred to 96 well plates. The cells were pipetted up and down to obtain a single cell suspension. The plates were centrifuged at 2,500 rpm for 1 min using a Sorvall Legend RT™ tabletop centrifuge (Kendro Laboratory Products, Asheville, N.C.). The cells were then washed once in PBS containing 0.2% BSA and 0.2% sodium azide (BA buffer). Phycoerythrin (PE) conjugated anti HER2/ Neu antibody (Becton Dickinson, #340552), or PE conjugated anti-keyhole limpet hemocyanin [KLH] (Becton Dickinson, #340761) control antibody was added at a dilution of 1:20 and 1:40 respectively (final concentration was 1 µg/mL) and the cells were pipeted up and down to form a single cell suspension, and incubated for 15 mins. The cells were washed twice with 200 µL BA buffer, and resuspended in 200 µL BA buffer, and transferred to FACSCAN tubes with an additional 250 µL BA buffer. Samples were analyzed using a FACSCalibur™ flow cytometer (Becton Dickinson, San Jose, Calif.) equipped with Argon-ion laser that emits 15 mW of 488 nm light for excitation of the PE fluorochrome. 10,000 events were collected per sample. A fluorescence histogram was generated and the mean fluorescence intensity (MFI) of each sample was determined using Cellquest software. The background was defined as the MFI generated from cells incubated with control IgG-PE, and was subtracted from each sample stained with the HER2/Neu antibody. Cells incubated with DMSO were used as untreated controls since the compounds were resuspended in DMSO. Percent degradation of Her2 was calculated as follows:

% Her2 degraded=[(MFI untreated cells−MFI treated cells)/MFI untreated cell]×100.

The Her2 degradation ability of selected compounds of the invention based on this assay is summarized in Table 3. IC$_{50}$ is defined as the concentration at which there was 50% degradation of the HER2/Neu protein.

Example 68

MTS Assay 3-(4,5-dimethylthiazol-2-yl)-5-(3-carboxymethoxyphenyl)-2-(4-sulfophenyl)-2H-tetrazolium assays measure the cytotoxicity of geldanamycin derivatives. MTS (3-(4,5-dimethylthiazol-2-yl)-5-(3-carboxymethoxyphenyl)-2-(4-sulfophenyl)-2H-tetrazolium) is a tetrazolium dye that is converted to a formazan product by dehydrogenase enzymes of metabolically active cells (Corey, A. et al. "Use of an aqueous soluble tetrazolium/formazan assay for cell growth assays in culture," Cancer Commun. 1991, 3, 207-212). Cells were seeded in 96 well plates at 2000 cells/well and allowed to adhere overnight in Dulbecco's modified Eagle's medium supplemented with 10% fetal bovine serum. The final culture volume was 100 µl. Viable cell number was determined by using the Celltiter 96 AQ$_{ueous}$ Non-radioactive Cell Proliferation Assay (Promega, Madison Wis.). The MTS/PMS (phenazine methosulfate) solution was mixed at a ratio of 20:1, and 20 µL was added per well to 100 µl of culture medium. After 2-4 hours, the formation of the formazan product was measured at 490 nm absorbance using a multiwell plate spectrophotometer. Background was determined by measuring the Abs 490 nm of cell culture medium and MTS-PMS in the absence of cells and was subtracted from all values. Percent viable cells was calculated as follows:

% viable cells=(Abs at 490 nm treated cells/Abs at 490 nm untreated cells)×100

The effect of selected compounds of the invention on MCF7 breast carcinoma cells according to the MTS assay is summarized in table 3. $IC_{50}$ was defined as the concentration of the compound which gave rise to 50% reduction in viable cell number.

TABLE 3

Biological Activities of Selected Compounds of the Invention

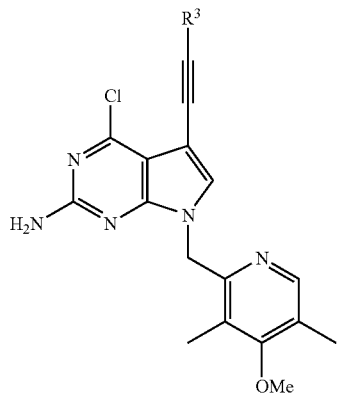

| Sample. No | Example | R³ | IC₅₀ (μM) Her2 | Lysate binding | MTS BT474 | MTS MCF7 |
|---|---|---|---|---|---|---|
| 1 | 1 | —CH₂OH | 0.012 | ND | 0.02 | 0.13 |
| 2 | 10 | —CH₂CH₂CON(Et)₂ | 0.03 | 0.018 | 0.05 | 0.7 |
| 3 | 2 | —CH₂CH₂OH | 0.006 | 0.003 | 0.006 | 0.013 |
| 4 | 3 | —CH₂CH₂CH₂OH | 0.006 | 0.003 | 0.008 | 0.013 |
| 5 | 5 | —CH₂N(iPr)₂ | 0.055 | ND | 0.08 | 0.1 |
| 6 | 11 | —CH₂CH₂C(O)—N⟨⟩N—Me | 0.018 | ND | 0.02 | 0.1 |
| 7 | 12 | —CH₂CH₂CONH₂ | 0.016 | 0.012 | 0.02 | 0.03 |
| 8 | 16 | —CH₂CH₂CH₂NH₂ | 0.028 | ND | >10 | 0.09 |
| 9 | 15 | —CH₂CH₂CH₂NHBOC | 0.009 | ND | 1.0 | 0.06 |
| 10 | 17 | —CH₂CH₂CH₂—N(phthalimide) | 0.007 | ND | 0.1 | 0.01 |
| 11 | 18 | —CH₂CH₂—N(morpholine) | 0.01 | ND | 1.0 | 0.05 |
| 12 | 19 | —CH₂CH₂CH₂—N(morpholine) | 0.015 | ND | 1.0 | 0.1 |
| 13 | 20 | —CH₂CH₂NHtBu | 0.012 | ND | 23 | 130 |
| 14 | 21 | —CH₂CH₂CH₂NHt-Bu | 0.015 | ND | 30 | 230 |
| 15 | 7 | —CH₂CH₂CH₂CH₂OH | 0.009 | ND | 20 | 200 |
| 16 | 22 | —CH₂O(CO)CH₂NMe₂ | 0.013 | ND | 20 | 200 |

ND, not determined.

Example 69

In Vivo Mouse Tumor Studies

Six to 8 week old Balb/C and nu/nu athymic female mice were obtained from Harlan Sprague Dawley, (Indianapolis, Ind.). The mice were maintained in sterilized filter topped cages or ventilated caging in a room with a 12 hour light/dark cycle. Irradiated pelleted food (Harlan Teklad #7912) and autoclaved deionized water were provided ad libitum. Animals were identified by the use of individually numbered ear tags. Experiments were carried out under institutional guidelines for the proper and human use of animals in research established by the Institute for Laboratory Animal Research (ILAR).

Tumor fragments (approximately 2 mm$^3$) or 5×10$^6$ tumor cells were inoculated subcutaneously in the right or left flank of the animal. Mice with established tumors (50-200 mm$^3$) were selected for study (n=7-10/treatment group). Tumor dimensions were measured using calipers and tumor volumes were calculated using the equation for an ellipsoid sphere (l×w$^2$)/2=mm$^3$, where l and w refer to the larger and smaller dimensions collected at each measurement.

Mice were followed until tumor volumes in the control group reached approximately 1000 mm$^3$ and were sacrificed by CO$_2$ euthanasia. The mean tumor volumes of each group were calculated. The change in mean treated tumor volume was divided by the change in mean control tumor volume, multiplied by 100 and subtracted from 100% to give the tumor growth inhibition for each group. Statistical analysis was performed using the standard T-test and using GraphPad Prism© Software.

Example 70

N87 Gastric Carcinoma Xenograft

Tumors were established in mice, by innoculation of human N87 stomach cancer cells, according to example 69. Four treatment groups (n=7-10/treatment group) were established for study:
I. 4-[2-Amino-4-chloro-7-(4-methoxy-3,5-dimethyl-pyridin-2-ylmethyl)-7H-pyrrolo[2,3-d]pyrimidin-5-yl]-but-3-yn-1-ol, prepared as described in example 2 above, was administered at 8 mg/kg po
II. 5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol, prepared as described in example 23 above, was administered at 8 mg/kg po
III. 5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol, prepared as described in example 23 above, was administered at 16 mg/kg po
IV. Vehicle alone was administered to the control group.

The results are shown in FIG. 1, a plot of tumor volume (mm$^3$) against time (days).

Example 71

NCI295 Adrenocortical Carcinoma Xenograft

Tumors were established in mice, by innoculation of NCI295 adrenocortical carcinoma cells, according to example 69. Two treatment groups (n=7-10/treatment group) were established for study:
I. 5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol, prepared as described in example 23 above, was administered at 8 mg/kg po
II. Vehicle alone was administered to the control group.

Figure 2:
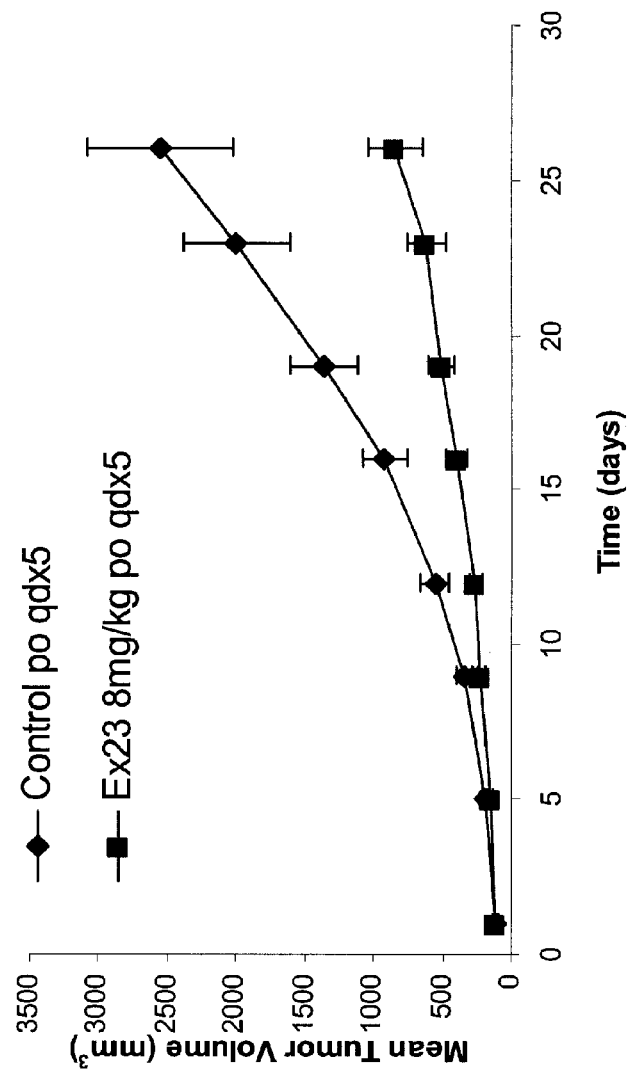
FIG. 2 represents a plot of tumor volume ($mm^3$) against time (days), for animals administered compounds of the present invention (and controls) in a mouse NCI295 Adrenocortical Carcinoma Xenograft model, as described in example 71.

The results are shown in FIG. 2, a plot of tumor volume (mm$^3$) against time (days).

Example 72

SK-MEL-28 Melanoma Xenograft

Tumors were established in mice, by innoculation of SK-MEL-28 melanoma cells, according to example 69. Two treatment groups (n=7-10/treatment group) were established for study:

I. 5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol, prepared as described in example 23 above, was administered at 8 mg/kg po
II. Vehicle alone was administered to the control group.

Figure 3:
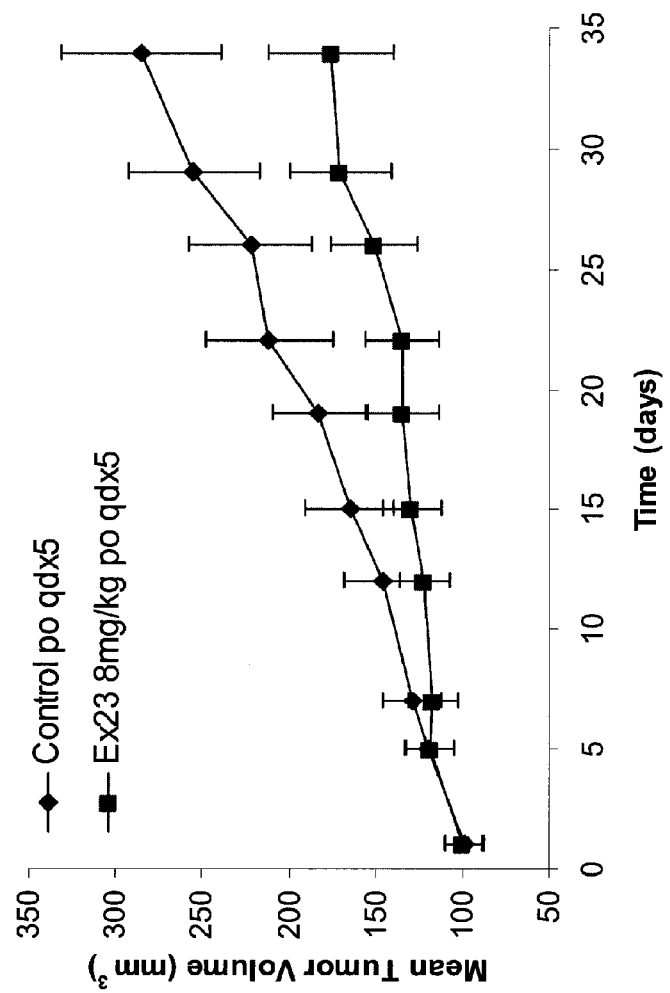
FIG. 3 represents a plot of tumor volume ($mm^3$) against time (days), for animals administered compounds of the present invention (and controls) in a mouse SK-MEL-28 Melanoma Xenograft model, as described in example 72.

The results are shown in FIG. 3, a plot of tumor volume (mm$^3$) against time (days).

Example 73

HT29 Colon Carcinoma Xenograft

Tumors were established in mice, by innoculation of HT29 Colon Carcinoma cells, according to example 69. Three treatment groups (n=7-10/treatment group) were established for study:
I. 5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol, prepared as described in example 23 above, was administered at 4 mg/kg po
II. 5-(2-amino-4-chloro-7-((4-methoxy-3,5-dimethylpyridin-2-yl)methyl)-7H-pyrrolo[2,3-d]pyrimidin-5-yl)-2-methylpent-4-yn-2-ol, prepared as described in example 23 above, was administered at 8 mg/kg po
III. Vehicle alone was administered to the control group.

Figure 4:
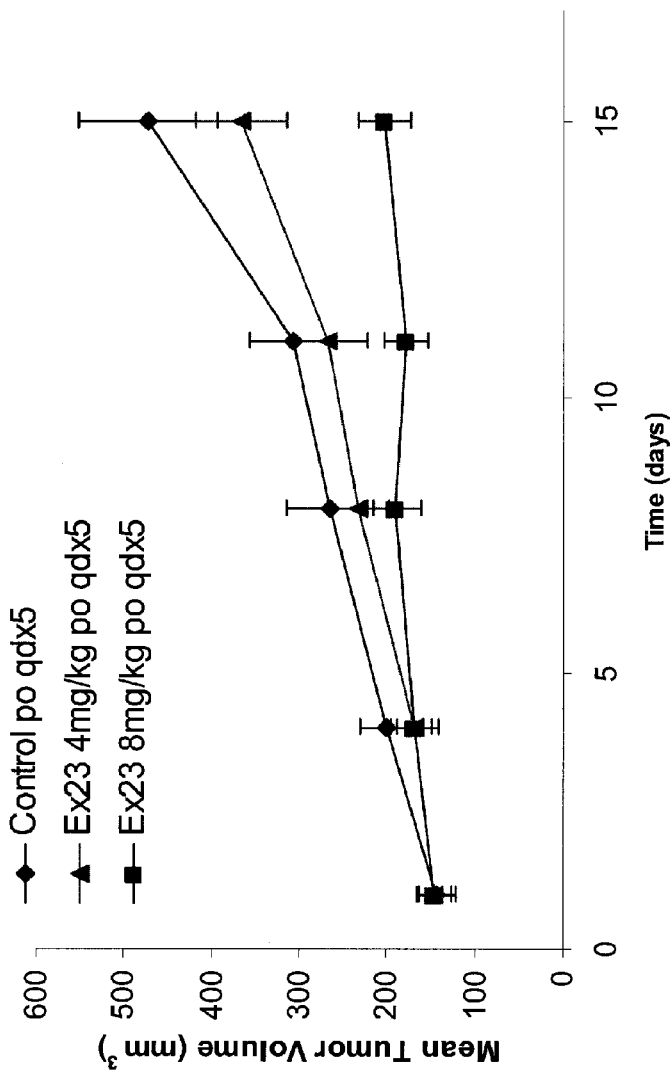
FIG. 4 represents a plot of tumor volume ($mm^3$) against time (days), for animals administered compounds of the present invention (and controls) in a mouse a plot of tumor volume ($mm^3$) against time (days), for animals administered compounds of the present invention (and controls) in a mouse HT29 Colon Carcinoma Xenograft model, as described in example 73.

The results are shown in FIG. 4, a plot of tumor volume (mm$^3$) against time (days).

Example 74

Pharmacodynamic Effects

Preparation of Buffers and Reagents

The following reagents and buffers are prepared ahead of the experiments.

Western Lysis Buffer (WLS) contains 10 mM HEPES, 42 mM KCl, 5 mM MgCl2, 0.1 mM EDTA, 0.1 mM EGTA, 1 mM DTT, 1 mM PMSF, 1 ug/ml Pepstatin A, 1 ug/ml Leupeptin, 5 ug/ml Aprotinin, and 1% Triton X-100. Aliquot and store at −20° C.

5× Western Sample Buffer (5× WSB) contains 20 ml glycerol, 4 ml β-mercaptoethanol, 5 g SDS, 12.5 ml 1M Tris pH 6.8, and 50 mg bormophenol blue. Add water to a final volume of 50 ml. Aliquot and store at −20° C.

Western Transfer Buffer contains 23.3 g Tris base, 116 g glycine and 1.6L methanol. Add water to a final volume of 8L and store at 4° C.

TBST (1×) contains 10 mM Tris pH8.0, 150 mM NaCl and 0.1% Tweene 20.

Blocking solution contains 5% nonfat dry milk in 1× TBST. Keep at 4° C.

Processing of Tumor Samples:

Snap-frozen N87 gastric carcinoma tumors are transferred from liquid nitrogen into −80° C. freezer. WLB is supplemented with protease inhibitor cocktail (stock at 100×) on ice. Each tumor is thawed on ice and transferred onto the lid of a Petri dish. It is covered with 50 ul of WLB and is dissected into smaller pieces with disposable scalpels. Any residual skin attached to the tumor is removed. The tumor pieces are then chopped further down, and transferred into 300-500 ul of ice-cold WLB. The minced sample is sonicated at setting 3 on Fisher Scientific's Sonic Dismembrator 550 untill no more solid pieces can be broken down. The suspension is then centrifuged at 15,000 g, 4° C. for 5 minutes. The supernatant is collected into a clean Eppendorf tube on ice as lysate. 2 ul of the lysate is used for total protein quantification by following directions in the BCA Protein Assay kit. The rest of the lysate is snap-frozen in liquid nitrogen while the BCA assay is in process. The total protein concentration in each lysate is calculated upon completion of BCA assay. The lysates are thawed in a water bath, and their total protein concentrations adjusted to 4-10 mg/ml using 5× WSB (to a final of 20% of the total volume) and WLB (if necessary). The adjusted lysates are boiled at 95° C. for 5 minutes and cooled to room temperature. At this stage, they are frozen at −20° C. for future Western blotting analysis.

Western Blotting Analysis:

The quantified and adjusted lysates from tumor or spleen samples are thawed in a water bath, and loaded at equal total protein amount onto 4-12% Tris-glycine precast gels together with biotinylated protein marker. Electrophoresis is carried out at 140V for 1.5 hours. The separated proteins in the gels are transferred onto PVDF membranes at 100V for about 1 hour in Western transfer buffer. The blots are incubated in blocking buffer at room temperature for 1 hour or at 4° C. overnight with gentle rocking. Primary antibodies against various HSP90 client proteins of interest are applied at room temperature for 1 hour with gentle rocking. Excess antibodies are washed off with six 5-minute washes in TBST. The blots are then incubated in HRP-conjugated secondary antibodies and streptavidin-HRP conjugate at room temperature for 1 hour with gentle rocking. Excess secondary antibodies and conjugate are washed off by six 5 minute washes in TBST. The blots are then developed using Pierce's SuperSignal West Femto chemilluminescent substrate by mixing freshly prepared equal volumes of luminal enhancer and peroxide buffer and adding the mixture onto the blots one at a time. The protein bands can be visualized on Bio-Rad's fluor-S Max2 MultiImager using Bio-Rad's Quantity One software.

Figure 5:
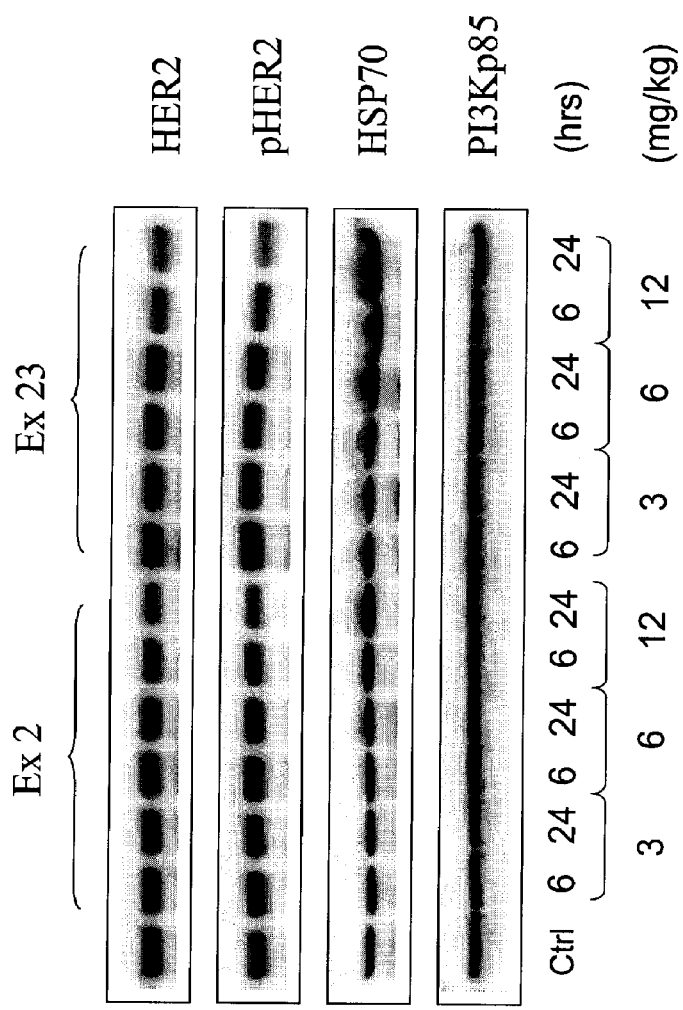
FIG. 5 represents Western Blot protein analysis of N87 gastric carcinoma cells after treatment with compounds 2 and 23 at varying concentrations and timepoints, as described in example 74.

The results of the Western Blott analysis are shown in FIG. 5.

The foregoing examples are not limiting and are merely illustrative of various aspects and embodiments of the present invention. All documents cited herein are indicative of the levels of skill in the art to which the invention pertains and are incorporated by reference herein in their entireties. None, however, is admitted to be prior art.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the spirit of the invention, as defined by the scope of the claims.

The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, e.g., genuses, those skilled in the art will recognize that the invention is also thereby described in terms of any individual member or subgroup of members of the Markush group or subgenus, and exclusions of individual members as appropriate, e.g., by proviso.

Other embodiments are within the following claims.

What is claimed is:

1. A compound represented by Formula I, or a pharmaceutically acceptable salt thereof,

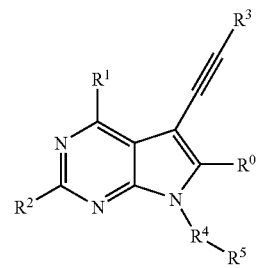

wherein:

$R^0$ is hydrogen;

$R^1$ is chloro;

$R^2$ is —$NH_2$;

$R^3$ is substituted lower alkyl wherein the substituent on $R^3$ is selected from —OP(O)(OH)$_2$ and —OR$^8$ wherein $R^8$ is selected from hydrogen, lower alkyl, and —C(O)R$^9$ wherein $R^9$ is selected from H, lower alkyl, —NR$^{10}$R$^{10}$ and —OR$^{11}$, wherein each $R^{10}$ is independently selected from hydrogen and lower alkyl, or $R^{10}$ and $R^{10}$ taken together with the N atom to which they are attached form an optionally substituted ring comprising 3-7 ring atoms, wherein, in addition to said N atom, 0-3 of the ring atoms are heteroatoms selected from O, S and N; and $R^{11}$ is lower alkyl;

$R^4$ is lower alkylene; and $R^5$ is 3,5-dimethyl-4-methoxy-pyridin-2-yl.

2. The compound of claim 1, or a pharmaceutically acceptable salt thereof, wherein $R^3$ is —(CH$_2$)$_n$OH, where n is 1, 2, or 3.

3. The compound of claim 1, or a pharmaceutically acceptable salt thereof, wherein $R^3$ is —(CH$_2$)$_m$C(R$^{12}$)$_2$(CH$_2$)$_n$OH, wherein m is 0, 1, or 2; n is 1 or 2; and each $R^{12}$ is independently hydrogen or lower alkyl.

4. The compound of claim 1, or a pharmaceutically acceptable salt thereof, wherein $R^3$ is lower alkyl substituted with the group —OP(O)(OH)$_2$.

5. The compound of claim 1, or a pharmaceutically acceptable salt thereof, wherein $R^4$ is —CH$_2$—.

6. A compound, or a pharmaceutically acceptable salt thereof, selected from

211
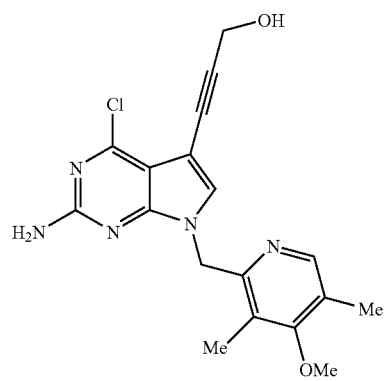
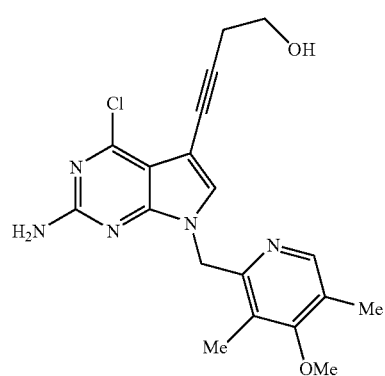
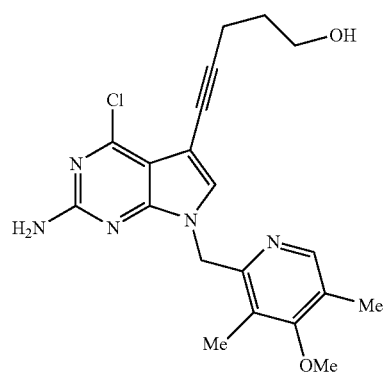
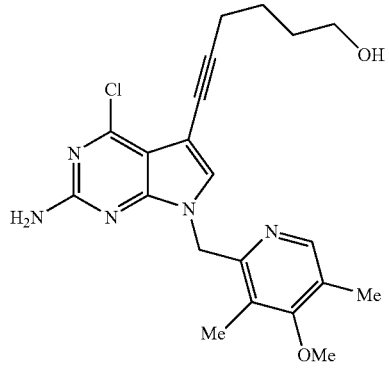
212
-continued
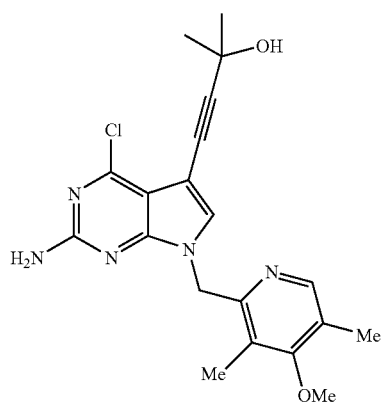
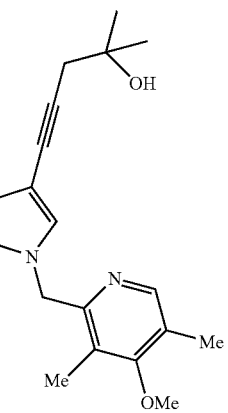
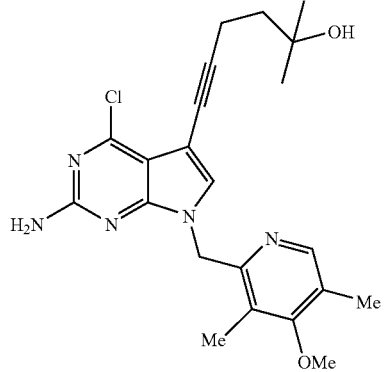
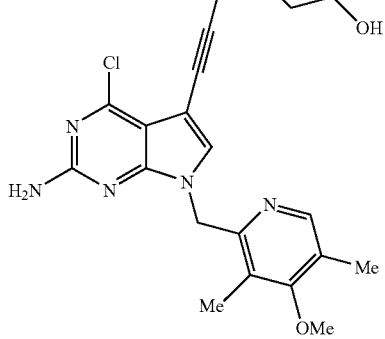

213
-continued
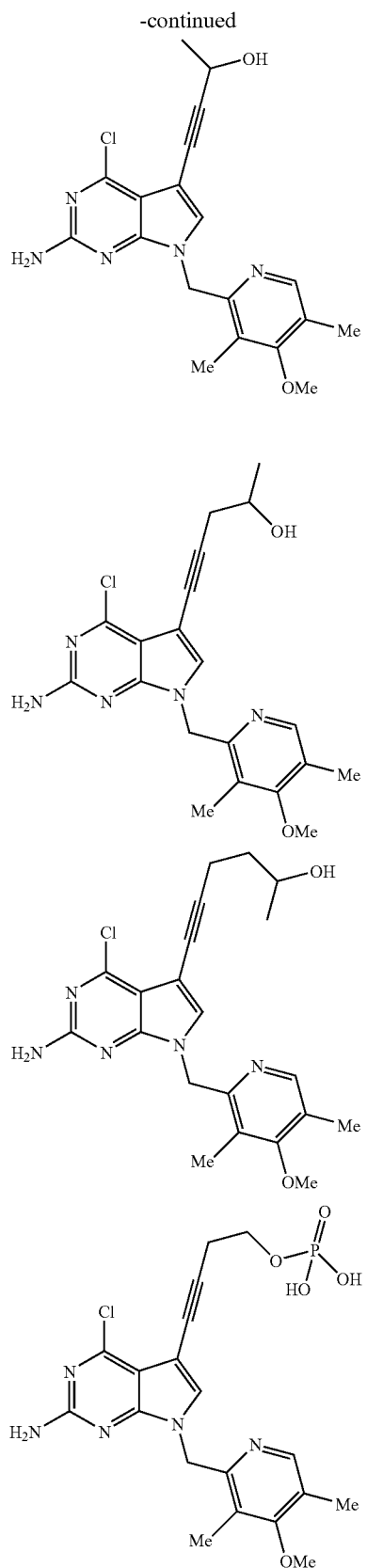
214
-continued
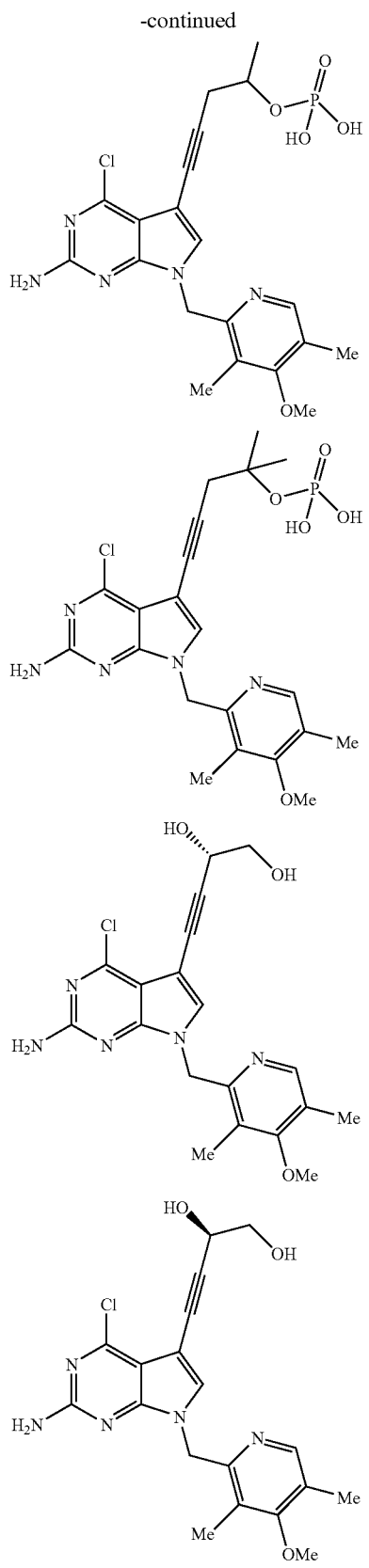

-continued

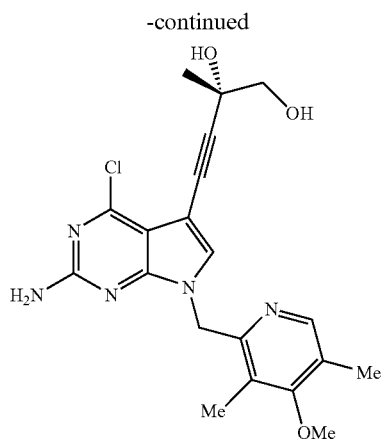

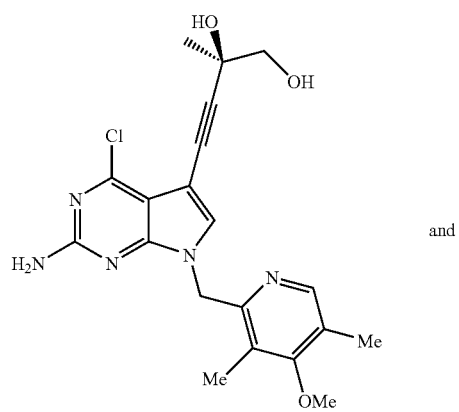

and

7. A compound, or a pharmaceutically acceptable salt thereof, of the formula:

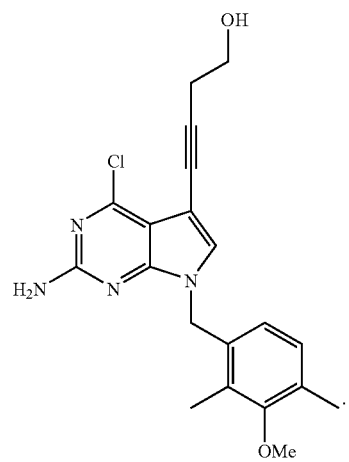

8. A compound, or a pharmaceutically acceptable salt thereof, of the formula:

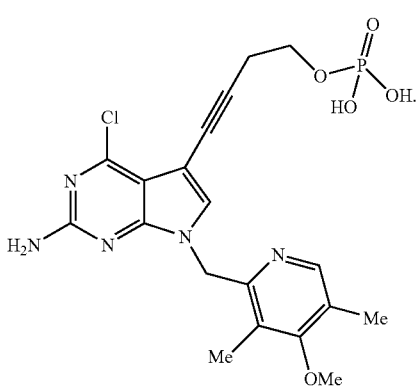

9. A compound, or a pharmaceutically acceptable salt thereof, of the formula:

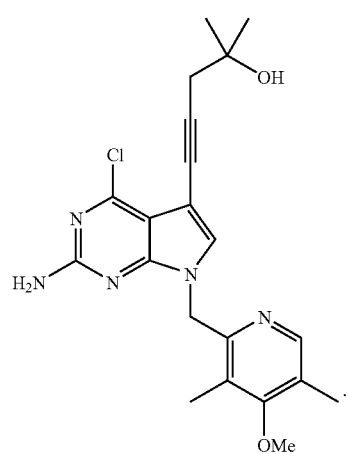

10. A pharmaceutical composition comprising a compound, or a pharmaceutically acceptable salt thereof, of claim 1, and one or more pharmaceutically acceptable excipients.

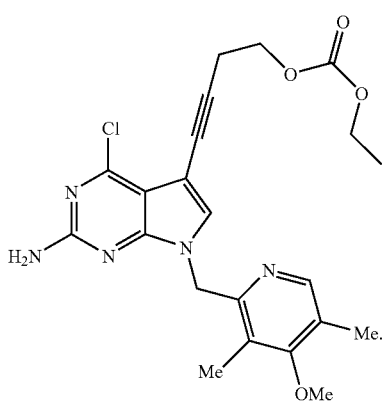

11. A pharmaceutical composition comprising a compound, or a pharmaceutically acceptable salt thereof, of claim 7, and one or more pharmaceutically acceptable excipients.

12. A pharmaceutical composition comprising a compound, or a pharmaceutically acceptable salt thereof, of claim 8, and one or more pharmaceutically acceptable excipients.

13. A pharmaceutical composition comprising a compound, or a pharmaceutically acceptable salt thereof, of claim 9, and one or more pharmaceutically acceptable excipients.

* * * * *

UNITED STATES PATENT AND TRADEMARK OFFICE
CERTIFICATE OF CORRECTION

PATENT NO. : 7,544,672 B2 Page 1 of 1
APPLICATION NO. : 11/277918
DATED : June 9, 2009
INVENTOR(S) : Srinivas Rao Kasibhatla et al.

It is certified that error appears in the above-identified patent and that said Letters Patent is hereby corrected as shown below:

In claim 1, column 210, lines 37-38, "-C(O) $R^9$" should read -- -C(O)$R^9$ --.

In claim 1, column 210, line 52, "3,5-dimethyl-4-methoxy-pyrid in-2-yl." should read -- 3,5-dimethyl-4-methoxy-pyridin-2-yl. --.

In claim 7, column 216, lines 1-20,

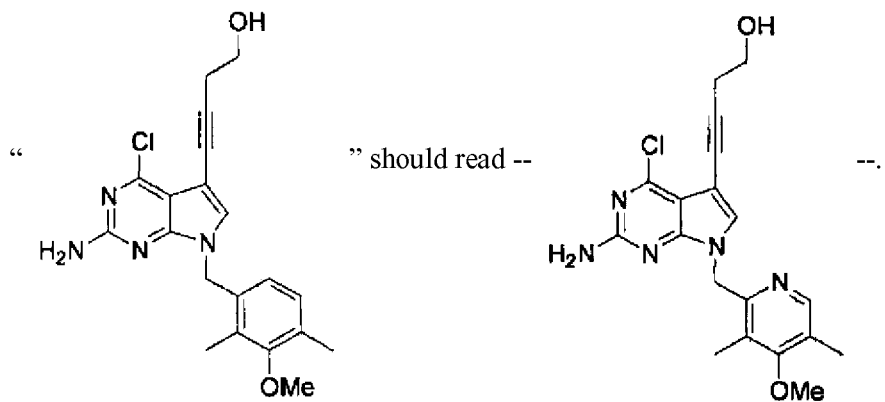

Signed and Sealed this

Eleventh Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,544,672 B2 | Page 1 of 1 |
| APPLICATION NO. | : 11/277918 | |
| DATED | : June 9, 2009 | |
| INVENTOR(S) | : Kasibhatla et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 115 days.

Signed and Sealed this
Sixteenth Day of August, 2011

David J. Kappos
*Director of the United States Patent and Trademark Office*